United States Patent
Egan et al.

(10) Patent No.: US 7,118,886 B1
(45) Date of Patent: Oct. 10, 2006

(54) ESE GENES AND PROTEINS

(75) Inventors: Sean E. Egan, Toronto (CA); Wei Wang, Toronto (CA); Ameet Sengar, Toronto (CA)

(73) Assignee: HSC Research and Development Limited Partnership, Ontario (CA)

( * ) Notice: Subject to any disclaimer, the term of this patent is extended or adjusted under 35 U.S.C. 154(b) by 0 days.

(21) Appl. No.: 09/674,237

(22) PCT Filed: Apr. 27, 1999

(86) PCT No.: PCT/CA99/00375

§ 371 (c)(1),
(2), (4) Date: Jul. 24, 2001

(87) PCT Pub. No.: WO99/55728

PCT Pub. Date: Nov. 4, 1999

Related U.S. Application Data

(60) Provisional application No. 60/118,739, filed on Feb. 5, 1999.

(30) Foreign Application Priority Data

Apr. 27, 1998 (CA) .................................. 2230201

(51) Int. Cl.
*C12P 21/06* (2006.01)

(52) U.S. Cl. ................. 435/69.1; 435/70.1; 435/252.3; 435/320.1; 435/325; 536/23.1; 536/23.5; 536/24.3; 536/24.31

(58) Field of Classification Search ............... 435/69.1, 435/70.1, 252.3, 320.1, 325; 536/23.1, 24.3, 536/23.5, 24.31
See application file for complete search history.

(56) References Cited

U.S. PATENT DOCUMENTS

| 5,717,067 | A | 2/1998 | Fazioli et al. | |
|---|---|---|---|---|
| 6,309,820 | B1 * | 10/2001 | Sparks et al. | .................. 435/6 |
| 2002/0034755 | A1 * | 3/2002 | Sparks et al. | |

FOREIGN PATENT DOCUMENTS

WO      WO 96 31625 A     10/1996

OTHER PUBLICATIONS

MPSRCH search report, 2002, us-09-674-237a-3.rai, pp. 1-2.*
Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
Gura (Science, 1997, 278:1041-1042).*
Jain (Sci. Am., 1994, 271:58-65).*
Curti (Crit. Rev. in Oncology/Hematology, 1993, 14:29-39).*
Hartwell et al (Science, 1997, 278:1064-1068).*
Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Harris et al. J. of The Am Society of Nephrology 6:1125-33, 1995.*
Ahn et al. Nature Genetics 3(4):283-91, 1993.*
Cawthon et al. Genomics 9(3):446-60, 1991.*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Sparks, AB et al, 1996, Genbank Sequence Database (Accession U61166), or Nat. Biotechnol, 14(6): 741-744, 1996, and MPSRCH search report, 2003, us-09-674-273a-1.rge, pp. 28-30.*
MPSRCH search report, 2003, us-09-674-273a-2.mpb, pp. 6-7.*
Muller et al, 1992, Mol Cell Biol, 12: 5087-5093.*
Sambrook et al, eds, 1989, Molecular Cloning, A laboratory manual, 2nd ed, Cold Spring Harbor Laboratory Press, Cold Spring Harbor, p. 14.2-14.3.*
H. Riezman, P. G. Woodman, G. van Meer, M. Marsh. Molecular mechanisms of Endocytosis. Cell 91: 731-738, 1997.
S. L. Schmid. Clathrin-coated vesicle formation and protein sorting: an integrated process. Annu. Rev. Biochem. 66: 511-548, 1997.
M. S. Robinson. Coats and budding vesicles. Trends Cell. Biol. 7: 99-102, 1997.
D. E. Warnock, S. L. Schmid. Dynamin GTPase, a force-generating molecular switch. BioEssays 18: 885-893, 1996.
R. Urrutia, J. R. Henley, T. Cook, M. A. McNiven. The dynamins: redundant or distinct functions for an expanding family of related GTPases? Proc. Natl. Acad. Sci. USA 94: 377-384, 1997.
P. Wigge, K. Kohler, Y. Vallis, C. A. Doyle, D. Owen, S. P. Hunt, H. T. McMahon. Amphiphysin Heterodimers: Potential Role in Clathrin-mediated Endocytosis. Molecular Biology of the Cell 8: 2003-2015, 1997.
A. L. Munn, B. J. Stevenson, M. J. Geli, H. Riezman. end5, end6 and end7:mutations that cause actin delocalization and block the internalization step of endocytosis in *Saccharomyces cerevisiae*. Molecular Biology of the Cell 6: 1721-1742, 1995.
O. Shupliakov, P. Low, D. Grabs, H. Gad, H. Chen, C. David, K. Takei, P. De Camilli, L. Brodin. Synaptic vesicle endocytosis impaired by disruption of dynamin-SH3 domain interactions. Science 276: 259-263, 1997.

(Continued)

*Primary Examiner*—Susan Ungar
*Assistant Examiner*—Minh-Tam Davis
(74) *Attorney, Agent, or Firm*—Meyers Bigel Sibley & Sajovec, P.A.

(57) ABSTRACT

The present invention describes the identification, isolation and characterization of novel mammalian proteins encoded by the Ese1 and Ese2 genes which are involved in endocytosis, vesicular trafficking and regulation of the actin cytoskeleton. Transcripts and products of these genes are useful for detecting abnormal cellular endocytosis processes as well as for developing assay systems to find and elucidate further binding partners of the proteins, to develop therapeutics to alter/restore protein function and for the isolation and manufacture of Ese proteins.

8 Claims, 9 Drawing Sheets

OTHER PUBLICATIONS

Figure 1:
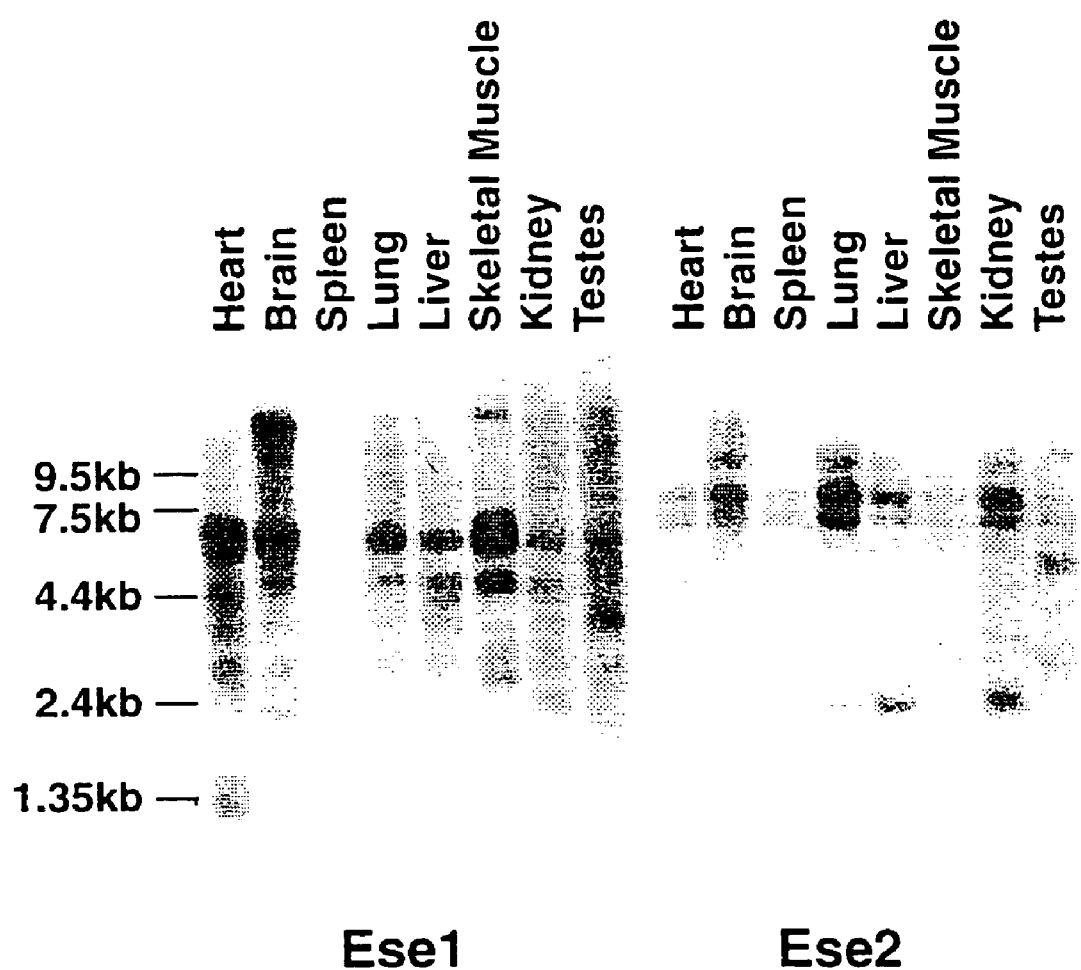

P. Wigge, Y. Vallis, H. T. McMahon. Inhibition of receptor-mediated endocytosis by the amphiphysin SH3 domain. Current Biology 7: 554-560, 1997.

H. McLauchlan, J. Newell, N. Morrice, A. Osborne, M. West, E. Smythe. A novel role for Rab5-GDI in ligand sequestration into clathrin-coated pits. Current Biology 8: 34-45, 1997.

P. J. Robinson, J.-M. Sontag, J.-P. Liu, E. M. Fykse, C. Slaughter, H. McMahon, T. C. Sudhof. Dynamin GTPase regulated by protein kinase C phosphorylation in nerve terminals. Nature 365: 163-166, 1993.

J.-P. Liu, A. T. R. Sim, P. J. Robinson. Calcineurin inhibition of Dynamin GTPase activity coupled to nerve terminal depolarization. Science 265: 970-973, 1994.

A. Wilde, F. M. Brodsky. In vivo phosphorylation of Adaptors regulates their interaction with Clathrin. The Journal of Cell Biology 135: 635-645, 1996.

R. Bauerfeind, K. Takei, P. De Camilli. Amphiphysin I is associated with coated endocytic intermediates and undergoes stimulation-dependent dephosphorylation in nerve terminals. J. Biol. Chem. 272: 30984-30992, 1997.

S. van Delft, R. Govers, G. J. Strous, A. J. Verkleij, P. M. P. van Bergen en Henegouwen. Epidermal growth factor induces ubiquitination of Eps15. Journal of Biological Chemistry 272: 14013-14016, 1997.

J.-M. Galan, R. Haguenauer-Tsapis. Ubiquitin Lys63 is involved in ubiquitination of a membrane plasma membrane protein. EMBO J 16: 5847-5854, 1997.

J. Terrel, S. Shih, R. Dunn, L. Hicke. A function for monoubiquitination in the internalization of a G protein-coupled receptor. Molecular Cell 1: 193-202, 1998.

R. Govers, P. van Kerkhof, A. L. Schwartz, G. J. Strous. Linkage of the ubiquitin-conjugating system and the endocytic pathway in ligand-induced internalization of the growth hormone receptor. EMBO J. 16: 4851-4858, 1997.

P. De Camilli, S. D. Emr, P. S. McPherson, P. Novick. Phosphoinositides as regulators in membrane traffic. Science 271: 1533-1539, 1996.

E. Kubler, H. Riezman. Actin and fimbrin are required for the internalization step of endocytosis in yeast. EMBO J. 12: 2855-2862, 1993.

H. Benedetti, S. Raths, F. Crausaz, H. Riezman. The END3 gene encodes a protein that is required for the internalization step of endocytosis and for actin cytoskeleton organization in yeast. Mol. Biol. Cell. 5: 1023-1037, 1994.

M. I. Geli, H. Riezman. Role of Type I Myosin in receptor-mediated endocytosis in yeast. Science 272: 533-535, 1996.

H.-Y. Tang, M. Cai. The EH-domain-containing protein Pan1 is required for normal organization of the actin cytoskeleton in Saccaromyces cerevisiae. Mol. Cell. Biol. 16: 4897-1914, 1996.

V. Moreau, J.-M. Galan, G. Devilliers, R. Haguenauer-Tsapis, B. Winsor. The yeast Actin-related protein Arp2p is required for the internalization step of endocytosis. Molecular Biology of the Cell 8: 1361-1375, 1997.

B. Wendland, S. D. Emr. Pan1p, Yeast eps15, functions as a multivalent adaptor that coordinates protein-protein interactions essential for endocytosis. Journal of Cell Biology 141: 71-84, 1998.

F. Fazioli, L. Minichiello, B. Matoskova, W. T. Wong, P. P. DiFiore. eps15, A novel tyrosine kinase substrate, exhibits transforming activity. Mol. Cell. Biol. 13: 5814-5828, 1993.

A. Benmerah, J. Gagnon, B. Begue, B. Megarbane, A. Dautry-Varsat, N. Cerf-Bensussan. The Tyrosine kinase substrate EPS15 is constitutively associated with the plasma membrane adaptor AP2. J. Cell Biol. 131: 1831-1838, 1995.

F. Tebar, T. Sorkina, A. Sorkin, M. Ericsson, T. Kirchausen. Eps15 Is a component of Clathrin-coated Pits and Vesicles and is located at the Rim of Coated Pits. Journal of Biological Chemistry 271: 28727-28730, 1996.

F. Tebar, S. Confalonieri, R. E. Carter, P. P. DiFiore, A. Sorkin. Eps15 is Constitutively Oligomerized due to Homolphilic interaction of its Coiled-coil domain. Journal of Biological Chemistry 272: 15413-15418, 1997.

R. Carbone, S. Fre, G. Iannolo, F. Belleudi, M. P., P. G. Pelicci, M. R. Torrisi, P. P. DiFiore. eps15 and eps15R are essential components of the endocytic pathway. Cancer Research 57: 5498-5504, 1997.

A. Benmerah, C. Lamaze, B. Begue, S. L. Schmid, A. Dautry-Varsat, N. Cerf-Bensussan. AP-2/Eps15 interaction is required for receptor-mediated endocytosis. Journal of Cell Biology 140: 1055-1062, 1998.

W. T. Wong, C. Schumacher, A. E. Salcini, A. Romano, P. Castagnino, P. G. Pelicci, P. P. Di Fiore. A protein-binding domain, EH, identified in the receptor tyrosine kinase substrate EPS15 and conserved in evolution. Proc. Natl. Acad. Sci. USA 92: 9530-9534, 1995.

P. P. Di Fiore, P. G. Pelicci, A. Sorkin. EH: a novel protein-protein interaction domain potentially involved in intracellular sorting. Trends. Biochem. Sci. 22: 411-413, 1997.

C. Schumacher, B. S. Knudsen, T. Ohuchi, P. P. Di Fiore, R. H. Glassman, H. Hanafusa. The SH3 domain of Crk binds specifically to a conserved proline-rich motif in Ep 15 and Eps15R. Journal of Biological Chemistry 270: 15341-15347, 1995.

A. Benmerah, B. Begue, A. Dautry-Vasat, N. Cerf-Bensussan. The Ear of alpha-Adaptin interacts with the COOH-terminal domain of the EPS15 protein. Journal of Biological Chemistry 271: 12111-12116, 1996.

G. Iannolo, A. E. Salcini, I. Gaidarov, O. B. J. Goodman, J. Baulida, G. Carpenter, P. G. Pelicci, P. P. Di Fiore, J. H. Keen. Mapping of the molecular determinants involved in the interaction between Eps15 and AP2. Cancer Research 57: 240-245, 1997.

L. Coda, A. E. Salcini, S. Confalonieri, G. Pelicci, T. Sorkina, A. Sorkin, P. G. Pelicci, P. P. Di Fiore. Eps15R is a tyrosine kinase substrate with characteristics of a docking protein possibly involved in coated pits-mediated internalization. Journal of Biological Chemistry 273: 3003-3012, 1998.

B. Wendland, J. M. McCaffery, Q. Xiao, S. D. Emr. A Novel Fluorescence-activated Cell-Sorter-based screen for yeast Endocytosis mutants identifies a yeast homologue of mammalian eps15. J Cell Biol. 135: 1485-1500, 1996.

S. Raths, J. Rohrer, F. Crausaz, H. Riezman. end3 and end4: Two mutants defective in receptor-mediated and fluid-phase endocytosis in Saccaromyces cerevisiae. The Journal of Cell Biology 120: 55-65, 1993.

H. Y. Tang, A. Munn, M. Cai. EH domain proteins Pan1p and End3p are components of a complex that plays a dual role in organization of the cortical actin cytoskeleton and endocytosis in Saccharomyces cerevisiae. Mol. Cell. Biol. 17: 4294-4304, 1997.

T. Zoladek, A. Tobiasz, G. Vaduva, M. Boguta, N. C. Martin, A. K. Hopper, MDPI, a Saccharomyces cerevisiae gene involved in mitochondrial/cytoplasmic protein distribution, is identical to the ubiquitin-protein ligase gene RSP5. Genetics 145: 595-603, 1997.

P. S. McPherson, E. P. Garcia, V. I. Slepnev, C. David, X. Zhang, D. Grabs, W. S. Sossin, R. Bauerfeind, Y. Nemoto, P. De Camilli. A presynaptic inositol-5-phosphatase. Nature 379: 353-357, 1996.

A. E. Salcini, S. Confalonieri, M. Doria, E. Santolini, E. Tassi, O. Minencova, G. Cesareni, P. G. Pelicci, P. P. Di Fiore. Binding specificty and in vivo targets of the EH domain, a novel protein-protein interaction module. Genes & Development 11: 2239-2249, 1997.

I. Gout, R. Dhand, I. D. Hiles, M. J. Fry, G. Panayotou, P. Das, O. Truong, N. F. Totty, J. Hsuan, G. W. Booker, I. D. Campbell, M. D. Waterfield. The GTPase dynamin binds to and is activated by a subset of SH3 domains. Cell 75: 25-36, 1993.

C. David, P. S. McPherson, O. Mundigl, P. De Camilli. A role of amphiphysin in synaptic vesicle endocytosis suggested by its binding to dynamin in nerve terminals. Proc. Natl. Acad. Sci. USA 93: 331-335, 1996.

M. H. Butler, C. David, G.-C. Ochoa, Z. Freyberg, L. Daniell, D. Grabs, O. Cremona, P. De Camilli. Amphiphysin II (SH3P9;BIN1), a member of the Amphiphysin/Rvs family, is concentrated in the cortical cytomatrix of axon initial segments and Nodes of Ranvier in brain and around T Tubules in skeletal muscle. Journal of Cell Biology 137: 1355-1367, 1997.

C. Leprince, F. Romero, D. Cussac, B. Vayssiere, R. Berger, A. Tavitian, J. H. Camonis. A new member of the Amphiphysin family connecting endocytosis and signal transduction pathways. J. Biol. Chem. 272: 15101-15105, 1997.

A. R. Ramjaun, K. D. Micheva, I. Bouchelet, P. S. McPherson. Identification and characterization of a nerve terminal-enriched amphiphysin isoform. J. Biol. Chem. 272: 16700-16706, 1997.

A. Wesp, L. Hicke, J. Palecek, R. Lombardi, T. Aust, A. L. Munn, H. Riezman. End4p/Sla2p Interacts with Actin-associated proteins for endocytosis in *Saccharomyces cerevisiae*. Molecular Biology of the Cell 8: 2291-2306, 1997.

E. de Heuvel, A. W. Bell, A. R. Ramjaun, K. Wong, W. S. Sossin, P. S. McPherson. Identification of the major Synaptojanin-binding proteins in the brain. J. Biol. Chem. 272: 8710-8716, 1997.

N. Ringstad, Y. Nemoto, P. De Camilli. The SH3p4/SH3p8/SH3p13 protein family: binding partners for synaptojanin and dynamin via a Grb2-like Src homology 3 domain. Proc. Natl. Acad. Sci. USA 94: 8569-8574, 1997.

Z. Wang, M. F. Moran. Requirement for the Adapter protein Grb2 in EGF receptor endocytosis. Science 272: 1935-1939, 1996.

A. B. Sparks, N. G. Hoffman, S. J. McConnel, D. M. Fowlkes, B. K. Kay. Cloning of ligand targets: Systematic isolation of SH3 domain-containing proteins. Nature Biotechnology 14: 741-744, 1996.

P. Cupers, E. ter Haar, W. Boll, T. Kirchhausen. Parallel dimers and anti-parallel tetramers formed by Epidermal Growth Factor Receptor Pathway Substrate Clone 15 (Eps15). Journal of Biological Chemistry 272: 33430-33434, 1997.

H. Stenmark, C. Bucci, M. Zerial. Expression of Rab GTPases using recombinant vaccinia virus. Meth. Enzymol. 257: 155-164, 1995.

S. van Delft, C. Schumacher, W. Hage, A. J. Verkleij, P. M. P. van Bergen en Henegouwen. Association and Colocalization of Eps15 with Adaptor Protein-2 and Clathrin. The Journal of Cell Biology 136: 811-821, 1997.

M. Toth, J. Grimsby, G. Buzsaki, G. P. Donovan. Epileptic seizures caused by inactivation of a novel gene, jerky, related to centromere binding protein-B in transgenic mice. Nature Genetics 11: 71-75, 1995.

Roos, J. and Kelly, R. B. Dap160, a Neural-specific Eps115 homology and multiple SH3 domain-containing protein that interacts with *Drosophila* Dynamin. *J. Biol. Chem.* 273, 19108-19119, 1998.

Ren, R., Mayer, B.J. Cicchetti, P. and Baltimore, D. Identification of a Ten-Amino Acid Proline-Rich SH3 Binding Site. *Science*, 259, 1157-1161, 1993.

Hall, A. Rho GTPases and the actin cytoskeleton. *Science*, 279, 509-514, 1998.

Nalefski, E.A. and Falke, J.J. The C2 domain calcium-binding motif: Structural and functional diversity, *Protein Science*. 5, 2375-2390, 1996.

Chen, H., et al., Epsin is an EH-domain binding protein implicated in clathrin-mediated endocytosis. *Nature*, 394, 793-797.

Stukenberg, P.T. et al., Systematic identification of mitotic phosphoproteins. *Current Biology*, 7, 338-348, 1997.

Tang, H. Y. and Cai, M. The EH-domain containing protein Pan1 is required for normal organization of the actin cytoskeleton in *Saccaromyces cerevisiae*. *Mol. Cell. Biol.* 16, 4897-4914, 1996.

Database EMVRT E.M.B.L. Databases, Accession No.: AF032118, Nov. 27, 1997.

Yamabhai, M. et al. (1998) "Intersectin, a novel adaptor protein with two Eps15 homology and five Src homology 3 domains" Journal of Biological Chemistry, v. 273, No. 47, pp. 31401-31407.

Database EMEST24, E.M.B.L. Databases, Accession No.: AA061808, Sep. 24, 1996, Marra, M. et al.

Database EMEST23, E.M.B.L. Databases, Accession No.: AA217338, Feb. 11, 1997, Marra M. et al.

Sengar, A. et al., (1999), "The EH and SH3 domain Ese proteins regulate endocytosis by linking to dynamin and Eps15" EMBO Journal, v. 18, No. 5, pp. 1159-1171.

Guipponi M et al., (1998), "Two isoforms of a human intersectin (ITSN) protein are produced by brain-specific alternative splicing in a stop codon", GENOMICS, v. 53, No. 3, pp. 369-376.

Salcini A. et al. "Binding specificity and in vivo targets of the EH domain, a novel protein-protein interaction module" (1997) Genes & Development, v. 11, No. 17, pp. 2239-2249.

\* cited by examiner

Ese1L:

Ese2L:

```
Ese1 1204 ········ LTTDMDPSQQWCSDLHLLDMLTPTERKRQGYIHELIVTEENYVN-DLQLV 1252
                  ::: :::::::: ::  ::  :::::::::::::::: :::  :  :::::
Ese2 1143 ········ MTTDSDPSQQWCADLQALDTMQPTERKRQGYIHELIQTEERYMDDDLQLV 1192
          DBL ━━━━━━
          TEIFQKPLTESELLTEKEVAMIFVNWKELIMCNIKLLKALRVRKKMSGEK 1302
          :::  :::::   ::  :::   : :::::::::::: ::: ::::::: :::
          IEVFQKRMAESGFLTEADMALIFVNWKELIMSNTKLLRALRVRKKTGGEK 1242

MPVKMIGDILSAQLPHMQPYIRFCSCQLNGAALIQQKTDEAPDFKEFVKR 1352
          ::: :::::: : ::: :::::::::::::: : ::::::   ::::: :
          MPVQMIGDILAAELSHMQAYIRFCSCQLNGATLLQQKTDEDTDFKEFLKK 1292

LAMDPRCKGMPLSSFILKPMQRVTRYPLIIKNILENTPENHPDHSHLKHA 1402
          :: ::::::::::: ::::::: ::::::  : :::::::: :  ::  :
          LASDPRCKGMPLSSFLLKPMQRITRYPLLIRSILENTPQSHVDHSSLKLA 1342

LEKAEELCSQVNEGVREKENSDRLEWIQAHVQCEGLSEQLVFNSVTNCLG 1452
          :::::::::::::::::::::::::::::::::::::  ::: ::: :::::
          LEKAEELCSQVNEGVREKENSDRLEWIQAHVQCEGLAEQLIFNSLTNCLG 1392
          PH ━━━━━━
          PRKFLHSGKLYKAKSNKELYGFLFNDFLLLTQITKP-LGSSGTDKVFSPK 1501
          ::: ::::::::: :::::::  :::::::: ::  :  :  :   :
          PRKLLHSGKLYKTKSNKELHAFLFNDFLLLTYLVRQFAAASGHEKLFNSK 1442

SNLQYKMYKTPIFLNEVLVKLPTDPSGDEPIFHISHIDRVYTLRAESINE 1551
          :  :   :::::::::::::::::::::::: :::::::::::  :::
          SSAQFRMYKTPIFLNEVLVKLPTDPSGDEPVFHISHIDRVYTLRTDNINE 1492

C2 ━━━━━━
          RTAWVQKIKAASELYIETEKKKREKAYLVRSQRATGIGRLMVNVVEGIEL 1601
          :::::::::::: :::  ::  :::::::::::  :::  :::::::: : : :::
          RTAWVQKIKGASEQYIDTEKKKREKAYQARSQKTSGIGRLMVHVIEATEL 1542

KPCRSHGKSNPYCEVTMGSQCHITKTIQDTLNPKWNSNCQFFIRDLEQEV 1651
          :  :  :::::::::  :::: ::::: ::  :::::::::::::::::  ::
          KACKPNGKSNPYCEVSMGSQSYTTRTLQDTLNPKWNFNCQFFIKDLYQDV 1592

LCITVFERDQFSPDDFLGRTEIRVADIKKDQGSKPVTKCLLLHEVPTGE 1701
          :: : : :::::::::::::::::: ::  : : :::: :  ::::::::::::::::
          LCLTMFDRDQFSPDDFLGRTEVPVAKIRTEQESKGPTTRRLLLHEVPTGE 1642

IVVRLDLQLFDEP     1714
          :: ::::::::::
          VWVRFDLQLFEQKTLL  1658
```

FIGURE 2B

A) Yeast two hybrid screen: Eps15 and Eps15R bind the Ese1 coiled-coil domain

A) Yeast two hybrid screen: Dynamin binds the Ese1 SH3 domains

B) Ese1 overexpression recruits endogenous Dynamin

SEQUENCE LISTING

<160> NUMBER OF SEQ ID NOS: 37

<210> SEQ ID NO 1
<211> LENGTH: 5084
<212> TYPE: DNA
<213> ORGANISM: Mus musculus

<400> SEQUENCE: 1

```
cggcacgagg aggagtggag cggcgcggga gggcgcgcag cttggttgct ccgtagtacg      60
gcggctcgca agggagcatc ccgagcgggc tccgggacgg ccgggaggca ggcaggcggg     120
cgggcgggga tggtgtgcgc ggctgcggac tcggcgttcc tcgcgcggcg tgcgggctgc     180
actgatttgt gtgaggggcg gccgcgcgca cccgcccgga gatgaggcgt cgatcagcaa     240
ggtgaacgta atagaaccat ggctcagttt cccacacctt tcggtggtag cctggatgtc     300
tgggccataa ctgtggagga aagggccaag catgaccagc agttccttag cctgaagccg     360
atagcgggat ttattactgg tgatcaagcg aggaactttt ttttccaatc tgggttacct     420
cagcctgtct tagcacaaat atgggcgcta gcggacatga ataacgatgg aaggatggat     480
caagtggaat tttccatagc catgaagctt atcaaactga agctacaagg atatcagctc     540
ccctccacac ttccccctgt catgaaacag caaccagtgg ctatttccag tgcaccagca     600
tttggtatag gagggattgc tagcatgcca ccactcacag ctgttgctcc tgtgccaatg     660
ggctccattc cagttgttgg aatgtctcca cccttagtat cttctgtccc tccagcagca     720
gtgcctcccc tggctaacgg ggctcctccc gtcatacagc ctctgcctgc gtttgcgcat     780
cctgcagcca catggccaaa gagttcttcc ttcagcagat ctggtccagg gtcacaatta     840
aacactaagt tacagaaggc acaatcattc gatgtcgcca gcgcccctcc agcagcagaa     900
tgggctgtgc ctcagtcatc aaggctgaaa tacaggcagt tattcaacag ccacgacaaa     960
actatgagtg gacacttaac aggtccccag gcaagaacta ttctcatgca atcaagttta    1020
ccccaggctc agctggcttc aatatggaat ctttctgaca ttgatcaaga tggaaaactc    1080
actgcagaag aatttatcct agctatgcac ctaattgatg ttgccatgtc tggtcagcca    1140
ctgccgcccg tcctgcctcc agaatacatc cctccttcct tcagaagagt tcgctccggc    1200
agtgggatgt ccgtcataag ctcttcttct gtggatcaga ggctgcctga ggagccgtcg    1260
tcagaggatg agcagcagcc agagaagaaa ctgcctgtga catttgaaga taagaagcgg    1320
gagaacttcg agcgaggcag tgtggagctg agaagcgcc gccaagcgct cttggagcag    1380
cagcgcaaag agcaggagcg gttggctcag ctggagcgcg ccgagcagga gaggaaagag    1440
cgggagcgcc aggagcagga ggccaagcgg cagctggagc tggagaagca gctggagaag    1500
cagcgggagc tggagcggca gcgagaggag gagaggagga aggagatcga gaggcgcgag    1560
gccgcaaaac gggaactgga aaggcagcga caacttgaat gggaacggaa ccggagacag    1620
gaactcctga atcagaggaa caaggagcag gagggcaccg tggtcctgaa ggcaaggagg    1680
aagactctgg agtttgagtt agaagctctg aatgacaaaa agcatcagct agaaggaaaa    1740
cttcaggata tcaggtgtcg actggcaacc cagaggcaag aaattgagag cacgaacaag    1800
tctagagagc taagaattgc tgaaatcacc cacttacagc agcagttgca ggaatctcag    1860
caaatgcttg gaagacttat tccagagaaa cagatactca gtgaccagtt aaaacaagtc    1920
cagcagaaca gtttgcatag agactcgctt cttaccctca aaagagcctt ggaagcaaag    1980
gagctggccc ggcagcagct ccgggagcag ctggacgagg tggagagaga gaccaggtca    2040
```

-continued

```
aagctgcagg agattgatgt tttcaacaac cagctgaagg aactgagaga gatacatagc    2100
aaacagcaac tccagaagca gaggtccctg gaggcagcgc gactgaagca gaaagagcag    2160
gagaggaaga gcctggagtt agagaagcaa aaggaagacg ctcagagacg agttcaggaa    2220
agggacaagc aatggctgga gcatgtgcag caggaggagc agccacgccc ccggaaaccc    2280
cacgaggagg acagactgaa gagggaagac agtgtcagga agaaggaggc ggaagagaga    2340
gccaagccgg aaatgcaaga caagcagagt cggcttttcc atccgcatca ggagccagct    2400
aagctggcca cccaggcacc ctggtctacc acagagaaag gcccgcttac catttctgca    2460
caggagagtg taaaagtggt atattaccga gcgctgtacc cctttgaatc agaagtcac     2520 gatgagatca ccatccagcc aggagatata gtcatggtgg atgaaagcca gactggagag    2580
ccaggatggc ttggaggaga gctgaaaggg aagacgggat ggttccctgc aaactatgca    2640
gaaaagattc cagaaaatga ggttcccact ccagccaaac cagtgaccga tctgacatct    2700
gcccctgccc ccaaactggc tctgcgtgag acccctgctc ctttgccagt gacctcttct    2760
gagccctcca caaccccaa caactgggca gacttcagtt ccacgtggcc cagcagctca    2820
aacgagaagc cagaaacgga caactgggat acgtgggcgg ctcagccttc tctgaccgta    2880
cctagtgctg gccagttacg gcagagatca gcctttaccc cagccacagc cactggctcc    2940
tccccatctc ccgtcctggg ccagggtgaa aaggtggaag ggctacaagc gcaagccctg    3000
tatccctgga gagccaaaaa agacaaccac ttaaattta acaaaagtga cgtcatcacc    3060
gttctggaac agcaagacat gtggtggttt ggagaagttc aaggtcagaa gggttggttc    3120
cccaagtctt acgtgaaact catttcaggg cccgtaagga atccacaag catcgatact    3180 ggccctactg aaagtcctgc tagtctaaag agagtggctt ccccggccgc caagccagcc    3240
attcccggag aagagtttat tgccatgtac acatacgaga gttctgagca aggagattta    3300
acctttcagc aaggggatgt gattgtggtt accaagaaag atggtgactg gtggacggga    3360
acggtgggcg acaagtccgg agtcttccct tctaactatg tgaggcttaa agattcagag    3420
ggctctggaa ctgctgggaa acagggagt ttaggaaaaa aacctgaaat tgcccaggtt    3480
attgcttcct acgctgctac tggtcccgaa caactcaccc tggctcctgg gcagctgatt    3540
ctgatccgga aaaagaaccc aggtggatgg tgggaaggag aactgcaagc tcagggaaa    3600 aagcgccaga tagggtggtt tccagcaaat tatgtcaaac ttctaagccc cggaacaagc    3660
aaaatcaccc caactgagct acccaagacc gcagtgcagc cagcagtgtg ccaggtgatc    3720
gggatgtacg attacaccgc ccagaacgat gacgaactag ccttcagcaa aggccagatc    3780
atcaacgtcc tcaacaagga ggacccggac tggtggaaag agaagtcag tgggcaagtt    3840 gggctcttcc catccaatta tgtaaagctg accacagaca tggaccccag ccagcaatga    3900
atcatatgtt gtccatcccc ccctcaggct tgaaagtcct caaagagacc cactatccca    3960
tatcactgcc cagagggatg atgggagatg cagccttgat catgtgactt gcagcatgat    4020
cacctactgc cttctgagta gaagaactca ctgcagagca gtttacctca tttgacctta    4080
gttgcatgtg atcgaaatgt ctgagtcact gcgtgcagag gcagaagcaa attgcagaac    4140
tgcacagggt ggtgggtcct tttgggggctt tcctagtcac tcagactgac cggccccgcc    4200
ttcacacggg cgctttcaat agttttaaga ttatttttaa atgtgtattt tagccttta    4260 ataaaaatct caatcaatta cttctttgcc tattttggtt ttacaaaaac acccactatc    4320
aaggagtgcc tgtctgcgga cgattaaaat gctgttccgg gcgtaccgta aactgagagc    4380
```

```
ttgctgtacc tttgccgttt gtccagtgtt cccaaccaca ttgtgtagtt tggggctgtt      4440
ccctgccgta gagcacagag gagatgggtg tacctgtttt gaaaatgtgt atgtagactg      4500
agcctgacta tggaaggggt tatgcttgtc tgtgaccatc acgtgtacct gtcgcgcatg      4560
taccatctgt accgaagaag tagctcttcc tccatggcta aacccaccac cgtgtacagt      4620
gctctcatct actgcattca ttttactttg cacagtgacc ttgtagccac ctgaggaagc      4680
acccatgttt ccgtttggtc tcagatgtac ctagttgtgc ccgtgttttg tttttatttt      4740
tcaatctggc atgtcttcac accataaact agtaagacgc caactgccca ggcggttacg      4800
atcatcagta cccaccgtct tagtctctgt tacgtgaagt ttattccagt tgctttttat      4860
ggaatatctt gaacaagtaa tcttcttgac aagaaagaat gtatagaagt ctccctgcaa      4920
ttaatttccc agtgtttaca tttttttaact agactgtggg ggttgctaca gattaatatg      4980
aaatggcgct cctggtccgt gtgtgtgtta acttgtgctg tagctgaagc cgtgtgtcct      5040
tagatattag ttggaagtcg ggaagagaat tcgatatcaa gctt                      5084

<210> SEQ ID NO 2
<211> LENGTH: 3642
<212> TYPE: DNA
<213> ORGANISM: Mus musculus
<220> FEATURE:
<221> NAME/KEY: CDS
<222> LOCATION: (1)..(3642)
<223> OTHER INFORMATION: Mouse Ese1

<400> SEQUENCE: 2 atg gct cag ttt ccc aca cct ttc ggt ggt agc ctg gat gtc tgg gcc       48
Met Ala Gln Phe Pro Thr Pro Phe Gly Gly Ser Leu Asp Val Trp Ala
1               5                   10                  15 ata act gtg gag gaa agg gcc aag cat gac cag cag ttc ctt agc ctg       96
Ile Thr Val Glu Glu Arg Ala Lys His Asp Gln Gln Phe Leu Ser Leu
            20                  25                  30 aag ccg ata gcg gga ttt att act ggt gat caa gcg agg aac ttt ttt      144
Lys Pro Ile Ala Gly Phe Ile Thr Gly Asp Gln Ala Arg Asn Phe Phe
        35                  40                  45 ttc caa tct ggg tta cct cag cct gtc tta gca caa ata tgg gcg cta      192
Phe Gln Ser Gly Leu Pro Gln Pro Val Leu Ala Gln Ile Trp Ala Leu
    50                  55                  60 gcg gac atg aat aac gat gga agg atg gat caa gtg gaa ttt tcc ata      240
Ala Asp Met Asn Asn Asp Gly Arg Met Asp Gln Val Glu Phe Ser Ile
65                  70                  75                  80 gcc atg aag ctt atc aaa ctg aag cta caa gga tat cag ctc ccc tcc      288
Ala Met Lys Leu Ile Lys Leu Lys Leu Gln Gly Tyr Gln Leu Pro Ser
                85                  90                  95 aca ctt ccc cct gtc atg aaa cag caa cca gtg gct att tcc agt gca      336
Thr Leu Pro Pro Val Met Lys Gln Gln Pro Val Ala Ile Ser Ser Ala
            100                 105                 110 cca gca ttt ggt ata gga ggg att gct agc atg cca cca ctc aca gct      384
Pro Ala Phe Gly Ile Gly Gly Ile Ala Ser Met Pro Pro Leu Thr Ala
        115                 120                 125 gtt gct cct gtg cca atg ggc tcc att cca gtt gtt gga atg tct cca      432
Val Ala Pro Val Pro Met Gly Ser Ile Pro Val Val Gly Met Ser Pro
    130                 135                 140 ccc tta gta tct tct gtc cct cca gca gca gtg cct ccc ctg gct aac      480
Pro Leu Val Ser Ser Val Pro Pro Ala Ala Val Pro Pro Leu Ala Asn
145                 150                 155                 160 ggg gct cct ccc gtc ata cag cct ctg cct gcg ttt gcg cat cct gca      528
Gly Ala Pro Pro Val Ile Gln Pro Leu Pro Ala Phe Ala His Pro Ala
                165                 170                 175
```

```
gcc aca tgg cca aag agt tct tcc ttc agc aga tct ggt cca ggg tca      576
Ala Thr Trp Pro Lys Ser Ser Ser Phe Ser Arg Ser Gly Pro Gly Ser
        180                 185                 190 caa tta aac act aag tta cag aag gca caa tca ttc gat gtc gcc agc      624
Gln Leu Asn Thr Lys Leu Gln Lys Ala Gln Ser Phe Asp Val Ala Ser
            195                 200                 205 gcc cct cca gca gca gaa tgg gct gtg cct cag tca tca agg ctg aaa      672
Ala Pro Pro Ala Ala Glu Trp Ala Val Pro Gln Ser Ser Arg Leu Lys
    210                 215                 220 tac agg cag tta ttc aac agc cac gac aaa act atg agt gga cac tta      720
Tyr Arg Gln Leu Phe Asn Ser His Asp Lys Thr Met Ser Gly His Leu
225                 230                 235                 240 aca ggt ccc cag gca aga act att ctc atg caa tca agt tta ccc cag      768
Thr Gly Pro Gln Ala Arg Thr Ile Leu Met Gln Ser Ser Leu Pro Gln
                245                 250                 255 gct cag ctg gct tca ata tgg aat ctt tct gac att gat caa gat gga      816
Ala Gln Leu Ala Ser Ile Trp Asn Leu Ser Asp Ile Asp Gln Asp Gly
            260                 265                 270 aaa ctc act gca gaa gaa ttt atc cta gct atg cac cta att gat gtt      864
Lys Leu Thr Ala Glu Glu Phe Ile Leu Ala Met His Leu Ile Asp Val
        275                 280                 285 gcc atg tct ggt cag cca ctg ccg ccc gtc ctg cct cca gaa tac atc      912
Ala Met Ser Gly Gln Pro Leu Pro Pro Val Leu Pro Pro Glu Tyr Ile
290                 295                 300 cct cct tcc ttc aga aga gtt cgc tcc ggc agt ggg atg tcc gtc ata      960
Pro Pro Ser Phe Arg Arg Val Arg Ser Gly Ser Gly Met Ser Val Ile
305                 310                 315                 320 agc tct tct tct gtg gat cag agg ctg cct gag gag ccg tcg tca gag     1008
Ser Ser Ser Ser Val Asp Gln Arg Leu Pro Glu Glu Pro Ser Ser Glu
                325                 330                 335 gat gag cag cag cca gag aag aaa ctg cct gtg aca ttt gaa gat aag     1056
Asp Glu Gln Gln Pro Glu Lys Lys Leu Pro Val Thr Phe Glu Asp Lys
            340                 345                 350 aag cgg gag aac ttc gag cga ggc agt gtg gag ctg gag aag cgc cgc     1104
Lys Arg Glu Asn Phe Glu Arg Gly Ser Val Glu Leu Glu Lys Arg Arg
        355                 360                 365 caa gcg ctc ttg gag cag cag cgc aaa gag cag gag cgg ttg gct cag     1152
Gln Ala Leu Leu Glu Gln Gln Arg Lys Glu Gln Glu Arg Leu Ala Gln
    370                 375                 380 ctg gag cgc gcc gag cag gag agg aaa gag cgg gag cgc cag gag cag     1200
Leu Glu Arg Ala Glu Gln Glu Arg Lys Glu Arg Glu Arg Gln Glu Gln
385                 390                 395                 400 gag gcc aag cgg cag ctg gag ctg gag aag cag ctg gag aag cag cgg     1248
Glu Ala Lys Arg Gln Leu Glu Leu Glu Lys Gln Leu Glu Lys Gln Arg
                405                 410                 415 gag ctg gag cgg cag cga gag gag gag agg agg aag gag atc gag agg     1296
Glu Leu Glu Arg Gln Arg Glu Glu Glu Arg Arg Lys Glu Ile Glu Arg
            420                 425                 430 cgc gag gcc gca aaa cgg gaa ctg gaa agg cag cga caa ctt gaa tgg     1344
Arg Glu Ala Ala Lys Arg Glu Leu Glu Arg Gln Arg Gln Leu Glu Trp
        435                 440                 445 gaa cgg aac cgg aga cag gaa ctc ctg aat cag agg aac aag gag cag     1392
Glu Arg Asn Arg Arg Gln Glu Leu Leu Asn Gln Arg Asn Lys Glu Gln
    450                 455                 460 gag ggc acc gtg gtc ctg aag gca agg agg aag act ctg gag ttt gag     1440
Glu Gly Thr Val Val Leu Lys Ala Arg Arg Lys Thr Leu Glu Phe Glu
465                 470                 475                 480 tta gaa gct ctg aat gac aaa aag cat cag cta gaa gga aaa ctt cag     1488
Leu Glu Ala Leu Asn Asp Lys Lys His Gln Leu Glu Gly Lys Leu Gln
```

-continued

```
                485                 490                 495
gat atc agg tgt cga ctg gca acc cag agg caa gaa att gag agc acg    1536
Asp Ile Arg Cys Arg Leu Ala Thr Gln Arg Gln Glu Ile Glu Ser Thr
            500                 505                 510 aac aag tct aga gag cta aga att gct gaa atc acc cac tta cag cag    1584
Asn Lys Ser Arg Glu Leu Arg Ile Ala Glu Ile Thr His Leu Gln Gln
        515                 520                 525 cag ttg cag gaa tct cag caa atg ctt gga aga ctt att cca gag aaa    1632
Gln Leu Gln Glu Ser Gln Gln Met Leu Gly Arg Leu Ile Pro Glu Lys
    530                 535                 540 cag ata ctc agt gac cag tta aaa caa gtc cag cag aac agt ttg cat    1680
Gln Ile Leu Ser Asp Gln Leu Lys Gln Val Gln Gln Asn Ser Leu His
545                 550                 555                 560 aga gac tcg ctt ctt acc ctc aaa aga gcc ttg gaa gca aag gag ctg    1728
Arg Asp Ser Leu Leu Thr Leu Lys Arg Ala Leu Glu Ala Lys Glu Leu
                565                 570                 575 gcc cgg cag cag ctc cgg gag cag ctg gac gag gtg gag aga gag acc    1776
Ala Arg Gln Gln Leu Arg Glu Gln Leu Asp Glu Val Glu Arg Glu Thr
            580                 585                 590 agg tca aag ctg cag gag att gat gtt ttc aac aac cag ctg aag gaa    1824
Arg Ser Lys Leu Gln Glu Ile Asp Val Phe Asn Asn Gln Leu Lys Glu
        595                 600                 605 ctg aga gag ata cat agc aaa cag caa ctc cag aag cag agg tcc ctg    1872
Leu Arg Glu Ile His Ser Lys Gln Gln Leu Gln Lys Gln Arg Ser Leu
    610                 615                 620 gag gca gcg cga ctg aag cag aaa gag cag gag agg aag agc ctg gag    1920
Glu Ala Ala Arg Leu Lys Gln Lys Glu Gln Glu Arg Lys Ser Leu Glu
625                 630                 635                 640 tta gag aag caa aag gaa gac gct cag aga cga gtt cag gaa agg gac    1968
Leu Glu Lys Gln Lys Glu Asp Ala Gln Arg Arg Val Gln Glu Arg Asp
                645                 650                 655 aag caa tgg ctg gag cat gtg cag cag gag gag cag cca cgc ccc cgg    2016
Lys Gln Trp Leu Glu His Val Gln Gln Glu Glu Gln Pro Arg Pro Arg
            660                 665                 670 aaa ccc cac gag gag gac aga ctg aag agg gaa gac agt gtc agg aag    2064
Lys Pro His Glu Glu Asp Arg Leu Lys Arg Glu Asp Ser Val Arg Lys
        675                 680                 685 aag gag gcg gaa gag aga gcc aag ccg gaa atg caa gac aag cag agt    2112
Lys Glu Ala Glu Glu Arg Ala Lys Pro Glu Met Gln Asp Lys Gln Ser
    690                 695                 700 cgg ctt ttc cat ccg cat cag gag cca gct aag ctg gcc acc cag gca    2160
Arg Leu Phe His Pro His Gln Glu Pro Ala Lys Leu Ala Thr Gln Ala
705                 710                 715                 720 ccc tgg tct acc aca gag aaa ggc ccg ctt acc att tct gca cag gag    2208
Pro Trp Ser Thr Thr Glu Lys Gly Pro Leu Thr Ile Ser Ala Gln Glu
                725                 730                 735 agt gta aaa gtg gta tat tac cga gcg ctg tac ccc ttt gaa tcc aga    2256
Ser Val Lys Val Val Tyr Tyr Arg Ala Leu Tyr Pro Phe Glu Ser Arg
            740                 745                 750 agt cac gat gag atc acc atc cag cca gga gat ata gtc atg gtg gat    2304
Ser His Asp Glu Ile Thr Ile Gln Pro Gly Asp Ile Val Met Val Asp
        755                 760                 765 gaa agc cag act gga gag cca gga tgg ctt gga gga gag ctg aaa ggg    2352
Glu Ser Gln Thr Gly Glu Pro Gly Trp Leu Gly Gly Glu Leu Lys Gly
    770                 775                 780 aag acg gga tgg ttc cct gca aac tat gca gaa aag att cca gaa aat    2400
Lys Thr Gly Trp Phe Pro Ala Asn Tyr Ala Glu Lys Ile Pro Glu Asn
785                 790                 795                 800 gag gtt ccc act cca gcc aaa cca gtg acc gat ctg aca tct gcc cct    2448
```

-continued

| | | |
|---|---|---|
| Glu Val Pro Thr Pro Ala Lys Pro Val Thr Asp Leu Thr Ser Ala Pro<br>805 810 815 | | |
| gcc ccc aaa ctg gct ctg cgt gag acc cct gct cct ttg cca gtg acc<br>Ala Pro Lys Leu Ala Leu Arg Glu Thr Pro Ala Pro Leu Pro Val Thr<br>820 825 830 | 2496 | |
| tct tct gag ccc tcc aca acc ccc aac aac tgg gca gac ttc agt tcc<br>Ser Ser Glu Pro Ser Thr Thr Pro Asn Asn Trp Ala Asp Phe Ser Ser<br>835 840 845 | 2544 | |
| acg tgg ccc agc agc tca aac gag aag cca gaa acg gac aac tgg gat<br>Thr Trp Pro Ser Ser Ser Asn Glu Lys Pro Glu Thr Asp Asn Trp Asp<br>850 855 860 | 2592 | |
| acg tgg gcg gct cag cct tct ctg acc gta cct agt gct ggc cag tta<br>Thr Trp Ala Ala Gln Pro Ser Leu Thr Val Pro Ser Ala Gly Gln Leu<br>865 870 875 880 | 2640 | |
| cgg cag aga tca gcc ttt acc cca gcc aca gcc act ggc tcc tcc cca<br>Arg Gln Arg Ser Ala Phe Thr Pro Ala Thr Ala Thr Gly Ser Ser Pro<br>885 890 895 | 2688 | |
| tct ccc gtc ctg ggc cag ggt gaa aag gtg gaa ggg cta caa gcg caa<br>Ser Pro Val Leu Gly Gln Gly Glu Lys Val Glu Gly Leu Gln Ala Gln<br>900 905 910 | 2736 | |
| gcc ctg tat ccc tgg aga gcc aaa aaa gac aac cac tta aat ttt aac<br>Ala Leu Tyr Pro Trp Arg Ala Lys Lys Asp Asn His Leu Asn Phe Asn<br>915 920 925 | 2784 | |
| aaa agt gac gtc atc acc gtt ctg gaa cag caa gac atg tgg tgg ttt<br>Lys Ser Asp Val Ile Thr Val Leu Glu Gln Gln Asp Met Trp Trp Phe<br>930 935 940 | 2832 | |
| gga gaa gtt caa ggt cag aag ggt tgg ttc ccc aag tct tac gtg aaa<br>Gly Glu Val Gln Gly Gln Lys Gly Trp Phe Pro Lys Ser Tyr Val Lys<br>945 950 955 960 | 2880 | |
| ctc att tca ggg ccc gta agg aaa tcc aca agc atc gat act ggc cct<br>Leu Ile Ser Gly Pro Val Arg Lys Ser Thr Ser Ile Asp Thr Gly Pro<br>965 970 975 | 2928 | |
| act gaa agt cct gct agt cta aag aga gtg gct tcc ccg gcc gcc aag<br>Thr Glu Ser Pro Ala Ser Leu Lys Arg Val Ala Ser Pro Ala Ala Lys<br>980 985 990 | 2976 | |
| cca gcc att ccc gga gaa gag ttt att gcc atg tac aca tac gag agt<br>Pro Ala Ile Pro Gly Glu Glu Phe Ile Ala Met Tyr Thr Tyr Glu Ser<br>995 1000 1005 | 3024 | |
| tct gag caa gga gat tta acc ttt cag caa ggg gat gtg att gtg<br>Ser Glu Gln Gly Asp Leu Thr Phe Gln Gln Gly Asp Val Ile Val<br>1010 1015 1020 | 3069 | |
| gtt acc aag aaa gat ggt gac tgg tgg acg gga acg gtg ggc gac<br>Val Thr Lys Lys Asp Gly Asp Trp Trp Thr Gly Thr Val Gly Asp<br>1025 1030 1035 | 3114 | |
| aag tcc gga gtc ttc cct tct aac tat gtg agg ctt aaa gat tca<br>Lys Ser Gly Val Phe Pro Ser Asn Tyr Val Arg Leu Lys Asp Ser<br>1040 1045 1050 | 3159 | |
| gag ggc tct gga act gct ggg aaa aca ggg agt tta gga aaa aaa<br>Glu Gly Ser Gly Thr Ala Gly Lys Thr Gly Ser Leu Gly Lys Lys<br>1055 1060 1065 | 3204 | |
| cct gaa att gcc cag gtt att gct tcc tac gct gct act ggt ccc<br>Pro Glu Ile Ala Gln Val Ile Ala Ser Tyr Ala Ala Thr Gly Pro<br>1070 1075 1080 | 3249 | |
| gaa caa ctc acc ctg gct cct ggg cag ctg att ctg atc cgg aaa<br>Glu Gln Leu Thr Leu Ala Pro Gly Gln Leu Ile Leu Ile Arg Lys<br>1085 1090 1095 | 3294 | |
| aag aac cca ggt gga tgg tgg gaa gga gaa ctg caa gct cga ggg<br>Lys Asn Pro Gly Gly Trp Trp Glu Gly Glu Leu Gln Ala Arg Gly<br>1100 1105 1110 | 3339 | |

```
aaa aag cgc cag ata ggg tgg ttt cca gca aat tat gtc aaa ctt    3384
Lys Lys Arg Gln Ile Gly Trp Phe Pro Ala Asn Tyr Val Lys Leu
1115                1120                1125 cta agc ccc gga aca agc aaa atc acc cca act gag cta ccc aag    3429
Leu Ser Pro Gly Thr Ser Lys Ile Thr Pro Thr Glu Leu Pro Lys
        1130                1135                1140 acc gca gtg cag cca gca gtg tgc cag gtg atc ggg atg tac gat    3474
Thr Ala Val Gln Pro Ala Val Cys Gln Val Ile Gly Met Tyr Asp
1145                1150                1155 tac acc gcc cag aac gat gac gaa cta gcc ttc agc aaa ggc cag    3519
Tyr Thr Ala Gln Asn Asp Asp Glu Leu Ala Phe Ser Lys Gly Gln
        1160                1165                1170 atc atc aac gtc ctc aac aag gag gac ccg gac tgg tgg aaa gga    3564
Ile Ile Asn Val Leu Asn Lys Glu Asp Pro Asp Trp Trp Lys Gly
1175                1180                1185 gaa gtc agt ggg caa gtt ggg ctc ttc cca tcc aat tat gta aag    3609
Glu Val Ser Gly Gln Val Gly Leu Phe Pro Ser Asn Tyr Val Lys
        1190                1195                1200 ctg acc aca gac atg gac ccc agc cag caa tga                    3642
Leu Thr Thr Asp Met Asp Pro Ser Gln Gln
1205                1210

<210> SEQ ID NO 3
<211> LENGTH: 1213
<212> TYPE: PRT
<213> ORGANISM: Mus musculus

<400> SEQUENCE: 3

Met Ala Gln Phe Pro Thr Pro Phe Gly Gly Ser Leu Asp Val Trp Ala
1               5                   10                  15

Ile Thr Val Glu Glu Arg Ala Lys His Asp Gln Gln Phe Leu Ser Leu
            20                  25                  30

Lys Pro Ile Ala Gly Phe Ile Thr Gly Asp Gln Ala Arg Asn Phe Phe
        35                  40                  45

Phe Gln Ser Gly Leu Pro Gln Pro Val Leu Ala Gln Ile Trp Ala Leu
    50                  55                  60

Ala Asp Met Asn Asn Asp Gly Arg Met Asp Gln Val Glu Phe Ser Ile
65                  70                  75                  80

Ala Met Lys Leu Ile Lys Leu Lys Leu Gln Gly Tyr Gln Leu Pro Ser
                85                  90                  95

Thr Leu Pro Pro Val Met Lys Gln Gln Pro Val Ala Ile Ser Ser Ala
            100                 105                 110

Pro Ala Phe Gly Ile Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Pro Leu Val Ser Ser Val Pro Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Trp Pro Lys Ser Ser Phe Ser Arg Ser Gly Pro Gly Ser
        180                 185                 190

Gln Leu Asn Thr Lys Leu Gln Lys Ala Gln Ser Phe Asp Val Ala Ser
    195                 200                 205

Ala Pro Pro Ala Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
```

-continued

```
            225                 230                 235                 240
Thr Gly Pro Gln Ala Arg Thr Ile Leu Met Gln Ser Ser Leu Pro Gln
                245                 250                 255
Ala Gln Leu Ala Ser Ile Trp Asn Leu Ser Asp Ile Asp Gln Asp Gly
                260                 265                 270
Lys Leu Thr Ala Glu Glu Phe Ile Leu Ala Met His Leu Ile Asp Val
                275                 280                 285
Ala Met Ser Gly Gln Pro Leu Pro Pro Val Leu Pro Pro Glu Tyr Ile
                290                 295                 300
Pro Pro Ser Phe Arg Arg Val Arg Ser Gly Ser Gly Met Ser Val Ile
305                 310                 315                 320
Ser Ser Ser Ser Val Asp Gln Arg Leu Pro Glu Glu Pro Ser Ser Glu
                325                 330                 335
Asp Glu Gln Gln Pro Glu Lys Lys Leu Pro Val Thr Phe Glu Asp Lys
                340                 345                 350
Lys Arg Glu Asn Phe Glu Arg Gly Ser Val Glu Leu Glu Lys Arg Arg
                355                 360                 365
Gln Ala Leu Leu Glu Gln Gln Arg Lys Glu Gln Glu Arg Leu Ala Gln
                370                 375                 380
Leu Glu Arg Ala Glu Gln Glu Arg Lys Glu Arg Glu Arg Gln Glu Gln
385                 390                 395                 400
Glu Ala Lys Arg Gln Leu Glu Leu Glu Lys Gln Leu Glu Lys Gln Arg
                405                 410                 415
Glu Leu Glu Arg Gln Arg Glu Glu Arg Arg Lys Glu Ile Glu Arg
                420                 425                 430
Arg Glu Ala Ala Lys Arg Glu Leu Glu Arg Gln Arg Gln Leu Glu Trp
                435                 440                 445
Glu Arg Asn Arg Arg Gln Glu Leu Leu Asn Gln Arg Asn Lys Glu Gln
                450                 455                 460
Glu Gly Thr Val Val Leu Lys Ala Arg Arg Lys Thr Leu Glu Phe Glu
465                 470                 475                 480
Leu Glu Ala Leu Asn Asp Lys Lys His Gln Leu Glu Gly Lys Leu Gln
                485                 490                 495
Asp Ile Arg Cys Arg Leu Ala Thr Gln Arg Gln Glu Ile Glu Ser Thr
                500                 505                 510
Asn Lys Ser Arg Glu Leu Arg Ile Ala Glu Ile Thr His Leu Gln Gln
                515                 520                 525
Gln Leu Gln Glu Ser Gln Gln Met Leu Gly Arg Leu Ile Pro Glu Lys
                530                 535                 540
Gln Ile Leu Ser Asp Gln Leu Lys Gln Val Gln Gln Asn Ser Leu His
545                 550                 555                 560
Arg Asp Ser Leu Leu Thr Leu Lys Arg Ala Leu Glu Ala Lys Glu Leu
                565                 570                 575
Ala Arg Gln Gln Leu Arg Glu Gln Leu Asp Glu Val Glu Arg Glu Thr
                580                 585                 590
Arg Ser Lys Leu Gln Glu Ile Asp Val Phe Asn Asn Gln Leu Lys Glu
                595                 600                 605
Leu Arg Glu Ile His Ser Lys Gln Gln Leu Gln Lys Gln Arg Ser Leu
                610                 615                 620
Glu Ala Ala Arg Leu Lys Gln Lys Glu Gln Glu Arg Lys Ser Leu Glu
625                 630                 635                 640
Leu Glu Lys Gln Lys Glu Asp Ala Gln Arg Arg Val Gln Glu Arg Asp
                645                 650                 655
```

```
Lys Gln Trp Leu Glu His Val Gln Gln Glu Gln Pro Arg Pro Arg
            660                 665                 670

Lys Pro His Glu Glu Asp Arg Leu Lys Arg Glu Asp Ser Val Arg Lys
            675                 680                 685

Lys Glu Ala Glu Glu Arg Ala Lys Pro Glu Met Gln Asp Lys Gln Ser
            690                 695                 700

Arg Leu Phe His Pro His Gln Glu Pro Ala Lys Leu Ala Thr Gln Ala
705                 710                 715                 720

Pro Trp Ser Thr Thr Glu Lys Gly Pro Leu Thr Ile Ser Ala Gln Glu
                725                 730                 735

Ser Val Lys Val Val Tyr Arg Ala Leu Tyr Pro Phe Glu Ser Arg
            740                 745                 750

Ser His Asp Glu Ile Thr Ile Gln Pro Gly Asp Ile Val Met Val Asp
            755                 760                 765

Glu Ser Gln Thr Gly Glu Pro Gly Trp Leu Gly Gly Glu Leu Lys Gly
            770                 775                 780

Lys Thr Gly Trp Phe Pro Ala Asn Tyr Ala Glu Lys Ile Pro Glu Asn
785                 790                 795                 800

Glu Val Pro Thr Pro Ala Lys Pro Val Thr Asp Leu Thr Ser Ala Pro
                805                 810                 815

Ala Pro Lys Leu Ala Leu Arg Glu Thr Pro Ala Pro Leu Pro Val Thr
            820                 825                 830

Ser Ser Glu Pro Ser Thr Thr Pro Asn Asn Trp Ala Asp Phe Ser Ser
            835                 840                 845

Thr Trp Pro Ser Ser Ser Asn Glu Lys Pro Glu Thr Asp Asn Trp Asp
850                 855                 860

Thr Trp Ala Ala Gln Pro Ser Leu Thr Val Pro Ser Ala Gly Gln Leu
865                 870                 875                 880

Arg Gln Arg Ser Ala Phe Thr Pro Ala Thr Ala Thr Gly Ser Ser Pro
            885                 890                 895

Ser Pro Val Leu Gly Gln Gly Glu Lys Val Glu Gly Leu Gln Ala Gln
            900                 905                 910

Ala Leu Tyr Pro Trp Arg Ala Lys Lys Asp Asn His Leu Asn Phe Asn
            915                 920                 925

Lys Ser Asp Val Ile Thr Val Leu Glu Gln Gln Asp Met Trp Trp Phe
            930                 935                 940

Gly Glu Val Gln Gly Gln Lys Gly Trp Phe Pro Lys Ser Tyr Val Lys
945                 950                 955                 960

Leu Ile Ser Gly Pro Val Arg Lys Ser Thr Ser Ile Asp Thr Gly Pro
                965                 970                 975

Thr Glu Ser Pro Ala Ser Leu Lys Arg Val Ala Ser Pro Ala Ala Lys
            980                 985                 990

Pro Ala Ile Pro Gly Glu Glu Phe Ile Ala Met Tyr Thr Tyr Glu Ser
            995                 1000                1005

Ser Glu Gln Gly Asp Leu Thr Phe Gln Gln Gly Asp Val Ile Val
            1010                1015                1020

Val Thr Lys Lys Asp Gly Asp Trp Trp Thr Gly Thr Val Gly Asp
            1025                1030                1035

Lys Ser Gly Val Phe Pro Ser Asn Tyr Val Arg Leu Lys Asp Ser
            1040                1045                1050

Glu Gly Ser Gly Thr Ala Gly Lys Thr Gly Ser Leu Gly Lys Lys
            1055                1060                1065
```

-continued

| | | | | | | | | | | |
|---|---|---|---|---|---|---|---|---|---|---|
| Pro | Glu | Ile | Ala | Gln | Val | Ile | Ala | Ser | Tyr | Ala | Thr | Gly | Pro |
| | 1070 | | | | 1075 | | | | 1080 | |

| Glu | Gln | Leu | Thr | Leu | Ala | Pro | Gly | Gln | Leu | Ile | Leu | Ile | Arg | Lys |
| | 1085 | | | | 1090 | | | | 1095 | |

| Lys | Asn | Pro | Gly | Gly | Trp | Trp | Glu | Gly | Glu | Leu | Gln | Ala | Arg | Gly |
| | 1100 | | | | 1105 | | | | 1110 | |

| Lys | Lys | Arg | Gln | Ile | Gly | Trp | Phe | Pro | Ala | Asn | Tyr | Val | Lys | Leu |
| | 1115 | | | | 1120 | | | | 1125 | |

| Leu | Ser | Pro | Gly | Thr | Ser | Lys | Ile | Thr | Pro | Thr | Glu | Leu | Pro | Lys |
| | 1130 | | | | 1135 | | | | 1140 | |

| Thr | Ala | Val | Gln | Pro | Ala | Val | Cys | Gln | Val | Ile | Gly | Met | Tyr | Asp |
| | 1145 | | | | 1150 | | | | 1155 | |

| Tyr | Thr | Ala | Gln | Asn | Asp | Asp | Glu | Leu | Ala | Phe | Ser | Lys | Gly | Gln |
| | 1160 | | | | 1165 | | | | 1170 | |

| Ile | Ile | Asn | Val | Leu | Asn | Lys | Glu | Asp | Pro | Asp | Trp | Trp | Lys | Gly |
| | 1175 | | | | 1180 | | | | 1185 | |

| Glu | Val | Ser | Gly | Gln | Val | Gly | Leu | Phe | Pro | Ser | Asn | Tyr | Val | Lys |
| | 1190 | | | | 1195 | | | | 1200 | |

| Leu | Thr | Thr | Asp | Met | Asp | Pro | Ser | Gln | Gln |
| | 1205 | | | | 1210 |

<210> SEQ ID NO 4
<211> LENGTH: 4625
<212> TYPE: DNA
<213> ORGANISM: Mus musculus

<400> SEQUENCE: 4

```
cccttcctttcctttttttg tgttcgcctt cggccgtgcc ggctgagagc ccagcagccg     60
tgacaggctg cgcaacaggt tcgctgcggc cggcctgacg actgacccgg cggcggcggc    120
cgcggcacgg cagggtcttc ccggagcttg gccgcgccca cgcgccggtg tcgaggagcg    180
cgcggggtcg cgccgggacg tgcgcgaggc gccagatggc tgagagctgc aagaagaagt    240
caggatcatg atggctcagt ttcccacagc gatgaatgga gggccaaata tgtgggctat    300
tacatctgaa gaacgtacta agcatgataa acagtttgat aacctcaaac cttcaggagg    360
ttacataaca ggtgatcaag cccgtacttt tttcctacag tcaggtctgc cggccccggt    420
tttagctgaa atatgggcct tatcagatct gaacaaggat gggaagatgg accagcaaga    480
gttctctata gctatgaaac tcatcaagtt aaagttgcag ggccaacagc tgcctgtagt    540
cctccctcct atcatgaaac aacccccctat gttctctcca ctaatctctg ctcgttttgg    600
gatgggaagc atgcccaatc tgtccattca tcagccattg cctccagttg cacctatagc    660
aacacccttg tcttctgcta cgtcagggac cagtattcct cccctaatga tgcctgctcc    720
cctagtgcct tctgttagta catcctcatt accaaatgga actgccagtc tcattcagcc    780
tttatccatt cctattcttcttcaacatt gcctcatgca tcatcttaca gcctgatgat    840
gggaggattt ggtggtgcta gtatccagaa ggcccagtct ctgattgatt aggatctag    900
tagctcaact tcctcaactg cttccctctc agggaactca cctaagacag ggacctcaga    960
gtgggcagtt cctcagcctt caagattaaa gtatcggcaa aaatttaata gtctagacaa   1020
aggcatgagc ggatacctct caggttttca agctagaaat gcccttcttc agtcaaatct   1080
ctctcaaact cagctagcta ctatttggac tctggctgac atcgatggtg acggacagtt   1140
gaaagctgaa gaatttattc tggcgatgca cctcactgac atggccaaag ctggacagcc   1200
actaccactg acgttgcctc ccgagcttgt ccctccatct ttcagagggg gaaagcaagt   1260
```

-continued

```
tgattctgtt aatggaactc tgccttcata tcagaaaaca caagaagaag agcctcagaa    1320
gaaactgcca gttacttttg aggacaaacg gaaagccaac tatgaacgag gaaacatgga    1380
gctggagaag cgacgccaag tgttgatgga gcagcagcag agggaggctg aacgcaaagc    1440
ccagaaagag aaggaagagt gggagcggaa acagagagaa ctgcaagagc aagaatggaa    1500
gaagcagctg gagttggaga aacgcttgga gaaacagaga gagctggaga gacagcggga    1560
ggaagagagg agaaaggaga tagaaagacg agaggcagca aaacaggagc ttgagagaca    1620
acgccgttta gaatgggaaa gactccgtcg gcaggagctg ctcagtcaga agaccaggga    1680
acaagaagac attgtcaggc tgagctccag aaagaaaagt ctccacctgg aactggaagc    1740
agtgaatgga aaacatcagc agatctcagg cagactacaa gatgtccaaa tcagaaagca    1800
aacacaaaag actgagctag aagttttgga taaacagtgt gacctggaaa ttatggaaat    1860
caaacaactt caacaagagc ttaaggaata tcaaaataag cttatctatc tggtccctga    1920
gaagcagcta ttaaacgaaa gaattaaaaa catgcagctc agtaacacac ctgattcagg    1980
gatcagttta cttcataaaa agtcatcaga aaggaagaa ttatgccaaa gacttaaaga    2040
acaattagat gctcttgaaa agaaaactgc atctaagctc tcagaaatgg attcatttaa    2100
caatcagctg aaggaactca gagaaagcta taatacacag cagttagccc ttgaacaact    2160
tcataaaatc aaacgtgaca aattgaagga atcgaaaga aaaagattag agcaaattca    2220 aaaaagaaa ctagaagatg aggctgcaag gaaagcaaag caaggaaaag aaaacttgtg    2280
gagagaaagt attagaaagg aagaagagga aaagcaaaaa cgactccagg aagaaaagtc    2340
acaggacaaa actcaagaag aggaacgaaa agctgaggca aaacaaagtg agacagccag    2400
tgctttggtg aattacagag cactgtaccc ttttgaagca agaaaccatg atgagatgag    2460
ttttagttct ggggatataa ttcaggttga tgaaaaaact gtaggagagc ctggttggct    2520
ttatggtagt tttcagggaa agtttggctg gttcccctgc aactatgtag aaaaagtgct    2580
gtcaagtgaa aaagctctgt ctcctaagaa ggccttactt cctcctacag tgtctctctc    2640
tgctacctca acttcttccc agccaccagc atcagtgact gattatcaca atgtatcctt    2700
ctcaaacctt actgttaata caacatggca gcagaagtca gcttttaccc gcactgtgtc    2760
ccctggatct gtgtccccca ttcacggaca ggggcaggct gtagaaaacc tgaaagccca    2820
ggccctttgt tcctggacgg caaagaagga gaaccacctg aacttctcaa agcacgacgt    2880
catcactgtc ctggagcagc aggaaaactg gtggtttggg gaggtgcacg gaggaagagg    2940
atggttcccc aagtcttatg tcaagctcat tcctgggaat gaagtacagc gaggagagcc    3000
agaagctttg tatgcagctg tgactaagaa acctacctcc acagcctatc cagttacctc    3060
cacagcctat ccagttggag aagactacat tgcactttat tcatactcaa gtgtagagcc    3120
cggggatttg actttcactg aaggtgaaga aattctagtg acccagaaag atggagagtg    3180
gtggacagga agtattggag agagaactgg aatcttcccg tccaactacg tcagaccaaa    3240
ggatcaagag aattttggga atgctagcaa atctggagca tcaaacaaaa acccgagat    3300 cgctcaagta acttcagcat atgctgcttc agggactgag cagctcagcc ttgcgccagg    3360
acagttaata ttaatcttaa agaaaaacac aagcgggtgg tggcaaggag agctacaggc    3420
cagagggaag aaacgacaga agggatggtt tcctgccagc catgtaaagc tgctaggtcc    3480
aagcagtgaa agaaccatgc ctactttca cgctgtatgt caagtgattg ctatgtatga    3540
ctacatggcg aataacgaag atgagctcaa tttctccaaa ggacagctga ttaatgttat    3600
```

-continued

```
gaacaaagat gaccctgact ggtggcaagg agaaaccaat ggtctgactg gtctctttcc      3660
ttcaaactat gttaagatga caacagactc agatccaagt caacagtggt gtgctgacct      3720
ccaagccctg gacacaatgc agcctacgga gaggaagcga cagggctaca ttcacgagct      3780
cattcagaca gaggagcggt acatggacga cctgcaactt tttgaacaaa aaactctcct      3840
ttgagggcct ggggaagcca gaaccagggg agctgcccac aaggctgggt ctaaagacag      3900
attttgctct cccaggacag aggagcatca atcggcttc atccatccaa acaagccaca      3960
ctcgctgggc ctggtatttt attgcaccac taaaattgct agcaatctat gcaaacatga      4020 tcttttaaa caaacgccac agcacagtgc cttgtactag tgttaacctg ttcagctgtg      4080
ttagatgcca gggtttccat tttcagggct ataaagtat tatgtgggaa atgagacatc      4140
agaccaccgg acgttaccac ttggcaaatc tgtccactgt ggagttggtg atgttggaac      4200
cattccacac tatgtgacct ctgctgggtc acacactcag gaggtgaagg gctgagatga      4260
aatgctgcag ccttggggct tgtgcagcct gatactgaaa tagcatccac ttgtgcactg      4320
aataaataga aacttgatcg ttttattctg actagatatt atcattctct gctaagacaa      4380
tatagtttga aatattatag tttgaatata aggaggaaag cttgatgtac tttaaatata      4440
ctgtgaactc taataatgtg gggatatttt tcaactttaa ttttcttaag tataaattat      4500
ttatgtaaat tctttgtttt gcatatttca tagaacatgc atctttaagc tttatcattg      4560
ccaacaatgt acagaaagag aataaaagta taagtttatg aatgtaaaaa aaaaaaaaaa      4620
aaaaa                                                                 4625
```

<210> SEQ ID NO 5
<211> LENGTH: 3594
<212> TYPE: DNA
<213> ORGANISM: Mus musculus
<220> FEATURE:
<221> NAME/KEY: CDS
<222> LOCATION: (1)..(3594)
<223> OTHER INFORMATION: Mouse Ese2

<400> SEQUENCE: 5

```
atg gct cag ttt ccc aca gcg atg aat gga ggg cca aat atg tgg gct        48
Met Ala Gln Phe Pro Thr Ala Met Asn Gly Gly Pro Asn Met Trp Ala
1               5                   10                  15 att aca tct gaa gaa cgt act aag cat gat aaa cag ttt gat aac ctc        96
Ile Thr Ser Glu Glu Arg Thr Lys His Asp Lys Gln Phe Asp Asn Leu
                20                  25                  30 aaa cct tca gga ggt tac ata aca ggt gat caa gcc cgt act ttt ttc       144
Lys Pro Ser Gly Gly Tyr Ile Thr Gly Asp Gln Ala Arg Thr Phe Phe
            35                  40                  45 cta cag tca ggt ctg ccg gcc ccg gtt tta gct gaa ata tgg gcc tta       192
Leu Gln Ser Gly Leu Pro Ala Pro Val Leu Ala Glu Ile Trp Ala Leu
        50                  55                  60 tca gat ctg aac aag gat ggg aag atg gac cag caa gag ttc tct ata       240
Ser Asp Leu Asn Lys Asp Gly Lys Met Asp Gln Gln Glu Phe Ser Ile
65                  70                  75                  80 gct atg aaa ctc atc aag tta aag ttg cag ggc caa cag ctg cct gta       288
Ala Met Lys Leu Ile Lys Leu Lys Leu Gln Gly Gln Gln Leu Pro Val
                85                  90                  95 gtc ctc cct cct atc atg aaa caa ccc cct atg ttc tct cca cta atc       336
Val Leu Pro Pro Ile Met Lys Gln Pro Pro Met Phe Ser Pro Leu Ile
            100                 105                 110 tct gct cgt ttt ggg atg gga agc atg ccc aat ctg tcc att cat cag       384
Ser Ala Arg Phe Gly Met Gly Ser Met Pro Asn Leu Ser Ile His Gln
        115                 120                 125
```

| | | |
|---|---|---|
| cca ttg cct cca gtt gca cct ata gca aca ccc ttg tct tct gct acg<br>Pro Leu Pro Pro Val Ala Pro Ile Ala Thr Pro Leu Ser Ser Ala Thr<br>130                        135                    140 | | 432 |
| tca ggg acc agt att cct ccc cta atg atg cct gct ccc cta gtg cct<br>Ser Gly Thr Ser Ile Pro Pro Leu Met Met Pro Ala Pro Leu Val Pro<br>145                        150                    155                    160 | | 480 |
| tct gtt agt aca tcc tca tta cca aat gga act gcc agt ctc att cag<br>Ser Val Ser Thr Ser Ser Leu Pro Asn Gly Thr Ala Ser Leu Ile Gln<br>                    165                    170                    175 | | 528 |
| cct tta tcc att cct tat tct tct tca aca ttg cct cat gca tca tct<br>Pro Leu Ser Ile Pro Tyr Ser Ser Ser Thr Leu Pro His Ala Ser Ser<br>              180                    185                    190 | | 576 |
| tac agc ctg atg atg gga gga ttt ggt ggt gct agt atc cag aag gcc<br>Tyr Ser Leu Met Met Gly Gly Phe Gly Gly Ala Ser Ile Gln Lys Ala<br>          195                    200                    205 | | 624 |
| cag tct ctg att gat tta gga tct agc tca act tcc tca act gct<br>Gln Ser Leu Ile Asp Leu Gly Ser Ser Ser Thr Ser Ser Thr Ala<br>210                        215                    220 | | 672 |
| tcc ctc tca ggg aac tca cct aag aca ggg acc tca gag tgg gca gtt<br>Ser Leu Ser Gly Asn Ser Pro Lys Thr Gly Thr Ser Glu Trp Ala Val<br>225                        230                    235                    240 | | 720 |
| cct cag cct tca aga tta aag tat cgg caa aaa ttt aat agt cta gac<br>Pro Gln Pro Ser Arg Leu Lys Tyr Arg Gln Lys Phe Asn Ser Leu Asp<br>                    245                    250                    255 | | 768 |
| aaa ggc atg agc gga tac ctc tca ggt ttt caa gct aga aat gcc ctt<br>Lys Gly Met Ser Gly Tyr Leu Ser Gly Phe Gln Ala Arg Asn Ala Leu<br>              260                    265                    270 | | 816 |
| ctt cag tca aat ctc tct caa act cag cta gct act att tgg act ctg<br>Leu Gln Ser Asn Leu Ser Gln Thr Gln Leu Ala Thr Ile Trp Thr Leu<br>          275                    280                    285 | | 864 |
| gct gac atc gat ggt gac gga cag ttg aaa gct gaa gaa ttt att ctg<br>Ala Asp Ile Asp Gly Asp Gly Gln Leu Lys Ala Glu Glu Phe Ile Leu<br>          290                    295                    300 | | 912 |
| gcg atg cac ctc act gac atg gcc aaa gct gga cag cca cta cca ctg<br>Ala Met His Leu Thr Asp Met Ala Lys Ala Gly Gln Pro Leu Pro Leu<br>305                        310                    315                    320 | | 960 |
| acg ttg cct ccc gag ctt gtc cct cca tct ttc aga ggg gga aag caa<br>Thr Leu Pro Pro Glu Leu Val Pro Pro Ser Phe Arg Gly Gly Lys Gln<br>                    325                    330                    335 | | 1008 |
| gtt gat tct gtt aat gga act ctg cct tca tat cag aaa aca caa gaa<br>Val Asp Ser Val Asn Gly Thr Leu Pro Ser Tyr Gln Lys Thr Gln Glu<br>              340                    345                    350 | | 1056 |
| gaa gag cct cag aag aaa ctg cca gtt act ttt gag gac aaa cgg aaa<br>Glu Glu Pro Gln Lys Lys Leu Pro Val Thr Phe Glu Asp Lys Arg Lys<br>          355                    360                    365 | | 1104 |
| gcc aac tat gaa cga gga aac atg gag ctg gag aag cga cgc caa gtg<br>Ala Asn Tyr Glu Arg Gly Asn Met Glu Leu Glu Lys Arg Arg Gln Val<br>370                        375                    380 | | 1152 |
| ttg atg gag cag cag cag agg gag gct gaa cgc aaa gcc cag aaa gag<br>Leu Met Glu Gln Gln Gln Arg Glu Ala Glu Arg Lys Ala Gln Lys Glu<br>385                        390                    395                    400 | | 1200 |
| aag gaa gag tgg gag cgg aaa cag aga gaa ctg caa gag caa gaa tgg<br>Lys Glu Glu Trp Glu Arg Lys Gln Arg Glu Leu Gln Glu Gln Glu Trp<br>                    405                    410                    415 | | 1248 |
| aag aag cag ctg gag ttg gag aaa cgc ttg gag aaa cag aga gag ctg<br>Lys Lys Gln Leu Glu Leu Glu Lys Arg Leu Glu Lys Gln Arg Glu Leu<br>              420                    425                    430 | | 1296 |
| gag aga cag cgg gag gaa gag agg aga aag gag ata gaa aga cga gag<br>Glu Arg Gln Arg Glu Glu Glu Arg Arg Lys Glu Ile Glu Arg Arg Glu | | 1344 |

```
                435                 440                 445
gca gca aaa cag gag ctt gag aga caa cgc cgt tta gaa tgg gaa aga    1392
Ala Ala Lys Gln Glu Leu Glu Arg Gln Arg Arg Leu Glu Trp Glu Arg
        450                 455                 460 ctc cgt cgg cag gag ctg ctc agt cag aag acc agg gaa caa gaa gac    1440
Leu Arg Arg Gln Glu Leu Leu Ser Gln Lys Thr Arg Glu Gln Glu Asp
465                 470                 475                 480 att gtc agg ctg agc tcc aga aag aaa agt ctc cac ctg gaa ctg gaa    1488
Ile Val Arg Leu Ser Ser Arg Lys Lys Ser Leu His Leu Glu Leu Glu
            485                 490                 495 gca gtg aat gga aaa cat cag cag atc tca ggc aga cta caa gat gtc    1536
Ala Val Asn Gly Lys His Gln Gln Ile Ser Gly Arg Leu Gln Asp Val
                500                 505                 510 caa atc aga aag caa aca caa aag act gag cta gaa gtt ttg gat aaa    1584
Gln Ile Arg Lys Gln Thr Gln Lys Thr Glu Leu Glu Val Leu Asp Lys
            515                 520                 525 cag tgt gac ctg gaa att atg gaa atc aaa caa ctt caa caa gag ctt    1632
Gln Cys Asp Leu Glu Ile Met Glu Ile Lys Gln Leu Gln Gln Glu Leu
        530                 535                 540 aag gaa tat caa aat aag ctt atc tat ctg gtc cct gag aag cag cta    1680
Lys Glu Tyr Gln Asn Lys Leu Ile Tyr Leu Val Pro Glu Lys Gln Leu
545                 550                 555                 560 tta aac gaa aga att aaa aac atg cag ctc agt aac aca cct gat tca    1728
Leu Asn Glu Arg Ile Lys Asn Met Gln Leu Ser Asn Thr Pro Asp Ser
            565                 570                 575 ggg atc agt tta ctt cat aaa aag tca tca gaa aag gaa gaa tta tgc    1776
Gly Ile Ser Leu Leu His Lys Lys Ser Ser Glu Lys Glu Glu Leu Cys
        580                 585                 590 caa aga ctt aaa gaa caa tta gat gct ctt gaa aaa gaa act gca tct    1824
Gln Arg Leu Lys Glu Gln Leu Asp Ala Leu Glu Lys Glu Thr Ala Ser
            595                 600                 605 aag ctc tca gaa atg gat tca ttt aac aat cag ctg aag gaa ctc aga    1872
Lys Leu Ser Glu Met Asp Ser Phe Asn Asn Gln Leu Lys Glu Leu Arg
        610                 615                 620 gaa agc tat aat aca cag cag tta gcc ctt gaa caa ctt cat aaa atc    1920
Glu Ser Tyr Asn Thr Gln Gln Leu Ala Leu Glu Gln Leu His Lys Ile
625                 630                 635                 640 aaa cgt gac aaa ttg aag gaa atc gaa aga aaa aga tta gag caa att    1968
Lys Arg Asp Lys Leu Lys Glu Ile Glu Arg Lys Arg Leu Glu Gln Ile
            645                 650                 655 caa aaa aag aaa cta gaa gat gag gct gca agg aaa gca aag caa gga    2016
Gln Lys Lys Lys Leu Glu Asp Glu Ala Ala Arg Lys Ala Lys Gln Gly
        660                 665                 670 aaa gaa aac ttg tgg aga gaa agt att aga aag gaa gag gaa aag        2064
Lys Glu Asn Leu Trp Arg Glu Ser Ile Arg Lys Glu Glu Glu Lys
675                 680                 685 caa aaa cga ctc cag gaa gaa aag tca cag gac aaa act caa gaa gag    2112
Gln Lys Arg Leu Gln Glu Glu Lys Ser Gln Asp Lys Thr Gln Glu Glu
        690                 695                 700 gaa cga aaa gct gag gca aaa caa agt gag aca gcc agt gct ttg gtg    2160
Glu Arg Lys Ala Glu Ala Lys Gln Ser Glu Thr Ala Ser Ala Leu Val
705                 710                 715                 720 aat tac aga gca ctg tac cct ttt gaa gca aga aac cat gat gag atg    2208
Asn Tyr Arg Ala Leu Tyr Pro Phe Glu Ala Arg Asn His Asp Glu Met
            725                 730                 735 agt ttt agt tct ggg gat ata att cag gtt gat gaa aaa act gta gga    2256
Ser Phe Ser Ser Gly Asp Ile Ile Gln Val Asp Glu Lys Thr Val Gly
        740                 745                 750 gag cct ggt tgg ctt tat ggt agt ttt cag gga aag ttt ggc tgg ttc    2304
```

-continued

```
                Glu Pro Gly Trp Leu Tyr Gly Ser Phe Gln Gly Lys Phe Gly Trp Phe
                            755                 760                 765 ccc tgc aac tat gta gaa aaa gtg ctg tca agt gaa aaa gct ctg tct              2352
Pro Cys Asn Tyr Val Glu Lys Val Leu Ser Ser Glu Lys Ala Leu Ser
            770                 775                 780 cct aag aag gcc tta ctt cct cct aca gtg tct ctc tct gct acc tca              2400
Pro Lys Lys Ala Leu Leu Pro Pro Thr Val Ser Leu Ser Ala Thr Ser
785                 790                 795                 800 act tct tcc cag cca cca gca tca gtg act gat tat cac aat gta tcc              2448
Thr Ser Ser Gln Pro Pro Ala Ser Val Thr Asp Tyr His Asn Val Ser
                805                 810                 815 ttc tca aac ctt act gtt aat aca aca tgg cag cag aag tca gct ttt              2496
Phe Ser Asn Leu Thr Val Asn Thr Thr Trp Gln Gln Lys Ser Ala Phe
            820                 825                 830 acc cgc act gtg tcc cct gga tct gtg tcc ccc att cac gga cag ggg              2544
Thr Arg Thr Val Ser Pro Gly Ser Val Ser Pro Ile His Gly Gln Gly
        835                 840                 845 cag gct gta gaa aac ctg aaa gcc cag gcc ctt tgt tcc tgg acg gca              2592
Gln Ala Val Glu Asn Leu Lys Ala Gln Ala Leu Cys Ser Trp Thr Ala
    850                 855                 860 aag aag gag aac cac ctg aac ttc tca aag cac gac gtc atc act gtc              2640
Lys Lys Glu Asn His Leu Asn Phe Ser Lys His Asp Val Ile Thr Val
865                 870                 875                 880 ctg gag cag cag gaa aac tgg tgg ttt ggg gag gtg cac gga gga aga              2688
Leu Glu Gln Gln Glu Asn Trp Trp Phe Gly Glu Val His Gly Gly Arg
                885                 890                 895 gga tgg ttc ccc aag tct tat gtc aag ctc att cct ggg aat gaa gta              2736
Gly Trp Phe Pro Lys Ser Tyr Val Lys Leu Ile Pro Gly Asn Glu Val
            900                 905                 910 cag cga gga gag cca gaa gct ttg tat gca gct gtg act aag aaa cct              2784
Gln Arg Gly Glu Pro Glu Ala Leu Tyr Ala Ala Val Thr Lys Lys Pro
        915                 920                 925 acc tcc aca gcc tat cca gtt acc tcc aca gcc tat cca gtt gga gaa              2832
Thr Ser Thr Ala Tyr Pro Val Thr Ser Thr Ala Tyr Pro Val Gly Glu
    930                 935                 940 gac tac att gca ctt tat tca tac tca agt gta gag ccc ggg gat ttg              2880
Asp Tyr Ile Ala Leu Tyr Ser Tyr Ser Ser Val Glu Pro Gly Asp Leu
945                 950                 955                 960 act ttc act gaa ggt gaa gaa att cta gtg acc cag aaa gat gga gag              2928
Thr Phe Thr Glu Gly Glu Glu Ile Leu Val Thr Gln Lys Asp Gly Glu
                965                 970                 975 tgg tgg aca gga agt att gga gag aga act gga atc ttc ccg tcc aac              2976
Trp Trp Thr Gly Ser Ile Gly Glu Arg Thr Gly Ile Phe Pro Ser Asn
            980                 985                 990 tac gtc aga cca aag gat caa gag  aat ttt ggg aat gct  agc aaa tct            3024
Tyr Val Arg Pro Lys Asp Gln Glu  Asn Phe Gly Asn Ala  Ser Lys Ser
        995                 1000                1005 gga gca  tca aac aaa aaa ccc  gag atc gct caa gta  act tca gca               3069
Gly Ala  Ser Asn Lys Lys Pro  Glu Ile Ala Gln Val  Thr Ser Ala
    1010                1015                1020 tat gct  gct tca ggg act gag  cag ctc agc ctt gcg  cca gga cag               3114
Tyr Ala  Ala Ser Gly Thr Glu  Gln Leu Ser Leu Ala  Pro Gly Gln
    1025                1030                1035 tta ata  tta atc tta aag aaa  aac aca agc ggg tgg  tgg caa gga               3159
Leu Ile  Leu Ile Leu Lys Lys  Asn Thr Ser Gly Trp  Trp Gln Gly
    1040                1045                1050 gag cta  cag gcc aga ggg aag  aaa cga cag aag gga  tgg ttt cct               3204
Glu Leu  Gln Ala Arg Gly Lys  Lys Arg Gln Lys Gly  Trp Phe Pro
    1055                1060                1065
```

```
gcc agc cat gta aag ctg cta ggt cca agc agt gaa aga acc atg      3249
Ala Ser His Val Lys Leu Leu Gly Pro Ser Ser Glu Arg Thr Met
    1070            1075                1080 cct act ttt cac gct gta tgt caa gtg att gct atg tat gac tac      3294
Pro Thr Phe His Ala Val Cys Gln Val Ile Ala Met Tyr Asp Tyr
        1085            1090                1095 atg gcg aat aac gaa gat gag ctc aat ttc tcc aaa gga cag ctg      3339
Met Ala Asn Asn Glu Asp Glu Leu Asn Phe Ser Lys Gly Gln Leu
    1100            1105                1110 att aat gtt atg aac aaa gat gac cct gac tgg tgg caa gga gaa      3384
Ile Asn Val Met Asn Lys Asp Asp Pro Asp Trp Trp Gln Gly Glu
        1115            1120                1125 acc aat ggt ctg act ggt ctc ttt cct tca aac tat gtt aag atg      3429
Thr Asn Gly Leu Thr Gly Leu Phe Pro Ser Asn Tyr Val Lys Met
    1130            1135                1140 aca aca gac tca gat cca agt caa cag tgg tgt gct gac ctc caa      3474
Thr Thr Asp Ser Asp Pro Ser Gln Gln Trp Cys Ala Asp Leu Gln
        1145            1150                1155 gcc ctg gac aca atg cag cct acg gag agg aag cga cag ggc tac      3519
Ala Leu Asp Thr Met Gln Pro Thr Glu Arg Lys Arg Gln Gly Tyr
    1160            1165                1170 att cac gag ctc att cag aca gag gag cgg tac atg gac gac ctg      3564
Ile His Glu Leu Ile Gln Thr Glu Glu Arg Tyr Met Asp Asp Leu
        1175            1180                1185 caa ctt ttt gaa caa aaa act ctc ctt tga                          3594
Gln Leu Phe Glu Gln Lys Thr Leu Leu
    1190            1195

<210> SEQ ID NO 6
<211> LENGTH: 1197
<212> TYPE: PRT
<213> ORGANISM: Mus musculus

<400> SEQUENCE: 6

Met Ala Gln Phe Pro Thr Ala Met Asn Gly Gly Pro Asn Met Trp Ala
1               5                   10                  15

Ile Thr Ser Glu Glu Arg Thr Lys His Asp Lys Gln Phe Asp Asn Leu
                20                  25                  30

Lys Pro Ser Gly Gly Tyr Ile Thr Gly Asp Gln Ala Arg Thr Phe Phe
            35                  40                  45

Leu Gln Ser Gly Leu Pro Ala Pro Val Leu Ala Glu Ile Trp Ala Leu
        50                  55                  60

Ser Asp Leu Asn Lys Asp Gly Lys Met Asp Gln Gln Glu Phe Ser Ile
65                  70                  75                  80

Ala Met Lys Leu Ile Lys Leu Lys Leu Gln Gly Gln Gln Leu Pro Val
                85                  90                  95

Val Leu Pro Pro Ile Met Lys Gln Pro Pro Met Phe Ser Pro Leu Ile
            100                 105                 110

Ser Ala Arg Phe Gly Met Gly Ser Met Pro Asn Leu Ser Ile His Gln
        115                 120                 125

Pro Leu Pro Pro Val Ala Pro Ile Ala Thr Pro Leu Ser Ser Ala Thr
    130                 135                 140

Ser Gly Thr Ser Ile Pro Pro Leu Met Met Pro Ala Pro Leu Val Pro
145                 150                 155                 160

Ser Val Ser Thr Ser Ser Leu Pro Asn Gly Thr Ala Ser Leu Ile Gln
                165                 170                 175

Pro Leu Ser Ile Pro Tyr Ser Ser Thr Leu Pro His Ala Ser Ser
            180                 185                 190
```

```
Tyr Ser Leu Met Met Gly Gly Phe Gly Gly Ala Ser Ile Gln Lys Ala
        195                 200                 205

Gln Ser Leu Ile Asp Leu Gly Ser Ser Ser Thr Ser Ser Thr Ala
    210                 215                 220

Ser Leu Ser Gly Asn Ser Pro Lys Thr Gly Thr Ser Glu Trp Ala Val
225                 230                 235                 240

Pro Gln Pro Ser Arg Leu Lys Tyr Arg Gln Lys Phe Asn Ser Leu Asp
                245                 250                 255

Lys Gly Met Ser Gly Tyr Leu Ser Gly Phe Gln Ala Arg Asn Ala Leu
            260                 265                 270

Leu Gln Ser Asn Leu Ser Gln Thr Gln Leu Ala Thr Ile Trp Thr Leu
        275                 280                 285

Ala Asp Ile Asp Gly Asp Gly Gln Leu Lys Ala Glu Glu Phe Ile Leu
        290                 295                 300

Ala Met His Leu Thr Asp Met Ala Lys Ala Gly Gln Pro Leu Pro Leu
305                 310                 315                 320

Thr Leu Pro Pro Glu Leu Val Pro Pro Ser Phe Arg Gly Gly Lys Gln
                325                 330                 335

Val Asp Ser Val Asn Gly Thr Leu Pro Ser Tyr Gln Lys Thr Gln Glu
            340                 345                 350

Glu Glu Pro Gln Lys Lys Leu Pro Val Thr Phe Glu Asp Lys Arg Lys
        355                 360                 365

Ala Asn Tyr Glu Arg Gly Asn Met Glu Leu Glu Lys Arg Arg Gln Val
        370                 375                 380

Leu Met Glu Gln Gln Arg Glu Ala Glu Arg Lys Ala Gln Lys Glu
385                 390                 395                 400

Lys Glu Glu Trp Glu Arg Lys Gln Arg Glu Leu Gln Glu Gln Glu Trp
                405                 410                 415

Lys Lys Gln Leu Glu Leu Glu Lys Arg Leu Glu Lys Gln Arg Glu Leu
            420                 425                 430

Glu Arg Gln Arg Glu Glu Glu Arg Lys Glu Ile Glu Arg Arg Glu
        435                 440                 445

Ala Ala Lys Gln Glu Leu Glu Arg Gln Arg Arg Leu Glu Trp Glu Arg
        450                 455                 460

Leu Arg Arg Gln Glu Leu Leu Ser Gln Lys Thr Arg Glu Gln Glu Asp
465                 470                 475                 480

Ile Val Arg Leu Ser Ser Arg Lys Lys Ser Leu His Leu Glu Leu Glu
                485                 490                 495

Ala Val Asn Gly Lys His Gln Gln Ile Ser Gly Arg Leu Gln Asp Val
            500                 505                 510

Gln Ile Arg Lys Gln Thr Gln Lys Thr Glu Leu Glu Val Leu Asp Lys
        515                 520                 525

Gln Cys Asp Leu Glu Ile Met Glu Ile Lys Gln Leu Gln Gln Glu Leu
        530                 535                 540

Lys Glu Tyr Gln Asn Lys Leu Ile Tyr Leu Val Pro Glu Lys Gln Leu
545                 550                 555                 560

Leu Asn Glu Arg Ile Lys Asn Met Gln Leu Ser Asn Thr Pro Asp Ser
                565                 570                 575

Gly Ile Ser Leu Leu His Lys Lys Ser Ser Glu Lys Glu Leu Cys
            580                 585                 590

Gln Arg Leu Lys Glu Gln Leu Asp Ala Leu Glu Lys Glu Thr Ala Ser
        595                 600                 605
```

```
Lys Leu Ser Glu Met Asp Ser Phe Asn Asn Gln Leu Lys Glu Leu Arg
    610                 615                 620

Glu Ser Tyr Asn Thr Gln Gln Leu Ala Leu Glu Gln Leu His Lys Ile
625                 630                 635                 640

Lys Arg Asp Lys Leu Lys Glu Ile Glu Arg Lys Arg Leu Glu Gln Ile
                645                 650                 655

Gln Lys Lys Lys Leu Glu Asp Glu Ala Ala Arg Lys Ala Lys Gln Gly
            660                 665                 670

Lys Glu Asn Leu Trp Arg Glu Ser Ile Arg Lys Glu Glu Glu Lys
        675                 680                 685

Gln Lys Arg Leu Gln Glu Glu Lys Ser Gln Asp Lys Thr Gln Glu Glu
    690                 695                 700

Glu Arg Lys Ala Glu Ala Lys Gln Ser Glu Thr Ala Ser Ala Leu Val
705                 710                 715                 720

Asn Tyr Arg Ala Leu Tyr Pro Phe Glu Ala Arg Asn His Asp Glu Met
                725                 730                 735

Ser Phe Ser Ser Gly Asp Ile Ile Gln Val Asp Glu Lys Thr Val Gly
            740                 745                 750

Glu Pro Gly Trp Leu Tyr Gly Ser Phe Gln Gly Lys Phe Gly Trp Phe
        755                 760                 765

Pro Cys Asn Tyr Val Glu Lys Val Leu Ser Ser Glu Lys Ala Leu Ser
770                 775                 780

Pro Lys Lys Ala Leu Leu Pro Pro Thr Val Ser Leu Ser Ala Thr Ser
785                 790                 795                 800

Thr Ser Ser Gln Pro Pro Ala Ser Val Thr Asp Tyr His Asn Val Ser
                805                 810                 815

Phe Ser Asn Leu Thr Val Asn Thr Thr Trp Gln Gln Lys Ser Ala Phe
            820                 825                 830

Thr Arg Thr Val Ser Pro Gly Ser Val Ser Pro Ile His Gly Gln Gly
        835                 840                 845

Gln Ala Val Glu Asn Leu Lys Ala Gln Ala Leu Cys Ser Trp Thr Ala
    850                 855                 860

Lys Lys Glu Asn His Leu Asn Phe Ser Lys His Asp Val Ile Thr Val
865                 870                 875                 880

Leu Glu Gln Gln Glu Asn Trp Trp Phe Gly Glu Val His Gly Gly Arg
                885                 890                 895

Gly Trp Phe Pro Lys Ser Tyr Val Lys Leu Ile Pro Gly Asn Glu Val
            900                 905                 910

Gln Arg Gly Glu Pro Glu Ala Leu Tyr Ala Ala Val Thr Lys Lys Pro
        915                 920                 925

Thr Ser Thr Ala Tyr Pro Val Thr Ser Thr Ala Tyr Pro Val Gly Glu
    930                 935                 940

Asp Tyr Ile Ala Leu Tyr Ser Tyr Ser Ser Val Glu Pro Gly Asp Leu
945                 950                 955                 960

Thr Phe Thr Glu Gly Glu Glu Ile Leu Val Thr Gln Lys Asp Gly Glu
                965                 970                 975

Trp Trp Thr Gly Ser Ile Gly Glu Arg Thr Gly Ile Phe Pro Ser Asn
            980                 985                 990

Tyr Val Arg Pro Lys Asp Gln Glu  Asn Phe Gly Asn Ala  Ser Lys Ser
        995                 1000                1005

Gly Ala  Ser Asn Lys Lys Pro  Glu Ile Ala Gln Val  Thr Ser Ala
    1010                1015                1020

Tyr Ala  Ala Ser Gly Thr Glu  Gln Leu Ser Leu Ala  Pro Gly Gln
```

```
            1025                1030                1035
Leu Ile Leu Ile Leu Lys Lys Asn Thr Ser Gly Trp Trp Gln Gly
        1040                1045                1050

Glu Leu Gln Ala Arg Gly Lys Lys Arg Gln Lys Gly Trp Phe Pro
        1055                1060                1065

Ala Ser His Val Lys Leu Leu Gly Pro Ser Ser Glu Arg Thr Met
        1070                1075                1080

Pro Thr Phe His Ala Val Cys Gln Val Ile Ala Met Tyr Asp Tyr
        1085                1090                1095

Met Ala Asn Asn Glu Asp Glu Leu Asn Phe Ser Lys Gly Gln Leu
        1100                1105                1110

Ile Asn Val Met Asn Lys Asp Asp Pro Asp Trp Trp Gln Gly Glu
        1115                1120                1125

Thr Asn Gly Leu Thr Gly Leu Phe Pro Ser Asn Tyr Val Lys Met
        1130                1135                1140

Thr Thr Asp Ser Asp Pro Ser Gln Gln Trp Cys Ala Asp Leu Gln
        1145                1150                1155

Ala Leu Asp Thr Met Gln Pro Thr Glu Arg Lys Arg Gln Gly Tyr
        1160                1165                1170

Ile His Glu Leu Ile Gln Thr Glu Glu Arg Tyr Met Asp Asp Leu
        1175                1180                1185

Gln Leu Phe Glu Gln Lys Thr Leu Leu
        1190                1195
```

<210> SEQ ID NO 7
<211> LENGTH: 738
<212> TYPE: DNA
<213> ORGANISM: Mus musculus

<400> SEQUENCE: 7

```
ccgtcttcca catttcccac attgatcgtg tgtacacact ccgaacagac aacatcaacg    60
agaggacggc ctgggtccag aagatcaagg gtgcctcaga gcagtacatc gacactgaga   120
agaagaaacg ggaaaaggct taccaagccc gttctcaaaa gacttcaggt attgggcgtc   180
tgatggtgca tgtcattgaa gctacagaat aaaagcctg caaaccaaac gggaaaagta    240
atccatactg tgaagtcagc atgggctccc aaagctatac caccaggacc ctgcaggaca   300
cactaaaccc caagtggaac ttcaactgcc agttcttcat caaggatctt taccaggacg   360
ttctgtgtct cactatgttt gacagagacc agttttctcc agatgacttc ttgggtcgta   420
ctgaagttcc agtggcaaaa atccgaacag aacaggaaag caaaggcccc accacccgcc   480
gactactact gcacgaagtc cccactggag aagtctgggt ccgctttgac ctgcaacttt   540
ttgaacaaaa aactctcctt tgagggcctg gggaagccag aaccagggga gctgcccaca   600
aggctgggtc taaagacaga ttttgctctc ccaggacaga ggagcatcac atggcttcat   660
ccatcaaaca gccacactcg ctgggcctgt attttattgc acactaaatt gctagcaatc   720
tatgcaaaca tgatctttt                                               738
```

<210> SEQ ID NO 8
<211> LENGTH: 186
<212> TYPE: PRT
<213> ORGANISM: Mus musculus

<400> SEQUENCE: 8

```
Val Phe His Ile Ser His Ile Asp Arg Val Tyr Thr Leu Arg Thr Asp
1               5                   10                  15
```

Asn Ile Asn Glu Arg Thr Ala Trp Val Gln Lys Ile Lys Gly Ala Ser
            20                  25                  30

Glu Gln Tyr Ile Asp Thr Glu Lys Lys Arg Glu Lys Ala Tyr Gln
        35                  40                  45

Ala Arg Ser Gln Lys Thr Ser Gly Ile Gly Arg Leu Met Val His Val
 50                  55                  60

Ile Glu Ala Thr Glu Leu Lys Ala Cys Lys Pro Asn Gly Lys Ser Asn
 65                  70                  75                  80

Pro Tyr Cys Glu Val Ser Met Gly Ser Gln Ser Tyr Thr Thr Arg Thr
                85                  90                  95

Leu Gln Asp Thr Leu Asn Pro Lys Trp Asn Phe Asn Cys Gln Phe Phe
            100                 105                 110

Ile Lys Asp Leu Tyr Gln Asp Val Leu Cys Leu Thr Met Phe Asp Arg
        115                 120                 125

Asp Gln Phe Ser Pro Asp Phe Leu Gly Arg Thr Glu Val Pro Val
130                 135                 140

Ala Lys Ile Arg Thr Glu Gln Glu Ser Lys Gly Pro Thr Thr Arg Arg
145                 150                 155                 160

Leu Leu Leu His Glu Val Pro Thr Gly Glu Val Trp Val Arg Phe Asp
                165                 170                 175

Leu Gln Leu Phe Glu Gln Lys Thr Leu Leu
            180                 185

<210> SEQ ID NO 9
<211> LENGTH: 1078
<212> TYPE: DNA
<213> ORGANISM: Mus musculus

<400> SEQUENCE: 9

```
gaattcggca cgagggctga gagaagcgga ctccgaggac tctgatgctg aagagaagcc      60
tgttaagcag gaggacttcc cgaagattta ggaccaaaga agttaaagac gggtggcaat     120
tttaagccca gccagaaagg cttttcagga ggaaccaagt ccttcatgga ctttggcagc     180
tgggagagac acacgaaagg gatcgggcag aagctgctgc agaagatggg ctacgtccct     240
gggcgtggcc tggggaagaa cgcacagggg atcatcaacc catcgaagc caaacagaga     300
aaaggcaagg gagccgtggg ggcctatggc tcggagagga ccactcagtc tctgcaggac     360
ttccccgtgg ccgactcgga agaggaggca gaagaggagt tcagaagga gctgagccaa     420
tggaggaaag accccagcgg gagcaagaag aagccaaagt actcttacaa gactgtggag     480
gagctgaagg ccaagggcag ggtcagcaag aagctcacag cacctcagaa ggaactgtct     540
caggtcaagg tgatcgacat gacaggccgg gagcagaagg tgtactacag ctacagccaa     600
atcagccaca agcacagcgt gcccgatgaa ggggtgccat tgctggcgca gctgcccccc     660
acagccggca aggaagccag gatgccgggc tttgcactgc tgagctggga gcacaacctg     720
cagctgctca ttgagcgcac ggagcaggag atcatccaga gcgaccggca gctccagtat     780
gagcgggaca tggtggtcag cctgtcgcat gagctggaga gacggccga ggttcttgca     840
catgaggagc gtgtcatctc taacctcagc aaggtgctgg ccctggtgga ggaatgtgag     900
cgccgcatgc agccccatgg caccgacccc tcactctgg atgagtgtgc ccgcatcttt     960
gagacactac aggacaagta ttatgaggag taccgcctgg cggaccgcgc agacctcgct    1020
gtggccattg tctacccgct cgtgaaggac tactttaagg attggcaccc ctcgaggg     1078
```

```
<210> SEQ ID NO 10
<211> LENGTH: 309
<212> TYPE: PRT
<213> ORGANISM: Mus musculus

<400> SEQUENCE: 10

Gly Thr Lys Ser Phe Met Asp Phe Gly Ser Trp Glu Arg His Thr Lys
1               5                   10                  15

Gly Ile Gly Gln Lys Leu Leu Gln Lys Met Gly Tyr Val Pro Gly Arg
            20                  25                  30

Gly Leu Gly Lys Asn Ala Gln Gly Ile Ile Asn Pro Ile Glu Ala Lys
        35                  40                  45

Gln Arg Lys Gly Lys Gly Ala Val Gly Ala Tyr Gly Ser Glu Arg Thr
    50                  55                  60

Thr Gln Ser Leu Gln Asp Phe Pro Val Ala Asp Ser Glu Glu Glu Ala
65                  70                  75                  80

Glu Glu Glu Phe Gln Lys Glu Leu Ser Gln Trp Arg Lys Asp Pro Ser
                85                  90                  95

Gly Ser Lys Lys Lys Pro Lys Tyr Ser Tyr Lys Thr Val Glu Glu Leu
            100                 105                 110

Lys Ala Lys Gly Arg Val Ser Lys Lys Leu Thr Ala Pro Gln Lys Glu
        115                 120                 125

Leu Ser Gln Val Lys Val Ile Asp Met Thr Gly Arg Glu Gln Lys Val
    130                 135                 140

Tyr Tyr Ser Tyr Ser Gln Ile Ser His Lys His Ser Val Pro Asp Glu
145                 150                 155                 160

Gly Val Pro Leu Leu Ala Gln Leu Pro Pro Thr Ala Gly Lys Glu Ala
                165                 170                 175

Arg Met Pro Gly Phe Ala Leu Pro Glu Leu Glu His Asn Leu Gln Leu
            180                 185                 190

Leu Ile Glu Arg Thr Glu Gln Glu Ile Ile Gln Ser Asp Arg Gln Leu
    195                 200                 205

Gln Tyr Glu Arg Asp Met Val Val Ser Leu Ser His Glu Leu Glu Lys
210                 215                 220

Thr Ala Glu Val Leu Ala His Glu Glu Arg Val Ile Ser Asn Leu Ser
225                 230                 235                 240

Lys Val Leu Ala Leu Val Glu Glu Cys Glu Arg Arg Met Gln Pro His
                245                 250                 255

Gly Thr Asp Pro Leu Thr Leu Asp Glu Cys Ala Arg Ile Phe Glu Thr
            260                 265                 270

Leu Gln Asp Lys Tyr Tyr Glu Glu Tyr Arg Leu Ala Asp Arg Ala Asp
    275                 280                 285

Leu Ala Val Ala Ile Val Tyr Pro Leu Val Lys Asp Tyr Phe Lys Asp
290                 295                 300

Trp His Pro Ser Arg
305

<210> SEQ ID NO 11
<211> LENGTH: 97
<212> TYPE: DNA
<213> ORGANISM: Mus musculus

<400> SEQUENCE: 11
catggcggcg gctgcggagg gcgtcccggc gacgcgacgg aggacgagcc acctcgagat    60
gatgctgcgg tggagacagc cgaggaagca aggagc                             97
```

<210> SEQ ID NO 12
<211> LENGTH: 123
<212> TYPE: DNA
<213> ORGANISM: Mus musculus

<400> SEQUENCE: 12

```
cttgagtcta ctgaaaatac cctgcaggaa gctacatcat ccatgtcttt gatgacccaa      60
tttgaacagg aagtatctgg cctccaaaga ccatacgtga tattgagact agcgaagaga     120
tgc                                                                   123
```

<210> SEQ ID NO 13
<211> LENGTH: 140
<212> TYPE: DNA
<213> ORGANISM: Mus musculus

<400> SEQUENCE: 13

```
gaattcggca cgagggagtc tggttctgga aagccgacag aagctgagct tgtcaactta      60
gatttcttgg gagatttgga tgttccggta tctgccccac ccctgtgtgt ctgagctcga     120
gtctctctgc tggactatgg                                                 140
```

<210> SEQ ID NO 14
<211> LENGTH: 2855
<212> TYPE: DNA
<213> ORGANISM: Mus musculus

<400> SEQUENCE: 14

```
ctttacgagc agagggagcc aaattcagag ccgttttaga taaagctgtg caagcggatg      60
gacaggtgaa ggagcgctac cagtcccatc gagacaccat cgcacttctg tgtaagccgg     120
agccagagct gaatgctgcc atcccctctg ctaacccagc aaagaccatg cagggcagcg     180
aggttgtaag tgtcttaaag tccttattat caaatcttga tgaaatcaag aaggaaagag     240
agagtcttga gaatgacctg aagtcagtga attttgacat gacaagcaag tttttgacag     300
ctctggccca agatggcgtg ataaatgagg aggctctctc tgtcactgag ctggatcgga     360
tctatggcgg tctaacaagt aaagttcaag agtctctgaa gaaacaagag ggacttctaa     420
aaaatataca ggtctcacac caagaattct ccaaaatgaa gcaatctaac aacgaggcta     480
acttgagaga agaagttctg aagaacctag caactgcgta tgacaacttt gttgagcttg     540
tagctaactt gaaggagggc acaaagtttt acaatgagct gactgagatc ctggtcaggt     600
tccagaacaa atgcagtgac atagtgtttg cacggaagac agaaagagac gagctcttga     660
aggatctgca gcagagcatt gccagagagc ccagcgctcc ttcaatccct cctccagcct     720
atcagtcctc cccagcagcg gggcatgcag cagcgcctcc aactccagcc caagaaccaa     780
tgccgcctgc taagcccag cctcagccc ggcctccacc tctgtgcttt cctgcaaacc      840
gagttcctcc tgcttctgct gctgctgccc ctgcaggcgt ggggacggct tcagcagcgc     900
cgccacagac ccctggctct gctccccgc cacaggctca gggaccacca taccctacct      960
atccaggata tcccgggtat tgccaaatgc ccatgcccat gggctacaac ccctacgcat    1020
atggccagta caatatgccg tacccaccgg tgtatcacca gagccccgga caggctccat    1080
acccaggacc ccagcagcct acctacccct ccctcagcc ccgcagcag tcctactatc      1140
cacagcagta acgctgccac gtgctgctgg ttcagatcag agcgacagga cagcagctgc    1200
caccagctct aagccacgct ctggccactc gagagtatct tgctctattg attgctgtgg    1260
atgatttctg tctgtggcta aagccgaagg ctgggcccca cctccacatt tgatcgcact    1320
```

-continued

```
cgtgagattc tgctgctgtt gcagtataaa cgctagctat aatagcattt gaaaaaaatt    1380
acagttccat aaaatgctga aaatgagaaa ttaaacctgc aagtgaaaca tttgaaatta    1440
gcatacttta taagatgcag ttgggacaaa gatggcttaa gtactgatat ttaaggaaaa    1500
agttttcttt ctcttttggt ttattgattt agtttaattt ctattatgat attttgcata    1560
atcaaggcat tgtaaatctt ataatttaaa aataaaattac ttacgaacag ttgtcattgt    1620
tatgttttgt cattgattct cattgctgtc tagttccttt ctggtattag cctctccttc    1680
tgtatgttca caggctccat tactgtgttg aattgcgtga cgtcaggtga gcagtcaggg    1740
agggctgctc tgcggacgcc aagcgcacac cagcttgtct caggctcagc agtcagctca    1800
tctggacatt tctatttaaa agtcctttaa tgtggaagat acacacaatt gttaccaaag    1860
gttcttccaa ttaattttac aatttaaaaa gtatgtatta atgttttatt gttagatttt    1920
ccaaaaaaat gatgcaaatt ctggtaatat tcatttccct cacccataat ttggttaaaa    1980
tgagtagttt tagccataca gtctcatctg ctgtggagga acctggagaa agtcccctgt    2040
gcctttctag cccttgggtt ctattcttat cctgcaatgt ctactgcaca gtgtgtttga    2100
gcagatccta accctccttt tacagtttct tcttcttact tctttattct ttttgtggct    2160
cctgaaatct gaggttattt tgtaattcag gagcatgcag acaattgtt gggacatgtg    2220 cctagtccgg aatacagccc aggacagcaa ggagatgcgt cctgcaccag gaagccgtgc    2280
aggcaggagc tgtccaaggt cccggcggct ctgcctgtgt gaggcaggag aatgagcaga    2340
ttccctaatc tatgttctcg aagtttaatg ctgatgttgt cttgccttat cctcatttaa    2400
ctgatactgt cacccagtcc acctttgctc tcattgcaaa gtgatagtgt aatttcaaat    2460
gtaagactga agatacgatt gtaaaaggga gtaaactggt ttaaacgtgt tattctaaag    2520
caccttactt tgttgttgta tgcagaaaac acagatgcgc taattcagta taaatgactg    2580
attgcctgga atttggacgt tggcttaaag tccgatagct aaaccttggc aaaacataac    2640
aaacatttca ttgctcagcc tcagtgctct ggagtattca gtgtatgaga caggtttatt    2700
tgagtcctct gtaaatggca tttgaatttt atattctccc ctcccgagta tcttataaga    2760
catcccctga gttagggagt tcccagactg ctactctatt ccttatgaat gcaaacaac    2820 caccaataga acaaaaaaaa aaaaaaaaac tcgag                              2855
```

<210> SEQ ID NO 15
<211> LENGTH: 1151
<212> TYPE: DNA
<213> ORGANISM: Mus musculus

<400> SEQUENCE: 15

```
ctttacgagc agagggagcc aaattcagag ccgttttaga taaagctgtg caagcggatg     60
gacaggtgaa ggagcgctac cagtcccatc gagacaccat cgcacttctg tgtaagccgg    120
agccagagct gaatgctgcc atcccctctg ctaacccagc aaagaccatg cagggcagcg    180
aggttgtaag tgtcttaaag tccttattat caaatcttga tgaaatcaag aaggaaagag    240
agagtcttga gaatgacctg aagtcagtga attttgacat gacaagcaag ttttttgacag    300 ctctggccca gatggcgtg ataaatgagg aggctctctc tgtcactgag ctggatcgga    360
tctatggcgg tctaacaagt aaagttcaag agtctctgaa gaaacaagag ggacttctaa    420
aaaatataca ggtctcacac caagaattct ccaaaatgaa gcaatctaac aacgaggcta    480
acttgagaga agaagttctg aagaacctag caactgcgta tgacaacttt gttgagcttg    540
```

```
tagctaactt gaaggagggc acaaagtttt acaatgagct gactgagatc ctggtcaggt      600
tccagaacaa atgcagtgac atagtgtttg cacggaagac agaaagagac gagctcttga      660
aggatctgca gcagagcatt gccagagagc ccagcgctcc ttcaatccct cctccagcct      720
atcagtcctc cccagcagcg gggcatgcag cagcgcctcc aactccagcc caagaaccag      780
tgccgcctgc taagccccag cctccagccc ggcctccacc tcctgtgctt cctgcaaacc      840
gagttcctcc tgcttctgct gctgctgccc ctgcaggcgt ggggacggct tcagcagcgc      900
cgccacagac ccctggctct gctccccgc cacaggctca gggaccacca tacctacct        960 atccaggata tccgggtat tgccaaatgc ccatgcccat gggctacaac ccctacgcat      1020
atggccagta caatatgccg tacccaccgg tgtatcacca gaccccgga caggctccat      1080 acccaggacc ccagcagcct acctacccct tccctcagcc cccgcagcag tcctactatc      1140
cacagcagta a                                                            1151
```

```
<210> SEQ ID NO 16
<211> LENGTH: 382
<212> TYPE: PRT
<213> ORGANISM: Mus musculus

<400> SEQUENCE: 16
```

```
Leu Arg Ala Glu Gly Ala Lys Phe Arg Ala Val Leu Asp Lys Ala Val
1               5                   10                  15

Gln Ala Asp Gly Gln Val Lys Glu Arg Tyr Gln Ser His Arg Asp Thr
            20                  25                  30

Ile Ala Leu Leu Cys Lys Pro Glu Pro Glu Leu Asn Ala Ala Ile Pro
        35                  40                  45

Ser Ala Asn Pro Ala Lys Thr Met Gln Gly Ser Glu Val Val Ser Val
    50                  55                  60

Leu Lys Ser Leu Leu Ser Asn Leu Asp Glu Ile Lys Lys Glu Arg Glu
65                  70                  75                  80

Ser Leu Glu Asn Asp Leu Lys Ser Val Asn Phe Asp Met Thr Ser Lys
                85                  90                  95

Phe Leu Thr Ala Leu Ala Gln Asp Gly Val Ile Asn Glu Glu Ala Leu
            100                 105                 110

Ser Val Thr Glu Leu Asp Arg Ile Tyr Gly Gly Leu Thr Ser Lys Val
        115                 120                 125

Gln Glu Ser Leu Lys Lys Gln Glu Gly Leu Leu Lys Asn Ile Gln Val
    130                 135                 140

Ser His Gln Glu Phe Ser Lys Met Lys Gln Ser Asn Asn Glu Ala Asn
145                 150                 155                 160

Leu Arg Glu Glu Val Leu Lys Asn Leu Ala Thr Ala Tyr Asp Asn Phe
                165                 170                 175

Val Glu Leu Val Ala Asn Leu Lys Glu Gly Thr Lys Phe Tyr Asn Glu
            180                 185                 190

Leu Thr Glu Ile Leu Val Arg Phe Gln Asn Lys Cys Ser Asp Ile Val
        195                 200                 205

Phe Ala Arg Lys Thr Glu Arg Asp Glu Leu Leu Lys Asp Leu Gln Gln
    210                 215                 220

Ser Ile Ala Arg Glu Pro Ser Ala Pro Ser Ile Pro Pro Ala Tyr
225                 230                 235                 240

Gln Ser Ser Pro Ala Ala Gly His Ala Ala Pro Thr Pro Ala
                245                 250                 255

Pro Arg Thr Met Pro Pro Ala Lys Pro Gln Pro Pro Ala Arg Pro Pro
```

```
            260              265              270
Pro Pro Val Leu Pro Ala Asn Arg Val Pro Ala Ser Ala Ala Ala
            275              280              285
Ala Pro Ala Gly Val Gly Thr Ala Ser Ala Ala Pro Pro Gln Thr Pro
    290                  295              300
Gly Ser Ala Pro Pro Gln Ala Gln Gly Pro Pro Tyr Pro Thr Tyr
305              310              315              320
Pro Gly Tyr Pro Gly Tyr Cys Gln Met Pro Met Met Gly Tyr Asn
                325              330              335
Pro Tyr Ala Tyr Gly Gln Tyr Asn Met Pro Tyr Pro Val Tyr His
            340              345              350
Gln Ser Pro Gly Gln Ala Pro Tyr Pro Gly Pro Gln Gln Pro Thr Tyr
            355              360              365
Pro Phe Pro Gln Pro Pro Gln Gln Ser Tyr Tyr Pro Gln Gln
    370              375              380
```

<210> SEQ ID NO 17
<211> LENGTH: 1738
<212> TYPE: DNA
<213> ORGANISM: Mus musculus

<400> SEQUENCE: 17

```
ggtcttggct agaattttaa atttcttctc atttgagtaa aatgttgcat tctgaagtcc      60
catgctacct gaagttgcat ttggagtccc aagctactgg aatgtttata tgtgaccgtt     120
tcccaggagg cttacactgc agaaggaaga atgaatctag gtgaggtggg cagctgcttg     180
gcagtcctct cttgtgcccc aactgtaaac cagatagaaa tgttcagggg aggatacttt     240
cattattgtg gtttgtagtg ttaagatgat tgcttctgcc ttggaaatac ctcaagctgt     300
tcttatttaa caggtaagtg actgagtata atattccaga aaaatttgaa atcctaatt     360
cttccatatt tcattaaatt ttttgcatac aggtctaaca aatatggata tgtatacaca     420
tcctctttaa tgaaggtatt attttggtta cttttcctaa gatataccct aaaagatgtt     480
ctatacattt cctacttaaa ttctgggga tttggagtat gtacatgata aaaaagatta      540
taatatatcg attgaagtta ctttattttc taattagaat tattttaata gtcctttatt     600
gaataagtgc tgtaatttgt ttgctatgag acttattcct gatgtgaatg taaattattt     660
ttccacatgc atgaaaaaat gtatgtacta atcagagttg tctccattgc attgaaatta     720
cttgttttga actaaagtaa ctcatattta tgtagtagaa tgcttatgtt ttcagacttt     780
gtaatgattt cctttggatg tattttaaat caatcggtct gggtaacata tcagtttaga     840
ttaatatgtg cttaaaagaa gaaaaaaatt caatggttca tagtagaaat gtgccacact     900
taaataagct ctgtatgaca tgaaattctg ttaaaacatt gtaattcatg gtgacttta      960
acttataaaa atactacttg cacgggttac ttgatttatg gatatatgaa aacttctcag    1020
gacgaaagtt cttctttctc tagaactatt cttctgtcgg tcatgcagaa tgctgttatt    1080
ctgaaaagtg tccctgttgc atatgatggt cactttattt gggggattc ttcataagat     1140
gtgagatgtt gatgccagtc tttcccaagt aagtgctcgt aaaaaaggac tactaactag    1200
cctgcatctg tctctaactg ggaccaaggg gtctgctgaa ggaaactgaa gagctctaac    1260
attttcacag cttggagaag atagaatctt taaaagtaca actgaagctt gatctatttt    1320
acaagtgcat tgatggcccc tgtccttctc tggttcctgt catttgaaac caactcctgt    1380
tgtaaatagg aagaatatgg gacattcata tttaagaaaa tttgatgtca ttaggtgact    1440
```

-continued

```
aagtagaagg cttagaaaaa tgtattcatt tgcaagtatt ttggcacaag aaattttcca    1500
actgaatagt aagcaaaagc taagttgttt cattgaaatc ataaggcagt ttaagataaa    1560
ctggagaaga taactgttct aatagaggat aatcgaattg attgtcaagt ggatgttatt    1620
tattggatag tgacagagtt tatttgtaac cttaattata ttaaaagtta ttctgttagg    1680
atgttttgta ttaataaacg tgaacaaaat taaaaaaaaa aaaaaaaaaa ctcgaggg     1738
```

<210> SEQ ID NO 18
<211> LENGTH: 1521
<212> TYPE: DNA
<213> ORGANISM: Mus musculus
<220> FEATURE:
<221> NAME/KEY: misc_feature
<222> LOCATION: (102)..(103)
<223> OTHER INFORMATION: "n" represents any nucleotide.

<400> SEQUENCE: 18

```
gagaaggcgg cctgccgcag cgggacaacc tagagcgcga cgtggaggcg cgtagcggag    60
ctggagcaac tgcgcaccga ggtggatgtg cgcattagcg cnntggacac ctgcgtcaag    120
gccaagtcgc tgccagccgt cccgccgaga gtctcaggcc accccccgaa ccctccaccc    180
attgatccag ctagcctgga ggaattcaag aaaaggatcc tggagtctca gcggctccct    240
gtagtcaacc ctgcwgccca acccagcggt tgagraccca gctgccgcag gacgctgggt    300
gccagaatcg cccacctgtg gatgggggca gccaggtgcc cacagtgctg gacacccgcc    360
gtgcctgccg gcagcctcca cccccagcgc cttctctggc accccttcac tgtcccstgc    420
atccccrcca ttcsscasws askggattta aggcacacac agctgtgaga tgacttcaca    480 tcgaccccctt gtgcagtgac ccggatggtg ccccacccac acatgaagca cccacagctc    540
agctgccacc ctaggcaact cctccggttt cctatcactc tgctcctgac ccgggaggtg    600
agaacaggaa gccagccttt cagctcccctt gggagtttcc agcctccctc ttaaaggcca    660
ctagggtttc cagatcctat ttgagagtct ccaggcctcc cctgaagggt tctagccacc    720
acgcccacag gattcccatt aggttttaaa gtcttttcca gagtccgctg gttccctcc     780 tcctcacaag gaagggcctc aattgtagat gagcgttccg ggtggatctt agagcctag     840 agggaggctt ttgcttgtar cccctaaag atattactgg cacataataa atatgaaagt    900
cctttgaaag ttggacactg cgcaaatggg gctctccatg gaccgcagcc catacgcccg    960
cacgggggac cagcagcgcg gctctggttc tacctgcgct atttcttcct cttcgtgtcg    1020
ctcattcagt tcctcatcat cctgggcctg gtcctcttca tgatctatgg caatgtgcac    1080
gccaccactg agtccagcct gcgcgccacg gagatccgcg ccgacagcct gtacagccag    1140
gtggttggac tatcggcctc acaggctaac ctgagcaaac agctgaacat cagcttgctt    1200
gtcaaggaaa cagtcatgca gcaactgttg actacgcgac gtgagatgga gcgcatcaac    1260
gccagcttcc gccagtgcca aggcgacctg atcacctaca taaactataa tcgcttcatc    1320
gccgctatca tcctgagcga gaagcagtgc aggaacagc tgaaggaggt caacaagacc    1380
tgcgaacttt actcttcaag ctgggagaaa aagttaagac actggagatg gaggtggcca    1440
aggagaaggc agtgtgctcc aaggacaagg agagcctgct ggcaggaaag cggcagacgg    1500
aagagcagct ggaggcctgt g                                              1521
```

<210> SEQ ID NO 19
<211> LENGTH: 720
<212> TYPE: DNA
<213> ORGANISM: Mus musculus

<400> SEQUENCE: 19

```
tgtgcgccgc ctctagaact agtggatccc ccgggcctgc aggaattccg gcacgacggc    60
cgagcgccgc ggaccacccg cggctgcccg ccgagccgtc gacatgtggg gggactgggg   120
tgggagcggc cggagcagcg ccaggtaccc gggcgcgcag aaccatggct ctcgctcgcc   180
tgtcctgacc tggcttgctc gccccaccga agaatgtcag ccaagtccaa ggggaaccct   240
cctcgtcctc cgcagccgag ggaccgccgg cagcctccaa aaccaaggtg aaggagcaga   300
tcaagatcat agtggaggat ctggaattag tcctgggcga cctgaaggac gtggccaaag   360
aacttaagga ggtggttgac cagattgaca ccctgacctc tgatctacag ctggaagatg   420
agatgaccga cagctccaaa acagacactc tgaacagcag ctccagtggg acaacagcct   480
ccagcataga gaagatcaaa gaacaggcca atgctcccct cattaaacct ccagcacacc   540
cgtctgctat cctgactgtc ctgagaaagc caaaccctcc accgcctcct ccaaggttga   600
cacccgtgag gtgtgaagag cctcagagag tggtgccgac tgccaaccct gtaaagacca   660
atggcactct tctgcggaat ggaggcttag cggggaggcc aacaaaaatt ccaaatggag   720
```

<210> SEQ ID NO 20
<211> LENGTH: 801
<212> TYPE: DNA
<213> ORGANISM: Mus musculus

<400> SEQUENCE: 20

```
ctcgagtttt ttttttttt ttttttttt tttcattatt tactattatt tattgacata    60
tttccaaagc tcaaaatatt ttattataca tatagttgaa catatgtttc aaattgtata   120
gtatagaaaa taaacttttt tgtagtgtcc tcagcatttc atgatgcaaa actattgaca   180
aacatcttta gaaaataat aaaatagtcc ttcggtatta aaattcttat taaaaagcat   240
tagatcaaag ggagaactat gacatcatca atgcatagat gagataggca tgaatggaat   300
gagttgccct ggctttatca acaaatcaaa atatctgaca tcccagctct tataatagac   360
caaaatactt ggaatcagaa ggtcacagtt tgttttaggt caatcacaaa aaaataaaat   420
tcattcatac tttctcaatt ttccgcagtt tctgatgatg aacatagaa acaatgtac    480
gtccaggaca gaggcgctac tctgcatact taccacgtga tttttatgc cactttgttg    540
aatgcagatt aatatatttg ggctttttat tgcttgagta gaaagtgctc attacttatt   600
attttacgtt tatcatatag aaaattaaaa acaaacagaa cgttttctta aatggcagat   660
atcacactgt ggtagtggtg gatttcctca ggatggtctt ctgtggtttt ggtgcagcgg   720
gaggaggcac ggttgcaggt gtgggagggg ggaaactgtt actgtggctt attcccagtc   780
ccccattttc taatgggaaa t                                             801
```

<210> SEQ ID NO 21
<211> LENGTH: 119
<212> TYPE: DNA
<213> ORGANISM: Mus musculus

<400> SEQUENCE: 21

```
gcacagcccc cctccatcct gaagaaaacc tcagcgtatg ggcctccagc ttcgggccgt    60
gtctatcctt cctctcctgg gacatggtgt tccccgcttg ccccctggc agaaaaccg    119
```

<210> SEQ ID NO 22
<211> LENGTH: 5738
<212> TYPE: DNA

-continued

<213> ORGANISM: Mus musculus

<400> SEQUENCE: 22

```
cggcacgagg aggagtggag cggcgcgggg agggcgcgca gcttggttgc tccgtagtac      60
ggcggctcgc aagggagcat cccgagcggg ctccgggacg gccgggaggc aggcaggcgg     120
gcgggcgggg atggtgtgcg cggctgcgga ctcggcgttc ctcgcgcggc gtgcgggctg     180
cactgatttg tgtgagggc ggccgcgcgc acccgcccgg agatgaggcg tcgatcagca      240
aggtgaacgt aatagaacca tggctcagtt tcccacacct ttcggtggta gcctggatgt     300
ctgggccata actgtggagg aaagggccaa gcatgaccag cagttcctta gcctgaagcc     360
gatagcggga tttattactg gtgatcaagc gaggaacttt tttttccaat ctgggttacc     420
tcagcctgtc ttagcacaaa tatgggcgct agcggacatg aataacgatg aaggatgga     480
tcaagtggaa ttttccatag ccatgaagct tatcaaactg aagctacaag gatatcagct     540
cccctccaca cttcccctg tcatgaaaca gcaaccagtg gctatttcca gtgcaccagc     600
atttggtata ggagggattg ctagcatgcc accactcaca gctgttgctc ctgtgccaat     660
gggctccatt ccagttgttg gaatgtctcc acccttagta tcttctgtcc ctccagcagc     720
agtgcctccc ctggctaacg gggctcctcc cgtcatacag cctctgcctg cgtttgcgca     780
tcctgcagcc acatggccaa agagttcttc cttcagcaga tctggtccag ggtcacaatt     840
aaacactaag ttacagaagg cacaatcatt cgatgtcgcc agcgcccctc cagcagcaga     900
atgggctgtg cctcagtcat caaggctgaa atacaggcag ttattcaaca gccacgacaa     960
aactatgagt ggacacttaa caggtcccca ggcaagaact attctcatgc aatcaagttt    1020
accccaggct cagctggctt caatatggaa tctttctgac attgatcaag atggaaaact    1080
cactgcagaa gaatttatcc tagctatgca cctaattgat gttgccatgt ctggtcagcc    1140
actgccgccc gtcctgcctc cagaatacat ccctccttcc ttcagaagag ttcgctccgg    1200
cagtgggatg tccgtcataa gctcttcttc tgtggatcag aggctgcctg aggagccgtc    1260
gtcagaggat gagcagcagc cagagaagaa actgcctgtg acatttgaag ataagaagcg    1320
ggagaacttc gagcgaggca gtgtggagct ggagaagcgc cggcaagcgc tcttggagca    1380
gcagcgcaaa gagcaggagc ggttggctca gctggagcgc gccgagcagg agaggaaaga    1440
gcgggagcgc caggagcagg aggccaagcg gcagctggag ctggagaagc agctggagaa    1500
gcagcgggag ctggagcggc agcgagagga ggagaggagg aaggagatcg agaggcgcga    1560
ggccgcaaaa cgggaactgg aaaggcagcg acaacttgaa tgggaacgga accggagaca    1620
ggaactcctg aatcagagga acaaggagca ggagggcacc gtggtcctga aggcaaggag    1680
gaagactctg gagtttgagt tagaagctct gaatgacaaa aagcatcagc tagaaggaaa    1740
acttcaggat atcaggtgtc gactggcaac ccagaggcaa gaaattgaga gcacgaacaa    1800
gtctagagag ctaagaattg ctgaaatcac ccacttacag cagcagttgc aggaatctca    1860
gcaaatgctt ggaagactta ttccagagaa acagatactc agtgaccagt taaacaagt     1920
ccagcagaac agtttgcata gagactcgct tcttaccctc aaaagagcct tggaagcaaa    1980
ggagctggcc cggcagcagc tccgggagca gctggacgag gtggagagag agaccaggtc    2040
aaagctgcag gagattgatg ttttcaacaa ccagctgaag gaactgagag agatacatag    2100
caaacagcaa ctccagaagc agaggtccct ggaggcagcg cgactgaagc agaaagagca    2160
ggagaggaag agcctggagt tagagaagca aaaggaagac gctcagagac gagttcagga    2220
aagggacaag caatggctgg agcatgtgca gcaggaggag cagccacgcc cccggaaacc    2280
```

```
ccacgaggag  acagactga  agagggaaga  cagtgtcagg  aagaaggagg  cggaagagag   2340
agccaagccg  gaaatgcaag  acaagcagag  tcggcttttc  catccgcatc  aggagccagc   2400
taagctggcc  acccaggcac  cctggtctac  cacagagaaa  ggcccgctta  ccatttctgc   2460
acaggagagt  gtaaaagtgg  tatattaccg  agcgctgtac  ccctttgaat  ccagaagtca   2520
cgatgagatc  accatccagc  caggagatat  agtcatggtg  gatgaaagcc  agactggaga   2580
gccaggatgg  cttggaggag  agctgaaagg  gaagacggga  tggttccctg  caaactatgc   2640
agaaaagatt  ccagaaaatg  aggttcccac  tccagccaaa  ccagtgaccg  atctgacatc   2700
tgcccctgcc  cccaaactgg  ctctgcgtga  gacccctgct  cctttgccag  tgacctcttc   2760
tgagccctcc  acaaccccca  caactgggc   agacttcagt  tccacgtggc  ccagcagctc   2820
aaacgagaag  ccagaaacgg  acaactggga  tacgtgggcg  gctcagcctt  ctctgaccgt   2880
acctagtgct  ggccagttac  ggcagagatc  agcctttacc  ccagccacag  ccactggctc   2940
ctccccatct  cccgtcctgg  gccagggtga  aaaggtggaa  gggctacaag  cgcaagccct   3000
gtatccctgg  agagccaaaa  aagacaacca  cttaaatttt  aacaaaagtg  acgtcatcac   3060
cgttctggaa  cagcaagaca  tgtggtggtt  tggagaagtt  caaggtcaga  agggttggtt   3120
ccccaagtct  tacgtgaaac  tcatttcagg  gcccgtaagg  aaatccacaa  gcatcgatac   3180
tggccctact  gaaagtcctg  ctagtctaaa  gagagtggct  tccccggccg  ccaagccagc   3240
cattcccgga  gaagagtttta  ttgccatgta  cacatacgag  agttctgagc  aaggagattt   3300
aacctttcag  caagggggatg  tgattgtggt  taccaagaaa  gatggtgact  ggtggacggg   3360
aacggtgggc  gacaagtccg  gagtcttccc  ttctaactat  gtgaggctta  agattcaga   3420
gggctctgga  actgctggga  aaacaggag   tttaggaaaa  aaacctgaaa  ttgcccaggt   3480
tattgcttcc  tacgctgcta  ctggtcccga  acaactcacc  ctggctcctg  ggcagctgat   3540
tctgatccgg  aaaaagaacc  caggtggatg  gtgggaagga  gaactgcaag  ctcgagggaa   3600
aaagcgccag  atagggtggt  ttccagcaaa  ttatgtcaaa  cttctaagcc  ccggaacaag   3660
caaaatcacc  ccaactgagc  tacccaagac  cgcagtgcag  ccagcagtgt  gccaggtgat   3720
cgggatgtac  gattacaccg  cccagaacga  tgacgaacta  gccttcagca  aaggccagat   3780
catcaacgtc  ctcaacaagg  aggacccgga  ctggtggaaa  ggagaagtca  gtgggcaagt   3840
tgggctcttc  ccatccaatt  atgtaaagct  gaccacagac  atggaccca   gccagcaatg   3900
gtgctcagac  ctgcatctct  tagatatgct  gacccccgact  gagaggaagc  ggcaaggcta   3960
catccatgaa  ctcattgtca  cggaggagaa  ctacgtgaac  gacttgcagc  tggtcacaga   4020
gatctttcag  aaaccctga   cggagtctga  gctgctgaca  gaaaaagagg  ttgctatgat   4080
ttttgttaac  tggaaggagc  tgatcatgtg  taatatcaaa  ctgctgaaag  cgctgagagt   4140
ccgcaagaag  atgtctgggg  agaagatgcc  ggtgaagatg  attggcgaca  tcctgagcgc   4200
ccagctgccg  cacatgcagc  cttacatccg  cttctgcagc  tgccagctca  atgggctgc    4260
cctcatccag  cagaagacgg  acgaggctcc  agacttcaag  gagttcgtca  aaagactggc   4320
aatggaccct  cggtgcaaag  gaatgcctct  gtccagcttt  atactgaagc  ctatgcagcg   4380
tgtcacaaga  tacccgctga  tcattaaaaa  catcctggaa  aacactcctg  agaaccatcc   4440
agaccacagc  cacctgaagc  atgccctgga  aaaggcggag  gagctgtgct  cccaggtgaa   4500
cgagggagtt  cgagagaagg  agaactcaga  ccggctggag  tggatccaag  cccacgtgca   4560
gtgtgaaggc  cttttctgagc  aactggtgtt  caattcagtg  accaactgct  tgggaccacg   4620
```

-continued

```
caagtttctg cacagcggga agctctacaa ggccaagagc aataaagaac tgtatggctt    4680
cctcttcaac gacttcctcc tgctgaccca aatcacaaag cccttaggct cttccggcac    4740
cgacaaagtc ttcagcccca aatctaacct tcagtataaa atgtacaaaa cgcccatttt    4800
cttaaatgag gttctagtaa aattgcccac ggacccttct ggagatgagc ctatcttcca    4860
catttcccac atcgaccggg tctacaccct ccgagcagag agcataaatg agaggactgc    4920
ctgggtgcag aaaatcaagg cggcgtctga gctctacata gagacggaga aaagaagcg    4980 agagaaggcg tacctggtcc gttcccagcg ggcgaccggt attggaaggt tgatggtgaa    5040
cgtggtagaa ggcattgagc tgaagccctg tcggtcacat ggaaagagca acccgtactg    5100
tgaggtgacc atgggctctc agtgccacat caccaagaca atccaggaca cgctaaaccc    5160
caagtggaat tctaactgcc agttcttcat cagagacctg gagcaggagg ttctctgcat    5220
cacagtgttt gagagggacc agttctcgcc tgatgatttt ttgggtcgga cagagatccg    5280
agtggccgac atcaagaaag accagggctc aaggggccg gttacgaagt gtctcctgct    5340
gcatgaggtc cccacgggag agattgtggt ccgccttgac ctgcagttgt ttgatgagcc    5400
gtagcagccc tgcgatgatc gtagatgact tcctcctcaa ggccccgtgc gggcgtgctg    5460
tctggtggtc agcctcagag caacggggat gaagcaaaga cgaagcccct cgaggctgct    5520
aggagtcgtt ctcgacaatc ctgcccttca aaccatgtct cattttatga atccaaattc    5580
tcttttcctt tgctctccct atggtctcat catggcttct agagtctctg aaatctgtga    5640
cctttaacta ggttccattg ggagcctggc tccttccctg gctggaggt gtgggtctgg    5700 tttctataaa atagattata aactcgagaa tcactagt                           5738
```

<210> SEQ ID NO 23
<211> LENGTH: 5145
<212> TYPE: DNA
<213> ORGANISM: Mus musculus
<220> FEATURE:
<221> NAME/KEY: CDS
<222> LOCATION: (1)..(5145)
<223> OTHER INFORMATION: Mouse Esel1L

<400> SEQUENCE: 23

```
atg gct cag ttt ccc aca cct ttc ggt ggt agc ctg gat gtc tgg gcc     48
Met Ala Gln Phe Pro Thr Pro Phe Gly Gly Ser Leu Asp Val Trp Ala
1               5                   10                  15 ata act gtg gag gaa agg gcc aag cat gac cag cag ttc ctt agc ctg     96
Ile Thr Val Glu Glu Arg Ala Lys His Asp Gln Gln Phe Leu Ser Leu
            20                  25                  30 aag ccg ata gcg gga ttt att act ggt gat caa gcg agg aac ttt ttt    144
Lys Pro Ile Ala Gly Phe Ile Thr Gly Asp Gln Ala Arg Asn Phe Phe
        35                  40                  45 ttc caa tct ggg tta cct cag cct gtc tta gca caa ata tgg gcg cta    192
Phe Gln Ser Gly Leu Pro Gln Pro Val Leu Ala Gln Ile Trp Ala Leu
    50                  55                  60 gcg gac atg aat aac gat gga agg atg gat caa gtg gaa ttt tcc ata    240
Ala Asp Met Asn Asn Asp Gly Arg Met Asp Gln Val Glu Phe Ser Ile
65                  70                  75                  80 gcc atg aag ctt atc aaa ctg aag cta caa gga tat cag ctc ccc tcc    288
Ala Met Lys Leu Ile Lys Leu Lys Leu Gln Gly Tyr Gln Leu Pro Ser
                85                  90                  95 aca ctt ccc cct gtc atg aaa cag caa cca gtg gct att tcc agt gca    336
Thr Leu Pro Pro Val Met Lys Gln Gln Pro Val Ala Ile Ser Ser Ala
            100                 105                 110 cca gca ttt ggt ata gga ggg att gct agc atg cca cca ctc aca gct    384
```

```
                Pro Ala Phe Gly Ile Gly Gly Ile Ala Ser Met Pro Pro Leu Thr Ala
                        115                 120                 125 gtt gct cct gtg cca atg ggc tcc att cca gtt gtt gga atg tct cca         432
Val Ala Pro Val Pro Met Gly Ser Ile Pro Val Val Gly Met Ser Pro
130                 135                 140 ccc tta gta tct tct gtc cct cca gca gca gtg cct ccc ctg gct aac         480
Pro Leu Val Ser Ser Val Pro Pro Ala Ala Val Pro Pro Leu Ala Asn
145                 150                 155                 160 ggg gct cct ccc gtc ata cag cct ctg cct gcg ttt gcg cat cct gca         528
Gly Ala Pro Pro Val Ile Gln Pro Leu Pro Ala Phe Ala His Pro Ala
                165                 170                 175 gcc aca tgg cca aag agt tct tcc ttc agc aga tct ggt cca ggg tca         576
Ala Thr Trp Pro Lys Ser Ser Ser Phe Ser Arg Ser Gly Pro Gly Ser
            180                 185                 190 caa tta aac act aag tta cag aag gca caa tca ttc gat gtc gcc agc         624
Gln Leu Asn Thr Lys Leu Gln Lys Ala Gln Ser Phe Asp Val Ala Ser
        195                 200                 205 gcc cct cca gca gca gaa tgg gct gtg cct cag tca tca agg ctg aaa         672
Ala Pro Pro Ala Ala Glu Trp Ala Val Pro Gln Ser Ser Arg Leu Lys
    210                 215                 220 tac agg cag tta ttc aac agc cac gac aaa act atg agt gga cac tta         720
Tyr Arg Gln Leu Phe Asn Ser His Asp Lys Thr Met Ser Gly His Leu
225                 230                 235                 240 aca ggt ccc cag gca aga act att ctc atg caa tca agt tta ccc cag         768
Thr Gly Pro Gln Ala Arg Thr Ile Leu Met Gln Ser Ser Leu Pro Gln
                245                 250                 255 gct cag ctg gct tca ata tgg aat ctt tct gac att gat caa gat gga         816
Ala Gln Leu Ala Ser Ile Trp Asn Leu Ser Asp Ile Asp Gln Asp Gly
            260                 265                 270 aaa ctc act gca gaa gaa ttt atc cta gct atg cac cta att gat gtt         864
Lys Leu Thr Ala Glu Glu Phe Ile Leu Ala Met His Leu Ile Asp Val
        275                 280                 285 gcc atg tct ggt cag cca ctg ccg ccc gtc ctg cct cca gaa tac atc         912
Ala Met Ser Gly Gln Pro Leu Pro Pro Val Leu Pro Pro Glu Tyr Ile
    290                 295                 300 cct cct tcc ttc aga aga gtt cgc tcc ggc agt ggg atg tcc gtc ata         960
Pro Pro Ser Phe Arg Arg Val Arg Ser Gly Ser Gly Met Ser Val Ile
305                 310                 315                 320 agc tct tct tct gtg gat cag agg ctg cct gag gag ccg tcg tca gag        1008
Ser Ser Ser Ser Val Asp Gln Arg Leu Pro Glu Glu Pro Ser Ser Glu
                325                 330                 335 gat gag cag cag cca gag aag aaa ctg cct gtg aca ttt gaa gat aag        1056
Asp Glu Gln Gln Pro Glu Lys Lys Leu Pro Val Thr Phe Glu Asp Lys
            340                 345                 350 aag cgg gag aac ttc gag cga ggc agt gtg gag ctg gag aag cgc cgg        1104
Lys Arg Glu Asn Phe Glu Arg Gly Ser Val Glu Leu Glu Lys Arg Arg
        355                 360                 365 caa gcg ctc ttg gag cag cag cgc aaa gag cag gag cgg ttg gct cag        1152
Gln Ala Leu Leu Glu Gln Gln Arg Lys Glu Gln Glu Arg Leu Ala Gln
    370                 375                 380 ctg gag cgc gcc gag cag gag agg aaa gag cgg gag cgc cag gag cag        1200
Leu Glu Arg Ala Glu Gln Glu Arg Lys Glu Arg Glu Arg Gln Glu Gln
385                 390                 395                 400 gag gcc aag cgg cag ctg gag ctg gag aag cag ctg gag aag cag cgg        1248
Glu Ala Lys Arg Gln Leu Glu Leu Glu Lys Gln Leu Glu Lys Gln Arg
                405                 410                 415 gag ctg gag cgg cag cga gag gag gag agg agg aag gag atc gag agg        1296
Glu Leu Glu Arg Gln Arg Glu Glu Glu Arg Arg Lys Glu Ile Glu Arg
            420                 425                 430
```

```
cgc gag gcc gca aaa cgg gaa ctg gaa agg cag cga caa ctt gaa tgg       1344
Arg Glu Ala Ala Lys Arg Glu Leu Glu Arg Gln Arg Gln Leu Glu Trp
        435                 440                 445 gaa cgg aac cgg aga cag gaa ctc ctg aat cag agg aac aag gag cag       1392
Glu Arg Asn Arg Arg Gln Glu Leu Leu Asn Gln Arg Asn Lys Glu Gln
450                 455                 460 gag ggc acc gtg gtc ctg aag gca agg agg aag act ctg gag ttt gag       1440
Glu Gly Thr Val Val Leu Lys Ala Arg Arg Lys Thr Leu Glu Phe Glu
465                 470                 475                 480 tta gaa gct ctg aat gac aaa aag cat cag cta gaa gga aaa ctt cag       1488
Leu Glu Ala Leu Asn Asp Lys Lys His Gln Leu Glu Gly Lys Leu Gln
                485                 490                 495 gat atc agg tgt cga ctg gca acc cag agg caa gaa att gag agc acg       1536
Asp Ile Arg Cys Arg Leu Ala Thr Gln Arg Gln Glu Ile Glu Ser Thr
            500                 505                 510 aac aag tct aga gag cta aga att gct gaa atc acc cac tta cag cag       1584
Asn Lys Ser Arg Glu Leu Arg Ile Ala Glu Ile Thr His Leu Gln Gln
        515                 520                 525 cag ttg cag gaa tct cag caa atg ctt gga aga ctt att cca gag aaa       1632
Gln Leu Gln Glu Ser Gln Gln Met Leu Gly Arg Leu Ile Pro Glu Lys
    530                 535                 540 cag ata ctc agt gac cag tta aaa caa gtc cag cag aac agt ttg cat       1680
Gln Ile Leu Ser Asp Gln Leu Lys Gln Val Gln Gln Asn Ser Leu His
545                 550                 555                 560 aga gac tcg ctt ctt acc ctc aaa aga gcc ttg gaa gca aag gag ctg       1728
Arg Asp Ser Leu Leu Thr Leu Lys Arg Ala Leu Glu Ala Lys Glu Leu
                565                 570                 575 gcc cgg cag cag ctc cgg gag cag ctg gac gag gtg gag aga gag acc       1776
Ala Arg Gln Gln Leu Arg Glu Gln Leu Asp Glu Val Glu Arg Glu Thr
            580                 585                 590 agg tca aag ctg cag gag att gat gtt ttc aac aac cag ctg aag gaa       1824
Arg Ser Lys Leu Gln Glu Ile Asp Val Phe Asn Asn Gln Leu Lys Glu
        595                 600                 605 ctg aga gag ata cat agc aaa cag caa ctc cag aag cag agg tcc ctg       1872
Leu Arg Glu Ile His Ser Lys Gln Gln Leu Gln Lys Gln Arg Ser Leu
    610                 615                 620 gag gca gcg cga ctg aag cag aaa gag cag gag agg aag agc ctg gag       1920
Glu Ala Ala Arg Leu Lys Gln Lys Glu Gln Glu Arg Lys Ser Leu Glu
625                 630                 635                 640 tta gag aag caa aag gaa gac gct cag aga cga gtt cag gaa agg gac       1968
Leu Glu Lys Gln Lys Glu Asp Ala Gln Arg Arg Val Gln Glu Arg Asp
                645                 650                 655 aag caa tgg ctg gag cat gtg cag cag gag gag cag cca cgc ccc cgg       2016
Lys Gln Trp Leu Glu His Val Gln Gln Glu Glu Gln Pro Arg Pro Arg
            660                 665                 670 aaa ccc cac gag gag gac aga ctg aag agg gaa gac agt gtc agg aag       2064
Lys Pro His Glu Glu Asp Arg Leu Lys Arg Glu Asp Ser Val Arg Lys
        675                 680                 685 aag gag gcg gaa gag aga gcc aag ccg gaa atg caa gac aag cag agt       2112
Lys Glu Ala Glu Glu Arg Ala Lys Pro Glu Met Gln Asp Lys Gln Ser
    690                 695                 700 cgg ctt ttc cat ccg cat cag gag cca gct aag ctg gcc acc cag gca       2160
Arg Leu Phe His Pro His Gln Glu Pro Ala Lys Leu Ala Thr Gln Ala
705                 710                 715                 720 ccc tgg tct acc aca gag aaa ggc ccg ctt acc att tct gca cag gag       2208
Pro Trp Ser Thr Thr Glu Lys Gly Pro Leu Thr Ile Ser Ala Gln Glu
                725                 730                 735 agt gta aaa gtg gta tat tac cga gcg ctg tac ccc ttt gaa tcc aga       2256
Ser Val Lys Val Val Tyr Tyr Arg Ala Leu Tyr Pro Phe Glu Ser Arg
            740                 745                 750
```

```
agt cac gat gag atc acc atc cag cca gga gat ata gtc atg gtg gat    2304
Ser His Asp Glu Ile Thr Ile Gln Pro Gly Asp Ile Val Met Val Asp
        755                 760                 765 gaa agc cag act gga gag cca gga tgg ctt gga gga gag ctg aaa ggg    2352
Glu Ser Gln Thr Gly Glu Pro Gly Trp Leu Gly Gly Glu Leu Lys Gly
770                 775                 780 aag acg gga tgg ttc cct gca aac tat gca gaa aag att cca gaa aat    2400
Lys Thr Gly Trp Phe Pro Ala Asn Tyr Ala Glu Lys Ile Pro Glu Asn
785                 790                 795                 800 gag gtt ccc act cca gcc aaa cca gtg acc gat ctg aca tct gcc cct    2448
Glu Val Pro Thr Pro Ala Lys Pro Val Thr Asp Leu Thr Ser Ala Pro
                805                 810                 815 gcc ccc aaa ctg gct ctg cgt gag acc cct gct cct ttg cca gtg acc    2496
Ala Pro Lys Leu Ala Leu Arg Glu Thr Pro Ala Pro Leu Pro Val Thr
            820                 825                 830 tct tct gag ccc tcc aca acc ccc aac aac tgg gca gac ttc agt tcc    2544
Ser Ser Glu Pro Ser Thr Thr Pro Asn Asn Trp Ala Asp Phe Ser Ser
        835                 840                 845 acg tgg ccc agc agc tca aac gag aag cca gaa acg gac aac tgg gat    2592
Thr Trp Pro Ser Ser Ser Asn Glu Lys Pro Glu Thr Asp Asn Trp Asp
850                 855                 860 acg tgg gcg gct cag cct tct ctg acc gta cct agt gct ggc cag tta    2640
Thr Trp Ala Ala Gln Pro Ser Leu Thr Val Pro Ser Ala Gly Gln Leu
865                 870                 875                 880 cgg cag aga tca gcc ttt acc cca gcc aca gcc act ggc tcc tcc cca    2688
Arg Gln Arg Ser Ala Phe Thr Pro Ala Thr Ala Thr Gly Ser Ser Pro
                885                 890                 895 tct ccc gtc ctg ggc cag ggt gaa aag gtg gaa ggg cta caa gcg caa    2736
Ser Pro Val Leu Gly Gln Gly Glu Lys Val Glu Gly Leu Gln Ala Gln
            900                 905                 910 gcc ctg tat ccc tgg aga gcc aaa aaa gac aac cac tta aat ttt aac    2784
Ala Leu Tyr Pro Trp Arg Ala Lys Lys Asp Asn His Leu Asn Phe Asn
        915                 920                 925 aaa agt gac gtc atc acc gtt ctg gaa cag caa gac atg tgg tgg ttt    2832
Lys Ser Asp Val Ile Thr Val Leu Glu Gln Gln Asp Met Trp Trp Phe
930                 935                 940 gga gaa gtt caa ggt cag aag ggt tgg ttc ccc aag tct tac gtg aaa    2880
Gly Glu Val Gln Gly Gln Lys Gly Trp Phe Pro Lys Ser Tyr Val Lys
945                 950                 955                 960 ctc att tca ggg cca gta agg aaa tcc aca agc atc gat act ggc cct    2928
Leu Ile Ser Gly Pro Val Arg Lys Ser Thr Ser Ile Asp Thr Gly Pro
                965                 970                 975 act gaa agt cct gct agt cta aag aga gtg gct tcc ccg gcc gcc aag    2976
Thr Glu Ser Pro Ala Ser Leu Lys Arg Val Ala Ser Pro Ala Ala Lys
            980                 985                 990 cca gcc att ccc gga gaa gag ttt att gcc atg tac aca tac gag agt    3024
Pro Ala Ile Pro Gly Glu Glu Phe Ile Ala Met Tyr Thr Tyr Glu Ser
        995                 1000                1005 tct gag caa gga gat tta acc ttt cag caa ggg gat gtg att gtg        3069
Ser Glu Gln Gly Asp Leu Thr Phe Gln Gln Gly Asp Val Ile Val
        1010                1015                1020 gtt acc aag aaa gat ggt gac tgg tgg acg gga acg gtg ggc gac        3114
Val Thr Lys Lys Asp Gly Asp Trp Trp Thr Gly Thr Val Gly Asp
    1025                1030                1035 aag tcc gga gtc ttc cct tct aac tat gtg agg ctt aaa gat tca        3159
Lys Ser Gly Val Phe Pro Ser Asn Tyr Val Arg Leu Lys Asp Ser
1040                1045                1050 gag ggc tct gga act gct ggg aaa aca ggg agt tta gga aaa aaa        3204
Glu Gly Ser Gly Thr Ala Gly Lys Thr Gly Ser Leu Gly Lys Lys
```

|  |  |  |  |  |  |  |  |  |  |  |  |  |  |  |
|---|---|---|---|---|---|---|---|---|---|---|---|---|---|---|
|  |  | 1055 |  |  |  | 1060 |  |  |  |  | 1065 |  |  |  |
| cct | gaa | att | gcc | cag | gtt | att | gct | tcc | tac | gct | gct | act | ggt | ccc | 3249 |
| Pro | Glu | Ile | Ala | Gln | Val | Ile | Ala | Ser | Tyr | Ala | Ala | Thr | Gly | Pro |  |
|  | 1070 |  |  |  | 1075 |  |  |  |  | 1080 |  |  |  |  |
| gaa | caa | ctc | acc | ctg | gct | cct | ggg | cag | ctg | att | ctg | atc | cgg | aaa | 3294 |
| Glu | Gln | Leu | Thr | Leu | Ala | Pro | Gly | Gln | Leu | Ile | Leu | Ile | Arg | Lys |  |
|  | 1085 |  |  |  | 1090 |  |  |  |  | 1095 |  |  |  |  |
| aag | aac | cca | ggt | gga | tgg | tgg | gaa | gga | gaa | ctg | caa | gct | cga | ggg | 3339 |
| Lys | Asn | Pro | Gly | Gly | Trp | Trp | Glu | Gly | Glu | Leu | Gln | Ala | Arg | Gly |  |
|  | 1100 |  |  |  | 1105 |  |  |  |  | 1110 |  |  |  |  |
| aaa | aag | cgc | cag | ata | ggg | tgg | ttt | cca | gca | aat | tat | gtc | aaa | ctt | 3384 |
| Lys | Lys | Arg | Gln | Ile | Gly | Trp | Phe | Pro | Ala | Asn | Tyr | Val | Lys | Leu |  |
|  | 1115 |  |  |  | 1120 |  |  |  |  | 1125 |  |  |  |  |
| cta | agc | ccc | gga | aca | agc | aaa | atc | acc | cca | act | gag | cta | ccc | aag | 3429 |
| Leu | Ser | Pro | Gly | Thr | Ser | Lys | Ile | Thr | Pro | Thr | Glu | Leu | Pro | Lys |  |
|  | 1130 |  |  |  | 1135 |  |  |  |  | 1140 |  |  |  |  |
| acc | gca | gtg | cag | cca | gca | gtg | tgc | cag | gtg | atc | ggg | atg | tac | gat | 3474 |
| Thr | Ala | Val | Gln | Pro | Ala | Val | Cys | Gln | Val | Ile | Gly | Met | Tyr | Asp |  |
|  | 1145 |  |  |  | 1150 |  |  |  |  | 1155 |  |  |  |  |
| tac | acc | gcc | cag | aac | gat | gac | gaa | cta | gcc | ttc | agc | aaa | ggc | cag | 3519 |
| Tyr | Thr | Ala | Gln | Asn | Asp | Asp | Glu | Leu | Ala | Phe | Ser | Lys | Gly | Gln |  |
|  | 1160 |  |  |  | 1165 |  |  |  |  | 1170 |  |  |  |  |
| atc | atc | aac | gtc | ctc | aac | aag | gag | gac | ccg | gac | tgg | tgg | aaa | gga | 3564 |
| Ile | Ile | Asn | Val | Leu | Asn | Lys | Glu | Asp | Pro | Asp | Trp | Trp | Lys | Gly |  |
|  | 1175 |  |  |  | 1180 |  |  |  |  | 1185 |  |  |  |  |
| gaa | gtc | agt | ggg | caa | gtt | ggg | ctc | ttc | cca | tcc | aat | tat | gta | aag | 3609 |
| Glu | Val | Ser | Gly | Gln | Val | Gly | Leu | Phe | Pro | Ser | Asn | Tyr | Val | Lys |  |
|  | 1190 |  |  |  | 1195 |  |  |  |  | 1200 |  |  |  |  |
| ctg | acc | aca | gac | atg | gac | ccc | agc | cag | caa | tgg | tgc | tca | gac | ctg | 3654 |
| Leu | Thr | Thr | Asp | Met | Asp | Pro | Ser | Gln | Gln | Trp | Cys | Ser | Asp | Leu |  |
|  | 1205 |  |  |  | 1210 |  |  |  |  | 1215 |  |  |  |  |
| cat | ctc | tta | gat | atg | ctg | acc | ccg | act | gag | agg | aag | cgg | caa | ggc | 3699 |
| His | Leu | Leu | Asp | Met | Leu | Thr | Pro | Thr | Glu | Arg | Lys | Arg | Gln | Gly |  |
|  | 1220 |  |  |  | 1225 |  |  |  |  | 1230 |  |  |  |  |
| tac | atc | cat | gaa | ctc | att | gtc | acg | gag | gag | aac | tac | gtg | aac | gac | 3744 |
| Tyr | Ile | His | Glu | Leu | Ile | Val | Thr | Glu | Glu | Asn | Tyr | Val | Asn | Asp |  |
|  | 1235 |  |  |  | 1240 |  |  |  |  | 1245 |  |  |  |  |
| ttg | cag | ctg | gtc | aca | gag | atc | ttt | cag | aaa | ccc | ctg | acg | gag | tct | 3789 |
| Leu | Gln | Leu | Val | Thr | Glu | Ile | Phe | Gln | Lys | Pro | Leu | Thr | Glu | Ser |  |
|  | 1250 |  |  |  | 1255 |  |  |  |  | 1260 |  |  |  |  |
| gag | ctg | ctg | aca | gaa | aaa | gag | gtt | gct | atg | att | ttt | gtt | aac | tgg | 3834 |
| Glu | Leu | Leu | Thr | Glu | Lys | Glu | Val | Ala | Met | Ile | Phe | Val | Asn | Trp |  |
|  | 1265 |  |  |  | 1270 |  |  |  |  | 1275 |  |  |  |  |
| aag | gag | ctg | atc | atg | tgt | aat | atc | aaa | ctg | ctg | aaa | gcg | ctg | aga | 3879 |
| Lys | Glu | Leu | Ile | Met | Cys | Asn | Ile | Lys | Leu | Leu | Lys | Ala | Leu | Arg |  |
|  | 1280 |  |  |  | 1285 |  |  |  |  | 1290 |  |  |  |  |
| gtc | cgc | aag | aag | atg | tct | ggg | gag | aag | atg | ccg | gtg | aag | atg | att | 3924 |
| Val | Arg | Lys | Lys | Met | Ser | Gly | Glu | Lys | Met | Pro | Val | Lys | Met | Ile |  |
|  | 1295 |  |  |  | 1300 |  |  |  |  | 1305 |  |  |  |  |
| ggc | gac | atc | ctg | agc | gcc | cag | ctg | ccg | cac | atg | cag | cct | tac | atc | 3969 |
| Gly | Asp | Ile | Leu | Ser | Ala | Gln | Leu | Pro | His | Met | Gln | Pro | Tyr | Ile |  |
|  | 1310 |  |  |  | 1315 |  |  |  |  | 1320 |  |  |  |  |
| cgc | ttc | tgc | agc | tgc | cag | ctc | aat | ggg | gct | gcc | ctc | atc | cag | cag | 4014 |
| Arg | Phe | Cys | Ser | Cys | Gln | Leu | Asn | Gly | Ala | Ala | Leu | Ile | Gln | Gln |  |
|  | 1325 |  |  |  | 1330 |  |  |  |  | 1335 |  |  |  |  |
| aag | acg | gac | gag | gct | cca | gac | ttc | aag | gag | ttc | gtc | aaa | aga | ctg | 4059 |
| Lys | Thr | Asp | Glu | Ala | Pro | Asp | Phe | Lys | Glu | Phe | Val | Lys | Arg | Leu |  |
|  | 1340 |  |  |  | 1345 |  |  |  |  | 1350 |  |  |  |  |
| gca | atg | gac | cct | cgg | tgc | aaa | gga | atg | cct | ctg | tcc | agc | ttt | ata | 4104 |

-continued

| | | | | | | | | | | | | | | |
|---|---|---|---|---|---|---|---|---|---|---|---|---|---|---|
| Ala | Met | Asp | Pro | Arg | Cys | Lys | Gly | Met | Pro | Leu | Ser | Ser | Phe | Ile |
| | 1355 | | | | 1360 | | | | 1365 | | | | | |

| ctg | aag | cct | atg | cag | cgt | gtc | aca | aga | tac | ccg | ctg | atc | att | aaa | 4149 |
|---|---|---|---|---|---|---|---|---|---|---|---|---|---|---|---|
| Leu | Lys | Pro | Met | Gln | Arg | Val | Thr | Arg | Tyr | Pro | Leu | Ile | Ile | Lys | |
| 1370 | | | | 1375 | | | | | 1380 | | | | | | |

| aac | atc | ctg | gaa | aac | act | cct | gag | aac | cat | cca | gac | cac | agc | cac | 4194 |
|---|---|---|---|---|---|---|---|---|---|---|---|---|---|---|---|
| Asn | Ile | Leu | Glu | Asn | Thr | Pro | Glu | Asn | His | Pro | Asp | His | Ser | His | |
| 1385 | | | | 1390 | | | | | 1395 | | | | | | |

| ctg | aag | cat | gcc | ctg | gaa | aag | gcg | gag | gag | ctg | tgc | tcc | cag | gtg | 4239 |
|---|---|---|---|---|---|---|---|---|---|---|---|---|---|---|---|
| Leu | Lys | His | Ala | Leu | Glu | Lys | Ala | Glu | Glu | Leu | Cys | Ser | Gln | Val | |
| 1400 | | | | 1405 | | | | | 1410 | | | | | | |

| aac | gag | gga | gtt | cga | gag | aag | gag | aac | tca | gac | cgg | ctg | gag | tgg | 4284 |
|---|---|---|---|---|---|---|---|---|---|---|---|---|---|---|---|
| Asn | Glu | Gly | Val | Arg | Glu | Lys | Glu | Asn | Ser | Asp | Arg | Leu | Glu | Trp | |
| 1415 | | | | 1420 | | | | | 1425 | | | | | | |

| atc | caa | gcc | cac | gtg | cag | tgt | gaa | ggc | ctt | tct | gag | caa | ctg | gtg | 4329 |
|---|---|---|---|---|---|---|---|---|---|---|---|---|---|---|---|
| Ile | Gln | Ala | His | Val | Gln | Cys | Glu | Gly | Leu | Ser | Glu | Gln | Leu | Val | |
| 1430 | | | | 1435 | | | | | 1440 | | | | | | |

| ttc | aat | tca | gtg | acc | aac | tgc | ttg | gga | cca | cgc | aag | ttt | ctg | cac | 4374 |
|---|---|---|---|---|---|---|---|---|---|---|---|---|---|---|---|
| Phe | Asn | Ser | Val | Thr | Asn | Cys | Leu | Gly | Pro | Arg | Lys | Phe | Leu | His | |
| 1445 | | | | 1450 | | | | | 1455 | | | | | | |

| agc | ggg | aag | ctc | tac | aag | gcc | aag | agc | aat | aaa | gaa | ctg | tat | ggc | 4419 |
|---|---|---|---|---|---|---|---|---|---|---|---|---|---|---|---|
| Ser | Gly | Lys | Leu | Tyr | Lys | Ala | Lys | Ser | Asn | Lys | Glu | Leu | Tyr | Gly | |
| 1460 | | | | 1465 | | | | | 1470 | | | | | | |

| ttc | ctc | ttc | aac | gac | ttc | ctc | ctg | ctg | acc | caa | atc | aca | aag | ccc | 4464 |
|---|---|---|---|---|---|---|---|---|---|---|---|---|---|---|---|
| Phe | Leu | Phe | Asn | Asp | Phe | Leu | Leu | Leu | Thr | Gln | Ile | Thr | Lys | Pro | |
| 1475 | | | | 1480 | | | | | 1485 | | | | | | |

| tta | ggc | tct | tcc | ggc | acc | gac | aaa | gtc | ttc | agc | ccc | aaa | tct | aac | 4509 |
|---|---|---|---|---|---|---|---|---|---|---|---|---|---|---|---|
| Leu | Gly | Ser | Ser | Gly | Thr | Asp | Lys | Val | Phe | Ser | Pro | Lys | Ser | Asn | |
| 1490 | | | | 1495 | | | | | 1500 | | | | | | |

| ctt | cag | tat | aaa | atg | tac | aaa | acg | ccc | att | ttc | tta | aat | gag | gtt | 4554 |
|---|---|---|---|---|---|---|---|---|---|---|---|---|---|---|---|
| Leu | Gln | Tyr | Lys | Met | Tyr | Lys | Thr | Pro | Ile | Phe | Leu | Asn | Glu | Val | |
| 1505 | | | | 1510 | | | | | 1515 | | | | | | |

| cta | gta | aaa | ttg | ccc | acg | gac | cct | tct | gga | gat | gag | cct | atc | ttc | 4599 |
|---|---|---|---|---|---|---|---|---|---|---|---|---|---|---|---|
| Leu | Val | Lys | Leu | Pro | Thr | Asp | Pro | Ser | Gly | Asp | Glu | Pro | Ile | Phe | |
| 1520 | | | | 1525 | | | | | 1530 | | | | | | |

| cac | att | tcc | cac | atc | gac | cgg | gtc | tac | acc | ctc | cga | gca | gag | agc | 4644 |
|---|---|---|---|---|---|---|---|---|---|---|---|---|---|---|---|
| His | Ile | Ser | His | Ile | Asp | Arg | Val | Tyr | Thr | Leu | Arg | Ala | Glu | Ser | |
| 1535 | | | | 1540 | | | | | 1545 | | | | | | |

| ata | aat | gag | agg | act | gcc | tgg | gtg | cag | aaa | atc | aag | gcg | gcg | tct | 4689 |
|---|---|---|---|---|---|---|---|---|---|---|---|---|---|---|---|
| Ile | Asn | Glu | Arg | Thr | Ala | Trp | Val | Gln | Lys | Ile | Lys | Ala | Ala | Ser | |
| 1550 | | | | 1555 | | | | | 1560 | | | | | | |

| gag | ctc | tac | ata | gag | acg | gag | aaa | aag | aag | cga | gag | aag | gcg | tac | 4734 |
|---|---|---|---|---|---|---|---|---|---|---|---|---|---|---|---|
| Glu | Leu | Tyr | Ile | Glu | Thr | Glu | Lys | Lys | Lys | Arg | Glu | Lys | Ala | Tyr | |
| 1565 | | | | 1570 | | | | | 1575 | | | | | | |

| ctg | gtc | cgt | tcc | cag | cgg | gcg | acc | ggt | att | gga | agg | ttg | atg | gtg | 4779 |
|---|---|---|---|---|---|---|---|---|---|---|---|---|---|---|---|
| Leu | Val | Arg | Ser | Gln | Arg | Ala | Thr | Gly | Ile | Gly | Arg | Leu | Met | Val | |
| 1580 | | | | 1585 | | | | | 1590 | | | | | | |

| aac | gtg | gta | gaa | ggc | att | gag | ctg | aag | ccc | tgt | cgg | tca | cat | gga | 4824 |
|---|---|---|---|---|---|---|---|---|---|---|---|---|---|---|---|
| Asn | Val | Val | Glu | Gly | Ile | Glu | Leu | Lys | Pro | Cys | Arg | Ser | His | Gly | |
| 1595 | | | | 1600 | | | | | 1605 | | | | | | |

| aag | agc | aac | ccg | tac | tgt | gag | gtg | acc | atg | ggc | tct | cag | tgc | cac | 4869 |
|---|---|---|---|---|---|---|---|---|---|---|---|---|---|---|---|
| Lys | Ser | Asn | Pro | Tyr | Cys | Glu | Val | Thr | Met | Gly | Ser | Gln | Cys | His | |
| 1610 | | | | 1615 | | | | | 1620 | | | | | | |

| atc | acc | aag | aca | atc | cag | gac | acg | cta | aac | ccc | aag | tgg | aat | tct | 4914 |
|---|---|---|---|---|---|---|---|---|---|---|---|---|---|---|---|
| Ile | Thr | Lys | Thr | Ile | Gln | Asp | Thr | Leu | Asn | Pro | Lys | Trp | Asn | Ser | |
| 1625 | | | | 1630 | | | | | 1635 | | | | | | |

| aac | tgc | cag | ttc | ttc | atc | aga | gac | ctg | gag | cag | gag | gtt | ctc | tgc | 4959 |
|---|---|---|---|---|---|---|---|---|---|---|---|---|---|---|---|
| Asn | Cys | Gln | Phe | Phe | Ile | Arg | Asp | Leu | Glu | Gln | Glu | Val | Leu | Cys | |
| 1640 | | | | 1645 | | | | | 1650 | | | | | | |

-continued

```
atc aca gtg ttt gag agg gac cag ttc tcg cct gat gat ttt ttg     5004
Ile Thr Val Phe Glu Arg Asp Gln Phe Ser Pro Asp Asp Phe Leu
1655                1660                1665 ggt cgg aca gag atc cga gtg gcc gac atc aag aaa gac cag ggc     5049
Gly Arg Thr Glu Ile Arg Val Ala Asp Ile Lys Lys Asp Gln Gly
    1670                1675                1680 tcc aag ggg ccg gtt acg aag tgt ctc ctg ctg cat gag gtc ccc     5094
Ser Lys Gly Pro Val Thr Lys Cys Leu Leu Leu His Glu Val Pro
1685                1690                1695 acg gga gag att gtg gtc cgc ctt gac ctg cag ttg ttt gat gag     5139
Thr Gly Glu Ile Val Val Arg Leu Asp Leu Gln Leu Phe Asp Glu
1700                1705                1710 ccg tag                                                          5145
Pro
```

<210> SEQ ID NO 24
<211> LENGTH: 1714
<212> TYPE: PRT
<213> ORGANISM: Mus musculus

<400> SEQUENCE: 24

```
Met Ala Gln Phe Pro Thr Pro Phe Gly Gly Ser Leu Asp Val Trp Ala
1               5                   10                  15

Ile Thr Val Glu Glu Arg Ala Lys His Asp Gln Gln Phe Leu Ser Leu
            20                  25                  30

Lys Pro Ile Ala Gly Phe Ile Thr Gly Asp Gln Ala Arg Asn Phe Phe
        35                  40                  45

Phe Gln Ser Gly Leu Pro Gln Pro Val Leu Ala Gln Ile Trp Ala Leu
    50                  55                  60

Ala Asp Met Asn Asn Asp Gly Arg Met Asp Gln Val Glu Phe Ser Ile
65                  70                  75                  80

Ala Met Lys Leu Ile Lys Leu Lys Leu Gln Gly Tyr Gln Leu Pro Ser
                85                  90                  95

Thr Leu Pro Pro Val Met Lys Gln Gln Pro Val Ala Ile Ser Ser Ala
            100                 105                 110

Pro Ala Phe Gly Ile Gly Gly Ile Ala Ser Met Pro Pro Leu Thr Ala
        115                 120                 125

Val Ala Pro Val Pro Met Gly Ser Ile Pro Val Val Gly Met Ser Pro
    130                 135                 140

Pro Leu Val Ser Ser Val Pro Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Trp Pro Lys Ser Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Ala Pro Pro Ala Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
```

-continued

```
                275                 280                 285
Ala Met Ser Gly Gln Pro Leu Pro Pro Val Leu Pro Pro Glu Tyr Ile
    290                 295                 300
Pro Pro Ser Phe Arg Arg Val Arg Ser Gly Ser Gly Met Ser Val Ile
305                 310                 315                 320
Ser Ser Ser Ser Val Asp Gln Arg Leu Pro Glu Glu Pro Ser Ser Glu
                325                 330                 335
Asp Glu Gln Gln Pro Glu Lys Lys Leu Pro Val Thr Phe Glu Asp Lys
            340                 345                 350
Lys Arg Glu Asn Phe Glu Arg Gly Ser Val Glu Leu Glu Lys Arg Arg
            355                 360                 365
Gln Ala Leu Leu Glu Gln Gln Arg Lys Glu Gln Glu Arg Leu Ala Gln
    370                 375                 380
Leu Glu Arg Ala Glu Gln Arg Lys Glu Arg Glu Arg Gln Glu Gln
385                 390                 395                 400
Glu Ala Lys Arg Gln Leu Glu Leu Glu Lys Gln Leu Glu Lys Gln Arg
                405                 410                 415
Glu Leu Glu Arg Gln Arg Glu Glu Arg Arg Lys Glu Ile Glu Arg
            420                 425                 430
Arg Glu Ala Ala Lys Arg Glu Leu Glu Arg Gln Arg Gln Leu Glu Trp
            435                 440                 445
Glu Arg Asn Arg Arg Gln Glu Leu Leu Asn Gln Arg Asn Lys Glu Gln
    450                 455                 460
Glu Gly Thr Val Val Leu Lys Ala Arg Lys Thr Leu Glu Phe Glu
465                 470                 475                 480
Leu Glu Ala Leu Asn Asp Lys Lys His Gln Leu Glu Gly Lys Leu Gln
                485                 490                 495
Asp Ile Arg Cys Arg Leu Ala Thr Gln Arg Gln Glu Ile Glu Ser Thr
            500                 505                 510
Asn Lys Ser Arg Glu Leu Arg Ile Ala Glu Ile Thr His Leu Gln Gln
            515                 520                 525
Gln Leu Gln Glu Ser Gln Gln Met Leu Gly Arg Leu Ile Pro Glu Lys
    530                 535                 540
Gln Ile Leu Ser Asp Gln Leu Lys Gln Val Gln Gln Asn Ser Leu His
545                 550                 555                 560
Arg Asp Ser Leu Leu Thr Leu Lys Arg Ala Leu Glu Ala Lys Glu Leu
                565                 570                 575
Ala Arg Gln Gln Leu Arg Glu Gln Leu Asp Glu Val Glu Arg Glu Thr
            580                 585                 590
Arg Ser Lys Leu Gln Glu Ile Asp Val Phe Asn Asn Gln Leu Lys Glu
            595                 600                 605
Leu Arg Glu Ile His Ser Lys Gln Gln Leu Gln Lys Gln Arg Ser Leu
    610                 615                 620
Glu Ala Ala Arg Leu Lys Gln Lys Gln Glu Arg Lys Ser Leu Glu
625                 630                 635                 640
Leu Glu Lys Gln Lys Glu Asp Ala Gln Arg Arg Val Gln Glu Arg Asp
                645                 650                 655
Lys Gln Trp Leu Glu His Val Gln Gln Glu Gln Pro Arg Pro Arg
            660                 665                 670
Lys Pro His Glu Glu Asp Arg Leu Lys Arg Glu Asp Ser Val Arg Lys
            675                 680                 685
Lys Glu Ala Glu Glu Arg Ala Lys Pro Glu Met Gln Asp Lys Gln Ser
    690                 695                 700
```

```
Arg Leu Phe His Pro His Gln Glu Pro Ala Lys Leu Ala Thr Gln Ala
705                 710                 715                 720

Pro Trp Ser Thr Thr Glu Lys Gly Pro Leu Thr Ile Ser Ala Gln Glu
            725                 730                 735

Ser Val Lys Val Val Tyr Tyr Arg Ala Leu Tyr Pro Phe Glu Ser Arg
            740                 745                 750

Ser His Asp Glu Ile Thr Ile Gln Pro Gly Asp Ile Val Met Val Asp
        755                 760                 765

Glu Ser Gln Thr Gly Glu Pro Gly Trp Leu Gly Gly Glu Leu Lys Gly
770                 775                 780

Lys Thr Gly Trp Phe Pro Ala Asn Tyr Ala Glu Lys Ile Pro Glu Asn
785                 790                 795                 800

Glu Val Pro Thr Pro Ala Lys Pro Val Thr Asp Leu Thr Ser Ala Pro
                805                 810                 815

Ala Pro Lys Leu Ala Leu Arg Glu Thr Pro Ala Pro Leu Pro Val Thr
            820                 825                 830

Ser Ser Glu Pro Ser Thr Thr Pro Asn Asn Trp Ala Asp Phe Ser Ser
            835                 840                 845

Thr Trp Pro Ser Ser Ser Asn Glu Lys Pro Glu Thr Asp Asn Trp Asp
850                 855                 860

Thr Trp Ala Ala Gln Pro Ser Leu Thr Val Pro Ser Ala Gly Gln Leu
865                 870                 875                 880

Arg Gln Arg Ser Ala Phe Thr Pro Ala Thr Ala Thr Gly Ser Ser Pro
                885                 890                 895

Ser Pro Val Leu Gly Gln Gly Glu Lys Val Glu Gly Leu Gln Ala Gln
            900                 905                 910

Ala Leu Tyr Pro Trp Arg Ala Lys Lys Asp Asn His Leu Asn Phe Asn
            915                 920                 925

Lys Ser Asp Val Ile Thr Val Leu Glu Gln Gln Asp Met Trp Trp Phe
930                 935                 940

Gly Glu Val Gln Gly Gln Lys Gly Trp Phe Pro Lys Ser Tyr Val Lys
945                 950                 955                 960

Leu Ile Ser Gly Pro Val Arg Lys Ser Thr Ser Ile Asp Thr Gly Pro
                965                 970                 975

Thr Glu Ser Pro Ala Ser Leu Lys Arg Val Ala Ser Pro Ala Ala Lys
            980                 985                 990

Pro Ala Ile Pro Gly Glu Glu Phe Ile Ala Met Tyr Thr Tyr Glu Ser
            995                 1000                1005

Ser Glu Gln Gly Asp Leu Thr Phe Gln Gln Gly Asp Val Ile Val
    1010                1015                1020

Val Thr Lys Lys Asp Gly Asp Trp Trp Thr Gly Thr Val Gly Asp
    1025                1030                1035

Lys Ser Gly Val Phe Pro Ser Asn Tyr Val Arg Leu Lys Asp Ser
    1040                1045                1050

Glu Gly Ser Gly Thr Ala Gly Lys Thr Gly Ser Leu Gly Lys Lys
    1055                1060                1065

Pro Glu Ile Ala Gln Val Ile Ala Ser Tyr Ala Ala Thr Gly Pro
    1070                1075                1080

Glu Gln Leu Thr Leu Ala Pro Gly Gln Leu Ile Leu Ile Arg Lys
    1085                1090                1095

Lys Asn Pro Gly Gly Trp Trp Glu Gly Glu Leu Gln Ala Arg Gly
    1100                1105                1110
```

-continued

```
Lys Lys Arg Gln Ile Gly Trp Phe Pro Ala Asn Tyr Val Lys Leu
1115                1120                1125

Leu Ser Pro Gly Thr Ser Lys Ile Thr Pro Thr Glu Leu Pro Lys
1130                1135                1140

Thr Ala Val Gln Pro Ala Val Cys Gln Val Ile Gly Met Tyr Asp
1145                1150                1155

Tyr Thr Ala Gln Asn Asp Asp Glu Leu Ala Phe Ser Lys Gly Gln
1160                1165                1170

Ile Ile Asn Val Leu Asn Lys Glu Asp Pro Asp Trp Trp Lys Gly
1175                1180                1185

Glu Val Ser Gly Gln Val Gly Leu Phe Pro Ser Asn Tyr Val Lys
1190                1195                1200

Leu Thr Thr Asp Met Asp Pro Ser Gln Gln Trp Cys Ser Asp Leu
1205                1210                1215

His Leu Leu Asp Met Leu Thr Pro Thr Glu Arg Lys Arg Gln Gly
1220                1225                1230

Tyr Ile His Glu Leu Ile Val Thr Glu Glu Asn Tyr Val Asn Asp
1235                1240                1245

Leu Gln Leu Val Thr Glu Ile Phe Gln Lys Pro Leu Thr Glu Ser
1250                1255                1260

Glu Leu Leu Thr Glu Lys Glu Val Ala Met Ile Phe Val Asn Trp
1265                1270                1275

Lys Glu Leu Ile Met Cys Asn Ile Lys Leu Leu Lys Ala Leu Arg
1280                1285                1290

Val Arg Lys Lys Met Ser Gly Glu Lys Met Pro Val Lys Met Ile
1295                1300                1305

Gly Asp Ile Leu Ser Ala Gln Leu Pro His Met Gln Pro Tyr Ile
1310                1315                1320

Arg Phe Cys Ser Cys Gln Leu Asn Gly Ala Ala Leu Ile Gln Gln
1325                1330                1335

Lys Thr Asp Glu Ala Pro Asp Phe Lys Glu Phe Val Lys Arg Leu
1340                1345                1350

Ala Met Asp Pro Arg Cys Lys Gly Met Pro Leu Ser Ser Phe Ile
1355                1360                1365

Leu Lys Pro Met Gln Arg Val Thr Arg Tyr Pro Leu Ile Ile Lys
1370                1375                1380

Asn Ile Leu Glu Asn Thr Pro Glu Asn His Pro Asp His Ser His
1385                1390                1395

Leu Lys His Ala Leu Glu Lys Ala Glu Glu Leu Cys Ser Gln Val
1400                1405                1410

Asn Glu Gly Val Arg Glu Lys Glu Asn Ser Asp Arg Leu Glu Trp
1415                1420                1425

Ile Gln Ala His Val Gln Cys Glu Gly Leu Ser Glu Gln Leu Val
1430                1435                1440

Phe Asn Ser Val Thr Asn Cys Leu Gly Pro Arg Lys Phe Leu His
1445                1450                1455

Ser Gly Lys Leu Tyr Lys Ala Lys Ser Asn Lys Glu Leu Tyr Gly
1460                1465                1470

Phe Leu Phe Asn Asp Phe Leu Leu Leu Thr Gln Ile Thr Lys Pro
1475                1480                1485

Leu Gly Ser Ser Gly Thr Asp Lys Val Phe Ser Pro Lys Ser Asn
1490                1495                1500

Leu Gln Tyr Lys Met Tyr Lys Thr Pro Ile Phe Leu Asn Glu Val
```

-continued

| | | | | | 1505 | | | | | 1510 | | | | | 1515 | |
|---|---|---|---|---|---|---|---|---|---|---|---|---|---|---|---|---|

Leu Val Lys Leu Pro Thr Asp Pro Ser Gly Asp Glu Pro Ile Phe
1520                    1525                      1530

His Ile Ser His Ile Asp Arg Val Tyr Thr Leu Arg Ala Glu Ser
1535                    1540                      1545

Ile Asn Glu Arg Thr Ala Trp Val Gln Lys Ile Lys Ala Ala Ser
1550                    1555                      1560

Glu Leu Tyr Ile Glu Thr Glu Lys Lys Lys Arg Glu Lys Ala Tyr
1565                    1570                      1575

Leu Val Arg Ser Gln Arg Ala Thr Gly Ile Gly Arg Leu Met Val
1580                    1585                      1590

Asn Val Val Glu Gly Ile Glu Leu Lys Pro Cys Arg Ser His Gly
1595                    1600                      1605

Lys Ser Asn Pro Tyr Cys Glu Val Thr Met Gly Ser Gln Cys His
1610                    1615                      1620

Ile Thr Lys Thr Ile Gln Asp Thr Leu Asn Pro Lys Trp Asn Ser
1625                    1630                      1635

Asn Cys Gln Phe Phe Ile Arg Asp Leu Glu Gln Glu Val Leu Cys
1640                    1645                      1650

Ile Thr Val Phe Glu Arg Asp Gln Phe Ser Pro Asp Asp Phe Leu
1655                    1660                      1665

Gly Arg Thr Glu Ile Arg Val Ala Asp Ile Lys Lys Asp Gln Gly
1670                    1675                      1680

Ser Lys Gly Pro Val Thr Lys Cys Leu Leu Leu His Glu Val Pro
1685                    1690                      1695

Thr Gly Glu Ile Val Val Arg Leu Asp Leu Gln Leu Phe Asp Glu
1700                    1705                      1710

Pro

<210> SEQ ID NO 25
<211> LENGTH: 6014
<212> TYPE: DNA
<213> ORGANISM: Mus musculus

<400> SEQUENCE: 25

```
cccttccttt cctttttttg tgttcgcctt cggccgtgcc ggctgagagc ccagcagccg      60
tgacaggctg cgcaacaggt tcgctgcggc cggcctgacg actgacccgg cggcggcggc     120
cgcggcacgg cagggtcttc ccggagcttg gccgcgccca cgcgccggtg tcgaggagcg     180
cgcggggtcg cgccgggacg tgcgcgaggc gccagatggc tgagagctgc aagaagaagt     240
caggatcatg atggctcagt tcccacagc gatgaatgga gggccaaata tgtgggctat      300
tacatctgaa gaacgtacta agcatgataa acagtttgat aacctcaaac cttcaggagg     360
ttacataaca ggtgatcaag cccgtacttt tttcctacag tcaggtctgc cggccccggt     420
tttagctgaa atatgggcct tatcagatct gaacaaggat gggaagatgg accagcaaga     480
gttctctata gctatgaaac tcatcaagtt aaagttgcag gccaacagc tgcctgtagt      540
cctccctcct atcatgaaac aaccccctat gttctctcca ctaatctctg ctcgttttgg     600
gatgggaagc atgcccaatc tgtccattca tcagccattg cctccagttg cacctatagc     660
aacacccttg tcttctgcta cgtcagggac cagtattcct cccctaatga tgcctgctcc     720
cctagtgcct tctgttagta catcctcatt accaaatgga actgccagtc tcattcagcc     780
tttatccatt ccttattctt cttcaacatt gcctcatgca tcatcttaca gcctgatgat     840
```

-continued

```
gggaggattt ggtggtgcta gtatccagaa ggcccagtct ctgattgatt taggatctag    900
tagctcaact tcctcaactg cttccctctc agggaactca cctaagacag ggacctcaga    960
gtgggcagtt cctcagcctt caagattaaa gtatcggcaa aaatttaata gtctagacaa   1020
aggcatgagc ggatacctct caggttttca agctagaaat gcccttcttc agtcaaatct   1080
ctctcaaact cagctagcta ctatttggac tctggctgac atcgatggtg acggacagtt   1140
gaaagctgaa gaatttattc tggcgatgca cctcactgac atggccaaag ctggacagcc   1200
actaccactg acgttgcctc ccgagcttgt ccctccatct ttcagagggg gaaagcaagt   1260
tgattctgtt aatggaactc tgccttcata tcagaaaaca caagaagaag agcctcagaa   1320
gaaactgcca gttacttttg aggacaaacg gaaagccaac tatgaacgag gaaacatgga   1380
gctggagaag cgacgccaag tgttgatgga gcagcagcag agggaggctg aacgcaaagc   1440
ccagaaagag aaggaagagt gggagcggaa acagagagaa ctgcaagagc aagaatggaa   1500
gaagcagctg gagttggaga aacgcttgga gaaacagaga gagctggaga cagcgggaa   1560
ggaagagagg agaaaggaga tagaaagacg agaggcagca aaacaggagc ttgagagaca   1620
acgccgttta gaatgggaaa gactccgtcg gcaggagctg ctcagtcaga agaccaggga   1680
acaagaagac attgtcaggc tgagctccag aaagaaaagt ctccacctgg aactggaagc   1740
agtgaatgga aaacatcagc agatctcagg cagactacaa gatgtccaaa tcagaaagca   1800
aacacaaaag actgagctag aagtttggga taaacagtgt gacctggaaa ttatggaaat   1860
caaacaactt caacaagagc ttaaggaata tcaaaataag cttatctatc tggtccctga   1920
gaagcagcta ttaaacgaaa gaattaaaaa catgcagctc agtaacacac ctgattcagg   1980
gatcagttta cttcataaaa agtcatcaga aaggaagaa ttatgccaaa gacttaaaga   2040
acaattagat gctcttgaaa agaaaactgc atctaagctc tcagaaatgg attcatttaa   2100
caatcagctg aaggaactca gagaaagcta taatacacag cagttagccc ttgaacaact   2160
tcataaaatc aaacgtgaca aattgaagga atcgaaaga aaaagattag agcaaattca   2220
aaaaagaaa ctagaagatg aggctgcaag gaaagcaaag caaggaaaag aaaacttgtg   2280
gagagaaagt attagaaagg aagaagagga aaagcaaaaa cgactccagg aagaaaagtc   2340
acaggacaaa actcaagaag aggaacgaaa agctgaggca aaacaaagtg agacagccag   2400
tgctttggtg aattacagag cactgtaccc ttttgaagca agaaaccatg atgagatgag   2460
ttttagttct ggggatataa ttcaggttga tgaaaaaact gtaggagagc ctggttggct   2520
ttatggtagt tttcagggaa agtttggctg gttccctgc aactatgtag aaaaagtgct   2580
gtcaagtgaa aaagctctgt ctcctaagaa ggccttactt cctcctacag tgtctctctc   2640
tgctacctca acttcttccc agccaccagc atcagtgact gattatcaca atgtatcctt   2700
ctcaaacctt actgttaata caacatggca gcagaagtca gcttttaccc gcactgtgtc   2760
ccctggatct gtgtccccca ttcacggaca ggggcaggct gtagaaaacc tgaaagccca   2820
ggccctttgt tcctggacgg caaagaagga gaaccacctg aacttctcaa agcacgacgt   2880
catcactgtc ctggagcagc aggaaaactg gtggtttggg gaggtgcacg gaggaagagg   2940
atggttcccc aagtcttatg tcaagctcat tcctgggaat gaagtacagc gaggagagcc   3000
agaagctttg tatgcagctg tgactaagaa acctacctcc acagcctatc cagttaccct   3060
cacagcctat ccagttggag aagactacat tgcactttat tcatactcaa gtgtagagcc   3120
cggggatttg actttcactg aagttgaaga aattctagtg acccagaaag atggagagtg   3180
gtggacagga agtattggag agagaactgg aatcttcccg tccaactacg tcagaccaaa   3240
```

```
ggatcaagag aattttggga atgctagcaa atctggagca tcaaacaaaa aacccgagat    3300
cgctcaagta acttcagcat atgctgcttc agggactgag cagctcagcc ttgcgccagg    3360
acagttaata ttaatcttaa agaaaaacac aagcgggtgg tggcaaggag agctacaggc    3420
cagagggaag aaacgacaga agggatggtt tcctgccagc catgtaaagc tgctaggtcc    3480
aagcagtgaa agaaccatgc ctactttca cgctgtatgt caagtgattg ctatgtatga     3540
ctacatggcg aataacgaag atgagctcaa tttctccaaa ggacagctga ttaatgttat    3600
gaacaaagat gaccctgact ggtggcaagg agaaaccaat ggtctgactg gtctctttcc    3660
ttcaaactat gttaagatga caacagactc agatccaagt caacagtggt gtgctgacct    3720
ccaagccctg gacacaatgc agcctacgga gaggaagcga cagggctaca ttcacgagct    3780
cattcagaca gaggagcggt acatggacga cgacctgcag ctggtcatcg aggtcttcca    3840
gaaacggatg gctgaggaag gcttcctcac tgaagcagac atggctctga tctttgtgaa    3900
ctggaaagag ctcatcatgt ccaacacgaa gctgctgagg gccttgcggg tgaggaagaa    3960
gactgggggt gagaagatgc cagttcagat gattggagac atcctggcgg cagagctgtc    4020
ccacatgcag gcctacatcc gcttctgcag ctgtcagctt aatggggcaa ccctgttaca    4080
gcagaagaca gacgaggaca cggacttcaa ggaatttcta aagaagttgg catcagaccc    4140
acgatgcaaa gggatgcccc tctccagctt cctgctgaag cccatgcaga ggatcactcg    4200
ctacccgctg ctcatccgaa gtatcctgga gaacactcca cagagtcatg ttgaccactc    4260
ctccctgaag ctgccctag aacgtgctga ggagctgtgc tctcaggtga acgagggagt     4320 ccggagaag gaaaattcag accggctgga gtggatccag gcacacgtgc agtgcgaagg     4380
cttggcagag caacttattt tcaactccct caccaactgc ctgggccccc ggaagcttct    4440
gcacagcggg aagctgtaca agaccaagag caataaggag ctgcacgcct tcctcttcaa    4500
cgacttcctg ctgctcacct acctggtcag gcagtttgcc gccgcctctg ccacgagaa     4560 gctcttcaac tccaagtcca gtgctcagtt ccggatgtac aaaacgccca ttttcctgaa    4620
tgaagtgttg gtgaaacttc ccacagaccc ttccggcgat gagcccgtct tccacatttc    4680
ccacattgat cgtgtgtaca cactccgaac agacaacatc aacgagagga cggcctgggt    4740
ccagaagatc aagggtgcct cagagcagta catcgacact gagaagaaga acgggaaaa     4800 ggcttaccaa gcccgttctc aaaagacttc aggtattggg cgtctgatgg tgcatgtcat    4860
tgaagctaca gaattaaaag cctgcaaacc aaacgggaaa agtaatccat actgtgaagt    4920
cagcatgggc tcccaaagct ataccaccag gaccctgcag gacacactaa accccaagtg    4980
gaacttcaac tgccagttct tcatcaagga tctttaccag gacgttctgt gtctcactat    5040
gtttgacaga gaccagtttt ctccagatga cttcttgggt cgtactgaag ttccagtggc    5100
aaaaatccga acagaacagg aaagcaaagg ccccaccacc cgccgactac tactgcacga    5160
agtccccact ggagaagtct gggtccgctt tgacctgcaa cttttgaac aaaaaactct     5220 cctttgaggg cctggggaag ccagaaccag gggagctgcc cacaaggctg ggtctaaaga    5280
cagattttgc tctcccagga cagaggagca tcacatggct tcatccatca aacagccaca    5340
ctcgctgggc ctgtattta ttgcacacta aattgctagc aatctatgca aacatgatct     5400
tttaaacaaa cgccacagca cagtgccttg tactagtgtt aacctgttca gctgtgttag    5460
atgccagggt ttccattttc agggctataa aagtattatg tggaaatgag gcatcagacc    5520
accggacgtt accacttggc aaatctgtcc actgtggagt tggtgatgtt ggaaccattc    5580
```

-continued

```
cacactatgt gacctctgct gggtcacaca ctcaggaggt gaagggctga gatgaaatgc    5640
tgcagccttg gggcttgtgc agcctgatac tgaaatagca tccacttgtg cactgaataa    5700
atagaaactt gatcgtttta ttctgactag atattatcat tctctgctaa gacaatatag    5760
tttgaaatat tatagtttga atataaggag gaaagcttga tgtactttaa atatactgtg    5820
aactctaata atgtggggat attttttcaac tttaattttc ttaagtataa attatttatg    5880
taaattcttt gttttgcata tttcatgaa catgcatctt taagctttat cattgccaac     5940
aatgtacaga aagagaataa aagtataagt ttatgaatgt aaaaaaaaaa aaaaaaaaa     6000 aaaaaaaaaa aaaa                                                       6014
```

<210> SEQ ID NO 26
<211> LENGTH: 4977
<212> TYPE: DNA
<213> ORGANISM: Mus musculus
<220> FEATURE:
<221> NAME/KEY: CDS
<222> LOCATION: (1)..(4977)
<223> OTHER INFORMATION: Mouse Ese2L

<400> SEQUENCE: 26

```
atg gct cag ttt ccc aca gcg atg aat gga ggg cca aat atg tgg gct      48
Met Ala Gln Phe Pro Thr Ala Met Asn Gly Gly Pro Asn Met Trp Ala
1               5                   10                  15 att aca tct gaa gaa cgt act aag cat gat aaa cag ttt gat aac ctc      96
Ile Thr Ser Glu Glu Arg Thr Lys His Asp Lys Gln Phe Asp Asn Leu
            20                  25                  30 aaa cct tca gga ggt tac ata aca ggt gat caa gcc cgt act ttt ttc     144
Lys Pro Ser Gly Gly Tyr Ile Thr Gly Asp Gln Ala Arg Thr Phe Phe
        35                  40                  45 cta cag tca ggt ctg ccg gcc ccg gtt tta gct gaa ata tgg gcc tta     192
Leu Gln Ser Gly Leu Pro Ala Pro Val Leu Ala Glu Ile Trp Ala Leu
    50                  55                  60 tca gat ctg aac aag gat ggg aag atg gac cag caa gag ttc tct ata     240
Ser Asp Leu Asn Lys Asp Gly Lys Met Asp Gln Gln Glu Phe Ser Ile
65                  70                  75                  80 gct atg aaa ctc atc aag tta aag ttg cag ggc caa cag ctg cct gta     288
Ala Met Lys Leu Ile Lys Leu Lys Leu Gln Gly Gln Gln Leu Pro Val
                85                  90                  95 gtc ctc cct cct atc atg aaa caa ccc cct atg ttc tct cca cta atc     336
Val Leu Pro Pro Ile Met Lys Gln Pro Pro Met Phe Ser Pro Leu Ile
            100                 105                 110 tct gct cgt ttt ggg atg gga agc atg ccc aat ctg tcc att cat cag     384
Ser Ala Arg Phe Gly Met Gly Ser Met Pro Asn Leu Ser Ile His Gln
        115                 120                 125 cca ttg cct cca gtt gca cct ata gca aca ccc ttg tct tct gct acg     432
Pro Leu Pro Pro Val Ala Pro Ile Ala Thr Pro Leu Ser Ser Ala Thr
    130                 135                 140 tca ggg acc agt att cct ccc cta atg atg cct gct ccc cta gtg cct     480
Ser Gly Thr Ser Ile Pro Pro Leu Met Met Pro Ala Pro Leu Val Pro
145                 150                 155                 160 tct gtt agt aca tcc tca tta cca aat gga act gcc agt ctc att cag     528
Ser Val Ser Thr Ser Ser Leu Pro Asn Gly Thr Ala Ser Leu Ile Gln
                165                 170                 175 cct tta tcc att cct tat tct tct tca aca ttg cct cat gca tca tct     576
Pro Leu Ser Ile Pro Tyr Ser Ser Ser Thr Leu Pro His Ala Ser Ser
            180                 185                 190 tac agc ctg atg atg gga gga ttt ggt ggt gct agt atc cag aag gcc     624
Tyr Ser Leu Met Met Gly Gly Phe Gly Gly Ala Ser Ile Gln Lys Ala
        195                 200                 205
```

```
cag tct ctg att gat tta gga tct agt agc tca act tcc tca act gct      672
Gln Ser Leu Ile Asp Leu Gly Ser Ser Ser Thr Ser Ser Thr Ala
    210                 215                 220 tcc ctc tca ggg aac tca cct aag aca ggg acc tca gag tgg gca gtt      720
Ser Leu Ser Gly Asn Ser Pro Lys Thr Gly Thr Ser Glu Trp Ala Val
225                 230                 235                 240 cct cag cct tca aga tta aag tat cgg caa aaa ttt aat agt cta gac      768
Pro Gln Pro Ser Arg Leu Lys Tyr Arg Gln Lys Phe Asn Ser Leu Asp
                245                 250                 255 aaa ggc atg agc gga tac ctc tca ggt ttt caa gct aga aat gcc ctt      816
Lys Gly Met Ser Gly Tyr Leu Ser Gly Phe Gln Ala Arg Asn Ala Leu
            260                 265                 270 ctt cag tca aat ctc tct caa act cag cta gct act att tgg act ctg      864
Leu Gln Ser Asn Leu Ser Gln Thr Gln Leu Ala Thr Ile Trp Thr Leu
        275                 280                 285 gct gac atc gat ggt gac gga cag ttg aaa gct gaa gaa ttt att ctg      912
Ala Asp Ile Asp Gly Asp Gly Gln Leu Lys Ala Glu Glu Phe Ile Leu
    290                 295                 300 gcg atg cac ctc act gac atg gcc aaa gct gga cag cca cta cca ctg      960
Ala Met His Leu Thr Asp Met Ala Lys Ala Gly Gln Pro Leu Pro Leu
305                 310                 315                 320 acg ttg cct ccc gag ctt gtc cct cca tct ttc aga ggg gga aag caa     1008
Thr Leu Pro Pro Glu Leu Val Pro Pro Ser Phe Arg Gly Gly Lys Gln
                325                 330                 335 gtt gat tct gtt aat gga act ctg cct tca tat cag aaa aca caa gaa     1056
Val Asp Ser Val Asn Gly Thr Leu Pro Ser Tyr Gln Lys Thr Gln Glu
            340                 345                 350 gaa gag cct cag aag aaa ctg cca gtt act ttt gag gac aaa cgg aaa     1104
Glu Glu Pro Gln Lys Lys Leu Pro Val Thr Phe Glu Asp Lys Arg Lys
        355                 360                 365 gcc aac tat gaa cga gga aac atg gag ctg gag aag cga cgc caa gtg     1152
Ala Asn Tyr Glu Arg Gly Asn Met Glu Leu Glu Lys Arg Arg Gln Val
    370                 375                 380 ttg atg gag cag cag cag agg gag gct gaa cgc aaa gcc cag aaa gag     1200
Leu Met Glu Gln Gln Gln Arg Glu Ala Glu Arg Lys Ala Gln Lys Glu
385                 390                 395                 400 aag gaa gag tgg gag cgg aaa cag aga gaa ctg caa gag caa gaa tgg     1248
Lys Glu Glu Trp Glu Arg Lys Gln Arg Glu Leu Gln Glu Gln Glu Trp
                405                 410                 415 aag aag cag ctg gag ttg gag aaa cgc ttg gag aaa cag aga gag ctg     1296
Lys Lys Gln Leu Glu Leu Glu Lys Arg Leu Glu Lys Gln Arg Glu Leu
            420                 425                 430 gag aga cag cgg gag gaa gag agg aga aag gag ata gaa aga cga gag     1344
Glu Arg Gln Arg Glu Glu Glu Arg Arg Lys Glu Ile Glu Arg Arg Glu
        435                 440                 445 gca gca aaa cag gag ctt gag aga caa cgc cgt tta gaa tgg gaa aga     1392
Ala Ala Lys Gln Glu Leu Glu Arg Gln Arg Arg Leu Glu Trp Glu Arg
    450                 455                 460 ctc cgt cgg cag gag ctg ctc agt cag aag acc agg gaa caa gaa gac     1440
Leu Arg Arg Gln Glu Leu Leu Ser Gln Lys Thr Arg Glu Gln Glu Asp
465                 470                 475                 480 att gtc agg ctg agc tcc aga aag aaa agt ctc cac ctg gaa ctg gaa     1488
Ile Val Arg Leu Ser Ser Arg Lys Lys Ser Leu His Leu Glu Leu Glu
                485                 490                 495 gca gtg aat gga aaa cat cag cag atc tca ggc aga cta caa gat gtc     1536
Ala Val Asn Gly Lys His Gln Gln Ile Ser Gly Arg Leu Gln Asp Val
            500                 505                 510 caa atc aga aag caa aca caa aag act gag cta gaa gtt ttg gat aaa     1584
Gln Ile Arg Lys Gln Thr Gln Lys Thr Glu Leu Glu Val Leu Asp Lys
```

```
                515                 520                 525
cag tgt gac ctg gaa att atg gaa atc aaa caa ctt caa caa gag ctt        1632
Gln Cys Asp Leu Glu Ile Met Glu Ile Lys Gln Leu Gln Gln Glu Leu
        530                 535                 540 aag gaa tat caa aat aag ctt atc tat ctg gtc cct gag aag cag cta        1680
Lys Glu Tyr Gln Asn Lys Leu Ile Tyr Leu Val Pro Glu Lys Gln Leu
545                 550                 555                 560 tta aac gaa aga att aaa aac atg cag ctc agt aac aca cct gat tca        1728
Leu Asn Glu Arg Ile Lys Asn Met Gln Leu Ser Asn Thr Pro Asp Ser
                565                 570                 575 ggg atc agt tta ctt cat aaa aag tca tca gaa aag gaa gaa tta tgc        1776
Gly Ile Ser Leu Leu His Lys Lys Ser Ser Glu Lys Glu Glu Leu Cys
            580                 585                 590 caa aga ctt aaa gaa caa tta gat gct ctt gaa aaa gaa act gca tct        1824
Gln Arg Leu Lys Glu Gln Leu Asp Ala Leu Glu Lys Glu Thr Ala Ser
        595                 600                 605 aag ctc tca gaa atg gat tca ttt aac aat cag ctg aag gaa ctc aga        1872
Lys Leu Ser Glu Met Asp Ser Phe Asn Asn Gln Leu Lys Glu Leu Arg
610                 615                 620 gaa agc tat aat aca cag cag tta gcc ctt gaa caa ctt cat aaa atc        1920
Glu Ser Tyr Asn Thr Gln Gln Leu Ala Leu Glu Gln Leu His Lys Ile
625                 630                 635                 640 aaa cgt gac aaa ttg aag gaa atc gaa aga aaa aga tta gag caa att        1968
Lys Arg Asp Lys Leu Lys Glu Ile Glu Arg Lys Arg Leu Glu Gln Ile
                645                 650                 655 caa aaa aag aaa cta gaa gat gag gct gca agg aaa gca aag caa gga        2016
Gln Lys Lys Lys Leu Glu Asp Glu Ala Ala Arg Lys Ala Lys Gln Gly
            660                 665                 670 aaa gaa aac ttg tgg aga gaa agt att aga aag gaa gaa gag gaa aag        2064
Lys Glu Asn Leu Trp Arg Glu Ser Ile Arg Lys Glu Glu Glu Glu Lys
        675                 680                 685 caa aaa cga ctc cag gaa gaa aag tca cag gac aaa act caa gaa gag        2112
Gln Lys Arg Leu Gln Glu Glu Lys Ser Gln Asp Lys Thr Gln Glu Glu
690                 695                 700 gaa cga aaa gct gag gca aaa caa agt gag aca gcc agt gct ttg gtg        2160
Glu Arg Lys Ala Glu Ala Lys Gln Ser Glu Thr Ala Ser Ala Leu Val
705                 710                 715                 720 aat tac aga gca ctg tac cct ttt gaa gca aga aac cat gat gag atg        2208
Asn Tyr Arg Ala Leu Tyr Pro Phe Glu Ala Arg Asn His Asp Glu Met
                725                 730                 735 agt ttt agt tct ggg gat ata att cag gtt gat gaa aaa act gta gga        2256
Ser Phe Ser Ser Gly Asp Ile Ile Gln Val Asp Glu Lys Thr Val Gly
            740                 745                 750 gag cct ggt tgg ctt tat ggt agt ttt cag gga aag ttt ggc tgg ttc        2304
Glu Pro Gly Trp Leu Tyr Gly Ser Phe Gln Gly Lys Phe Gly Trp Phe
        755                 760                 765 ccc tgc aac tat gta gaa aaa gtg ctg tca agt gaa aaa gct ctg tct        2352
Pro Cys Asn Tyr Val Glu Lys Val Leu Ser Ser Glu Lys Ala Leu Ser
770                 775                 780 cct aag aag gcc tta ctt cct cct aca gtg tct ctc tct gct acc tca        2400
Pro Lys Lys Ala Leu Leu Pro Pro Thr Val Ser Leu Ser Ala Thr Ser
785                 790                 795                 800 act tct tcc cag cca cca gca tca gtg act gat tat cac aat gta tcc        2448
Thr Ser Ser Gln Pro Pro Ala Ser Val Thr Asp Tyr His Asn Val Ser
                805                 810                 815 ttc tca aac ctt act gtt aat aca aca tgg cag cag aag tca gct ttt        2496
Phe Ser Asn Leu Thr Val Asn Thr Thr Trp Gln Gln Lys Ser Ala Phe
            820                 825                 830 acc cgc act gtg tcc cct gga tct gtg tcc ccc att cac gga cag ggg        2544
```

```
                Thr Arg Thr Val Ser Pro Gly Ser Val Ser Pro Ile His Gly Gln Gly
                    835                 840                 845 cag gct gta gaa aac ctg aaa gcc cag gcc ctt tgt tcc tgg acg gca        2592
Gln Ala Val Glu Asn Leu Lys Ala Gln Ala Leu Cys Ser Trp Thr Ala
850                 855                 860 aag aag gag aac cac ctg aac ttc tca aag cac gac gtc atc act gtc        2640
Lys Lys Glu Asn His Leu Asn Phe Ser Lys His Asp Val Ile Thr Val
865                 870                 875                 880 ctg gag cag cag gaa aac tgg tgg ttt ggg gag gtg cac gga gga aga        2688
Leu Glu Gln Gln Glu Asn Trp Trp Phe Gly Glu Val His Gly Gly Arg
                    885                 890                 895 gga tgg ttc ccc aag tct tat gtc aag ctc att cct ggg aat gaa gta        2736
Gly Trp Phe Pro Lys Ser Tyr Val Lys Leu Ile Pro Gly Asn Glu Val
            900                 905                 910 cag cga gga gag cca gaa gct ttg tat gca gct gtg act aag aaa cct        2784
Gln Arg Gly Glu Pro Glu Ala Leu Tyr Ala Ala Val Thr Lys Lys Pro
        915                 920                 925 acc tcc aca gcc tat cca gtt acc tcc aca gcc tat cca gtt gga gaa        2832
Thr Ser Thr Ala Tyr Pro Val Thr Ser Thr Ala Tyr Pro Val Gly Glu
    930                 935                 940 gac tac att gca ctt tat tca tac tca agt gta gag ccc ggg gat ttg        2880
Asp Tyr Ile Ala Leu Tyr Ser Tyr Ser Ser Val Glu Pro Gly Asp Leu
945                 950                 955                 960 act ttc act gaa ggt gaa gaa att cta gtg acc cag aaa gat gga gag        2928
Thr Phe Thr Glu Gly Glu Glu Ile Leu Val Thr Gln Lys Asp Gly Glu
                    965                 970                 975 tgg tgg aca gga agt att gga gag aga act gga atc ttc ccg tcc aac        2976
Trp Trp Thr Gly Ser Ile Gly Glu Arg Thr Gly Ile Phe Pro Ser Asn
            980                 985                 990 tac gtc aga cca aag gat caa gag aat ttt ggg aat gct agc aaa tct        3024
Tyr Val Arg Pro Lys Asp Gln Glu Asn Phe Gly Asn Ala Ser Lys Ser
        995                 1000                1005 gga gca tca aac aaa aaa ccc gag atc gct caa gta act tca gca            3069
Gly Ala Ser Asn Lys Lys Pro Glu Ile Ala Gln Val Thr Ser Ala
    1010                1015                1020 tat gct gct tca ggg act gag cag ctc agc ctt gcg cca gga cag            3114
Tyr Ala Ala Ser Gly Thr Glu Gln Leu Ser Leu Ala Pro Gly Gln
    1025                1030                1035 tta ata tta atc tta aag aaa aac aca agc ggg tgg tgg caa gga            3159
Leu Ile Leu Ile Leu Lys Lys Asn Thr Ser Gly Trp Trp Gln Gly
    1040                1045                1050 gag cta cag gcc aga ggg aag aaa cga cag aag gga tgg ttt cct            3204
Glu Leu Gln Ala Arg Gly Lys Lys Arg Gln Lys Gly Trp Phe Pro
    1055                1060                1065 gcc agc cat gta aag ctg cta ggt cca agc agt gaa aga acc atg            3249
Ala Ser His Val Lys Leu Leu Gly Pro Ser Ser Glu Arg Thr Met
    1070                1075                1080 cct act ttt cac gct gta tgt caa gtg att gct atg tat gac tac            3294
Pro Thr Phe His Ala Val Cys Gln Val Ile Ala Met Tyr Asp Tyr
    1085                1090                1095 atg gcg aat aac gaa gat gag ctc aat ttc tcc aaa gga cag ctg            3339
Met Ala Asn Asn Glu Asp Glu Leu Asn Phe Ser Lys Gly Gln Leu
    1100                1105                1110 att aat gtt atg aac aaa gat gac cct gac tgg tgg caa gga gaa            3384
Ile Asn Val Met Asn Lys Asp Asp Pro Asp Trp Trp Gln Gly Glu
    1115                1120                1125 acc aat ggt ctg act ggt ctc ttt cct tca aac tat gtt aag atg            3429
Thr Asn Gly Leu Thr Gly Leu Phe Pro Ser Asn Tyr Val Lys Met
    1130                1135                1140
```

```
aca aca gac tca gat cca agt caa cag tgg tgt gct gac ctc caa    3474
Thr Thr Asp Ser Asp Pro Ser Gln Gln Trp Cys Ala Asp Leu Gln
    1145            1150                1155 gcc ctg gac aca atg cag cct acg gag agg aag cga cag ggc tac    3519
Ala Leu Asp Thr Met Gln Pro Thr Glu Arg Lys Arg Gln Gly Tyr
    1160            1165                1170 att cac gag ctc att cag aca gag gag cgg tac atg gac gac gac    3564
Ile His Glu Leu Ile Gln Thr Glu Glu Arg Tyr Met Asp Asp Asp
    1175            1180                1185 ctg cag ctg gtc atc gag gtc ttc cag aaa cgg atg gct gag gaa    3609
Leu Gln Leu Val Ile Glu Val Phe Gln Lys Arg Met Ala Glu Glu
    1190            1195                1200 ggc ttc ctc act gaa gca gac atg gct ctg atc ttt gtg aac tgg    3654
Gly Phe Leu Thr Glu Ala Asp Met Ala Leu Ile Phe Val Asn Trp
    1205            1210                1215 aaa gag ctc atc atg tcc aac acg aag ctg ctg agg gcc ttg cgg    3699
Lys Glu Leu Ile Met Ser Asn Thr Lys Leu Leu Arg Ala Leu Arg
    1220            1225                1230 gtg agg aag aag act ggg ggt gag aag atg cca gtt cag atg att    3744
Val Arg Lys Lys Thr Gly Gly Glu Lys Met Pro Val Gln Met Ile
    1235            1240                1245 gga gac atc ctg gcg gca gag ctg tcc cac atg cag gcc tac atc    3789
Gly Asp Ile Leu Ala Ala Glu Leu Ser His Met Gln Ala Tyr Ile
    1250            1255                1260 cgc ttc tgc agc tgt cag ctt aat ggg gca acc ctg tta cag cag    3834
Arg Phe Cys Ser Cys Gln Leu Asn Gly Ala Thr Leu Leu Gln Gln
    1265            1270                1275 aag aca gac gag gac acg gac ttc aag gaa ttt cta aag aag ttg    3879
Lys Thr Asp Glu Asp Thr Asp Phe Lys Glu Phe Leu Lys Lys Leu
    1280            1285                1290 gca tca gac cca cga tgc aaa ggg atg ccc ctc tcc agc ttc ctg    3924
Ala Ser Asp Pro Arg Cys Lys Gly Met Pro Leu Ser Ser Phe Leu
    1295            1300                1305 ctg aag ccc atg cag agg atc act cgc tac ccg ctg ctc atc cga    3969
Leu Lys Pro Met Gln Arg Ile Thr Arg Tyr Pro Leu Leu Ile Arg
    1310            1315                1320 agt atc ctg gag aac act cca cag agt cat gtt gac cac tcc tcc    4014
Ser Ile Leu Glu Asn Thr Pro Gln Ser His Val Asp His Ser Ser
    1325            1330                1335 ctg aag ctg gcc cta gaa cgt gct gag gag ctg tgc tct cag gtg    4059
Leu Lys Leu Ala Leu Glu Arg Ala Glu Glu Leu Cys Ser Gln Val
    1340            1345                1350 aac gag gga gtc cgg gag aag gaa aat tca gac cgg ctg gag tgg    4104
Asn Glu Gly Val Arg Glu Lys Glu Asn Ser Asp Arg Leu Glu Trp
    1355            1360                1365 atc cag gca cac gtg cag tgc gaa ggc ttg gca gag caa ctt att    4149
Ile Gln Ala His Val Gln Cys Glu Gly Leu Ala Glu Gln Leu Ile
    1370            1375                1380 ttc aac tcc ctc acc aac tgc ctg ggc ccc cgg aag ctt ctg cac    4194
Phe Asn Ser Leu Thr Asn Cys Leu Gly Pro Arg Lys Leu Leu His
    1385            1390                1395 agc ggg aag ctg tac aag acc aag agc aat aag gag ctg cac gcc    4239
Ser Gly Lys Leu Tyr Lys Thr Lys Ser Asn Lys Glu Leu His Ala
    1400            1405                1410 ttc ctc ttc aac gac ttc ctg ctc acc tac ctg gtc agg cag        4284
Phe Leu Phe Asn Asp Phe Leu Leu Leu Thr Tyr Leu Val Arg Gln
    1415            1420                1425 ttt gcc gcc gcc tct ggc cac gag aag ctc ttc aac tcc aag tcc    4329
Phe Ala Ala Ala Ser Gly His Glu Lys Leu Phe Asn Ser Lys Ser
    1430            1435                1440
```

| | | |
|---|---|---|
| agt gct cag ttc cgg atg tac aaa acg ccc att ttc ctg aat gaa<br>Ser Ala Gln Phe Arg Met Tyr Lys Thr Pro Ile Phe Leu Asn Glu<br>    1445                            1450                      1455 | | 4374 |
| gtg ttg gtg aaa ctt ccc aca gac cct tcc ggc gat gag ccc gtc<br>Val Leu Val Lys Leu Pro Thr Asp Pro Ser Gly Asp Glu Pro Val<br>1460                        1465                      1470 | | 4419 |
| ttc cac att tcc cac att gat cgt gtg tac aca ctc cga aca gac<br>Phe His Ile Ser His Ile Asp Arg Val Tyr Thr Leu Arg Thr Asp<br>    1475                        1480                    1485 | | 4464 |
| aac atc aac gag agg acg gcc tgg gtc cag aag atc aag ggt gcc<br>Asn Ile Asn Glu Arg Thr Ala Trp Val Gln Lys Ile Lys Gly Ala<br>1490                        1495                      1500 | | 4509 |
| tca gag cag tac atc gac act gag aag aag aaa cgg gaa aag gct<br>Ser Glu Gln Tyr Ile Asp Thr Glu Lys Lys Lys Arg Glu Lys Ala<br>    1505                        1510                    1515 | | 4554 |
| tac caa gcc cgt tct caa aag act tca ggt att ggg cgt ctg atg<br>Tyr Gln Ala Arg Ser Gln Lys Thr Ser Gly Ile Gly Arg Leu Met<br>1520                        1525                      1530 | | 4599 |
| gtg cat gtc att gaa gct aca gaa tta aaa gcc tgc aaa cca aac<br>Val His Val Ile Glu Ala Thr Glu Leu Lys Ala Cys Lys Pro Asn<br>    1535                        1540                    1545 | | 4644 |
| ggg aaa agt aat cca tac tgt gaa gtc agc atg ggc tcc caa agc<br>Gly Lys Ser Asn Pro Tyr Cys Glu Val Ser Met Gly Ser Gln Ser<br>1550                        1555                      1560 | | 4689 |
| tat acc acc agg acc ctg cag gac aca cta aac ccc aag tgg aac<br>Tyr Thr Thr Arg Thr Leu Gln Asp Thr Leu Asn Pro Lys Trp Asn<br>    1565                        1570                    1575 | | 4734 |
| ttc aac tgc cag ttc ttc atc aag gat ctt tac cag gac gtt ctg<br>Phe Asn Cys Gln Phe Phe Ile Lys Asp Leu Tyr Gln Asp Val Leu<br>1580                        1585                      1590 | | 4779 |
| tgt ctc act atg ttt gac aga gac cag ttt tct cca gat gac ttc<br>Cys Leu Thr Met Phe Asp Arg Asp Gln Phe Ser Pro Asp Asp Phe<br>    1595                        1600                    1605 | | 4824 |
| ttg ggt cgt act gaa gtt cca gtg gca aaa atc cga aca gaa cag<br>Leu Gly Arg Thr Glu Val Pro Val Ala Lys Ile Arg Thr Glu Gln<br>1610                        1615                      1620 | | 4869 |
| gaa agc aaa ggc ccc acc acc cgc cga cta cta ctg cac gaa gtc<br>Glu Ser Lys Gly Pro Thr Thr Arg Arg Leu Leu Leu His Glu Val<br>    1625                        1630                    1635 | | 4914 |
| ccc act gga gaa gtc tgg gtc cgc ttt gac ctg caa ctt ttt gaa<br>Pro Thr Gly Glu Val Trp Val Arg Phe Asp Leu Gln Leu Phe Glu<br>1640                        1645                      1650 | | 4959 |
| caa aaa act ctc ctt tga<br>Gln Lys Thr Leu Leu<br>    1655 | | 4977 |

<210> SEQ ID NO 27
<211> LENGTH: 1658
<212> TYPE: PRT
<213> ORGANISM: Mus musculus

<400> SEQUENCE: 27

Met Ala Gln Phe Pro Thr Ala Met Asn Gly Gly Pro Asn Met Trp Ala
1               5                   10                  15

Ile Thr Ser Glu Glu Arg Thr Lys His Asp Lys Gln Phe Asp Asn Leu
            20                  25                  30

Lys Pro Ser Gly Gly Tyr Ile Thr Gly Asp Gln Ala Arg Thr Phe Phe
        35                  40                  45

Leu Gln Ser Gly Leu Pro Ala Pro Val Leu Ala Glu Ile Trp Ala Leu

-continued

```
             50                  55                  60
Ser Asp Leu Asn Lys Asp Gly Lys Met Asp Gln Gln Glu Phe Ser Ile
 65                  70                  75                  80
Ala Met Lys Leu Ile Lys Leu Lys Leu Gln Gly Gln Gln Leu Pro Val
                     85                  90                  95
Val Leu Pro Pro Ile Met Lys Gln Pro Pro Met Phe Ser Pro Leu Ile
                100                 105                 110
Ser Ala Arg Phe Gly Met Gly Ser Met Pro Asn Leu Ser Ile His Gln
                115                 120                 125
Pro Leu Pro Pro Val Ala Pro Ile Ala Thr Pro Leu Ser Ser Ala Thr
130                 135                 140
Ser Gly Thr Ser Ile Pro Pro Leu Met Met Pro Ala Pro Leu Val Pro
145                 150                 155                 160
Ser Val Ser Thr Ser Ser Leu Pro Asn Gly Thr Ala Ser Leu Ile Gln
                165                 170                 175
Pro Leu Ser Ile Pro Tyr Ser Ser Thr Leu Pro His Ala Ser Ser
                180                 185                 190
Tyr Ser Leu Met Met Gly Gly Phe Gly Gly Ala Ser Ile Gln Lys Ala
                195                 200                 205
Gln Ser Leu Ile Asp Leu Gly Ser Ser Ser Thr Ser Ser Thr Ala
210                 215                 220
Ser Leu Ser Gly Asn Ser Pro Lys Thr Gly Thr Ser Glu Trp Ala Val
225                 230                 235                 240
Pro Gln Pro Ser Arg Leu Lys Tyr Arg Gln Lys Phe Asn Ser Leu Asp
                245                 250                 255
Lys Gly Met Ser Gly Tyr Leu Ser Gly Phe Gln Ala Arg Asn Ala Leu
                260                 265                 270
Leu Gln Ser Asn Leu Ser Gln Thr Gln Leu Ala Thr Ile Trp Thr Leu
                275                 280                 285
Ala Asp Ile Asp Gly Asp Gly Gln Leu Lys Ala Glu Glu Phe Ile Leu
290                 295                 300
Ala Met His Leu Thr Asp Met Ala Lys Ala Gly Gln Pro Leu Pro Leu
305                 310                 315                 320
Thr Leu Pro Pro Glu Leu Val Pro Pro Ser Phe Arg Gly Gly Lys Gln
                325                 330                 335
Val Asp Ser Val Asn Gly Thr Leu Pro Ser Tyr Gln Lys Thr Gln Glu
                340                 345                 350
Glu Glu Pro Gln Lys Lys Leu Pro Val Thr Phe Glu Asp Lys Arg Lys
                355                 360                 365
Ala Asn Tyr Glu Arg Gly Asn Met Glu Leu Glu Lys Arg Arg Gln Val
                370                 375                 380
Leu Met Glu Gln Gln Arg Glu Ala Glu Arg Lys Ala Gln Lys Glu
385                 390                 395                 400
Lys Glu Glu Trp Glu Arg Lys Gln Arg Glu Leu Gln Glu Gln Trp
                405                 410                 415
Lys Lys Gln Leu Glu Leu Glu Lys Arg Leu Glu Lys Arg Glu Leu
                420                 425                 430
Glu Arg Gln Arg Glu Glu Arg Lys Glu Ile Glu Arg Glu
                435                 440                 445
Ala Ala Lys Gln Glu Leu Glu Arg Gln Arg Leu Glu Trp Glu Arg
                450                 455                 460
Leu Arg Arg Gln Glu Leu Leu Ser Gln Lys Thr Arg Glu Gln Glu Asp
465                 470                 475                 480
```

```
Ile Val Arg Leu Ser Ser Arg Lys Lys Ser Leu His Leu Glu Leu Glu
                485                 490                 495
Ala Val Asn Gly Lys His Gln Gln Ile Ser Gly Arg Leu Gln Asp Val
            500                 505                 510
Gln Ile Arg Lys Gln Thr Gln Lys Thr Glu Leu Glu Val Leu Asp Lys
        515                 520                 525
Gln Cys Asp Leu Glu Ile Met Glu Ile Lys Gln Leu Gln Gln Glu Leu
    530                 535                 540
Lys Glu Tyr Gln Asn Lys Leu Ile Tyr Leu Val Pro Glu Lys Gln Leu
545                 550                 555                 560
Leu Asn Glu Arg Ile Lys Asn Met Gln Leu Ser Asn Thr Pro Asp Ser
                565                 570                 575
Gly Ile Ser Leu Leu His Lys Lys Ser Ser Glu Lys Glu Glu Leu Cys
            580                 585                 590
Gln Arg Leu Lys Glu Gln Leu Asp Ala Leu Glu Lys Glu Thr Ala Ser
        595                 600                 605
Lys Leu Ser Glu Met Asp Ser Phe Asn Asn Gln Leu Lys Glu Leu Arg
    610                 615                 620
Glu Ser Tyr Asn Thr Gln Gln Leu Ala Leu Glu Gln Leu His Lys Ile
625                 630                 635                 640
Lys Arg Asp Lys Leu Lys Glu Ile Glu Arg Lys Arg Leu Glu Gln Ile
                645                 650                 655
Gln Lys Lys Lys Leu Glu Asp Glu Ala Ala Arg Lys Ala Lys Gln Gly
            660                 665                 670
Lys Glu Asn Leu Trp Arg Glu Ser Ile Arg Lys Glu Glu Glu Lys
        675                 680                 685
Gln Lys Arg Leu Gln Glu Glu Lys Ser Gln Asp Lys Thr Gln Glu Glu
    690                 695                 700
Glu Arg Lys Ala Glu Ala Lys Gln Ser Glu Thr Ala Ser Ala Leu Val
705                 710                 715                 720
Asn Tyr Arg Ala Leu Tyr Pro Phe Glu Ala Arg Asn His Asp Glu Met
                725                 730                 735
Ser Phe Ser Ser Gly Asp Ile Ile Gln Val Asp Glu Lys Thr Val Gly
            740                 745                 750
Glu Pro Gly Trp Leu Tyr Gly Ser Phe Gln Gly Lys Phe Gly Trp Phe
        755                 760                 765
Pro Cys Asn Tyr Val Glu Lys Val Leu Ser Ser Glu Lys Ala Leu Ser
    770                 775                 780
Pro Lys Lys Ala Leu Leu Pro Pro Thr Val Ser Leu Ala Thr Ser
785                 790                 795                 800
Thr Ser Ser Gln Pro Pro Ala Ser Val Thr Asp Tyr His Asn Val Ser
                805                 810                 815
Phe Ser Asn Leu Thr Val Asn Thr Thr Trp Gln Gln Lys Ser Ala Phe
            820                 825                 830
Thr Arg Thr Val Ser Pro Gly Ser Val Ser Pro Ile His Gly Gln Gly
        835                 840                 845
Gln Ala Val Glu Asn Leu Lys Ala Gln Ala Leu Cys Ser Trp Thr Ala
    850                 855                 860
Lys Lys Glu Asn His Leu Asn Phe Ser Lys His Asp Val Ile Thr Val
865                 870                 875                 880
Leu Glu Gln Gln Glu Asn Trp Trp Phe Gly Glu Val His Gly Gly Arg
                885                 890                 895
```

```
Gly Trp Phe Pro Lys Ser Tyr Val Lys Leu Ile Pro Gly Asn Glu Val
            900                 905                 910
Gln Arg Gly Glu Pro Glu Ala Leu Tyr Ala Ala Val Thr Lys Lys Pro
            915                 920                 925
Thr Ser Thr Ala Tyr Pro Val Thr Ser Thr Ala Tyr Pro Val Gly Glu
        930                 935                 940
Asp Tyr Ile Ala Leu Tyr Ser Tyr Ser Ser Val Glu Pro Gly Asp Leu
945                 950                 955                 960
Thr Phe Thr Glu Gly Glu Ile Leu Val Thr Gln Lys Asp Gly Glu
                965                 970                 975
Trp Trp Thr Gly Ser Ile Gly Glu Arg Thr Gly Ile Phe Pro Ser Asn
            980                 985                 990
Tyr Val Arg Pro Lys Asp Gln Glu Asn Phe Gly Asn Ala Ser Lys Ser
            995                 1000                1005
Gly Ala Ser Asn Lys Lys Pro Glu Ile Ala Gln Val Thr Ser Ala
        1010                1015                1020
Tyr Ala Ala Ser Gly Thr Glu Gln Leu Ser Leu Ala Pro Gly Gln
        1025                1030                1035
Leu Ile Leu Ile Leu Lys Lys Asn Thr Ser Gly Trp Trp Gln Gly
        1040                1045                1050
Glu Leu Gln Ala Arg Gly Lys Lys Arg Gln Lys Gly Trp Phe Pro
        1055                1060                1065
Ala Ser His Val Lys Leu Leu Gly Pro Ser Ser Glu Arg Thr Met
        1070                1075                1080
Pro Thr Phe His Ala Val Cys Gln Val Ile Ala Met Tyr Asp Tyr
        1085                1090                1095
Met Ala Asn Asn Glu Asp Glu Leu Asn Phe Ser Lys Gly Gln Leu
        1100                1105                1110
Ile Asn Val Met Asn Lys Asp Asp Pro Asp Trp Trp Gln Gly Glu
        1115                1120                1125
Thr Asn Gly Leu Thr Gly Leu Phe Pro Ser Asn Tyr Val Lys Met
        1130                1135                1140
Thr Thr Asp Ser Asp Pro Ser Gln Gln Trp Cys Ala Asp Leu Gln
        1145                1150                1155
Ala Leu Asp Thr Met Gln Pro Thr Glu Arg Lys Arg Gln Gly Tyr
        1160                1165                1170
Ile His Glu Leu Ile Gln Thr Glu Glu Arg Tyr Met Asp Asp Asp
        1175                1180                1185
Leu Gln Leu Val Ile Glu Val Phe Gln Lys Arg Met Ala Glu Glu
        1190                1195                1200
Gly Phe Leu Thr Glu Ala Asp Met Ala Leu Ile Phe Val Asn Trp
        1205                1210                1215
Lys Glu Leu Ile Met Ser Asn Thr Lys Leu Leu Arg Ala Leu Arg
        1220                1225                1230
Val Arg Lys Lys Thr Gly Gly Glu Lys Met Pro Val Gln Met Ile
        1235                1240                1245
Gly Asp Ile Leu Ala Ala Glu Leu Ser His Met Gln Ala Tyr Ile
        1250                1255                1260
Arg Phe Cys Ser Cys Gln Leu Asn Gly Ala Thr Leu Leu Gln Gln
        1265                1270                1275
Lys Thr Asp Glu Asp Thr Asp Phe Lys Glu Phe Leu Lys Lys Leu
        1280                1285                1290
Ala Ser Asp Pro Arg Cys Lys Gly Met Pro Leu Ser Ser Phe Leu
```

```
                 1295                1300                1305

Leu Lys Pro Met Gln Arg Ile Thr Arg Tyr Pro Leu Leu Ile Arg
1310                1315                1320

Ser Ile Leu Glu Asn Thr Pro Gln Ser His Val Asp His Ser Ser
1325                1330                1335

Leu Lys Leu Ala Leu Glu Arg Ala Glu Leu Cys Ser Gln Val
1340                1345                1350

Asn Glu Gly Val Arg Glu Lys Glu Asn Ser Asp Arg Leu Glu Trp
1355                1360                1365

Ile Gln Ala His Val Gln Cys Glu Gly Leu Ala Glu Gln Leu Ile
1370                1375                1380

Phe Asn Ser Leu Thr Asn Cys Leu Gly Pro Arg Lys Leu Leu His
1385                1390                1395

Ser Gly Lys Leu Tyr Lys Thr Lys Ser Asn Lys Glu Leu His Ala
1400                1405                1410

Phe Leu Phe Asn Asp Phe Leu Leu Leu Thr Tyr Leu Val Arg Gln
1415                1420                1425

Phe Ala Ala Ala Ser Gly His Glu Lys Leu Phe Asn Ser Lys Ser
1430                1435                1440

Ser Ala Gln Phe Arg Met Tyr Lys Thr Pro Ile Phe Leu Asn Glu
1445                1450                1455

Val Leu Val Lys Leu Pro Thr Asp Pro Ser Gly Asp Glu Pro Val
1460                1465                1470

Phe His Ile Ser His Ile Asp Arg Val Tyr Thr Leu Arg Thr Asp
1475                1480                1485

Asn Ile Asn Glu Arg Thr Ala Trp Val Gln Lys Ile Lys Gly Ala
1490                1495                1500

Ser Glu Gln Tyr Ile Asp Thr Glu Lys Lys Arg Glu Lys Ala
1505                1510                1515

Tyr Gln Ala Arg Ser Gln Lys Thr Ser Gly Ile Gly Arg Leu Met
1520                1525                1530

Val His Val Ile Glu Ala Thr Glu Leu Lys Ala Cys Lys Pro Asn
1535                1540                1545

Gly Lys Ser Asn Pro Tyr Cys Glu Val Ser Met Gly Ser Gln Ser
1550                1555                1560

Tyr Thr Thr Arg Thr Leu Gln Asp Thr Leu Asn Pro Lys Trp Asn
1565                1570                1575

Phe Asn Cys Gln Phe Phe Ile Lys Asp Leu Tyr Gln Asp Val Leu
1580                1585                1590

Cys Leu Thr Met Phe Asp Arg Asp Gln Phe Ser Pro Asp Asp Phe
1595                1600                1605

Leu Gly Arg Thr Glu Val Pro Val Ala Lys Ile Arg Thr Glu Gln
1610                1615                1620

Glu Ser Lys Gly Pro Thr Thr Arg Arg Leu Leu Leu His Glu Val
1625                1630                1635

Pro Thr Gly Glu Val Trp Val Arg Phe Asp Leu Gln Leu Phe Glu
1640                1645                1650

Gln Lys Thr Leu Leu
1655

<210> SEQ ID NO 28
<211> LENGTH: 30
<212> TYPE: DNA
<213> ORGANISM: Artificial
```

```
<220> FEATURE:
<223> OTHER INFORMATION: Primer

<400> SEQUENCE: 28
gaaggagaac tcagaccggc tggagtggat                                     30

<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
gacagaggag cggtacatgg a                                              21

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
agctcccctg gttctggctt c                                              21

<210> SEQ ID NO 31
<211> LENGTH: 51
<212> TYPE: DNA
<213> ORGANISM: Artificial
<220> FEATURE:
<223> OTHER INFORMATION: Primer

<400> SEQUENCE: 31
gaattcagaa ccatggaaca aaagcttatt tctgaagaag acttggggcc c             51

<210> SEQ ID NO 32
<211> LENGTH: 37
<212> TYPE: DNA
<213> ORGANISM: Artificial
<220> FEATURE:
<223> OTHER INFORMATION: Primer

<400> SEQUENCE: 32
cctggattac aaggatgatg atgacaaatg actcgag                             37

<210> SEQ ID NO 33
<211> LENGTH: 21
<212> TYPE: PRT
<213> ORGANISM: Artificial
<220> FEATURE:
<223> OTHER INFORMATION: Description of Artificial Sequence: Peptide

<400> SEQUENCE: 33

Met Ala Gln Phe Pro Thr Pro Phe Gly Gly Ser Leu Asp Val Trp Ala
1               5                   10                  15

Ile Thr Val Glu Glu
            20

<210> SEQ ID NO 34
<211> LENGTH: 1270
<212> TYPE: PRT
<213> ORGANISM: Xenopus laevis

<400> SEQUENCE: 34
```

```
Met Ala Gln Phe Gly Thr Pro Phe Gly Gly Asn Leu Asp Ile Trp Ala
1               5                   10                  15

Ile Thr Val Glu Glu Arg Ala Lys His Asp Gln Gln Phe His Gly Leu
            20                  25                  30

Lys Pro Thr Ala Gly Tyr Ile Thr Gly Asp Gln Ala Arg Asn Phe Phe
            35                  40                  45

Leu Gln Ser Gly Leu Pro Gln Pro Val Leu Ala Gln Ile Trp Ala Leu
50                  55                  60

Ala Asp Met Asn Asn Asp Gly Arg Met Asp Gln Leu Glu Phe Ser Ile
65                  70                  75                  80

Ala Met Lys Leu Ile Lys Leu Lys Leu Gln Gly Tyr Pro Leu Pro Ser
                85                  90                  95

Ile Leu Pro Ser Asn Met Leu Lys Gln Pro Val Ala Met Pro Ala Ala
            100                 105                 110

Ala Val Ala Gly Phe Gly Met Ser Gly Ile Val Gly Ile Pro Pro Leu
            115                 120                 125

Ala Ala Val Ala Pro Val Pro Met Pro Ser Ile Pro Val Val Gly Met
130                 135                 140

Ser Pro Pro Leu Val Ser Ser Val Pro Thr Val Pro Pro Leu Ser Asn
145                 150                 155                 160

Gly Ala Pro Ala Val Ile Gln Ser His Pro Ala Phe Ala His Ser Ala
            165                 170                 175

Thr Leu Pro Lys Ser Ser Ser Phe Gly Arg Ser Val Ala Gly Ser Gln
            180                 185                 190

Ile Asn Thr Lys Leu Gln Lys Ala Gln Ser Phe Asp Val Pro Ala Pro
            195                 200                 205

Pro Leu Val Val Glu Trp Ala Val Pro Ser Ser Arg Leu Lys Tyr
            210                 215                 220

Arg Gln Leu Phe Asn Ser Gln Asp Lys Thr Met Ser Gly Asn Leu Thr
225                 230                 235                 240

Gly Pro Gln Ala Arg Thr Ile Leu Met Gln Ser Ser Leu Pro Gln Ser
            245                 250                 255

Gln Leu Ala Thr Ile Trp Asn Leu Ser Asp Ile Asp Gln Asp Gly Lys
            260                 265                 270

Leu Thr Ala Glu Glu Phe Ile Leu Ala Met His Leu Ile Asp Val Ala
            275                 280                 285

Met Ser Gly Gln Pro Leu Pro Pro Ile Leu Pro Pro Glu Tyr Ile Pro
290                 295                 300

Pro Ser Phe Arg Arg Val Arg Ser Gly Ser Gly Leu Ser Ile Met Ser
305                 310                 315                 320

Ser Val Ser Val Asp Gln Arg Leu Pro Glu Pro Glu Glu Glu
            325                 330                 335

Pro Gln Asn Ala Asp Lys Lys Leu Pro Val Thr Phe Glu Asp Lys Lys
            340                 345                 350

Arg Glu Asn Phe Glu Arg Gly Asn Leu Glu Leu Glu Lys Arg Arg Gln
            355                 360                 365

Ala Leu Leu Glu Gln Gln Arg Lys Glu Gln Glu Arg Leu Ala Gln Leu
            370                 375                 380

Glu Arg Ala Glu Gln Glu Arg Lys Glu Arg Glu Arg Gln Asp Gln Glu
385                 390                 395                 400

Arg Lys Arg Gln Gln Asp Leu Glu Lys Gln Leu Glu Lys Gln Arg Glu
            405                 410                 415

Leu Glu Arg Gln Arg Glu Glu Arg Arg Lys Glu Ile Glu Arg Arg
```

-continued

```
                420             425             430
Glu Ala Ala Lys Arg Glu Leu Glu Arg Gln Arg Gln Leu Glu Trp Glu
            435                 440                 445
Arg Asn Arg Arg Gln Glu Leu Leu Asn Gln Arg Asn Arg Glu Gln Glu
450                 455                 460
Asp Ile Val Val Leu Lys Ala Lys Lys Thr Leu Glu Phe Glu Leu
465                 470                 475                 480
Glu Ala Leu Asn Asp Lys Lys His Gln Leu Glu Gly Lys Leu Gln Asp
                485                 490                 495
Ile Arg Cys Arg Leu Thr Thr Gln Arg His Glu Ile Glu Ser Thr Asn
            500                 505                 510
Lys Ser Arg Glu Leu Arg Ile Ala Glu Ile Thr His Leu Gln Gln Gln
            515                 520                 525
Leu Gln Glu Ser Gln Gln Leu Leu Gly Lys Met Ile Pro Glu Lys Gln
530                 535                 540
Ser Leu Ile Asp Gln Leu Lys Gln Val Gln Asn Ser Leu His Arg
545                 550                 555                 560
Asp Ser Leu Leu Thr Leu Lys Arg Ala Leu Glu Thr Lys Glu Ile Gly
                565                 570                 575
Arg Gln Gln Leu Arg Asp Gln Leu Asp Glu Val Glu Lys Glu Thr Arg
            580                 585                 590
Ala Lys Leu Gln Glu Ile Asp Val Phe Asn Asn Gln Leu Lys Glu Leu
            595                 600                 605
Arg Glu Leu Tyr Asn Lys Gln Gln Phe Gln Lys Gln Asp Phe Glu
610                 615                 620
Thr Glu Lys Ile Lys Gln Lys Glu Leu Glu Arg Lys Thr Ser Glu Leu
625                 630                 635                 640
Asp Lys Leu Lys Glu Glu Asp Lys Arg Arg Met Leu Glu Gln Asp Lys
                645                 650                 655
Leu Trp Gln Asp Arg Val Lys Gln Glu Glu Arg Tyr Lys Phe Gln
            660                 665                 670
Asp Glu Glu Lys Glu Lys Arg Glu Glu Ser Val Gln Lys Cys Glu Val
            675                 680                 685
Glu Lys Lys Pro Glu Ile Gln Glu Lys Pro Asn Lys Pro Phe His Gln
            690                 695                 700
Pro Pro Glu Pro Gly Lys Leu Gly Gly Gln Ile Pro Trp Met Asn Thr
705                 710                 715                 720
Glu Lys Ala Pro Leu Thr Ile Asn Gln Gly Asp Val Lys Val Tyr
                725                 730                 735
Tyr Arg Ala Leu Tyr Pro Phe Asp Ala Arg Ser His Asp Glu Ile Thr
            740                 745                 750
Ile Glu Pro Gly Asp Ile Ile Met Val Asp Glu Ser Gln Thr Gly Glu
            755                 760                 765
Pro Gly Trp Leu Gly Gly Glu Leu Lys Gly Lys Thr Gly Trp Phe Pro
            770                 775                 780
Ala Asn Tyr Ala Glu Arg Met Pro Glu Ser Glu Phe Pro Ser Thr Thr
785                 790                 795                 800
Lys Pro Ala Ala Glu Thr Thr Ala Lys Pro Thr Val His Val Ala Pro
                805                 810                 815
Ser Pro Val Ala Pro Ala Phe Thr Asn Thr Ser Thr Asn Ser Asn
            820                 825                 830
Asn Trp Ala Asp Phe Ser Ser Thr Trp Pro Thr Asn Asn Thr Asp Lys
            835                 840                 845
```

```
Val Glu Ser Asp Asn Trp Asp Thr Trp Ala Ala Gln Pro Ser Leu Thr
    850                 855                 860

Val Pro Ser Ala Gly Gln His Arg Gln Arg Ser Ala Phe Thr Pro Ala
865                 870                 875                 880

Thr Val Thr Gly Ser Ser Pro Ser Pro Val Leu Gly Gln Gly Glu Lys
                885                 890                 895

Val Glu Gly Leu Gln Ala Gln Ala Leu Tyr Pro Trp Arg Ala Lys Lys
            900                 905                 910

Asp Asn His Leu Asn Phe Asn Lys Asn Asp Val Ile Thr Val Leu Glu
                915                 920                 925

Gln Gln Asp Met Trp Trp Phe Gly Glu Val Gln Gly Gln Lys Gly Trp
930                 935                 940

Phe Pro Lys Ser Tyr Val Lys Leu Ile Ser Gly Pro Leu Arg Lys Ser
945                 950                 955                 960

Thr Ser Ile Asp Ser Thr Ser Ser Glu Ser Pro Ala Ser Leu Lys Arg
                965                 970                 975

Val Ser Ser Pro Ala Phe Lys Pro Ala Ile Gln Gly Glu Glu Tyr Ile
            980                 985                 990

Ser Met Tyr Thr Tyr Glu Ser Asn Glu Gln Gly Asp Leu Thr Phe Gln
        995                 1000                1005

Gln Gly Asp Leu Ile Val Val Ile Lys Lys Asp Gly Asp Trp Trp
    1010                1015                1020

Thr Gly Thr Val Gly Glu Lys Thr Gly Val Phe Pro Ser Asn Tyr
    1025                1030                1035

Val Arg Pro Lys Asp Ser Glu Ala Ala Gly Ser Gly Gly Lys Thr
    1040                1045                1050

Gly Ser Leu Gly Lys Lys Pro Glu Ile Ala Gln Val Ile Ala Ser
    1055                1060                1065

Tyr Ala Ala Thr Ala Pro Glu Gln Leu Thr Leu Ala Pro Gly Gln
    1070                1075                1080

Leu Ile Leu Ile Arg Lys Lys Asn Pro Gly Gly Trp Trp Glu Gly
    1085                1090                1095

Glu Leu Gln Ala Arg Gly Lys Lys Arg Gln Ile Gly Trp Phe Pro
    1100                1105                1110

Ala Asn Tyr Val Lys Leu Leu Ser Pro Gly Thr Asn Lys Ser Thr
    1115                1120                1125

Pro Thr Glu Pro Pro Lys Pro Thr Ser Leu Pro Pro Thr Cys Gln
    1130                1135                1140

Val Ile Gly Met Tyr Asp Tyr Ile Ala Gln Asn Asp Asp Glu Leu
    1145                1150                1155

Ala Phe Ser Lys Gly Gln Val Ile Asn Val Leu Asn Lys Glu Asp
    1160                1165                1170

Pro Asp Trp Trp Lys Gly Glu Leu Asn Gly His Val Gly Leu Phe
    1175                1180                1185

Pro Ser Asn Tyr Val Lys Leu Thr Thr Asp Met Asp Pro Ser Gln
    1190                1195                1200

Gln Phe Arg Leu Gly Val Lys Pro Ala Gly Gly Ile Pro Ala Thr
    1205                1210                1215

Gly Asp Arg Pro Phe Ile Leu Phe Pro Phe Arg Asp Gly Pro Ser
    1220                1225                1230

Leu Leu Pro Asn Ala Phe Gln Ala Pro Pro Leu Ser Val Val Met
    1235                1240                1245
```

-continued

```
Ile Lys Phe Arg Cys Phe Thr Ala Pro Arg Phe Cys Pro Asp Met
    1250                1255                1260

Asn Val Lys Tyr Ile Asn Ile
    1265            1270

<210> SEQ ID NO 35
<211> LENGTH: 1094
<212> TYPE: PRT
<213> ORGANISM: Drosophila melanogaster

<400> SEQUENCE: 35

Met Asn Ser Ala Val Asp Ala Trp Ala Val Thr Pro Arg Glu Arg Leu
1               5                   10                  15

Lys Tyr Gln Glu Gln Phe Arg Ala Leu Gln Pro Gln Ala Gly Phe Val
            20                  25                  30

Thr Gly Ala Gln Ala Lys Gly Phe Phe Leu Gln Ser Gln Leu Pro Pro
        35                  40                  45

Leu Ile Leu Gly Gln Ile Trp Ala Leu Ala Asp Thr Asp Ser Asp Gly
    50                  55                  60

Lys Met Asn Ile Asn Glu Phe Ser Ile Ala Cys Lys Leu Ile Asn Leu
65                  70                  75                  80

Lys Leu Arg Gly Met Asp Val Pro Lys Val Leu Pro Pro Ser Leu Leu
                85                  90                  95

Ser Ser Leu Thr Gly Asp Val Pro Ser Met Thr Pro Arg Gly Ser Thr
            100                 105                 110

Ser Ser Leu Ser Pro Leu Asp Pro Leu Lys Gly Ile Val Pro Ala Val
        115                 120                 125

Ala Pro Val Val Pro Val Ala Pro Pro Val Ala Val Ala Thr Val
    130                 135                 140

Ile Ser Pro Pro Gly Val Ser Val Pro Ser Gly Pro Thr Pro Pro Thr
145                 150                 155                 160

Ser Asn Pro Pro Ser Arg His Thr Ser Ile Ser Glu Arg Ala Pro Ser
                165                 170                 175

Ile Glu Ser Val Asn Gln Gly Glu Trp Ala Val Gln Ala Ala Gln Lys
            180                 185                 190

Arg Lys Tyr Thr Gln Val Phe Asn Ala Asn Asp Arg Thr Arg Ser Gly
        195                 200                 205

Tyr Leu Thr Gly Ser Gln Ala Arg Gly Val Leu Val Gln Ser Lys Leu
    210                 215                 220

Pro Gln Val Thr Leu Ala Gln Ile Trp Thr Leu Ser Asp Ile Asp Gly
225                 230                 235                 240

Asp Gly Arg Leu Asn Cys Asp Glu Phe Ile Leu Ala Met Phe Leu Cys
                245                 250                 255

Glu Lys Ala Met Ala Gly Glu Lys Ile Pro Val Thr Leu Pro Gln Glu
            260                 265                 270

Trp Val Pro Pro Asn Leu Arg Lys Ile Lys Ser Arg Pro Gly Ser Val
        275                 280                 285

Ser Gly Val Val Ser Arg Pro Gly Ser Gln Pro Ala Ser Arg His Ala
    290                 295                 300

Ser Val Ser Ser Gln Ser Gly Val Gly Val Val Asp Ala Asp Pro Thr
305                 310                 315                 320

Ala Gly Leu Pro Gly Gln Thr Ser Phe Glu Asp Lys Arg Lys Glu Asn
                325                 330                 335

Tyr Val Lys Gly Gln Ala Glu Leu Asp Arg Arg Arg Lys Ile Met Glu
            340                 345                 350
```

```
Asp Gln Gln Arg Lys Glu Arg Glu Arg Glu Arg Lys Arg Glu
        355                 360                 365
Glu Ala Asp Lys Arg Glu Lys Ala Arg Leu Glu Ala Glu Arg Lys Gln
        370                 375                 380
Gln Glu Glu Leu Glu Arg Gln Leu Gln Arg Gln Arg Glu Ile Glu Met
385                 390                 395                 400
Glu Lys Glu Glu Gln Arg Lys Arg Glu Leu Glu Ala Lys Glu Ala Ala
                405                 410                 415
Arg Lys Glu Leu Glu Lys Gln Arg Gln Glu Trp Glu Gln Ala Arg
                420                 425                 430
Ile Ala Glu Met Asn Ala Gln Lys Glu Arg Glu Gln Glu Arg Val Leu
        435                 440                 445
Lys Gln Lys Ala His Asn Thr Gln Leu Asn Val Glu Leu Ser Thr Leu
    450                 455                 460
Asn Glu Lys Ile Lys Glu Leu Ser Gln Arg Ile Cys Asp Thr Arg Ala
465                 470                 475                 480
Gly Val Thr Asn Val Lys Thr Val Ile Asp Gly Met Arg Thr Gln Arg
                485                 490                 495
Asp Thr Ser Met Ser Glu Met Ser Gln Leu Lys Ala Arg Ile Lys Glu
            500                 505                 510
Gln Asn Ala Lys Leu Leu Gln Leu Thr Gln Glu Arg Ala Lys Trp Glu
        515                 520                 525
Ala Lys Ser Lys Ala Ser Gly Ala Ala Leu Gly Gly Glu Asn Ala Gln
    530                 535                 540
Gln Glu Gln Leu Asn Ala Ala Phe Ala His Lys Gln Leu Ile Ile Asn
545                 550                 555                 560
Gln Ile Lys Asp Lys Val Glu Asn Ile Ser Lys Glu Ile Glu Ser Lys
                565                 570                 575
Lys Glu Asp Ile Asn Thr Asn Asp Val Gln Met Ser Glu Leu Lys Ala
            580                 585                 590
Glu Leu Ser Ala Leu Ile Thr Lys Cys Glu Asp Leu Tyr Lys Glu Tyr
        595                 600                 605
Asp Val Gln Arg Thr Ser Val Leu Glu Leu Lys Tyr Asn Arg Lys Asn
    610                 615                 620
Glu Thr Ser Val Ser Ser Ala Trp Asp Thr Gly Ser Ser Ser Ala Trp
625                 630                 635                 640
Glu Glu Thr Gly Thr Thr Val Thr Asp Pro Tyr Ala Val Ala Ser Asn
                645                 650                 655
Asp Ile Ser Ala Leu Ala Ala Pro Val Asp Leu Gly Gly Pro Ala
            660                 665                 670
Pro Glu Gly Phe Val Lys Tyr Gln Ala Val Tyr Glu Phe Asn Ala Arg
        675                 680                 685
Asn Ala Glu Glu Ile Thr Phe Val Pro Gly Asp Ile Ile Leu Val Pro
    690                 695                 700
Leu Glu Gln Asn Ala Glu Pro Gly Trp Leu Ala Gly Glu Ile Asn Gly
705                 710                 715                 720
His Thr Gly Trp Phe Pro Glu Ser Tyr Val Glu Lys Leu Glu Val Gly
                725                 730                 735
Glu Val Ala Pro Val Ala Ala Val Glu Ala Pro Val Asp Ala Gln Val
            740                 745                 750
Ala Asp Thr Tyr Asn Asp Asn Ile Asn Thr Ser Ser Ile Pro Ala Ala
        755                 760                 765
```

-continued

```
Ser Ala Asp Leu Thr Ala Ala Gly Asp Val Glu Tyr Tyr Ile Ala Ala
    770                 775                 780

Tyr Pro Tyr Glu Ser Ala Glu Glu Gly Asp Leu Ser Phe Ser Ala Gly
785                 790                 795                 800

Glu Met Val Met Val Ile Lys Lys Glu Gly Trp Trp Thr Gly Thr
                    805                 810                 815

Ile Gly Ser Arg Thr Gly Met Phe Pro Ser Asn Tyr Val Gln Lys Ala
            820                 825                 830

Asp Val Gly Thr Ala Ser Thr Ala Ala Glu Pro Val Glu Ser Leu
            835                 840                 845

Asp Gln Glu Thr Thr Leu Asn Gly Asn Ala Ala Tyr Thr Ala Ala Pro
    850                 855                 860

Val Glu Ala Gln Glu Gln Val Tyr Gln Pro Leu Pro Val Gln Glu Pro
865                 870                 875                 880

Ser Glu Gln Pro Ile Ser Ser Pro Gly Val Gly Ala Glu Glu Ala His
                    885                 890                 895

Glu Asp Leu Asp Thr Glu Val Ser Gln Ile Asn Thr Gln Ser Lys Thr
            900                 905                 910

Gln Ser Ser Glu Pro Ala Glu Ser Tyr Ser Arg Pro Met Ser Arg Thr
    915                 920                 925

Ser Ser Met Thr Pro Gly Met Arg Ala Lys Arg Ser Glu Ile Ala Gln
    930                 935                 940

Val Ile Ala Pro Tyr Glu Ala Thr Ser Thr Glu Gln Leu Ser Leu Thr
945                 950                 955                 960

Arg Gly Gln Leu Ile Met Ile Arg Lys Lys Thr Asp Ser Gly Trp Trp
                    965                 970                 975

Glu Gly Glu Leu Gln Ala Lys Gly Arg Arg Gln Ile Gly Trp Phe
            980                 985                 990

Pro Ala Thr Tyr Val Lys Val Leu  Gln Gly Gly Arg Asn  Ser Gly Arg
    995                 1000                1005

Asn Thr  Pro Val Ser Gly Ser  Arg Ile Glu Met Thr  Glu Gln Ile
    1010                1015                1020

Leu Asp  Lys Val Ile Ala Leu  Tyr Pro Tyr Lys Ala  Gln Asn Asp
    1025                1030                1035

Asp Glu  Leu Ser Phe Asp Lys  Asp Asp Ile Ile Ser  Val Leu Gly
    1040                1045                1050

Arg Asp  Glu Pro Glu Trp Trp  Arg Gly Glu Leu Asn  Gly Leu Ser
    1055                1060                1065

Gly Leu  Phe Pro Ser Asn Tyr  Val Gly Pro Phe Val  Thr Ser Gly
    1070                1075                1080

Lys Pro  Ala Lys Ala Asn Gly  Thr Thr Lys Lys
    1085                1090
```

<210> SEQ ID NO 36
<211> LENGTH: 12
<212> TYPE: DNA
<213> ORGANISM: Artificial
<220> FEATURE:
<223> OTHER INFORMATION: 5' UTR

<400> SEQUENCE: 36
ggatccacca tg                                                        12

<210> SEQ ID NO 37
<211> LENGTH: 12
<212> TYPE: DNA

```
-continued
<213> ORGANISM: Artificial
<220> FEATURE:
<223> OTHER INFORMATION: Portion of cloning linker sequence

<400> SEQUENCE: 37
aagcttgggc cc                                                        12
```

ESE GENES AND PROTEINS

This application claims the benefit under 35 U.S.C. 371 from PCT Application No. PCT/CA99/00375, filed Apr. 27, 1999, the disclosure of which is incorporated by reference herein in its entirety, which claims the benefit of Canadian Application Serial No. 2,230,201, filed Apr. 27, 1998 and U.S. Provisional Application Ser. No. 60/118,739, filed Feb. 5, 1999, now abandoned, the disclosures of which are incorporated by reference herein in their entirety.

FIELD OF THE INVENTION

This invention relates to novel mammalian proteins encoded by the Ese1 and Ese2 genes which are involved in endocytosis, vesicular trafficking and regulation of the actin cytoskeleton.

BACKGROUND OF THE INVENTION

Endocytosis via clathrin-coated pits is a multipstep process (1, 2). Clathrin heavy and light chains are brought to the plasma membrane through association with a heterotetrameric complex known as clathrin adaptor complex 2, o-r AP-2. At coated pits, the membrane is bent through the assembly of clathrin triskelion into a caged lattice. The GTPase Dynamin is also recruited to the neck of coated pits where it assembles into a collar for vesicle fission (4, 5). Recruitment of Dynamin to coated pits is believed to require the Amphiphysin I/II heterodimer (6), as these proteins bind Dynamin in vivo and amphiphysin proteins are required for endocytosis in yeast (7). In addition, ectopic expression of either Amphiphysin I or II by themselves (6), or the isolated SH3 domain of Amphiphysin I blocks endocytosis (8, 9). Recent data has revealed that the Rab5 small GTPase is required for sequestration of ligands such as transferrin and Epidermal Growth Factor into coated pits in vitro (10). The mechanism by which these components interact to regulate coated pit assembly, cargo sequestration, followed by vesicle fission is not yet understood.

From biochemical, cell biological and genetic analysis it is clear that additional components such as kinases, phosphatases, ubiquitin conjugating enzymes as well as lipid modifying enzymes are required for clathrin-coat and vesicle formation (1, 11, 12, 13, 14, 15, 16, 17, 18, 19). Indeed there is also strong evidence for a requirement of the actin cytoskeleton in endocytosis and several proteins which may facilitate this connection (1, 7, 20, 21, 22, 23, 24, 25).

The Eps15 protein was discovered in a search for substrates of the Epidermal Growth Factor Receptor (26). In 1995, Benmerah et. al. reported that Eps15 is constitutively associated with α-adaptin of the AP2 complex (27). The Eps15 protein has also been localized to the neck of clathrin-coated pits by immunoelectron microscopy (28, 29). Recently, two groups have used dominant inhibitory mutants of Eps15, or antibodies against Eps15 (or the related protein Eps15R), to demonstrate that Eps15 proteins are required for endocytosis via clathrin-coated pits (30, 31). Eps15 contains three large structural domains (26, 32). The N-terminal third contains three copies of an EH domain (for Eps15 Homology domain) (32, 33). The central region of Eps15 forms an extended coiled-coil, which is followed by a complex C-terminus containing SH3-binding motifs (34), a large number of DPF repeats (Aspartic acid-Proline-Phenylalanine), and α-adaptin binding sequences (31, 35, 36). The full length Eps15R protein has a similar overall organization (34). Both Eps15 and Eps15R can be alternatively spliced to produce numerous smaller proteins(37).

A protein with similar overall organization has been identified in *Saccharomyces cerevisiae* named Pan1p. Genetic analysis of PAN1 has revealed that this gene is required for endocytosis and for organization of the actin cytoskeleton (23, 38). Like Eps15 and Eps15R in mammals, the Pan1p protein has N-terminal EH domains followed by a central coiled-coil domain and C-terminal proline-rich sequences. A second EH domain containing protein, End3p, has also been described in *S. cerevisiae* which is required for endocytosis and regulation of the actin cytoskeleton (21, 39). Co-immunoprecipitation studies have shown that Pan1p and End3p form a complex in vivo (40). Indeed, overexpression of End3p can suppress the phenotype of pan1-4 hypomorphic mutants, and Pan1p is mislocalized in end3 mutants indicating that these proteins function together (40). Additional studies have revealed that the EH domains of Pan1p bind to yeast homologues of mammalian clathrin-binding proteins, AP180 and CALM (yAP180A and yAP180B), through NPF motifs (Asparagine-Proline-Phenylalanine) in the yAP180 C-termini(25). These data have led to a proposal that the Pan1p:End3p complex functions as a multivalent adaptor to coordinate protein—protein interactions during endocytosis (25, 40). At least two additional proteins are predicted to bind to the Pan1p:End3p complex in vivo, as strong genetic interactions have been detected between PAN1 and SJL1(25), and between PAN1 and RSP5 (41). SJL1 encodes a phosphatidylinositol polyphosphate-5-phosphatase protein which is related to mammalian synaptojanin (42) and has a C-terminal NPF motif predicted to bind to EH domains in Pan1p (or End3p) (25, 43). RSP5 encodes an E3 ubiquitin-protein ligase which may bind to the C-terminal polyproline sequences in Pan1p through one of its three WW domains (25).

Numerous SH3 domain containing proteins have been implicated in the regulation of endocytosis (44). These include Amphiphysin I(45) and II(6, 46, 47, 48), Rsv161/Rsv167(7), Actin Binding Protein-1(49), Endophilin/SH3P4/8/13 (50, 51) and Grb2 (52). Kay and coworkers have reported the isolation of several novel SH3 encoding cDNAs (53).

The present inventors have identified novel mammalian proteins containing both EH and SH3 domains, which have been named Ese1 and Ese2. Sequence and functional analysis of the full length proteins have implicated these proteins in receptor mediated endocytosis via clathrin coated pits and therefore the proteins have been named Ese1 and Ese2 respectively (Ese: for EH-domain and SH3 domain regulator of Endocytosis). Also identified are several mammalian alternative transcript proteins two of which are named Ese1L and Ese2L.

SUMMARY OF THE INVENTION

In accordance with one series of embodiments, this invention provides isolated nucleic acids corresponding to or relating to the nucleic acid sequences disclosed herein which encode the mammalian Ese1 and Ese2 proteins.

The invention more specifically provides isolated nucleic acids corresponding to or relating to the nucleic acid sequences disclosed herein which encode the mouse Ese1 and Ese2 proteins.

One of ordinary skill in the art is now able to identify and isolate mammalian Ese protein genes or cDNAs which are allelic variants of the disclosed sequences or are homologues thereof, in other species, including humans, using standard hybridisation screening and PCR techniques. The mammalian polynucleotide may be in the form of DNA, genomic DNA, cDNA, mRNA and various fragments and portions of the gene sequence encoding Ese proteins.

Homologues of the mammalian Ese protein genes are generally those sequences which share at least 80% sequence identity, preferably at least 90% sequence identity to the mammalian Ese gene sequence.

In a further embodiment, the invention provides cDNA sequences encoding murine Ese1 and Ese2 proteins comprising the nucleotide sequences of Sequence ID NOS: 1, 2, 4 and 5.

In a further embodiment, the invention provides cDNA sequences encoding murine Ese1L and Ese2L proteins comprising the nucleotides sequences of Sequence ID NOS: 22, 23, 25 and 26.

Also provided are portions of the Ese gene sequences useful as probes or PCR primers or for encoding fragments, functional domains or antigenic determinants of Ese proteins. The probes can be routinely used to screen and identify homologues of the Ese gene or portions thereof while primers are useful in PCR assays for the amplification of desired portions of the selected Ese gene.

The invention also provides portions of the disclosed nucleic acid sequences comprising about 10 consecutive nucleotides to nearly the complete disclosed nucleic acid sequences. The invention provides isolated nucleic acid sequences comprising sequences corresponding to at least 10, preferably 15 and more preferably at least 20 consecutive nucleotides of the Ese genes as disclosed or enabled herein or their complements.

In addition, the isolated nucleic acids of the invention include any of the above described nucleotide sequences included in a vector. Expression vectors comprising the nucleotide sequences are provided along with suitable host cells transfected with such expression vectors.

In accordance with a further series of embodiments, this invention provides substantially pure mammalian Ese proteins, fragments of these proteins and fusion proteins including these proteins and fragments.

In accordance with a further series of embodiments, this invention provides substantially pure mutant mammalian Ese proteins, fragments of these proteins and fusion proteins including these mutant proteins and fragments.

In a further embodiment, the invention provides amino acid sequences encoding murine Ese1 and Ese2 proteins comprising the amino acid sequences of Sequence ID NOS: 3 and 6.

In a further embodiment, the invention provides amino acid sequences encoding murine Ese1L and Ese2L proteins, which are alternative transcripts, comprising the amino acid sequences of Sequence ID NOS: 24 and 27.

The proteins, fragments and fusion proteins have utility, as described herein, for the preparation of polyclonal and monoclonal antibodies to murine and mammalian Ese proteins, for the identification of binding partners of the mammalian Ese proteins and for diagnostic and therapeutic methods, as described herein. For these uses, the present invention provides substantially pure proteins, polypeptides or derivatives of polypeptides which comprise portions of the mammalian Ese amino acid sequences disclosed or enabled herein and which may vary from about 4 to 5 amino acids to the complete amino acid sequence of the proteins. The invention provides substantially pure proteins or polypeptides comprising sequences corresponding to at least 5, preferably at least 10 and more preferably 50 or 100 consecutive amino acids of the mammalian Ese proteins disclosed or enabled herein. Monoclonal antibodies having suitably specific binding affinity for the antigenic regions of a mammalian Ese protein are prepared by the use of corresponding hybridoma cell lines. In addition, polyclonal antibodies may be prepared by inoculation of animals with suitable peptides which add suitable specific binding affinities for antigenic regions of an Ese protein.

In a further embodiment of the invention, a process is provided for producing mammalian Ese proteins comprising culturing one of the above described transfected host cells under suitable conditions, to produce the Ese protein by expressing the DNA sequence.

The proteins of the invention may be isolated and purified by any conventional method suitable in relation to the properties revealed by the amino acid sequences of these proteins.

Alternatively, cell lines may be produced which express or over-express the Ese gene products, allowing purification of the proteins for biochemical characterisation, large-scale production, antibody production and patient therapy.

For protein expression, eukaryotic or prokaryotic expression systems may be generated in which an Ese gene sequence is introduced into a plasmid or other vector which is then introduced into living cells. Constructs in which the Ese cDNA sequences containing the entire open reading frame is inserted in the correct orientation into an expression plasmid may be used for protein expression. Alternatively, only portions of the sequence may be inserted. Prokaryotic or eukaryotic expression systems allow various important functional domains of the proteins to be recovered as fusion proteins and used for binding, structural and functional studies and also for the generation of appropriate antibodies.

The present invention includes effective fragments, analogues of the Ese proteins described herein. "Effective" fragments or analogues retain the activity of the described Ese proteins to regulate endocytosis, vesicular trafficking and actin dynamics. The term "analogue" extends to any functional and/or chemical equivalent of a mammalian Ese protein including mimetics and includes proteins having one or more conservative amino acid substitutions, proteins incorporation unnatural amino acids and proteins having modified side chains.

In accordance with a further embodiment of the invention, antibodies are enabled which bind specifically to the Ese proteins disclosed herein. Polyclonal or monoclonal antibodies may be prepared using conventional methods. Antibodies may also be prepared to individual selected domains of the Ese proteins, as described herein.

In a further embodiment, the invention provides pharmaceutical compositions containing an Ese protein, fragment or mimetic thereof or a non-functional mutant Ese protein, fragment or mimetic thereof for the treatment of mammalian disorders which involve abnormal endocytosis, vesicular trafficking and actin dynamics leading to altered cellular functioning. Administration of a therapeutically active amount of a pharmaceutical composition of the present invention means an amount effective, at dosages and for periods of time necessary to achieve the desired result. The composition comprises an Ese protein and a pharmaceutically acceptable carrier.

In accordance with a further embodiment, the invention provides a method for identifying binding partners of the Ese proteins disclosed herein. Such methods in general include various assays including those including radiolabelling of the Ese proteins. Other methods may include but are not restricted to phage display, affinity purification techniques, expression cloning and the yeast 2-hybrid system, as described herein.

In accordance with a further embodiment of the present invention, is a method for identifying proteins which phosphorylate Ese proteins. Such method includes known phosphorylation assays.

The identification of proteins or peptides interact with or bind to Ese proteins can provide the basis for the design of peptide antagonists or agonists of Ese protein function or for the design of peptide antagonists or agonists of Ese protein binding partners which affect Ese protein function. Further, the structure of these peptides determined by standard techniques such as protein NMR or x-ray crystallography can provide the structural basis for the design of improved small molecule drugs.

In accordance with a further embodiment, the present invention also provides for the production of mouse models or transgenic non-human animal models for the study of mammalian Ese gene function, for the screening of candidate pharmaceutical compounds, for the creation of in vitro mammalian cell cultures which express the Ese proteins or in which an Ese gene has been inactivated by knock-out deletion, and for the evaluation of potential therapeutic interventions.

The invention enables a transgenic animal, including a transgenic insect, wherein the genome of the animal or of an ancestor of the animal has been modified by introduction of a transgene comprising mammalian Ese genes under the transcriptional control of tissue restricted regulatory elements including the mouse mammary-tumour virus long term repeat sequences.

Transgenic animals with inappropriate expression of Ese proteins may be examined for phenotypic changes, for example abnormal cellular development or abnormal cellular signalling, vesicular trafficking and actin dynamics and may be used to screen for compounds with potential as pharmaceuticals. Compounds which provide reversal of the phenotypic changes are candidates for development as pharmaceuticals.

Transgenic animals in accordance with the invention can be created by introducing a DNA sequence encoding a selected Ese protein either into embryonic stem (ES) cells of a suitable animal such as a mouse, by transfection or microinjection, or into a germ line or stem cell by a standard technique of oocyte microinjection. Such methods of producing animal models are fully described in the literature.

In accordance with another aspect of the present invention is a method for screening a candidate compound for effectiveness as an antagonist of an Ese protein comprising:
  (a) providing an assay method for determining the endocytotic regulatory capacity of an Ese protein; and
  (b) determining the endocytotic regulatory capacity of the Ese protein in the presence or absence of the candidate compound, wherein a reduced level of endocytosis in the presence of the candidate compound indicates antagonist activity of the compound.

In accordance with another aspect of the present invention is a method for treating in a mammal a disorder associated with an undesired level of endocytotic activity of an Ese protein comprising administering to the mammal an effective amount of a substance selected from the group consisting of:
  (a) an Ese protein antagonist;
  (b) an antibody which binds specifically to an Ese protein;
  (c) an antisense strand comprising a nucleic acid sequence complementary to the sequence or fragment of the sequence and capable of hybridizing to the nucleic acid sequence encoding an Ese protein;
  (d) an agent which down regulates the expression of the Ese gene encoding for an Ese protein;
  (e) an antagonist of an Ese protein binding partner; and
  (f) an Ese agonist.

According to another aspect of the present invention is a method for suppressing in a mammal, the abnormal proliferation of a cell capable of being stimulated to proliferate by a growth factor receptor, the method comprising administering to the mammal an effective amount of a Ese protein antagonist, an Ese agonist or an antibody which binds specifically to an Ese protein.

According to yet another aspect of the present invention is a method for preventing viral infection in a mammal, said method comprising administering to the mammal an effective amount of an Ese protein antagonist, an Ese agonist or an antibody which binds specifically to an Ese protein or an Ese mutant protein not capable of regulating endocytosis.

According to a further aspect of the present invention is a method for promoting endocytosis, vesicular trafficking and/or actin dynamics in selected cells in a mammal in need of such treatment, said method comprising administering to the mammal an effective amount of an Ese protein or an active analogue, mimic or fragment thereof.

According to a further aspect of the present invention is a method for blocking clathrin-mediated endocytosis in cultured cells or in selected cells in a mammal in need of such treatment, said method comprising overexpressing Ese1 protein or an active analogue, mimic or fragment thereof.

According to yet a further aspect of the present invention is a method for regulating endocytosis, vesicular trafficking and/or actin dynamics in cultured cells or in selected cells in a mammal in need of such treatment, said method comprising providing an Ese 1–Eps 15 complex and further providing a protein binding partner to bind to the complex to regulate components of the endocytic pathway. One such binding partner is dynamin.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

SUMMARY OF TABLES AND DRAWINGS

A detailed description of the preferred embodiments are provided herein below with reference to the following tables and drawings in which:

Table 1 shows the alignment of mouse Ese1 (SEQ ID NO:3) and Ese2 (SEQ ID NO:6) protein sequences. EH, coiled-coil and SH3 domains are as indicated.

Table 2 shows the alignment of protein sequences of the Ese family in mouse (Ese 1: SEQ ID NO:3; Ese 2: SEQ ID NO:6), *Xenopus* (SEQ ID NO:34) and *Drosophila* (SEQ ID NO:35). EH and SH3 domains are indicated with overlines. Amino acid identities are bolded and similarities are boxed.

FIG. 1 shows a Northern blot demonstrating expression of Ese1 and Ese2 genes in various adult tissues.

Figure 2A:
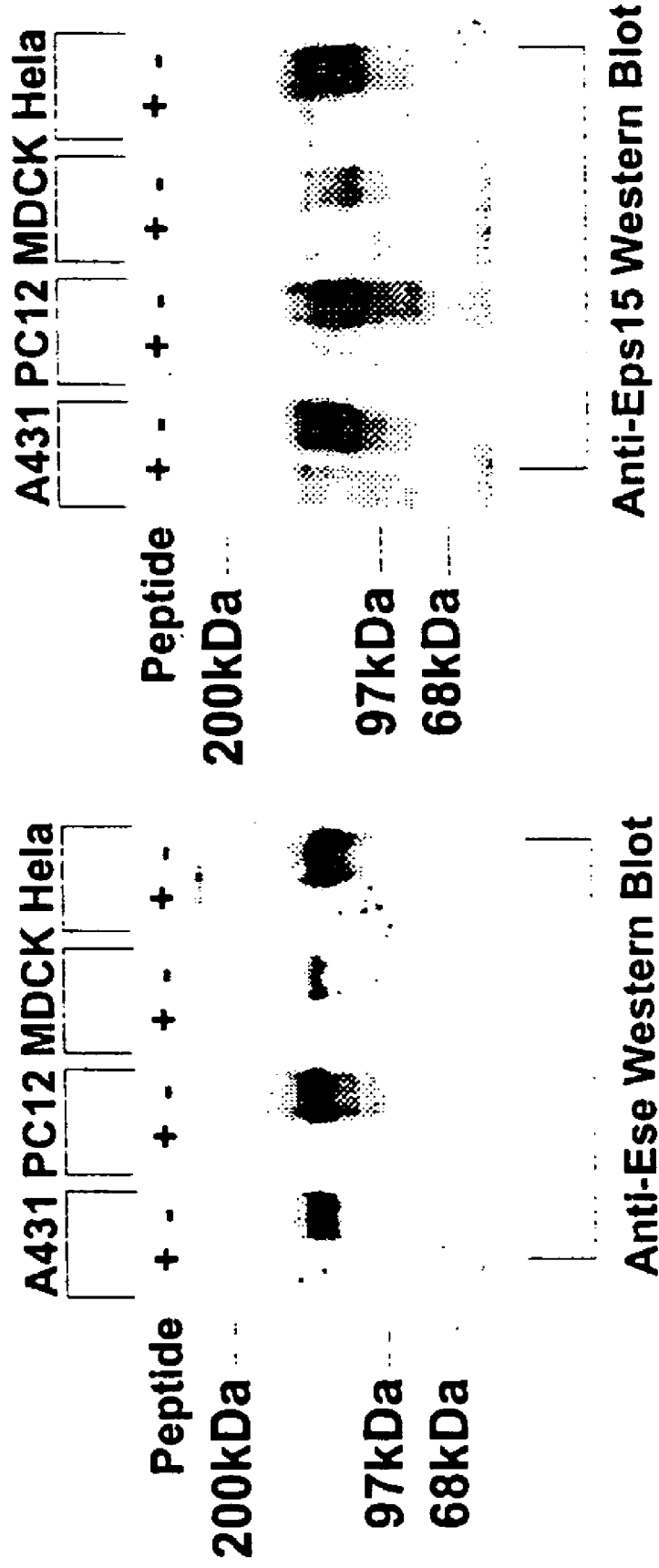

FIG. 2A shows Western blots demonstrating the association of Ese and Eps15 proteins in vivo. Endogenous Ese1 proteins were precipitated with Rabbit anti-peptide antisera against the N-terminus of Ese1. Immunoprecipitates were then analyzed on western blots for the presence of Ese1/2 with Chicken anti-Ese antisera or for co-precipitation of Eps15 with Rabbit antisera raised against the C-terminus of Eps15.

FIG. 2B shows alternative transcripts from the Ese1 and Ese 2 genes which code for Ese 1L (amino acids 1204 to 1714 of Sequence ID No:24) and Ese 2L (amino acids 1143 to 1658 of Sequence ID No:27) proteins respectively, with C-terminal DBL/PH and C2 domains. Ese 1 and Ese 2 sequence junctions are indicated in bold letters.

Figure 3A:
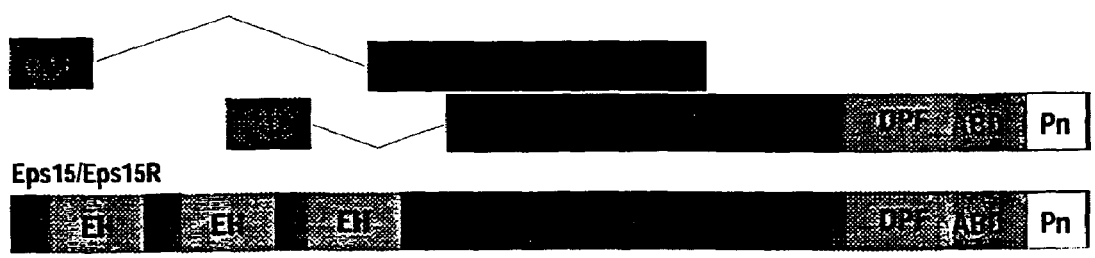

FIG. 3A shows Ese and Eps15 associate in vivo. This schematic representation of association of Eps15/Eps15R with Ese1 in the yeast two-hybrid screen. Ese1 coiled-coil domain fused with the Gal4 DNA binding domain (DBD) interacted with Eps15/Eps15R Gal4 activation domain (AD) fusions. The AD-Eps15/Eps15R diagram represents the shortest interacting coding region isolated.

Figure 3B:
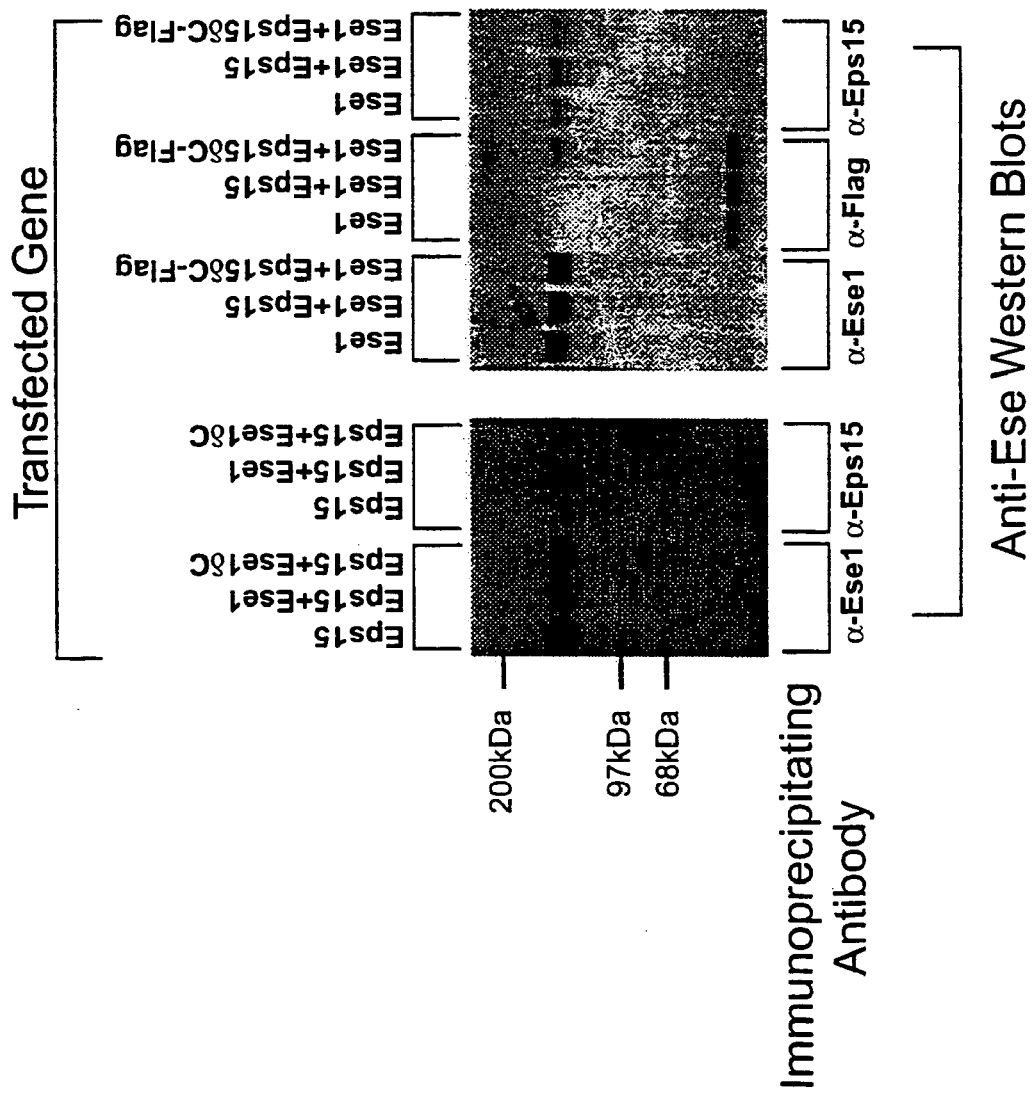

FIG. 3B shows association of Ese and Eps15 C-terminal deletion mutants. Cos-1 cells were transfected with pcDNA3Eps15, pcDNA3Ese1 or the C-terminal deletion mutants pcDNA3Ese1δC and pcDNA3Eps15δC-Flag as indicated. Cell lysates were immunoprecipitated with rabbit anti-Ese1 or rabbit anti-Eps15 (left panel); rabbit anti-Ese1, mouse anti-Flag or rabbit anti-Eps15 (right panel). Panels represent western blots to detect the presence of Ese1 in each immunoprecipitation. A 90 kDa Ese1 protein exists in the third and sixth lanes on the left panel which is the C-terminally truncated Ese1 protein which is co-immunoprecipitated in a complex with Eps15 in the sixth lane. Also, to be noted is the precipitation of Ese1 with anti-Flag monoclonal antibody in the sixth lane of the right panel experiment. In this case, Ese1 has been precipitated in a complex with the C-terminally truncated Eps15C protein.

Figure 4:
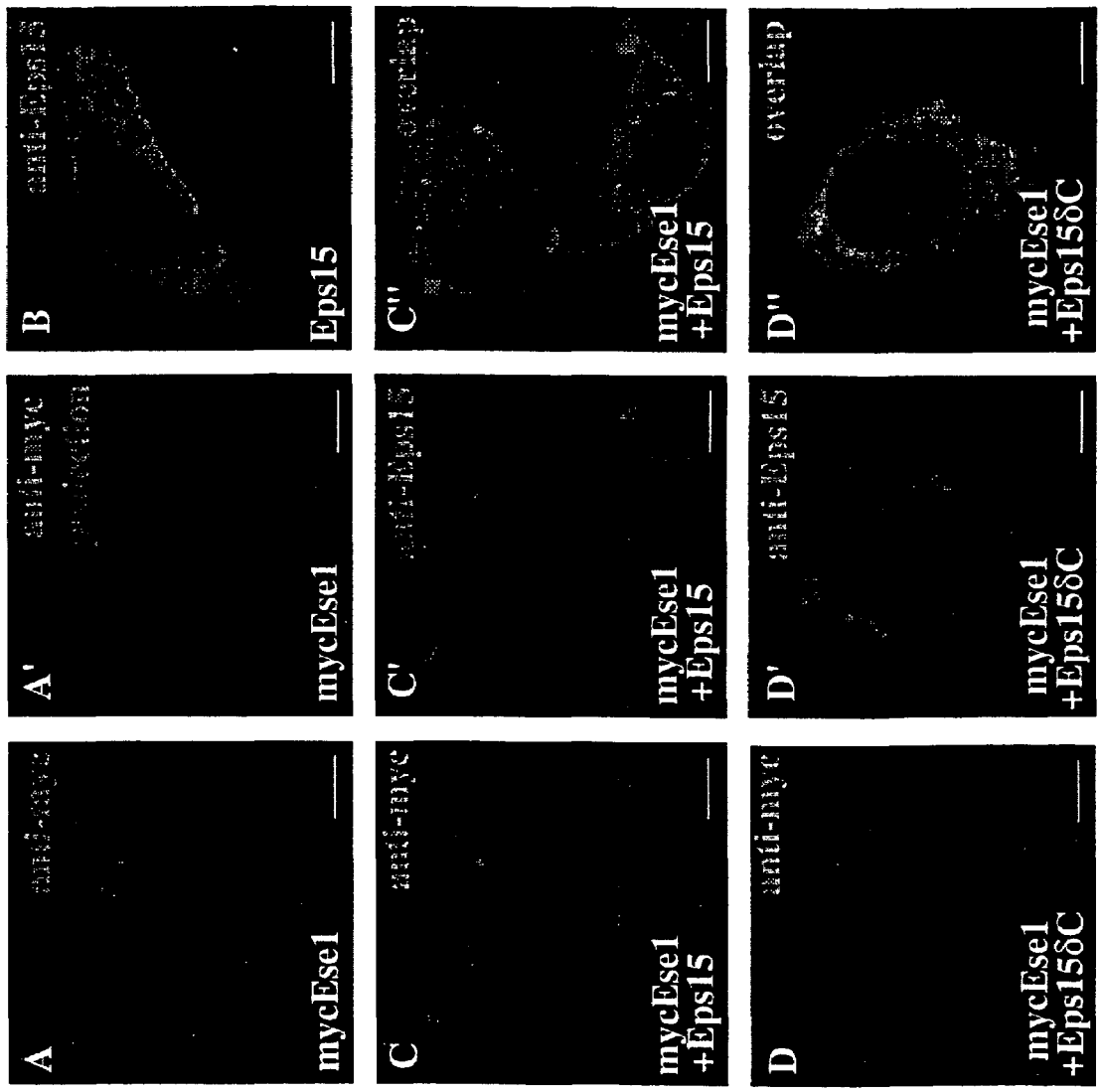

FIG. 4 shows confocal immunofluorescent micrographs of Cos cells transfected with myc-Ese1 (A, A'); Eps15 (B); myc-Ese1+Eps15 (C, C', C") or myc-Ese1+Eps15δC (D, D' and D"). Frames C" and D' represents the overlapping images from frames C/C' and D/D', respectively. Overlap in frames C" and D" are indicated in yellow. Scale bar is equal to 10 microns.

Figure 5A:
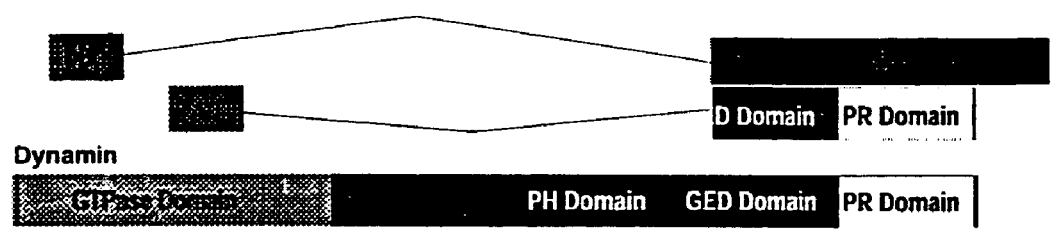
Figure 5B:
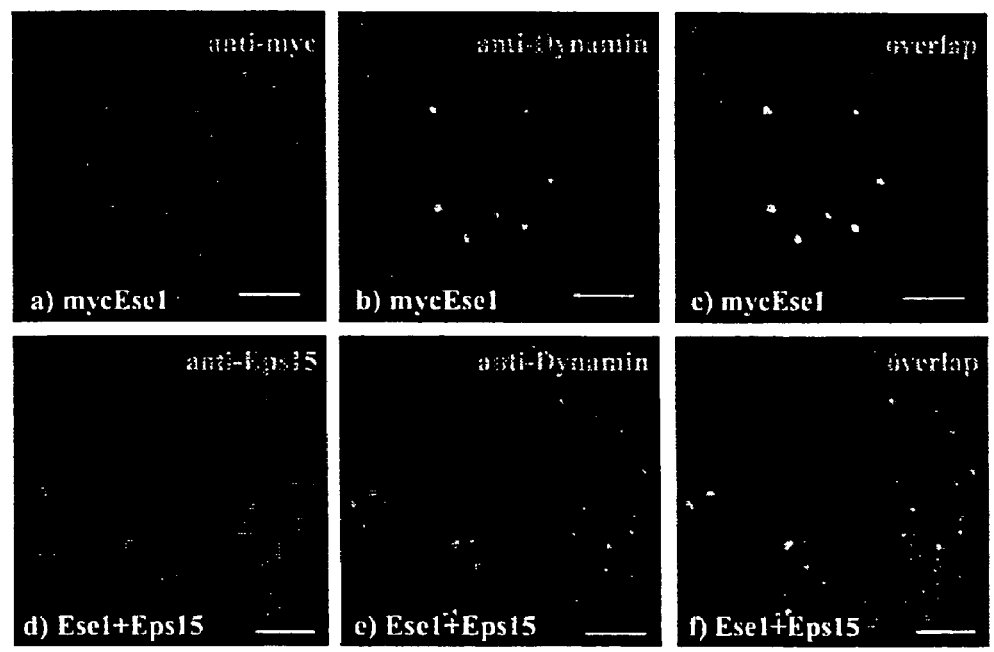

FIGS. 5A and 5B show that Ese1 links to Dynamin and Eps15. FIG. 5A is a schematic representation of association between Dynamin and Ese1 in the yeast two-hybrid screen. Ese1 SH3 domains fused with the Gal4 DNA binding domain (DBD) interacted with Dynamin Gal4 activation domain (AD) fusions. The AD-Dynamin diagram represents the shortest interacting coding region isolated. FIG. 5B shows confocal immunofluorescent microscopy to detect transfected mycEse1 (frame a), transfected Eps15 (frame d) or endogenous Dynamin (frames b and e) in transfected Cos cells. Frame c and f represents the overlapping images from frames a/b and d/e respectively. Scale bar is equal to 10 microns.

Figure 6:
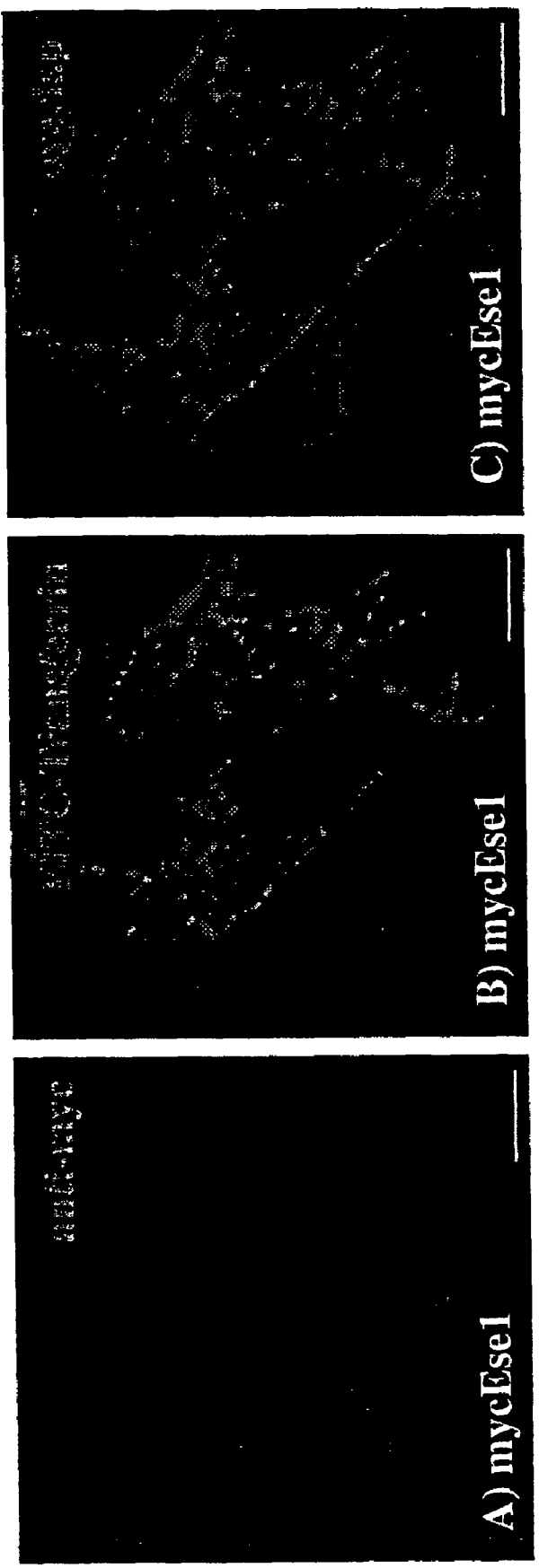

FIG. 6 shows Ese1 overexpression blocks endocytosis of Transferrin in Cos-1 cells. Confocal immunofluorescent microscopy was used to detect transfected mycEse1 (frame A), internalized FITC-labeled Transferrin (frame B). Overlapping images are shown in frame C revealing that Ese1 overexpression blocks clathrin-mediated endocytosis of Transferrin. Mononuclear morphologically normal cells from both transfected and untransfected groups where assessed for internalization of transferrin. Scale bar is equal to 10 microns.

Figure 7:
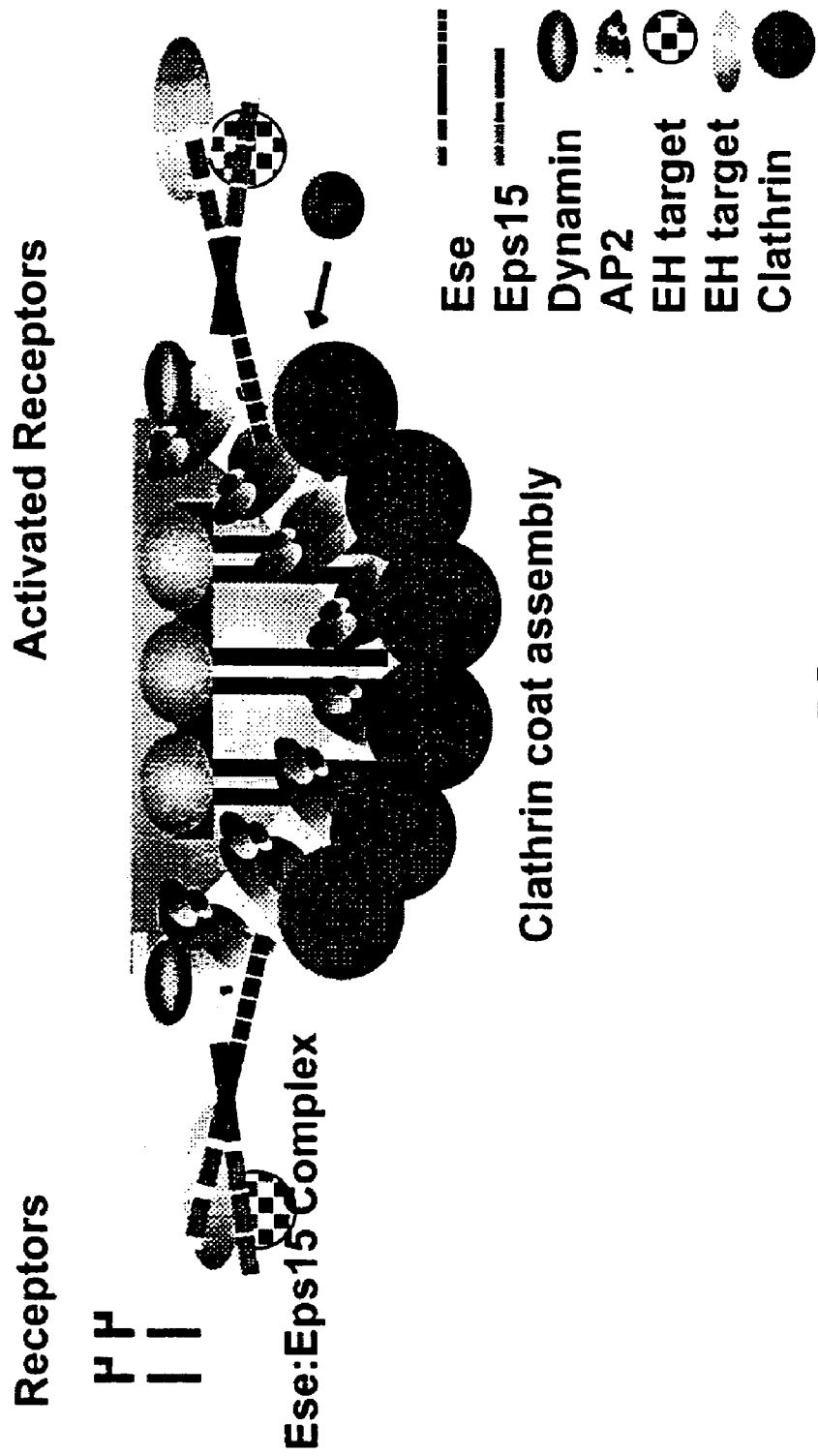

FIG. 7 shows a proposed model for Ese regulation of Endocytosis.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

Sequencing of Murine Ese1 and Ese2 Genes

The full length murine Ese1 cDNA was sequenced (Sequence ID NO:1). It encodes a sequence of 1213 amino (Sequence ID NO:3) having a predicted molecular weight of 137 kDa. Murine Ese2 cDNA was also sequenced (Sequence ID NO:4) and encodes a sequence of 1197 amino acids (Sequence ID NO:6) having a predicted molecular weight of 135.7 kDa.

The full length Ese proteins are predicted to encode two N-terminal EH domains followed by a coiled-coil domain and five SH3 domains (Tables 1 and 2). Several Ese1 isolated clones contain only $SH3_A$, $SH3_B$ and $SH3_E$ domains. Indeed, the $SH3_C$ domain was not included in the original human SH3P17 partial cDNA. In addition, expressed sequence tags from the Ese1 gene have been found in the public databases which skip sequences encoding individual EH domains or regions of the coiled-coil domain indicating that this gene is subject to complex alternative splicing and has the potential to encode for many distinct proteins. The predicted Ese2 protein on the other hand encodes a C-terminal extension of 45 amino acids in comparison to the human SH3P18 partial cDNA, suggesting that this gene is also alternatively spliced. The Ese proteins are 53% identical over the full length of Ese1 (645 of 1213 residues in Ese1 line up with identical residues in Ese2) and are related to the Ese protein from *Xenopus* which has recently been submitted to genebank (Accession # AF032118) and *Drosophila* (59) (Table 2). *Xenopus* Intersectin is 81% identical to mouse Ese1 and 54% identical to mouse Ese2 suggesting that Intersectin is an Ese1 orthologue (980/1213 residues of mouse Ese1 and 645/1198 residues of mouse Ese2 line up with identical residues in the *Xenopus* protein). *Drosophila* Dynamin associated protein, Dap160-1 is 32% identical to both mouse Ese proteins (393/1213 residues of mouse Ese1 and 387/1198 residues of mouse Ese2 line up with identical residues in the *Drosophila* protein). These homologies extend over the entire length of Dap160-1, except that Dap160-1 has only four SH3 domains corresponding to the first, second, fourth and fifth SH3 domains of the mouse Ese proteins. Additional sequence analysis reveals the presence of a very large number of potential phosphorylation sites and at least one SH3-binding consensus (60) in the N-terminus of each Ese protein.

The two EH domains of Ese 1 are highly related to the respective EH domains in Ese2 and these Ese EH domains are most closely related those found in Eps15 and Eps15R, two mammalian protein which are required for endocytosis through clathrin-coated pits. EH domains have also been identified in End3 and Pan1p which are yeast partners proteins required for endocytosis. The central third of both Ese proteins are predicted to encode an extended coiled-coil which is a domain typically associated with protein—protein association through dimerization or tetrarnerization as noted for Eps15 (29, 54). Besides the homology between Ese1 and Ese2, the Ese1 SH3 domains are most closely related to SH3 domains from Myosin IB in Acanthamoeba ($SH3_A$), Myosin IB in *Entamoeba* ($SH3_B$), the YFR024 hypothetic yeast protein (SH3$_C$), Myosin IB from Acanthamoeba (SH3$_D$) and Myosin IC from Acanthamoeba (SH3$_E$). The same homologies are noted for SH3 domains from Ese2 with the exception of SH3$_A$ which is most similar to the SH3 domain from βPIX, SH3$_C$ which is most similar to an SH3 domain from the mouse Ray protein and SH3$_D$ which is most similar to the SH3 domain from Dictyostelium myosin IB. Additional sequence analysis reveals the presence of a very large number of potential phosphorviation sites in the Ese proteins and a single SH3 binding consensus in the N-termini of each Ese protein.

With the knowledge of the amino acid sequences for Ese1 and Ese2 proteins and the alternative transcripts Ese1L and Ese2L, there is provided in accordance with the present invention antibodies which recognize epitopes within these proteins and which can be raised to provide information on the characteristics of the protein as well as for any mutant form of these proteins. The generation of antibodies enables the visualization of the protein in mammalian cells and tissues using Western blotting as described herein. Antibodies to the Ese1 or Ese2 proteins also allows for the use of immunocytochemistry and immunofluorescence techniques in which the proteins are visualized directly in cells and tissues as described herein. This is most helpful in order to establish the subcellular location of the protein and the tissue specificity of the protein.

In general, methods for the preparation of antibodies are well known. In order to prepare polyclonal antibodies, fusion proteins containing defined portions or all of the Ese1 or Ese2 proteins or any of their alternative transcripts can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by affinity chromatography. The sera can then be used to probe protein extracts run on a polyacrylamide gel to identify the Ese1 or Ese2 protein, alternative transcript or any mutant thereof. Alternatively, synthetic peptides can be made to the antigenic portions of these proteins and used to innoculate the animals.

Methods to produce monoclonal antibodies which specifically recognize mammalian Ese1 or Ese2 proteins or portions thereof, are known in the art. In general, cells actively expressing the protein are cultured or isolated from tissues and the cell extracts isolated. The extracts or recombinant protein extracts, containing the Ese1 or Ese2 protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable lines of clones is established which produce the antibody. The monoclonal antibody can then be purified by affinity chromatography using Protein A or Protein G Sepharose.

The Ese proteins may be isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chomatography) or by precipitation (immunoprecipitation). Polyacrylamide gel electrophoresis can also be used to isolate the Ese proteins based on the molecular weight of the protein, charge properties and hydrophobicity.

Similar procedures to those mentioned can be used to purify the protein from cells transfected with vectors containing an Ese gene (e.g. baculovirus systems, yeast expression systems and eukaryotic expression systems).

The purified proteins can be used in further biochemical analyses to establish secondary and tertiary structure which may aid in the design of pharmaceuticals to interact with the protein, alter the protein charge configuration or charge interaction with other proteins or alter its function.

The Ese proteins can also be purified from the creation of fusion proteins which are expressed and recovered from prokaryotic or eukaryotic cells. The fusion proteins can be purified by affinity chromatography based upon the fusion vector sequence. The Ese protein can then be further purified from the fusion protein by enzymatic cleavage of the fusion protein.

Expression of Ese Genes

In order to determine where the Ese genes are expressed Northern analysis was performed on mRNA derived from several adult mouse tissues (FIG. 1). These genes are both widely expressed and reveal a complex pattern of alternatively spliced transcripts. The highest levels of Ese1 mRNA were noted in brain, heart and skeletal muscle. Brain and skeletal muscle mRNA also contain an unusually large transcript which may be as much as 15 kb in length. Interestingly, these tissues express high levels of many proteins involved in synaptic vesicle recycling and endocytosis.

The Northern blot reveals the presence of many alternative mRNA transcripts for both Ese1 and Ese2. In addition, numerous Ese1 expressed sequence tags have been identified which skip sequences encoding individual EH domains or regions of the coiled-coil domain indicating that this gene has the potential to encode for many distinct proteins. Indeed, the SH3$_C$ domain was spliced out of the human SH3P17 partial cDNA described by Sparks 1996 (53). The predicted Ese2 protein on the other hand encodes a C-terminal extension of 45 amino acids in comparison to the human SH3P18 partial cDNA, revealing that this gene is also alternatively spliced. Lung, liver and kidney express high levels of a 2.4 kb Ese2 transcript which is significantly smaller than the 3591 bp sequence required to code for our full Ese2 protein as shown in Table 1 or 2, indicating that a major isoform of Ese2 has only a subset of the domains described above.

Alternative Splicing of Ese 1, Ese2 Transcripts

Additional transcripts from both Ese1 and Ese2 genes have also been characterized. One of the Ese1 clones isolated from a mouse brain cDNA library contained an extended reading frame. PCR was used from mouse brain cDNA libraries to identify the remaining coding sequences from this transcript. The splicing event which produces this extended protein adds an additional 501 amino acids to Ese1, and codes for a DBL homology domain, a Pleckstrin homology (PH) domain and a C2 domain (FIG. 2B). DBL and PH domains are found together in guanine nucleotide exchange factors for the Rho family of small GTPases. This long form of Ese1 is therefore expected to function as an activator of Rho-GTPases, which in turn regulate the actin cytoskeleton and numerous signal transduction pathways (61). C2 domains on the other hand are $Ca^{++}$ activated membrane binding domains and protein—protein interaction domains (62). A number of expressed sequence tages which code for a novel C2 domain fused to the sequence coding for the last 11 amino acids of Ese2 have been identified. PCR was used to isolate sequences coding for alternatively spliced exon(s) which can be included C-terminal to the SH3 domains but before the stop codon. The alternatively spliced exon(s) of Ese2 also code for a DBL/PH+C2 domain cassette which can be included within the Ese2 transcript (FIG. 2B).

As the Ese genes are subject to complex alternative splicing to produce proteins with novel predicted functions (eg. regulation of the cytoskeleton and membrane-binding), the alternative proteins are named as modifications of Ese. The Ese1 and Ese2 long forms described in FIG. 2B are called Ese1L and Ese2L, respectively. In the event that specific domains are spliced out from the transcripts coding for Ese1 and Ese2 proteins as shown in Table 2, then the name is listed as an Eseδ variant. The protein encoded by the spliced variant in the original SH3P17 clone is designated as $Ese1\delta S_C$ to indicate removal of $SH3_C$.

In an embodiment of the present invention the knowledge of the Ese1 and Ese2 gene sequences and their expression in heterologous cell systems can be used to demonstrate structure-function relationships as well as provide for cell lines for the purposes of drug screening. Ligating the Ese1 or Ese2 cDNA sequence into a plasmid expression vector to transfect cells is a useful method to test the proteins influence on various cellular biochemical parameters including the identification of substrates, binding partners as well as activators and inhibitors of the proteins. Plasmid expression vectors containing either the entire, or portions thereof, Ese1 or Ese2 can be used in in vitro mutagenesis experiments which will identify portions of the protein crucial for regulatory function.

The Ese1 or Ese2 cDNA sequence (or Ese1L and Ese2L cDNA sequence) can be manipulated in studies to understand the expression of the gene and its product, to achieve production of large quantities of the protein for functional analysis, for antibody production, and for patient therapy. The changes in the sequence may or may not alter the expression pattern in terms of relative quantities, tissue-specificity and functional properties. Partial or full-length cDNA sequences which encode for the Ese1 or Ese2 protein (or alternative transcripts thereof), modified or unmodified, may be ligated to bacterial expression vectors. *E. coli* can be used using the T7 RNA polymerase/promoter system using two plasmids or by labeling of plasmid-encoded proteins, or by expression by infection with M13 Phage mGPI-2. *E. coli* vectors can also be used with Phage lamba regulatory sequences, by fusion protein vectors (eg. lacZ and trpE), by maltose-binding protein fusions, and by glutathione-S-transferase fusion proteins.

Alternatively, the Ese 1 or Ese2 protein or alternative transcripts thereof can be expressed in insect cells using baculoviral vectors, or in mammalian cells using vaccinia virus. For expression in mammalian cells, the cDNA sequence may be ligated to heterologous promoters, such as the simian virus (SV40) promoter in the pSV2 vector and introduced into cells, such as COS cells to achieve transient or long-term expression. The stable integration of the chimeric gene construct may be maintained in mammalian cells by biochemical selection, such as neomycin, G418 and purimycin.

Any of the Ese1 or Ese2 cDNA sequences can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous Ese1 or Ese2 gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, electroporation, lipofection, DEAE dextran, microinjection, or by protoplast fusion. Alternatively, the cDNA can be introduced by infection using viral vectors.

Eukaryotic expression systems can be used for many studies of the Ese1 or Ese2 gene and gene product(s) including determination of proper expression and post-translational modifications for full biological activity, identifying regulatory elements located in the 5' region of the Ese1 or Ese2 gene and their role in tissue regulation of protein expression, production of large amounts of the normal and mutant protein for isolation and purification, to use cells expressing the Ese1 or Ese2 protein or alternative transcripts thereof as a functional assay system for antibodies generated against the protein or to test effectiveness of pharmacological agents, or as a component of a signal transduction system, to study the function of the normal complete protein, specific portions of the protein, or of naturally occurring and artificially produced mutant proteins.

Using the techniques mentioned, the expression vectors containing the Ese1 or Ese2 cDNA sequence or portions thereof can be introduced into a variety of mammalian cells from other species or into non-mammalian cells. It is understood that the cDNA sequences for use in the present invention include those sequences disclosed herein encoding Ese1, Ese1L, Ese2 and Ese2L proteins.

The recombinant cloning vector, according to this invention, comprises the selected DNA of the DNA sequences of this invention for expression in a suitable host. The DNA is operatively linked in the vector to an expression control sequence in the recombinant DNA molecule so that Ese1 or Ese2 proteins or alternative transcripts thereof can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cell which may be transfected with the vector of this invention may be selected from the group consisting of *E. coli, pseudomonas, bacillus subtillus, bacillus stearothermophilus*, or other bacili; other bacteria, yeast, fungi, insect, mouse or other animal, plant hosts, or human tissue cells.

Subcellular Localisation of Ese Proteins

To determine the subcellular localization of Ese1, a myc-epitope tagged version of this protein (mycEse1) was engineered. This tagged protein was expressed in Cos cells and detected by confocal immunofluoresence using the mouse anti-myc monoclonal antibody 9E10 (FIG. 4). Interestingly, the transfected Ese1 protein is highly concentrated into circular domains (FIGS. 4A and 4A') which are present throughout transfected cells (compare single optical section in FIG. 4A with the projection of all sections through the same cell shown in 4A'). In some optical sections rings of fluorescent staining surrounding a non-staining area were observed suggesting that the Ese1 induced structures are vesicles rather than inclusion bodies (data not shown and FIG. 6). Ese1 overexpressed in 10T1/2, BHK and Hela cells using the vaccinia virus T7 expression system is also localized to large circular domains (data not shown). This concentration of ectopically expressed Ese1 contrasts with the localization of Eps15 in transiently transfected cells, Eps15 being dispersed throughout the cell (FIG. 4B). Ese1 and Eps15 proteins form a complex in vivo and yet localize to distinct subcellular compartments in transfected Cos cells. We therefore determined the localization of both mycEse1 and Eps15 in Cos cells co-transfected with both genes. In co-transfected cells, mycEse1 is still found in circular domains (FIG. 4C). Interestingly, the transfected Eps15 is now also partially co-localized with Ese1 in the same circular domains (FIG. 4C' and C").

The C-terminal third of Eps15 contains several regions which are required for association with α-adaptin of the AP2 clathrin adaptor complex (31). It has been shown that this region of Eps15 is not required for its association with Ese1 (FIG. 4). In order to test whether Eps15 function may be required for Ese localization, mycEse1 and Eps15δC have been co-transfected. Interestingly, mycEse1 localization is still partially colocalized with Eps15δC (FIGS. 4D, D' and D") but is no longer found to be concentrated within circular structures, indicating that Ese1 requires Eps15 function for distinctive subcellular localization in transfected cells. In addition, these data suggest that the Ese1:Eps15 complex may require association with AP2 which binds to the Eps15 C-terminus in order to form the large circular domains in Ese1 transfected cells.

Identification of Binding Partners of Ese Proteins

In order to identify Ese partners, a systematic analysis was initiated of each domain for binding partners using the yeast two hybrid system. The central coiled-coil domain of Ese1 from amino acid 330 to 732 was fused to the GAL4 DNA binding domain and transformed into the Y190 reporter strain together with plasmid cDNA libraries from several tissue sources. Yeast colonies were selected for growth on Histidine minus plates in the presence of 40 mM 3-amino triazole to select for interaction between library encoded GAL4 activation domain fusions and the GAL4 DNA binding domain Ese1 coiled-coil bait. Yeast colonies which survived selection for expression of the His3 gene where also tested for induction of the integrated LacZ gene which is GAL4 responsive in Y190. Prey plasmids were recovered from 37 positive yeast colonies which were selected for expression of both His3 and LacZ. Several classes of cDNA were recovered in this screen. One class included Eps15 which was isolated twice and Eps15R which was isolated from four yeast colonies. Interestingly these clones were all partial cDNA fusions which minimally included C-terminal sequences from the central coiled-coil domain to the 3'UTR (FIG. 3A). In the case of Eps15, the positive clones start from amino acid 306 and 376 whereas in Eps15R the N-terminal boundary of clones were amino acid 4, 10, 222 and 386. These data indicate that minimal sequences required for interaction between the Ese1 coiled-coil domain and Eps15(R) include either or both of the central coiled-coil and/or the C-terminal third of these proteins.

The Ese proteins were analyzed in vivo to test for their association with Eps15 or Eps15R. Polyclonal antisera were raised in chickens against a GST fusion containing the C-terminus of Ese1 from amino acid 665 to the stop codon. This region of Ese1 contains all five of the SH3 domains. In addition, polyclonal antisera were generated in rabbits against a peptide representing the first 21 amino acids of Ese1. Cell lysates were prepared from A431, PC12, MDCK and Hela cells which represent cell lines from several distinct tissue types and species. The rabbit anti-peptide antisera were used to precipitate Ese1 from each lysate and precipitates were analyzed by western blotting using the chicken anti-Ese sera. In each cell line the presence of several specific bands in the range of 150 kDa were observed which were precipitated in the absence but not in the presence of the peptide to which the sera was generated (FIG. 3A). Thus the Ese1 protein is expressed in many tissue culture cells and runs in a range consistent with the predicted molecular weight of 137 kDa. The same samples were also analyzed for co-immunoprecipitation of Eps15 proteins. In each case multiple Eps15 proteins were detected which co-purify with Ese1. The anti-Ese1 peptide antisera and commercially available anti-Eps15 antisera which were used were raised against epitopes which are not shared by these proteins indicating that Ese1 and Eps15 are constitutively associated partners in vivo. This association is reminiscent of the previously detected complex between two EH domain containing yeast proteins, End3p and Pan1p.

Ese1 and Eps15 proteins both contain central coiled-coil motifs. In addition, Ese1 contains multiple C-terminal SH3 domains while Eps15 contains SH3-binding motifs. In order to map the regions of each protein which are required for their association in vivo, C-terminal truncations of each (Eps15δC and Ese1δC) were generated. Full length Eps15 was co-transfected into Cos-1 cells together with either full length Ese1 or C-terminally truncated Ese1δC. Cell lysates were precipitated with either rabbit anti-Eps15 or with rabbit anti-Ese1, and precipitates were western blotted with chicken anti Ese1 antisera. Interestingly, the C-terminally truncated Ese1 protein was efficiently immunoprecipitated in a complex with Eps15 using anti-Eps15 sera. In a reciprocal experiment Cos-1 cells were transfected with Ese1 alone or together with Eps15 or C-terminally truncated Eps15 which had been Flag-epitope tagged (Eps15δC-Flag). Cell lysates were prepared and immunoprecipitated with either rabbit anti-Ese1, mouse anti-Flag, or rabbit anti-Eps15 antibodies. These immunoprecipitations were also western blotted to analyze for the presence of Ese1 (FIG. 3B). The anti-Flag antibody efficiently precipitated Ese1 from cells expressing Flag-tagged Eps15δC indicating that the C-terminally truncated Eps15 protein can bind to Ese1 in vivo. The Ese1 and Eps15 proteins are therefore associated through interaction of their central coiled-coil regions and do not require the presence of SH3 and SH3-binding motifs in their respective C-termini.

In addition to the identification of Eps15 and Eps15R in the yeast two hybrid screen with the coiled-coil domain bait of Ese1, the following were also identified as Ese binding proteins: TSG101 (accession #U52945), meningioma expressed antigens 6/11 (accession #U94780 for mea6), β-tropomyosin, rabaptin5 (accession #D86066), Adora2a (accession #Y13345), L1 lipid binding protein (accession #K02109) and numerous cytokeratins and laminins. Novel genes identified in this screen are detailed below.

Also performed was a yeast two hybrid screen using amino acids 665–1213 of Ese1 as bait. This screen led to the isolation of the following clones which produced GAL4 Activation domain fusions which bound to this SH3 domain bait of Ese1. The Ese-binding proteins identified in our SH3 screen were the cb1-b oncoprotein (accession #U26712), Dynamin II (accession #L31398), KIAA0268 (accession #D87742), Jerky (accession #U35730), hnRNP-K (accession #L29769), SAP49 (accession #L35013) and SOS-1 (accession #Z11574). Novel genes identified in this screen are detailed below and several novel clones as outlined below.

These results demonstrate that the novel Ese genes and the proteins that they encode function in a complex with Eps15 proteins to regulate endocytosis together. In addition, this complex contains binding sites for numerous other proteins. Furthermore, with the identification of several potential phosphorylation sites on the Ese proteins, these results also suggest that whether or not complexed with Eps15, Ese proteins are involved in intracellular signalling processes which are likely to lead to altered cellular activity. Many Ese partners have been identified in these studies. Also revealed is a novel method to identify more Ese partners. Yeast cells have a complex formed by two EH domain proteins (Pan1p and End3p) which regulates both endocytosis as well as the actin cytoskeleton. Indeed, the Eps15 protein has been reported to regulate both endocytosis and the actin cytoskeleton (1). As Eps15 and Ese function together, and Ese contain many protein—protein interaction surfaces on this complex, strongly suggesting that the Ese proteins and their binding proteins are critical regulators of Eps15:Ese functions in vivo.

Ese and Dynamin

Yeast two-hybrid screens using baits composed of the GAL4 DNA-binding domain fused to individual SH3 domains of Ese1 were performed to identify Ese partners which bind the SH3s of this multi-domain protein. Initial screens with SH3B and SH3C domain fusions resulted in the artifactual isolation of many proline-rich fragments which did not represent real Ese partners. Screens were then done with GAL4 fusions containing all five SH3 domains from amino acid 665 to 1213. Forty one His3+/LacZ+ colonies from such screens were selected for further analysis. Six colonies were found to encode fragments of the Dynamin II gene and two encoded fragments of Dynamin I (FIG. 5A). All Dynamin II clones had 5' start sites between amino acid 252 and 278 and terminated within the 3' UTR. The two Dynamin I clones were identical and contained a small coding rregion from amino acid 673 to the C-terminus. Dynamin sequences contained within each Ese1-interacting clone therefore minimally code for the proline-rich motifs (FIG. 5A) which are known to bind SH3 domains in vitro (44). This result is consistent with the interaction between Dap160 and Dynamin that has been recently described in *Drosophila* (59). To determine the significance of Ese1: Dynamin binding, functional interactions between these proteins were tested for. MycEse1 was transfected into Cos cells. The subcellular localization of Dynamin in Ese1 overexpressing cells was analyzed by staining for endogenous Dynamin and the myc tag on Ese1. In many Ese1 transfectants, endogenous Dynamin was recrutied to the Ese1 staining vesicles and both proteins were co-localized (FIG. 5B, panel a, b and c). These results demonstrate that Ese proteins bind Dynamin and can regulate its subcellular localization. Given that Ese1 functions in a complex with Eps15 and Ese can regulate the subcellular distribution of Dynamin, it was investigated whether Eps15 also co-localized with Dynamin. Eps15 transfected into Cos cells was diffusely localized (FIG. 4). Endogenous Dynamin was not concentrated and was therefore not visable in Eps 15 transfected cells (data not shown). When Ese1 and Eps15 were co-transfected however, Eps15 and endogenous Dynamin are colocalized on the Ese1 induced circles (FIG. 5, panels d, e and f) indicating that all three proteins co-localize at these structures.

Ese and Epsin Family Proteins

In order to identify additional Ese partners, a fusion between GAL4-DBD and the N-terminal EH domain region of Ese1 (amino acids 1-393) was generated. This fusion protein was also used in yeast two hybrid screens with several GAL4 activation domain cDNA libraries. A total of 11 His3+/LacZ+ colonies were identified as containing library encoded fusion proteins which interact with the Ese1 EH-domain bait. Two of these clones coded for mouse homologues of the Epsin protein which was recently identified on the basis of its affinity for Eps15, and α-adaptin and is required for clathrin-mediated endocytosis (63). The two Epsin clones code for C-terminal fragments from amino acids 403 and 470 respectively. One of the Ese1 EH-domain interacting clones which was obtained coded for a C-terminal fragment of a novel Epsin-family protein (63, 64). This cDNA has been independently isolated and named Ibp-2 in accession #AF057286. The Ibp2 clone which has been identified includes amino acids 326 to 509 of the partial coding sequence in Genbank. Each Epsin family protein which has been isolated contains a C-terminal region which codes for three copies of an NPF motif. This is also the region of Epsin which binds to Eps15. It has previously been shown that AP-2 can independently bind both Epsin and Eps 15. It is now demonstrated that the C-terminus of Epsin family proteins can bind not only to the EH domains of Eps15 but also to the EH domains of Ese1. These data suggest that either multiple Epsin proteins exist in the Ese:Eps15 complex or the interaction between individual proteins in various AP-2:Epsin:Eps15:Ese:Dynamin complexes may be subject to dynamic rearrangement during clathrin coated pit formation, invagination and scission. Also identified was a mammalian homologue of *drosophila*, SINA, seven in absentia.

Ese1 Overexpression Blocks Endocytosis

Overexpression of Pan1p in yeast induces phenotypes which are identical to those observed in pan1 loss-of-fucntion mutants (65) suggesting that by altering the relative ratios of Pan1p to its numerous partners, the function of higher order Pan1p complexes may be blocked. As the Ese:Eps15 complex contains many protein—protein interaction domains which bind partners including Dynamin, Epsin and AP-2, it was thought that overexpressed Ese1 may disrupt the formation of higher order complexes between Ese proteins and partners. It was therefore tested whether clathrin-mediated endocytosis was functional in myc Ese1 overexpressing cells. Cos-1 cells were transfected with myc-tagged Ese1, and 48 hrs post transfection, FITC-labelled Transferrin was added to cultures for 30 minutes. Cells were then fixed and analyzed for expression of mycEse1 and for internalization of Transferrin. As shown in FIG. 6, transfected cells do not internalize transferrin in contrast to their untransfected neighbors. Cell counts in a representative experiment indicate that 96% of Ese1 overexpressing cells do not internalize labeled transferrin (N=46) whereas 100% of untransfected cells were capable of clathrin-mediated endocytosis (N=100). It appears that overexpression of Dynamin II may override the Ese1 induced endocytic block. These data indicate that overexpression of Ese1 blocks endocytosis and this may be through sequestration of Dynamin or other Ese1 partners into non-productive binary complexes during endocytosis or recycling of the tranferrin receptor. Overexpressed Ese1 would therefore be functioning as a dominant inhibitory protein through recruitment of partners into non-productive complexes which do not contain all of the necessary components for endocytosis to proceed.

Taken together, these studies demonstrate the identification and isolation of novel mammalian Ese proteins encoded by novel Ese genes which are involved in the regulation of endocytosis via clathrin-coated pits, vesicular trafficking and actin dynamics. These studies also demonstrate the identification and isolation of two alternative transcripts of the genes, named Ese1L and Ese2L. The process of endocytosis including receptor-mediated endocytosis as well as pinocytosis or non-eceptor mediated endocytosis. The novel Ese proteins of the present invention appear to function to regulate endocytosis involving the formation of clathrin-coated pits by the polymerization of clathrin into a lattice along the cytosolic face of a region of membrane causing the region to expand inward. Ultimately, the pit pinches off from the membrane, and the clathrin cage is completed thus producing a coated vesicle. Through the binding of Esp15 to form an Ese-Eps15 complex via a central binding region, the complex can recruit other proteins such as, Epsin, AP-2 and dynamin and promote coated vesicle formation and perhaps their transport to appropriate locations within the cell and release of internalized proteins and/or molecules (FIG. 7). The SH3 C-terminal domains of the Ese proteins can bind and interact with several other proteins leading to a host of protein-protein interactions involved in subcellular trafficking and signalling. The Ese proteins may be activated or inactivated via phosphorylation of the proteins at numerous phosphorylation sites by the action of activated receptors on cell surfaces.

Due to the fact that the Ese proteins appear to be a key central player in the complex process of endocytosis involving protein—protein interactions and intracellular signalling, these proteins are most likely involved in a myriad of clinical conditions and processes which are very likely to include but not be limited to regulation of endocytosis (as described above), cell division and cancer (Eps15 and cb1 are oncoproteins), cell migration (regulation of the actin cytoskeleton is required for many forms of cell migration), cell polarity, plane of cell division and cell fate specification (Eps15 binds to Numb in vivo which is required for these processes (43), RNA localization (several RNA binding proteins have been identified in the present screens) and viral infection and life cycle (Eps15 binds to RAB a cellular cofactor for HIV Rev (43)).

With respect to viral infection Ese proteins may play an important role and thus may be a target for developing therapeutic strategies against viral infection and virally-induced disease states. HIV is known to alter endocytosis of several important cell surface molecules including CD4 and MHC antigens. HIV-NEF has been demonstrated to bind to SH3 domains. NEF induces clathrin coated pit formation. As NEF binds SH3 domains and induces endocytosis, it is possible that Ese proteins may bind to NEF and are involved in NEF function. Therapeutic strategies to provide treatment for viral infection and virally induced disease states may therefore include the inhibition of Ese-NEF interactions, antibodies or other agents directed against Ese complexes to inhibit endocytosis and in this manner inhibit viral infection and virally induced disease states. It is also expected that many types of viruses will interact with the multi-component Eps15-Ese complex.

Synaptic transmission and abnormal or altered synaptic transmission as seen in various nervous disorders may also be a target for the therapeutic use of Ese proteins and/or antagonists. The Eps15:Ese complex has been demonstrated to regulate endocytosis, is highly expressed in the brain and Ese binds to Jerky; a protein required to prevent epilepsy in mice (57). Futhermore, Ese proteins are highly expressed not only in the brain but also in the heart and in skeletal muscle which are tissues involving high levels of synaptic transmission. This suggests that Ese protein may be used in the treatment of nervous system disorders involving altered synaptic transmission.

Receptor-mediated cell signaling such as seen with several different types of growth factors also involves endocytosis. Over-expression, mutation or over-stimulation of growth factor receptors has been demonstrated to lead to abnormal cell division and growth as seen in cancer. For example, EGF is a potent mitogen for many epithelial cells and EGF receptor activation is known to stimulate intracellular kinase pathways leading to cell proliferation. Such activity may play a role in cancer progression. By altering the rate of endocytosis by targeting Ese proteins, the cell proliferative effect of growth factor receptor stimulation may be counteracted.

Abnormal cell division and cell migration is seen in several diseases and involves the cell cytoskeleton. The intracellular cytoskeleton is highly organized and consists of microtubules, microfilaments and intermediate filaments acting as an internal reinforcement in the cytoplasm of a cell. Together these structures associate in a regular and defined manner which is regulated by extracellular signals and may transduce plasma membrane signals by association with other proteins or by second messengers. The Ese-Eps15 complex is very likely to regulate the cytoskeleton by analogy to the role of Pan1p:End3p in regulation of yeast cytoskeleton. Furthermore, endocytosis is known to involve a rearrangement of the intracellular cytoskeleton. Cell division and migration require the continual rearrangement of the intracellular cytoskeleton. Therefore, abnormal patterns of cell division and migration may involve altered Ese function and altered endocytosis. The Ese proteins or the genes may therefore be used to alter regulation of endocytosis or the association of the Ese proteins with the cytoskeleton and may restore cell division and migration to normal levels and patterns.

Tissue development also involves the continual remodeling of the cytoskeletal network along with its associated proteins. Developmental diseases can occur as a result of abnormal remodeling of the cytoskeleton leading to altered intracellular signaling. As Ese proteins are likely to be involved with both the cytoskeleton and intracellular signaling they may also be directly involved in the development of certain developmental diseases and therefore may be a target for therapeutic treatment of such diseases. Ese proteins may also be involved in normal development including that of stem cells which are self-renewing cells that divide to produce differentiated daughter cells in various tissues. As Ese proteins are associated with the cytoskeleton they may play a part in the formation of certain types of differentiated cells through the partitioning of RNA and proteins such as nuMb during cell division.

Transgenic Animal Models

The creation of transgenic animal models for abnormal endocytotic function characterized by altered Ese1 or Ese2 activity is important to the understanding of the function of these proteins in intracellular signaling and for the testing of possible therapies for abnormal endocytosis involving protein—protein interactions and intracellular signalling and leading to various clinical conditions. In general, techniques of generating transgenic animals are widely accepted and practiced.

There are several ways in which to create an animal model in which the Ese1 or Ese2 gene expression or function is altered. One could simply generate a specific mutation in the mouse Ese1 or Ese2 gene as one strategy. Secondly a wild type human Ese1 or Ese2 gene and/or a humanized murine gene could be inserted into the animals genome by homologous recombination. It is also possible to insert a mutant (single or multiple) human gene as genomic or minigene construct using wild type or mutant or artificial promoter elements. More commonly, and most preferred in the present invention, knock-out of the endogenous murine genes may be accomplished by the insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase. Gene knockout produces homozygous mutant mice, which show symptoms or phenotype similar to those exhibited by a human.

In general, for gene knock-out, embryonic stem cells heterozygous for a knockout mutation in a gene of interest (ie. Ese1 or Ese2 gene) and homozygous for a marker gene (eg. coat colour) are transplanted into the blastocoel cavity of 4.5 day embryos homozygous for an alternate market. The early embryos then are implanted into a pseudopregnant female. Some of the resulting progeny are chimeras. Chimeric mice then are backcrossed. Intercrossing will eventually produce individuals homozygous for the disrupted allele that is, knockout mice. (Capecchi, M R. 1989. Science. 244:1299–1291).

To inactivate the Ese1 or Ese2 mouse gene chemical or x-ray mutagenesis of mouse gametes, followed by fertilization, can be applied. Heterozygous offspring can then be identified by Southern blotting to demonstrate loss of one allele by dosage, or failure to inherit one parental allele using RFLP markers.

To create a transgenic mouse, a mutant or normal version of the human Ese1 or Ese2 gene can be inserted into a mouse germ line using standard techniques of oocyte microinjection or transfection or microinjection into stem cells. Alternatively, if it is desired to inactivate or replace the endogenous Ese1 or Ese2 gene, homologous recombination using embryonic stem cells may be applied.

For oocyte injection, one or more copies of a mutant or normal Ese1 or Ese2 gene can be inserted into the pronucleus of a just-fertilized mouse oocyte. This oocyte is then reimplanted into a pseudo-pregnant foster mother. The liveborn mice can then be screened for integrants using analysis of tail DNA for the presence of transgenic Ese1 or Ese2 gene sequences. The transgene can be either a complete genomic sequence injected as a YAC or chromosome fragment, a cDNA with either the natural promoter or a heterologous promoter, or a minigene containing all of the coding region and other elements found to be necessary for optimum expression.

Retroviral infection of early embryos can also be done to insert the human or mouse Ese1 or Ese2 gene. In this method, the Ese1 or Ese2 gene is inserted into a retroviral vector which is used to directly infect mouse embryos during the early stages of development to generate a chimera, some of which will lead to germline transmission.

Homologous recombination using stem cells allows for the screening of gene transfer cells to identify the rare homologous recombination events. Once identified, these can be used to generate chimeras by injection of mouse blastocysts, and a proportion of the resulting mice will show germline transmission from the recombinant line. This methodology is especially useful if inactivation of the Ese1 or Ese2 gene is desired. For example, inactivation of the Ese1 or Ese1 gene can be done by designing a DNA fragment which contains sequences from a Ese1 or Ese2 exon flanking a selectable marker. Homologous recombination leads to the insertion of the marker sequences in the middle of an exon, inactivating the Ese1 or Ese2 gene. DNA analysis of individual clones can then be used to recognize the homologous recombination events.

This embodiment of the invention has the most significant commercial value as a mouse model for abnormal endocytotic activity and this may include disorders such as those involving abnormal cell division, cancer, abnormal cell migration, viral infection, abnormal tissue development and abnormal synaptic transmission disorders.

Therapy

Gene therapy is another potential therapeutic approach for treating disorders involving abnormal endocytosis, vesicular trafficking and abnormal regulation of the actin cytoskeleton. Such disorders may include for example but not be limited to disorders such as those involving abnormal cell division, cancer, abnormal cell migration, viral infection, abnormal tissue development and abnormal synaptic transmission disorders.

In such therapy, normal copies of a mammalian Ese gene are introduced into patients to code successfully for normal protein in several different affected cell types. The gene must be delivered to those cells in a form in which it can be taken up and code for sufficient protein to provide effective function.

Retroviral vectors can be used for somatic cell gene therapy especially because of their high efficiency of infection and stable integration and expression. The targeted cells however must be able to divide and the expression of the levels or normal protein should be high. The full length Ese gene can be cloned into a retroviral vector and driven from its endogenous promoter or from the retroviral long terminal repeat or from a promoter specific for the target cell type of interest.

Other viral vectors which can be used include adeno-associated virus, vaccinia virus, bovine papilloma virus, or a herpevirus such as Epstein-Barr virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Antisense based strategies can employed to explore mammalian Ese gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target Ese mRNA. Hybridization is required for the antisense effect to occur, however the efficiency of intracellular hybridization is low and therefore the consequences of such an event may not be very successful. Antisense strategies may use a variety of approaches including the use of antisense oligonucleotides, injection of antisense RNA and transfection of antisense RNA expression vectors. Antisense effects can be induced by control (sense) sequences, however, the extend of phenotypic changes are highly variable. Phenotypic effects induced by antisense effects are based on changes in criteria such as protein levels. Protein activity measurement, and target mRNA levels. Multidrug resistance is a useful model to study molecular events associated with phenotypic changes due to antisense effects, since the multidrug resistance phenotype can be established by expression of a single gene mdr1 (MDR gene) encoding for P-glycoprotein.

Transplantation of normal genes into the affected area of the patient can also be useful therepy for any disease condition which includes abnormal endocytosis, vesicular trafficking and abnormal regulation of the actin cytoskeleton. In this procedure, a normal human Ese gene is transferred into a cultivatable cell type, either exogenously or endogenously to the patient. These cells are then injected serotologically into the disease-affected tissue or tissues.

Immunotherapy is also possible for treating disorders which includes abnormal endocytosis, vesicular trafficking and abnormal regulation of the actin cytoskeleton. Antibodies are raised to a mutant Ese protein (or a portion thereof) and are administered to the patient to bind or block the mutant protein and prevent its deleterious effects. Simultaneously, expression of the normal protein product could be encouraged. Alternatively, antibodies are raised to specific complexes between mutant or normal Ese proteins and their binding partners.

A further approach is to stimulate endogenous antibody production to the desired antigen. Administration could be in the form of a one time immunogenic preparation or vaccine immunization. An immunogenic composition may be prepared as injectables, as liquid solutions or emulsions. The Ese protein or other antigen may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectivess. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

Screening for Disease

In another embodiment of the invention the knowledge of mammalian Ese1 and Ese2 cDNA sequences provides for screening by conventional methods to obtain the corresponding human sequences and thus screening for various diseases involving abnormal Ese1 or Ese2 (or alternative transcripts thereof) in which the defect is due to a mutant Ese1 or Ese2 gene and thus an altered and abnormal endocytosis process involved in various disorders. Mutant forms of the protein may not be able to bind with their normal binding partners and thus endocytosis, vesicular trafficking and/or actin dynamics are negatively affected. Such defects may include, for example, cancer. Other defects may include abnormal cell division, abnormal cell migration, viral infection, abnormal receptor signalling, abnormal tissue development and abnormal synaptic transmission disorders. People at a risk for such an abnormality or, individuals not previously known to be at risk, or people in general may be screened routinely using probes to detect the presence of a mutant Ese1 or Ese2 gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences are then visualized using methods such as autoradiography, fluorometry, or calorimetric reaction. Suitable PCR primers can be generated which are useful for example in amplifying portions of the subject sequence containing identified mutations.

Direct DNA sequencing reveals sequence differences between normal and mutant Ese1 or Ese2 DNA. Cloned DNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as would be understood by those skilled in the art.

Sequence alterations may also generate fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis. Alternatively fluorography may be employed.

Genetic testing based on DNA sequence differences may be achieved by detection of alteration in electrophoretic mobility of DNA fragments in gels. Small sequence deletions and insertions can be visualized by high resolution gel electrophoresis. Small deletions may also be detected as changes in the migration pattern of DNA heteroduplexes in non-denaturing gel electrophoresis. Alternatively, a single base substitution mutation may be detected based on differential primer length in PCR. The PCR products of the normal and mutant gene could be differentially detected in acrylamide gels.

Nuclease protection assays (S1 or ligase-mediated) also reveal sequence changes at specific locations. Alternatively, to confirm or detect a polymorphism restriction mapping changes ligated PCR, ASO, REF-SSCP and SSCP may be used. Both REF-SSCP and SSCP are mobility shift assays which are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry, and fluorometry may also be used to identify specific individual genotypes.

According to an embodiment of the invention, the portion of the DNA segment that is informative for a mutation, can be amplified using PCR. The DNA segment immediately surrounding a specific mutation acquired from peripheral blood or other tissue samples from an individual can be screened using constructed oligonucleotide primers. This region would then be amplified by PCR, the products separated by electrophoresis, and transferred to membrane. Labeled probes are then hybridized to the DNA fragments and autoradiography performed.

In a further embodiment, the invention provides pharmaceutical compositions comprising Ese1 or Ese2 proteins or a functional analogue or mimetic of these proteins or their alternative transcripts for the treatment of certain disorders characterized by abnormal endocytosis and thus cell-signalling due to lack or absence of the proteins. Such disorders may include but are not limited to abnormal cell division, cancer, viral infection, abnormal synaptic transmission as seen in central nervous disorders and abnormal cell differentiation. Such compositions as provided herein can be appropriately packaged and targeted to specific cells and/or tissues.

Administration of a therapeutically active amount of a pharmaceutical composition of the present invention means an amount effective, at dosages and for periods of time necessary to achieve the desired result. This may also vary according to factors such as the disease state, age, sex, and weight of the subject, and the ability of the Ese1 or Ese2 proteins, peptides or alternative transcripts (for example Ese1L and Ese2L) to elicit a desired response in the subject. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples of pharmaceutically acceptable carriers are sugars, starches, cellulose and its derivatives, powdered tragacanth, malt, gelatin, collagen, talc, stearic acids, magnesium stearate, calcium sulfate, vegetable oils, polyols, agar, alginic acids, pyrogen-free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the active substance is combined in a mixture with a pharmaceutically acceptable carrier. Suitable carriers and formulations adapted for particular modes of administration are described, for example, in Remington's Pharmaceutical Sciences (Remington's Pharmaceutical Sciences, Mack Publishing Company, Easton, Pa., USA 1985). On this basis the compositions include, albeit not exclusively, solutions of the substance in association with one or more pharmaceutically acceptable vehicles or diluents, and contained in buffered solutions with a suitable pH and iso-osmotic with the physiological fluids.

The pharmaceutical compositions of the invention may be administered therapeutically by various routes such as by injection or by oral, nasal, buccal, rectal, vaginal, transdermal or ocular routes in a variety of formulations, as is known to those skilled in the art.

The present invention also enables the analysis of factors affecting the expression of the Ese1 or Ese2 gene in humans or in animal models. The invention further provides a system for screening candidate compounds for their ability to turn on or turn off expression of the Ese1 or Ese2 gene or to screen compounds which are binding partners of these proteins.

For example, a cell culture system can be used to identify compounds which activate production of Ese1 or Ese2 proteins or, once Ese1 or Ese2 production has been activated in the cells, they can be used to identify compounds which lead to suppression or switching off of Ese1 or Ese2 protein production. Compounds thus identified are useful as therapeutics in conditions where Ese1 or Ese2 production is deficient or excessive.

Compounds can also be screened in culture for their ability to overcome the effect of Ese protein expression in cell culture, tissue culture or in an animal model.

The present invention enables also a screening method for compounds of therapeutic utility as antagonists of the biological activity, binding activity, of Ese1 or Ese2 proteins and their binding partners. Those skilled in the art will be able to devise a number of possible screening methods for screening candidate compounds for Ese1 or Ese2 protein antagonism.

A screening method may also be based on binding to the Ese1 or Ese2 protein. Such competitive binding assays are well known to those skilled in the art. Once binding has been established for a particular compound, a biological activity assay is employed to determine agonist or antagonist potential.

Cell-free assays can also be readily designed by those skilled in the art to monitor and measure endocytosis, vesicular trafficking and actin dynamics.

To summarize, Ese proteins, Ese complexes including Eps 15, Eps15R and many of the proteins identified in the screens as well as others identified through similar screens can be targeted for use in therapies to treat diseases including cancer, viral infection based diseases, developmental diseases due to altered cell fate specification and/or division as well as neurological diseases and diseases of altered cell migration and other diseases due to defects in the actin cytoskeleton.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art.

Material and Methods

Ese Cloning and Plasmids

High Stringency screening was used to isolate the two mouse Ese cDNAs by previously described methodology (58). Ese1 was cloned from an adult mouse brain cDNA library using a PCR product from nt 1707–2197 of the coding sequence as probe. Ese2 was cloned from a mixed tissue adult mouse cDNA library using a mixture of three probes EST#583881 (Research Genetics Inc.), EST#652549 (Research Genetics Inc.) and a PCR product from nt 2712 to nt 3456 of the Ese2 coding sequence.

The Ese1 sequence was obtained from a single clone, whereas the Ese2 reading frame was predicted from the overlap of two cDNA clones. The DBL/PH/C2 region of Ese1L was obtained using PCR with an upstream primer designed from sequences within the DBL/PH domain region: GAAGGAGAACTCAGACCGGCTGGAGTGGAT (SEQ ID NO:28; this sequence was obtained from one partial Ese1L clone which we had isolated from a mouse brain cDNA library). This upstream primer was paired with downstream primers for the vector. The DBL/PH/C2 region of Ese2L was obtained using PCR with upstream and downstream primers flanking the site in Ese2 where sequence divergence had been noted within an EST clone (upstream Ese2 sequence: GACAGAGGAGCGGTA-CATGGA, SEQ ID NO:29; and downstream Ese2 sequence: AGCTCCCCTGGTTCTGGCTTC, SEQ ID NO:30). The mouse Eps15 cDNA was generated through a combination of high stringency library screening with Est sequences from the Eps15 gene and rt PCR according to established methods.

pcDNA3Ese1:

Full length Ese1 was cloned into the NotI site of pcDNA3 (Invitrogen Inc.). The Ese1 cDNA includes 53 nucleotides of 5' UTR plus a natural NotI site and 288 nucleotides of 3'UTR plus a small region of polylinker including a NotI site.

pcDNA3mycEse1:

The 5' end of pcDNA3Ese1 from the EcoRI site in the pcDNA3 polylinker to the start codon was replaced with the DNA sequence <u>GAATTC</u>AGAACCATG <u>GAACAAAAGCTTATTTCTGAAGAAGACTTGGGGC</u> CCATG (SEQ ID NO:31): where the first underlined sequence corresponds to an EcoRI site which was fused into the pcDNA3EcoRI site and the extended underlined sequence codes for a myc-epitope tag. This is followed by nine nucleotides which code for glycine, proline and the natural Ese1 start codon. This sequence was joined to the sequences coding for amino acids 2–1213 (the remainder of Ese1). The new start codon in this tagged Ese1 construct is bolded. The 3' end of Ese1 in this vector is the same as in pcDNA3Ese1 above.

pcDNA3Ese1δC:

The C-terminus of Ese1 was removed by replacing all sequences from nt 2209 of the coding sequence to the XhoI site in pcDNA3Ese1 with TGA<u>CTCGAG</u> where the stop codon is in bold and the XhoI site is underlined. This construct codes for amino acids 1–736 of Ese1.

pcDNA3Eps15:

This plasmid was constructed from four pieces. It contains the full length Eps15. The 5'UTR of this construct has been constructed to be <u>GGATCC</u>ACCATG (SEQ ID NO:36) where a BamHI site is underlined and the start codon is bolded. This BamHI site was fused to the BamHI site in pcDNA3. The 3'UTR in this vector is 204 nt of the mouse natural 3'UTR fused to a short cloning linker ending in the sequence AAGCTT<u>GGGCCC</u> (SEQ ID NO:37) where an ApaI site is underlined; this ApaI site was fused to the ApaI site in pcDNA3.

pcDNA3Eps15δC:

This vector is the same as pcDNA3Eps15 except that sequences downstream from and including mouse Eps15 coding nucleotide 1500 have been replaced with CCTG <u>GATTACMGGATGATGATGACAAA</u>TGA<u>CTCGAG</u> (SEQ ID NO:32) where the first underlined sequence codes for the Flag-epitope, an inframe stop codon is bolded and an XhoI site is underlined. This XhoI site was fused to the polylinker in pcDNA3. The resulting plasmid encodes amino acids 1–501 of mouse Eps15 fused to a C-terminal Flag epitope. The 5' end of Eps15 in this construct is as indicated above for pcDNA3Eps15.

pGBT9Ese1cc:

The Ese1 sequence coding for amino acids 330 to 732 were fused directly to <u>GAATTC</u> (EcoRI site) on the 5' end and to TA<u>GGATCC</u> (stop codon followed by a BamHI site) on the 3' end. This fragment was cloned into EcoRI/BamHI digested pGBT9 in frame with the GAL4 DBD.

pGBT9Ese1A3.3:

This plasmid encodes the bait for our SH3 screen. It encodes all five SH3 domains from amino acid 665–1213 and was subcloned into pGBT9 on an EcoRI fragment which fuses the Ese1 SH3 region in frame with the DBD of GAL4.

PGBT9Ese1Nterm:

This plasmid codes for the N-terminal 393 amino acids of Ese1, including both EH domains. It was subcloned into pGBT9 on an EcoRI/SalI fragment.

Yeast 2-Hybrid Screening pGBT9Ese1cc was transformed into S. cerevisiae strain Y190 using 45% PEG4000, 100 mM LiAc, 10 mM Tris-HCl (pH 7.5) as per standard protocols. Cells were plated onto Sc-Trp drop-out media. Single colonies were isolated and expression of bait was analyzed by Western Blot using antibodies against the GAL4 DBD. A clone expressing the bait fusion was used to inoculate a 100 mL Sc-Trp liquid culture grown overnight at 30° C. Cells were then re-inoculated into YPD at a density of $5 \times 10^6$ cells/mL and grown at 30° C. until the titer reached $2 \times 10^7$ cells/mL. Cells were pelleted, resuspended in 50 mL 100 mM LiAc and incubated for 10 min at 30° C. Once again the cells were pelleted, resuspended in 20 mL PLA [35% PEG, 100 mM LiAc, 2 mg/mL salmon sperm DNA] containing 30 µg plasmid library (cloned in pAD-GAL4) incubated at 30° C. for 30 min.; then heat shocked at 42° C. for 40 min., pelleted, resuspended in water and plated onto [Sc-Trp-Leu-His+40 mM 3-AT]. Plates were incubated at 30° C. until colonies were formed. Colonies were picked, patched and grown at 30° C. overnight on Whatman filter paper laid on top of Sc-Trp-Leu-His plates. Filters were submerged in liquid nitrogen for 15 seconds then placed on top of blotting paper soaked in Z-buffer+X-gal. β-galactosidase activity was measured by the appearance of blue colour. Plasmids from β-galactosidase positive colonies were shuttled to bacteria by electroporation and isolated for sequencing.

Northern Blot Analysis

A multiple tissue northern blot (Clontech) was prehybridized in 5 mL of ExpressHyb Solution (Clontech) at 68° C. for 30 min. Probe was added at $1\times10^6$ cpm/mL for 1 hr. The Blot was washed twice (2×SSC, 0.05% SDS) at room temperature, twice (0.1×SSC, 0.1% SDS) at 50° C. and then exposed to film overnight.

Antibodies and Western Blot Analysis

Western blot analysis was performed according to standard protocols. Briefly, cultured cell lines or 48 hours post tranfection Cos-1 cells where washed with PBS and lysed in one ml of cold lysis buffer (50 mM Hepes pH 7.4, 150 mM NaCl, 10% glycerol, 1% Triton X100, 1 mM EGTA, 1.5 mM $MgCl_2$, 10 mM NaF, 10 mg $ml^{-1}$ aprotinin, 1 mM PMSF, 10 mg $ml^{-1}$ leupeptin, 1 mM $Na_3VO_4$). Supernatants were clarified by centrifugation and immunoprecipitated with specific antiserum as indicated. Antigen-Antibody complexes where purified on anti-rabbit agarose or anti-mouse agarose (Sigma Chemical Co.) Samples were run on 7.5% PAGE gels and transferred to nitrocellulose membranes. Filters were blocked in 5% dry milk powder/0.05% Tween 20/PBS, washed in 1% dry milk powder/0.05% Tween 20/PBS, and probed with the appropriate antisera at 1 mg/ml in wash buffer (In the case of chicken anti-Ese1 we used 10 µg/ml to probe western blots). Probed filters were further washed, probed again with 1/5000 dilution of horseradish peroxidase conjugated anti-rabbit IgG, anti-mouse IgG antibodies (Amersham), or anti-chicken-IgY (Zymed); washed and signal detected using the Enhanced Chemiluminescence detection system as per manufacturers instructions (Amersham).

Rabbit anti-Ese1 antisera was raised against a peptide of the following sequence: MAQFPTPFGGSLDVWAITVEE (SEQ ID NO:33). The antisera was affinity purified over the same peptide (Research Genetics). This peptide was also used at 5 µg to compete for the 5 µg of antibody per immunoprecipitation reaction. Chicken anti-Ese1 antisera was raised against a fusion protein between GST and amino acids 665–1213 of mouse Ese1. This sera was cleared of antibodies reacting against GST by incubation with glutathione s-transferase on glutathione agarose beads.

Rabbit antibodies have also been raised against a peptide encoding the first twenty one amino acids of mouse Ese2. These antibodies were affinity purified and used to immunoprecipitate endogenous Ese1 containing protein complexes from cultured PC12 cells. A protein of approximately 130 kDa was co-immunoprecipitated in complex with Ese2. This protein was isolated from a silver stained gel slice, digested with trypsin and the resulting peptide fragments were analyzed using both MALDI-TOF and Q-TOF Mass Spectrometers. Taken together, these mass spec analyses revealed that the Ese-2 binding protein in question is a Rho-Family exchange protein variably known as KIAA0362, Dbs and Ost. The gene encoding KIAA0362, Dbs and Ost proteins is subject to complex alternative splicing but each protein is predicted to contain the DBL/PH exchange domain. Thus Ese proteins are found in complex with exchange proteins for the Rho-family of small GTP-binding proteins.

Monoclonal antibodies against Ese proteins were produced by immunizing mice with a GST fusion protein encoding the Ese1 C-terminus (from amino acid 665 to the stop codon) according to standard protocols. After multiple injections, the mouse spleens were removed and resuspended in phosphate buffered saline (PBS). The spleen cells served as a source of lymphocytes. These lymphocytes were fused with a permanently growing myeloma partner cell, and the products of the fusion were plated into 96 well plates in the presence of selective media. The culture supernatents were then screened by ELISA to identify those containing cells which were secreting anti-Ese antibodies. A histidine tagged version of the Ese1 C-terminus was used in these ELISA screens to ensure that anti-Ese antibodies were detected rather than antibodies directed against the GST portion of our original immunogen. From this procedure we isolated several independent stable hybridoma cloned lines which secrete anti-Ese antibodies. The monoclonal antibodies have then been purified on protein A/G columns as per standard protocols and demonstrated to bind Ese protein.

Immunofluorescence

For Immunofluorescent staining, Cos-1 cells were typically plated at a density of $2\times10^5$ per 22×50 mm coverglass and transfected with 2.5 µg of plasmid using Superfect (Qiagen Inc.). After 2 hours, the cells were washed with 10% FBS in Iscove's Media and fed with fresh 10% FBS in Iscove's Media. Two days later, these cultures where fixed with cold methanol for 30 minutes at room temperature. Cultures were washed three times 10 minutes with Phosphate buffered saline (PBS), blocked for one hour at room temperature with 1% BSA in PBS and then incubated with primary antibody in blocking solution for one hour, also at room temperature. Slides were then washed three times 10 minutes with PBS, incubated with secondary antibody/1% BSA/PBS in the dark for one hour at room temperature. Finally, slides were washed three times 10 minutes in the dark at room temperature and mounted using Dabco anti-fade solution (Sigma Chemical Co.). Slides were analyzed on the confocal microscope using the 63× objective and optical filters to separate signals on each channel.

For primary antibodies Mouse anti-myc monoclonal 9E10 (10 µg/ml: Santa CruzBiotech.), Rabbit anti-myc (5 µg/ml: Upstate Biotechnology Inc.), Rabbit anti-Eps D5 antisera #C20 (1 µg/ml: Santa Cruz Biotech), Rabbit anti-Flag epitope antisera (5 g/ml: Zymed) and mouse anti-Dynamin I #D25520, which recognizes Dynamin in Cos-1 cells by both immunoprecipitation and western blotting (data not shown) (20 µg/ml: Transduction labs, Inc.) were used. As secondary antibodies we used FITC-labelled goat anti-mouse (1:80 dilution) and Texas Red-labelled goat anti-rabbit antibodies (1:100 dilution) (Jackson Immuno Research Laboratories Inc.). Endogenous Eps15 staining above background in non-transfected cells was undetected. Prominent cytoplasmic Eps15 staining in transfected cells obscured the detection of clathrin-coated pit associated Eps15 at the membrane (FIG. 4B). In FIG. 5B panel a and b, Dynamin staining with both primary and secondary antibodies was performed first. MycEse1 was then stained for using biotinylated 9E10 followed by streptavidin conjugated to Texas Red. Following application of the secondary antibody to stain for Dynamin, all further incubations and washes were performed under dark condition. Endocytosis assays were performed as previously described (6, 9).

Mouse Ese1 cDNA—Sequence ID NO: 1

CGGCACGAGGAGGAGTGGAGCGGCGCGGGAGGGCGCGCAGCTTGGTTGC
TCCGTAGTACGGCGGCTCGCAAGGGAGCATCCCGAGCGGGCTCCGGACG
GCCGGGAGGCAGGCAGGCGGGCGGGCGGGATGGTGTGCGCGGCTGCGG
ACTCGGCGTTCCTCGCGCGGCGTGCGGGCTGCACTGATTTGTGTGAGGGG
CGGCCGCGCGCACCCGCCCGGAGATGAGGCGTCGATCAGCAAGGTGAAC
GTAATAGAACCATGGCTCAGTTTCCCACACCTTTCGGTGGTAGCCTGGATG
TCTGGGCCATAACTGTGGAGGAAAGGGCCAAGCATGACCAGCAGTTCCTT
AGCCTGAAGCCGATAGCGGGATTTATTACTGGTGATCAAGCGAGGAACTT
TTTTTTCCAATCTGGGTTACCTCAGCCTGTCTTAGCACAAATATGGGCGCT
AGCGGACATGAATAACGATGGAAGGATGGATCAAGTGGAATTTTCCATAG
CCATGAAGCTTATCAAACTGAAGCTACAAGGATATCAGCTCCCCTCCACA
CTTCCCCCTGTCATGAAACAGCAACCAGTGGCTATTTCCAGTGCACCAGCA
TTTGGTATAGGAGGGATTGCTAGCATGCCACCACTCACAGCTGTTGCTCCT
GTGCCAATGGGCTCCATTCCAGTTGTTGGAATGTCTCCACCCTTAGTATCT
TCTGTCCCTCCAGCAGCAGTGCCTCCCCTGGCTAACGGGGCTCCTCCCGTC
ATACAGCCTCTGCCTGCGTTTGCGCATCCTGCAGCCACATGGCCAAAGAG
TTCTTCCTTCAGCAGATCTGGTCCAGGGTCACAATTAAACACTAAGTTACA
GAAGGCACAATCATTCGATGTCGCCAGCGCCCCTCCAGCAGCAGAATGGG
CTGTGCCTCAGTCATCAAGGCTGAAATACAGGCAGTTATTCAACAGCCAC
GACAAAACTATGAGTGGACACTTAACAGGTCCCCAGGCAAGAACTATTCT
CATGCAATCAAGTTTACCCCAGGCTCAGCTGGCTTCAATATGGAATCTTTC
TGACATTGATCAAGATGGAAAACTCACTGCAGAAGAATTTATCCTAGCTA
TGCACCTAATTGATGTTGCCATGTCTGGTCAGCCACTGCCGCCCGTCCTGC
CTCCAGAATACATCCCTCCTTCCTTCAGAAGAGTTCGCTCCGGCAGTGGGA
TGTCCGTCATAAGCTCTTCTTCTGTGGATCAGAGGCTGCCTGAGGAGCCGT
CGTCAGAGGATGAGCAGCAGCCAGAGAAGAAACTGCCTGTGACATTTGAA
GATAAGAAGCGGGAGAACTTCGAGCGAGGCAGTGTGGAGCTGGAGAAGC
GCCGCCAAGCGCTCTTGGAGCAGGAGCGCAAAGAGCAGGAGCGGTTGGC
TCAGCTGGAGCGCGCCGAGCAGGAGAGGAAAGAGCGGGAGCGCCAGGAG
CAGGAGGCCAAGCGGCAGCTGGAGCTGGAGAAGCAGCTGGAGAAGCAGC
GGGAGCTGGAGCGGCAGCGAGAGGAGGAGAGGAGGAAGGAGATCGAGA
GGCGCGAGGCCGCAAAACGGGAACTGGAAAGGCAGCGACAACTTGAATG
GGAACGGAACCGGAGACAGGAACTCCTGAATCAGAGGAACAAGGAGCAG
GAGGGCACCGTGGTCCTGAAGGCAAGGAGGAAGACTCTGGAGTTTGAGTT
AGAAGCTCTGAATGACAAAAAGCATCAGCTAGAAGGAAAACTTCAGGAT

ATCAGGTGTCGACTGGCAACCCAGAGGCAAGAAATTGAGAGCACGAACA
AGTCTAGAGAGCTAAGAATTGCTGAAATCACCCACTTACAGCAGCAGTTG
CAGGAATCTCAGCAAATGCTTGGAAGACTTATTCCAGAGAAACAGATACT
CAGTGACCAGTTAAAACAAGTCCAGCAGAACAGTTTGCATAGAGACTCGC
TTCTTACCCTCAAAAGAGCCTTGGAAGCAAAGGAGCTGGCCCGGCAGCAG
CTCCGGGAGCAGCTGGACGAGGTGGAGAGAGAGACCAGGTCAAAGCTGC
AGGAGATTGATGTTTTCAACAACCAGCTGAAGGAACTGAGAGAGATACAT
AGCAAACAGCAACTCCAGAAGCAGAGGTCCCTGGAGGCAGCGCGACTGA
AGCAGAAAGAGCAGGAGAGGAAGAGCCTGGAGTTAGAGAAGCAAAAGG
AAGACGCTCAGAGACGAGTTCAGGAAAGGGACAAGCAATGGCTGGAGCA
TGTGCAGCAGGAGGAGCAGCCACGCCCCCGGAAACCCCACGAGGAGGAC
AGACTGAAGAGGGAAGACAGTGTCAGGAAGAAGGAGGCGGAAGAGAGA
GCCAAGCCGGAAATGCAAGACAAGCAGAGTCGGCTTTTCCATCCGCATCA
GGAGCCAGCTAAGCTGGCCACCCAGGCACCCTGGTCTACCACAGAGAAAG
GCCCGCTTACCATTTCTGCACAGGAGAGTGTAAAAGTGGTATATTACCGA
GCGCTGTACCCCTTTGAATCCAGAAGTCACGATGAGATCACCATCCAGCC
AGGAGATATAGTCATGGTGGATGAAAGCCAGACTGGAGAGCCAGGATGG
CTTGGAGGAGAGCTGAAAGGGAAGACGGGATGGTTCCCTGCAAACTATGC
AGAAAAGATTCCAGAAAATGAGGTTCCCACTCCAGCCAAACCAGTGACCG
ATCTGACATCTGCCCCTGCCCCCAAACTGGCTCTGCGTGAGACCCCTGCTC
CTTTGCCAGTGACCTCTTCTGAGCCCTCCACAACCCCCAACAACTGGGCAG
ACTTCAGTTCCACGTGGCCCAGCAGCTCAAACGAGAAGCCAGAAACGGAC
AACTGGGATACGTGGGCGGCTCAGCCTTCTCTGACCGTACCTAGTGCTGG
CCAGTTACGGCAGAGATCAGCCTTTACCCCAGCCACAGCCACTGGCTCCT
CCCCATCTCCCGTCCTGGGCCAGGGTGAAAAGGTGGAAGGGCTACAAGCG
CAAGCCCTGTATCCCTGGAGAGCCAAAAAAGACAACCACTTAAATTTTAA
CAAAAGTGACGTCATCACCGTTCTGGAACAGCAAGACATGTGGTGGTTTG
GAGAAGTTCAAGGTCAGAAGGGTTGGTTCCCCAAGTCTTACGTGAAACTC
ATTTCAGGGCCCGTAAGGAAATCCACAAGCATCGATACTGGCCCTACTGA
AAGTCCTGCTAGTCTAAAGAGAGTGGCTTCCCCGGCCGCCAAGCCAGCCA
TTCCCCGGAGAAGAGTTTATTGCCATGTACACATACGAGAGTTCTGAGCAA
GGAGATTTAACCTTTCAGCAAGGGGATGTGATTGTGGTTACCAAGAAAGA
TGGTGACTGGTGGACGGGAACGGTGGGCGACAAGTCCGGAGTCTTCCCTT
CTAACTATGTGAGGCTTAAAGATTCAGAGGGCTCTGGAACTGCTGGGAAA
ACAGGGAGTTTAGGAAAAAAACCTGAAATTGCCCAGGTTATTGCTTCCTA
CGCTGCTACTGGTCCCGAACAACTCACCCTGGCTCCTGGGCAGCTGATTCT
GATCCGGAAAAGAACCCAGGTGGATGGTGGGAAGGAGAACTGCAAGCT
CGAGGGAAAAAGCGCCAGATAGGGTGGTTTCCAGCAAATTATGTCAAACT
TCTAAGCCCCGGAACAAGCAAAATCACCCCAACTGAGCTACCCAAGACCG
CAGTGCAGCCAGCAGTGTGCCAGGTGATCGGGATGTACGATTACACCGCC

-continued

```
CAGAACGATGACGAACTAGCCTTCAGCAAAGGCCAGATCATCAACGTCCT
CAACAAGGAGGACCCGGACTGGTGGAAAGGAGAAGTCAGTGGGCAAGTT
GGGCTCTTCCCATCCAATTATGTAAAGCTGACCACAGACATGGACCCCAG
CCAGCAATGAATCATATGTTGTCCATCCCCCCCTCAGGCTTGAAAGTCCTC
AAAGAGACCCACTATCCCATATCACTGCCCAGAGGGATGATGGGAGATGC
AGCCTTGATCATGTGACTTGCAGCATGATCACCTACTGCCTTCTGAGTAGA
AGAACTCACTGCAGAGCAGTTTACCTCATTTGACCTTAGTTGCATGTGATC
GAAATGTCTGAGTCACTGCGTGCAGAGGCAGAAGCAAATTGCAGAACTGC
ACAGGGTGGTGGGTCCTTTTGGGGCTTTCCTAGTCACTCAGACTGACCGGC
CCCGCCTTCACACGGGCGCTTTCAATAGTTTTAAGATTATTTTTAAATGTG
TATTTTAGCCTTTTAATAAAAATCTCAATCAATTACTTCTTTGCCTATTTT
GGTTTTACAAAAACACCCACTATCAAGGAGTGCCTGTCTGCGGACGATTAA
AATGCTGTTCCGGGCGTACCGTAAACTGAGAGCTTGCTGTACCTTTGCCGT
TTGTCCAGTGTTCCCAACCACATTGTGTAGTTTGGGGCTGTTCCCTGCCGT
AGAGCACAGAGGAGATGGGTGTACCTGTTTTGAAAATGTGTATGTAGACT
GAGCCTGACTATGGAAGGGGTTATGCTTGTCTGTGACCATCACGTGTACCT
GTCGCGCATGTACCATCTGTACCGAAGAAGTAGCTCTTCCTCCATGGCTAA
ACCCACCACCGTGTACAGTGCTCTCATCTACTGCATTCATTTTACTTTGCA
CAGTGACCTTGTAGCCACCTGAGGAAGCACCCATGTTTCCGTTTGGTCTCA
GATGTACCTAGTTGTGCCCGTGTTTTGTTTTTATTTTTCAATCTGGCATGT
CTTCACACCATAAACTAGTAAGACGCCAACTGCCCAGGCGGTTACGATCAT
CAGTACCCACCGTCTTAGTCTCTGTTACGTGAAGTTTATTCCAGTTGCTTT
TTATGGAATATCTTGAACAAGTAATCTTCTTGACAAGAAAGAATGTATAGA
AGTCTCCCTGCAATTAATTTCCCAGTGTTTACATTTTTTAACTAGACTGTG
GGGGTTGCTACAGATTAATATGAAATGGCGCTCCTGGTCCGTGTGTGTT
AACTTGTGCTGTAGCTGAAGCCGTGTGTCCTTAGATATTAGTTGGAAGTCG
GGAAGAGAATTCGATATCAAGCTT
```

Mouse Ese1 Coding Sequence—Sequence ID NO:2

```
ATGGCTCAGTTTCCACACCTTTCGGTGGTAGCCTGGATGTCTGGGCCATA
ACTGTGGAGGAAAGGGCCAAGCATGACCAGCAGTTCCTTAGCCTGAAGCC
GATAGCGGGATTTATTACTGGTGATCAAGCGAGGAACTTTTTTTTCCAATC
TGGGTTACCTCAGCCTGTCTTAGCACAAATATGGGCGCTAGCGGACATGA
ATAACGATGGAAGGATGGATCAAGTGGAATTTTCCATAGCCATGAAGCTT
ATCAAACTGAAGCTACAAGGATATCAGCTCCCCTCCACACTTCCCCCTGTC
ATGAAACAGCAACCAGTGGCTATTTCCAGTGCACCAGCATTTGGTATAGG
AGGGATTGCTAGCATGCCACCACTCACAGCTGTTGCTCCTGTGCCAATGGG
CTCCATTCCAGTTGTTGGAATGTCTCCACCCTTAGTATCTTCTGTCCCTCC
AGCAGCAGTGCCTCCCCTGGCTAACGGGGCTCCTCCCGTCATACAGCCTCT
GCCTGCGTTTGCGCATCCTGCAGCCACATGGCCAAAGAGTTCTTCCTTCAG
```

-continued

```
CAGATCTGGTCCAGGGTCACAATTAAACACTAAGTTACAGAAGGCACAAT
CATTCGATGTCGCCAGCGCCCCTCCAGCAGCAGAATGGGCTGTGCCTCAG
TCATCAAGGCTGAAATACAGGCAGTTATTCAACAGCCACGACAAAACTAT
GAGTGGACACTTAACAGGTCCCCAGGCAAGAACTATTCTCATGCAATCAA
GTTTACCCCAGGCTCAGCTGGCTTCAATATGGAATCTTTCTGACATTGATC
AAGATGGAAAACTCACTGCAGAAGAATTTATCCTAGCTATGCACCTAATT
GATGTTGCCATGTCTGGTCAGCCACTGCCGCCCGTCCTGCCTCCAGAATAC
ATCCCTCCTTCCTTCAGAAGAGTTCGCTCCGGCAGTGGGATGTCCGTCATA
AGCTCTTCTTCTGTGGATCAGAGGCTGCCTGAGGAGCCGTCGTCAGAGGA
TGAGCAGCAGCCAGAGAAGAAACTGCCTGTGACATTTGAAGATAAGAAG
CGGGAGAACTTCGAGCGAGGCAGTGTGGAGCTGGAGAAGCGCCGCCAAG
CGCTCTTGGAGCAGCAGCGCAAAGAGCAGGAGCGGTTGGCTCAGCTGGA
GCGCGCCGAGCAGGAGAGGAAAGAGCGGGAGCGCCAGGAGCAGGAGGC
CAAGCGGCAGCTGGAGCTGGAGAAGCAGCTGGAGAAGCAGCGGGAGCTG
GAGCGGCAGCGAGAGGAGGAGAGGAGGAAGGAGATCGAGAGGCGCGAG
GCCGCAAAACGGGAACTGGAAAGGCAGCGACAACTTGAATGGGAACGGA
ACCGGAGACAGGAACTCCTGAATCAGAGGAACAAGGAGCAGGAGGGCAC
CGTGGTCCTGAAGGCAAGGAGGAAGACTCTGGAGTTTGAGTTAGAAGCTC
TGAATGACAAAAAGCATCAGCTAGAAGGAAAACTTCAGGATATCAGGTGT
CGACTGGCAACCCAGAGGCAAGAAATTGAGAGCACGAACAAGTCTAGAG
AGCTAAGAATTGCTGAAATCACCCACTTACAGCAGCAGTTGCAGGAATCT
CAGCAAATGCTTGGAAGACTTATTCCAGAGAAACAGATACTCAGTGACCA
GTTAAAACAAGTCCAGCAGAACAGTTTGCATAGAGACTCGCTTCTTACCC
TCAAAAGAGCCTTGGAAGCAAAGGAGCTGGCCCGGCAGCAGCTCCGGGA
GCAGCTGGACGAGGTGGAGAGAGAGACCAGGTCAAAGCTGCAGGAGATT
GATGTTTTCAACAACCAGCTGAAGGAACTGAGAGAGATACATAGCAAACA
GCAACTCCAGAAGCAGAGGTCCCTGGAGGCAGCGCGACTGAAGCAGAAA
GAGCAGGAGAGGAAGAGCCTGGAGTTAGAGAAGCAAAAGGAAGACGCTC
AGAGACGAGTTCAGGAAAGGGACAAGCAATGGCTGGAGCATGTGCAGCA
GGAGGAGCAGCCACGCCCCCGGAAACCCACGAGGAGGACAGACTGAAG
AGGGAAGACAGTGTCAGGAAGAAGGAGGCGGAAGAGAGAGCCAAGCCG
GAAATGCAAGACAAGCAGAGTCGGCTTTTCCATCCGCATCAGGAGCCAGC
TAAGCTGGCCACCCAGGCACCCTGGTCTACCACAGAGAAAGGCCCGCTTA
CCATTTCTGCACAGGAGAGTGTAAAAGTGGTATATTACCGAGCGCTGTAC
CCCTTTGAATCCAGAAGTCACGATGAGATACCATCCAGCCAGGAGATAT
AGTCATGGTGGATGAAAGCCAGACTGGAGAGCCAGGATGGCTTGGAGGA
GAGCTGAAAGGGAAGACGGGATGGTTCCCTGCAAACTATGCAGAAAAGA
TTCCAGAAAATGAGGTTCCCACTCCAGCCAAACCAGTGACCGATCTGACA
TCTGCCCCTGCCCCAAACTGGCTCTGCGTGAGACCCCTGCTCCTTTGCCA
GTGACCTCTTCTGAGCCCTCCACAACCCCCAACAACTGGGCAGACTTCAGT
```

-continued

```
TCCACGTGGCCCAGCAGCTCAAACGAGAAGCCAGAAACGGACAACTGGG
ATACGTGGGCGGCTCAGCCTTCTCTGACCGTACCTAGTGCTGGCCAGTTAC
GGCAGAGATCAGCCTTTACCCCAGCCACAGCCACTGGCTCCTCCCCATCTC
CCGTCCTGGGCCAGGGTGAAAAGGTGGAAGGGCTACAAGCGCAAGCCCT
GTATCCCTGGAGAGCCAAAAAAGACAACCACTTAAATTTTAACAAAAGTG
ACGTCATCACCGTTCTGGAACAGCAAGACATGTGGTGGTTTGGAGAAGTT
CAAGGTCAGAAGGGTTGGTTCCCCAAGTCTTACGTGAAACTCATTTCAGG
GCCCGTAAGGAAATCCACAAGCATCGATACTGGCCCTACTGAAAGTCCTG
CTAGTCTAAAGAGAGTGGCTTCCCCGGCCGCCAAGCCAGCCATTCCCGGA
GAAGAGTTTATTGCCATGTACACATACGAGAGTTCTGAGCAAGGAGATTT
AACCTTTCAGCAAGGGGATGTGATTGTGGTTACCAAGAAAGATGGTGACT
GGTGGACGGAACGGTGGGCGACAAGTCCGGAGTCTTCCCTTCTAACTAT
GTGAGGCTTAAAGATTCAGAGGGCTCTGGAACTGCTGGGAAAACAGGGA
GTTTAGGAAAAAAACCTGAAATTGCCCAGGTTATTGCTTCCTACGCTGCTA
CTGGTCCCGAACAACTCACCCTGGCTCCTGGGCAGCTGATTCTGATCCGGA
AAAAGAACCCAGGTGGATGGTGGGAAGGAGAACTGCAAGCTCGAGGGAA
AAAGCGCCAGATAGGGTGGTTTCCAGCAAATTATGTCAAACTTCTAAGCC
CCGGAACAAGCAAAATCACCCCAACTGAGCTACCCAAGACCGCAGTGCA
GCCAGCAGTGTGCCAGGTGATCGGGATGTACGATTACACCGCCCAGAACG
ATGACGAACTAGCCTTCAGCAAAGGCCAGATCATCAACGTCCTCAACAAG
GAGGACCCGGACTGGTGGAAAGGAGAAGTCAGTGGGCAAGTTGGGCTCTT
CCCATCCAATTATGTAAAGCTGACCACAGACATGGACCCCAGCCAGCAAT
GAATCATATGTTGTCCATCCCCCCCTCAGGCTTGAAAGTCCTCAAAGAGAC
CCACTATCCCATATCACTGCCCAGAGGGATGA
```

Mouse Ese1 Protein—Sequence ID NO:3

```
MAQFPTPFGGSLDVWAITVEERAKHDQQFLSLKPIAGFITGDQARNFFFQ
SGLPQPVLAQIWALADMNNDGRMDQVEFSIAMKLIKLKLQGYQLPSTLPP
VMKQQPVAISSAPAFGIGGIASMPPLTAVAPVPMGSIPVVGMSPPLVSSV
PPAAVPPLANGAPPVIQPLPAFAHPAATWPKSSSFSRSGPGSQLNTKLQK
AQSFDVASAPPAAEWAVPQSSRLKYRQLFNSHDKTMSGHLTGPQARTILM
QSSLPQAQLASIWNLSDIDQDGKLTAEEFILAMHLIDVAMSGQPLPPVLP
PEYIPPSFRRVRSGSGMSVISSSSVDQRLPEEPSSEDEQQPEKKLPVTFE
DKKRENFERGSVELEKRRQALLEQQRKEQERLAQLERAEQERKERERQEQ
EAKRQLELEKQLEKQRELERQREEERRKEIERREAAKRELERQRQLEWER
NRRQELLNQRNKEQEGTVVLKARRKTLEFELEALNDKKHQLEGKLQDIRC
RLATQRQEIESTNKSRELRIAEITHLQQQLQESQQMLGRLIPEKQILSDQ
LKQVQQNSLHRDSLLTLKRALEAKELARQQLREQLDEVERETRSKLQEID
VFNNQLKELREIHSKQQLQKQRSLEAARLKQKEQERKSLELEKQKEDAQR
RVQERDKQWLEHVQQEEQPRPRKPHEEDRLKREDSVRKKEAEERAKPEMQ
DKQSRLFHPHQEPAKLATQAPWSTTEKGPLTISAQESVKVVYYRALYPFE
SRSHDEITIQPGDIVMVDESQTGEPGWLGGELKGKTGWFPANYAEKIPEN
EVPTPAKPVTDLTSAPAPKLALRETPAPLPVTSSEPSTTPNNWADFSSTW
PSSSNEKPETDNWDTWAAQPSLTVPSAGQLRQRSAFTPATATGSSPSPVL
GQGEKVEGLQAQALYPWRAKKDNHLNFNKSDVITVLEQQDMWWFGEVQGQ
KGWFPKSYVKLISGPVRKSTSIDTGPTESPASLKRVASPAAKPAIPGEEF
IAMYTYESSEQGDLTFQQGDVIVVTKKDGDWWTGTVGDKSGVFPSNYVRL
KDSEGSGTAGKTGSLGKKPEIAQVIASYAATGPEQLTLAPGQLILIRKKN
PGGWWEGELQARGKKRQIGWFPANYVKLLSPGTSKITPTELPKTAVQPAV
CQVIGMYDYTAQNDDELAFSKGQIINVLNKEDPDWWKGEVSGQVGLFPSN
YVKLTTDMDPSQQ
```

Mouse Ese2 cDNA—Sequence ID NO:4

```
CCCTTCCTTTCCTTTTTTTGTGTTCGC-
CTTCGGCCGTGCCGGCTGAGAGCCC
AGCAGCCGTGACAGGCTGCGCAACAGGTTCGCTGCGGCCGGCCTGACGAC
TGACCCGGCGGCGGCCGCGGCACGGCAGGGTCTTCCCGGAGCTTGGC
CGCGCCCACGCGCCGGTGTCGAGGAGCGCGCGGGGTCGCGCCGGGACGT
GCGCGAGGCGCCAGATGGCTGAGAGCTGCAAGAAGAAGTCAGGATCATG
ATGGCTCAGTTTCCCACAGCGATGAATGGAGGGCCAAATATGTGGGCTAT
TACATCTGAAGAACGTACTAAGCATGATAAACAGTTTGATAACCTCAAAC
CTTCAGGAGGTTACATAACAGGTGATCAAGCCCGTACTTTTTTCCTACAGT
CAGGTCTGCCGGCCCCGGTTTTAGCTGAAATATGGGCCTTATCAGATCTGA
ACAAGGATGGGAAGATGGACCAGCAAGAGTTCTCTATAGCTATGAAACTC
ATCAAGTTAAAGTTGCAGGGCCAACAGCTGCCTGTAGTCCTCCCTCCTATC
ATGAAACAACCCCTATGTTCTCTCCACTAATCTCTGCTCGTTTTGGGATG
GGAAGCATGCCCAATCTGTCCATTCATCAGCCATTGCCTCCAGTTGCACCT
ATAGCAACACCCTTGTCTTCTGCTACGTCAGGGACCAGTATTCCTCCCCTA
ATGATGCCTGCTCCCCTAGTGCCTTCTGTTAGTACATCCTCATTACCAAAT
GGAACTGCCAGTCTCATTCAGCCTT-
TATCCATTCCTTATTCTTCTTCAACAT
TGCCTCATGCATCATCTTACAGCCTGATGATGGGAGGATTTGGTGGTGCTA
GTATCCAGAAGGCCCAGTCTCTGATTGATTTAGGATCTAGTAGCTAACTT
CCTCAACTGCTTCCCTCTCAGGGAACTCACCTAAGACAGGGACCTCAGAG
TGGGCAGTTCCTCAGCCTTCAAGATTAAAGTATCGGCAAAAATTTAATAGT
CTAGACAAAGGCATGAGCGGATACCTCTCAGGTTTTCAAGCTAGAAATGC
CCTTCTTCAGTCAAATCTCTCTCAAACTCAGCTAGCTACTATTTGGACTCT
GGCTGACATCGATGGTGACGGACAGTTGAAAGCTGAAGAATTTATTCTGG
CGATGCACCTCACTGACATGGCCAAAGCTGGACAGCCACTACCACTGACG
TTGCCTCCCGAGCTTGTCCCTCCATCTTTCAGAGGGGGAAGCAAGTTGAT
```

```
TCTGTTAATGGAACTCTGCCTTCATATCAGAAAACACAAGAAGAAGAGCC
TCAGAAGAAACTGCCAGTTACTTTTGAGGACAAACGGAAAGCCAACTATG
AACGAGGAAACATGGAGCTGGAGAAGCGACGCCAAGTGTTGATGGAGCA
GCAGCAGAGGGAGGCTGAACGCAAAGCCCAGAAAGAGAAGGAAGAGTG
GGAGCGGAAACAGAGAGAACTGCAAGAGCAAGAATGGAAGAAGCAGCTG
GAGTTGGAGAAACGCTTGGAGAAACAGAGAGAGCTGGAGAGACAGCGGG
AGGAAGAGAGGAGAAAGGAGATAGAAAGACGAGAGGCAGCAAAACAGG
AGCTTGAGAGACAACGCCGTTTAGAATGGGAAAGACTCCGTCGGCAGGAG
CTGCTCAGTCAGAAGACCAGGGAACAAGAAGACATTGTCAGGCTGAGCTC
CAGAAAGAAAAGTCTCCACCTGGAACTGGAAGCAGTGAATGGAAAACAT
CAGCAGATCTCAGGCAGACTACAAGATGTCCAAATCAGAAAGCAAACAC
AAAAGACTGAGCTAGAAGTTTTGGATAAACAGTGTGACCTGGAAATTATG
GAAATCAAACAACTTCAACAAGAGCTTAAGGAATATCAAAATAAGCTTAT
CTATCTGGTCCCTGAGAAGCAGCTATTAAACGAAAGAATTAAAAACATGC
AGCTCAGTAACACACCTGATTCAGGGATCAGTTTACTTCATAAAAAGTCA
TCAGAAAAGGAAGAATTATGCCAAAGACTTAAAGAACAATTAGATGCTCT
TGAAAAAGAAACTGCATCTAAGCTCTCAGAAATGGATTCATTTAACAATC
AGCTGAAGGAACTCAGAGAAAGCTATAATACACAGCAGTTAGCCCCTTGAA
CAACTTCATAAAATCAAACGTGACAAATTGAAGGAAATCGAAAGAAAAA
GATTAGAGCAAATTCAAAAAAAGAAACTAGAAGATGAGGCTGCAAGGAA
AGCAAAGCAAGGAAAAGAAAACTTGTGGAGAGAAAGTATTAGAAAGGAA
GAAGAGGAAAAGCAAAAACGACTCCAGGAAGAAAAGTCACAGGACAAA
ACTCAAGAAGAGGAACGAAAAGCTGAGGCAAAACAAAGTGAGACAGCCA
GTGCTTTGGTGAATTACAGAGCACTGTACCCTTTTGAAGCAAGAAACCAT
GATGAGATGAGTTTTAGTTCTGGGGATATAATTCAGGTTGATGAAAAAAC
TGTAGGAGAGCCTGGTTGGCTTTATGGTAGTTTTCAGGGAAAGTTTGGCTG
GTTCCCCTGCAACTATGTAGAAAAAGTGCTGTCAAGTGAAAAAGCTCTGT
CTCCTAAGAAGGCCTTACTTCCTCCTACAGTGTCTCTCTCTGCTACCTCAA
CTTCTTCCCAGCCACCAGCATCAGTGACTGATTATCACAATGTATCCTTCT
CAAACCTTACTGTTAATACAACATGGCAGCAGAAGTCAGCTTTTACCCGC
ACTGTGTCCCTGGATCTGTGTCCCCATTCACGGACAGGGGCAGGCTGTA
GAAAACCTGAAAGCCCAGGCCCTTTGTTCCTGGACGGCAAAGAAGGAGA
ACCACCTGAACTTCTCAAAGCACGACGTCATCACTGTCCTGGAGCAGCAG
GAAAACTGGTGGTTTGGGGAGGTGCACGGAGGAAGAGGATGGTTCCCCA
AGTCTTATGTCAAGCTCATTCCTGGGAATGAAGTACAGCGAGGAGACCA
GAAGCTTTGTATGCAGCTGTGACTAAGAAACCTACCTCCACAGCCTATCC
AGTTACCTCCACAGCCTATCCAGTTGGAGAAGACTACATTGCACTTTATTC
ATACTCAAGTGTAGAGCCCGGGGATTTGACTTTCACTGAAGGTGAAGAAA
TTCTAGTGACCCAGAAAGATGGAGAGTGGTGGACAGGAAGTATTGGAGA
GAGAACTGGAATCTTCCCGTCCAACTACGTCAGACCAAAGGATCAAGAGA
```

```
ATTTTGGGAATGCTAGCAAATCTGGAGCATCAAACAAAAAACCCGAGATC
GCTCAAGTAACTTCAGCATATGCTGCTTCAGGGACTGAGCAGCTCAGCCTT
GCGCCAGGACAGTTAATATTAATCTTAAAGAAAAACACAAGCGGGTGGTG
GCAAGGAGAGCTACAGGCCAGAGGGAAGAAACGACAGAAGGGATGGTTT
CCTGCCAGCCATGTAAAGCTGCTAGGTCCAAGCAGTGAAAGAACCATGCC
TACTTTTCACGCTGTATGTCAAGTGATTGCTATGTATGACTACATGGCGAA
TAACGAAGATGAGCTCAATTTCTCCAAAGGACAGCTGATTAATGTTATGA
ACAAAGATGACCCTGACTGGTGGCAAGGAGAAACCAATGGTCTGACTGGT
CTCTTTCCTTCAAACTATGTTAAGATGACAACAGACTCAGATCCAAGTCAA
CAGTGGTGTGCTGACCTCCAAGCCCTGGACACAATGCAGCCTACGGAGAG
GAAGCGACAGGGCTACATTCACGAGCTCATTCAGACAGAGGAGCGGTAC
ATGGACGACCTGCAACTTTTTGAACAAAAAAACTCTCCTTTGAGGGCCTGG
GGAAGCCAGAACCAGGGGAGCTGCCCACAAGGCTGGGTCTAAAGACAGA
TTTTGCTCTCCCAGGACAGAGGAGCATCACATCGGCTTCATCCATCCAAAC
AAGCCACACTCGCTGGGCCTGGTATTTTATTGCACCACTAAAATTGCTAGC
AATCTATGCAAACATGATCTTTTTAAACAAACGCCACAGCACAGTGCCTT
GTACTAGTGTTAACCTGTTCAGCTGTGTTAGATGCCAGGGTTTCCATTTC
AGGGCTATAAAAGTATTATGTGGGAAATGAGACATCAGACCACCGGACGT
TACCACTTGGCAAATCTGTCCACTGTGGAGTTGGTGATGTTGGAACCATTC
CACACTATGTGACCTCTGCTGGGTCACACACTCAGGAGGTGAAGGGCTGA
GATGAAATGCTGCAGCCTTGGGGCTTGTGCAGCCTGATACTGAAATAGCA
TCCACTTGTGCACTGAATAAATAGAAACTTGATCGTTTTATTCTGACTAGA
TATTATCATTCTCTGCTAAGACAATATAGTTTGAAATATTATAGTTTGAAT
ATAAGGAGGAAAGCTTGATGTACTTTAAATATACTGTGAACTCTAATAAT
GTGGGGATATTTTCAACTTTAATTTTCTTAAGTATAAATTATTTATGTAA
ATTCTTTGTTTTGCATATTTCATAGAACATGCATCTTTAAGCTTTATCATT
GCCAACAATGTACAGAAAGAGAATAAAAGTATAAGTTTATGAATGTAAAAA
AAAAAAAAAAAAAA
```

Mouse Ese2 Coding Sequence—Sequence ID NO:5

```
ATGGCTCAGTTTCCCACAGCGATGAATGGAGGGCCAAATATGTGGGCTAT
TACATCTGAAGAACGTACTAAGCATGATAAACAGTTTGATAACCTCAAAC
CTTCAGGAGGTTACATAACAGGTGATCAAGCCCGTACTTTTTTCCTACAG
TCAGGTCTGCCGGCCCCGGTTTTAGCTGAAATATGGGCCTTATCAGATCT
GAACAAGGATGGGAAGATGGACCAGCAAGAGTTCTCTATAGCTATGAAAC
TCATCAAGTTAAAGTTGCAGGGCCAACAGCTGCCTGTAGTCCTCCCTCCT
ATCATGAAACAACCCCCTATGTTCTCTCCACTAATCTCTGCTCGTTTTGG
GATGGGAAGCATGCCCAATCTGTCCATTCATCAGCCATTGCCTCCAGTTG
CACCTATAGCAACACCCTTGTCTTCTGCTACGTCAGGGACCAGTATTCCT
CCCCTAATGATGCCTGCTCCCCTAGTGCCTTCTGTTAGTACATCCTCATT
```

-continued

ACCAAATGGAACTGCCAGTCTCATTCAGCCTTTATCCATTCCTTATTCTT
CTTCAACATTGCCTCATGCATCATCTTACAGCCTGATGATGGGAGGATTT
GGTGGTGCTAGTATCCAGAAGGCCCAGTCTCTGATTGATTTAGGATCTAG
TAGCTCAACTTCCTCAACTGCTTCCCTCTCAGGGAACTCACCTAAGACAG
GGACCTCAGAGTGGGCAGTTCCTCAGCCTTCAAGATTAAAGTATCGGCAA
AAATTTAATAGTCTAGACAAAGGCATGAGCGGATACCTCTCAGGTTTTCA
AGCTAGAAATGCCCTTCTTCAGTCAAATCTCTCAAACTCAGCTAGCTA
CTATTTGGACTCTGGCTGACATCGATGGTGACGGACAGTTGAAAGCTGAA
GAATTTATTCTGGCGATGCACCTCACTGACATGGCCAAAGCTGGACAGCC
ACTACCACTGACGTTGCCTCCCGAGCTTGTCCCTCCATCTTTCAGAGGGG
GAAAGCAAGTTGATTCTGTTAATGGAACTCTGCCTTCATATCAGAAAACA
CAAGAAGAAGAGCCTCAGAAGAAACTGCCAGTTACTTTTGAGGACAAACG
GAAAGCCAACTATGAACGAGGAAACATGGAGCTGGAGAAGCGACGCCAAG
TGTTGATGGAGCAGCAGCAGAGGGAGGCTGAACGCAAAGCCCAGAAAGAG
AAGGAAGAGTGGGAGCGGAAACAGAGAGAACTGCAAGAGCAAGAATGGAA
GAAGCAGCTGGAGTTGGAGAAACGCTTGGAGAAACAGAGAGAGCTGGAGA
GACAGCGGGAGGAAGAGAGGAGAAAGGAGATAGAAAGACGAGAGGCAGCA
AAACAGGAGCTTGAGAGACAACGCCGTTTAGAATGGGAAAGACTCCGTCG
GCAGGAGCTGCTCAGTCAGAAGACCAGGGAACAAGAAGACATTGTCAGGC
TGAGCTCCAGAAAGAAAAGTCTCCACCTGGAACTGGAAGCAGTGAATGGA
AAACATCAGCAGATCTCAGGCAGACTACAAGATGTCCAAATCAGAAAGCA
AACACAAAAGACTGAGCTAGAAGTTTTGGATAAACAGTGTGACCTGGAAA
TTATGGAAATCAAACAACTTCAACAAGAGCTTAAGGAATATCAAAATAAG
CTTATCTATCTGGTCCCTGAGAAGCAGCTATTAAACGAAAGAATTAAAAA
CATGCAGCTCAGTAACACACCTGATTCAGGGATCAGTTTACTTCATAAAA
AGTCATCAGAAAAGGAAGAATTATGCCAAAGACTTAAAGAACAATTAGAT
GCTCTTGAAAAAGAAACTGCATCTAAGCTCTCAGAAATGGATTCATTTAA
CAATCAGCTGAAGGAACTCAGAGAAAGCTATAATACACAGCAGTTAGCCC
TTGAACAACTTCATAAAATCAAACGTGACAAATTGAAGGAAATCGAAAGA
AAAAGATTAGAGCAAATTCAAAAAAAGAAACTAGAAGATGAGGCTGCAAG
GAAAGCAAAGCAAGGAAAAGAAAACTTGTGGAGAGAAAGTATTAGAAAGG
AAGAAGAGGAAAAGCAAAAACGACTCCAGGAAGAAAAGTCACAGGACAAA
ACTCAAGAAGAGGAACGAAAAGCTGAGGCAAAACAAAGTGAGACAGCCA
GTGCTTTGGTGAATTACAGAGCACTGTACCCTTTTGAAGCAAGAAACCAT
GATGAGATGAGTTTTAGTTCTGGGGATATAATTCAGGTTGATGAAAAAAC
TGTAGGAGAGCCTGGTTGGCTTTATGGTAGTTTTCAGGGAAAGTTTGGCT
GGTTCCCCTGCAACTATGTAGAAAAAGTGCTGTCAAGTGAAAAAGCTCTG
TCTCCTAAGAAGGCCTTACTTCCTCCTACAGTGTCTCTCTCTGCTACCTC
AACTTCTTCCCAGCCACCAGCATCAGTGACTGATTATCACAATGTATCCT
TCTCAAACCTTACTGTTAATACAACATGGCAGCAGAAGTCAGCTTTTACC

-continued

CGCACTGTGTCCCCTGGATCTGTGTCCCCCATTCACGGACAGGGGCAGGC
TGTAGAAAACCTGAAAGCCCAGGCCCTTGTTCCTGGACGGCAAAGAAGG
AGAACCACCTGAACTTCTCAAAGCACGACGTCATCACTGTCCTGGAGCAG
CAGGAAAACTGGTGGTTTGGGGAGGTGCACGGAGGAAGAGGATGGTTCCC
CAAGTCTTATGTCAAGCTCATTCCTGGGAATGAAGTACAGCGAGGAGAGC
CAGAAGCTTTGTATGCAGCTGTGACTAAGAAACCTACCTCCACAGCCTAT
CCAGTTACCTCCACAGCCTATCCAGTTGGAGAAGACTACATTGCACTTTA
TTCATACTCAAGTGTAGAGCCCGGGGATTTGACTTTCACTGAAGGTGAAG
AAATTCTAGTGACCCAGAAAGATGGAGAGTGGTGGACAGGAAGTATTGGA
GAGAGAACTGGAATCTTCCCGTCCAACTACGTCAGACCAAAGGATCAAGA
GAATTTTGGGAATGCTAGCAAATCTGGAGCATCAAACAAAAAACCCGAGA
TCGCTCAAGTAACTTCAGCATATGCTGCTTCAGGGACTGAGCAGCTCAGC
CTTGCGCCAGGACAGTTAATATTAATCTTAAAGAAAAACACAAGCGGGTG
GTGGCAAGGAGAGCTACAGGCCAGAGGGAAGAAACGACAGAAGGGATGGT
TTCCTGCCAGCCATGTAAAGCTGCTAGGTCCAAGCAGTGAAAGAACCATG
CCTACTTTTCACGCTGTATGTCAAGTGATTGCTATGTATGACTACATGGC
GAATAACGAAGATGAGCTCAATTTCTCCAAAGGACAGCTGATTAATGTTA
TGAACAAAGATGACCCTGACTGGTGGCAAGGAGAAACCAATGGTCTGACT
GGTCTCTTTCCTTCAAACTATGTTAAGATGACAACAGACTCAGATCCAAG
TCAACAGTGGTGTGCTGACCTCCAAGCCCTGGACACAATGCAGCCTACGG
AGAGGAAGCGACAGGGCTACATTCACGAGCTCATTCAGACAGAGGAGCGG
TACATGGACGACCTGCAACTTTTTGAACAAAAAACTCTCCTTTGA

Mouse Ese2—Sequence ID NO:6

MAQFPTAMNGGPNMWAITSEERTKHDKQFDNLKPSGGYITGDQARTFFLQ
SGLPAPVLAEIWALSDLNKDGKMDQQEFSIAMKLIKLKLQGQQLPVVLPP
IMKQPPMFSPLISARFGMGSMPNLSIHQPLPPVAPIATPLSSATSGTSIP
PLMMPAPLVPSVSTSSLPNGTASLIQPLSIPYSSSTLPHASSYSLMMGGF
GGASIQKAQSLIDLGSSSSTSSTASLSGNSPKTGTSEWAVPQPSRLKYRQ
KFNSLDKGMSGYLSGFQARNALLQSNLSQTQLATIWTLADIDGDGQLKAE
EFILAMHLTDMAKAGQPLPLTLPPELVPPSFRGGKQVDSVNGTLPSYQKT
QEEEPQKKLPVTFEDKRKANYERGNMELEKRRQVLMEQQQREAERKAQKE
KEEWERKQRELQEQEWKKQLELEKRLEKQRELERQREEERRKEIERREAA
KQELERQRRLEWERLRRQELLSQKTREQEDIVRLSSRKKSLHLELEAVNG
KHQQISGRLQDVQIRKQTQKTELEVLDKQCDLEIMEIKQLQQELKEYQNK
LIYLVPEKQLLNERIKNMQLSNTPDSGISLLHKKSSEKEELCQRLKEQLD
ALEKETASKLSEMDSFNNQLKELRESYNTQQLALEQLHKIKRDKLKEIER
KRLEQIQKKKLEDEAARKAKQGKENLWRESIRKEEEEKQKRLQEEKSQDK
TQEEERKAEAKQSETASALVNYRALYPFEARNHDEMSFSSGDIIQVDEKT

-continued
VGEPGWLYGSFQGKFGWFPCNYVEKVLSSEKALSPKKALLPPTVSLSATS

TSSQPPASVTDYHNVSFSNLTVNTTWQQKSAFTRTVSPGSVSPIHGQGQA

VENLKAQALCSWTAKKENHLNFSKHDVITVLEQQENWWFGEVHGGRGWFP

KSYVKLIPGNEVVQRGEPEALYAAVTKKPTSTAYPVTSTAYPVGEDYIAL

YSYSSVEPGDLTFTEGEEILVTQKDGEWWTGSIGERTGIFPSNYVRPKDQ

ENFGNASKSGASNKKPEIAQVTSAYAASGTEQLSLAPGQLILILKKNTSG

WWQGELQARGKKRQKGWFPASHVKLLGPSSERTMPTFHAVCQVIAMYDYM

ANNEDELNFSKGQLINVMNKDDPDWWQGETNGLTGLFPSNYVKMTTDSDP

SQQWCADLQALDTMQPTERKRQGYIHELIQTEERYMDDLQLFEQKTLL

Mouse Ese2 Alternative Transcript Partial cDNA Sequence—Sequence ID NO:7

CCGTCTTCCACATTTCCCACATTGATCGTGTGTACACACTCCGAACAGAC

AACATCAACGAGAGGACGGCCTGGGTCCAGAAGATCAAGGGTGCCTCAGA

GCAGTACATCGACACTGAGAAGAAGAAACGGGAAAAGGCTTACCAAGCC

CGTTCTCAAAAGACTTCAGGTATTGGGCGTCTGATGGTGCATGTCATTGA

AGCTACAGAATTAAAAGCCTGCAAACCAAACGGGAAAAGTAATCCATACT

GTGAAGTCAGCATGGGCTCCCAAAGCTATACCACCAGGACCCTGCAGGAC

ACACTAAACCCCAAGTGGAACTTCAACTGCCAGTTCTTCATCAAGGATCT

TTACCAGGACGTTCTGTGTCTCACTATGTTTGACAGAGACCAGTTTTCTC

CAGATGACTTCTTGGGTCGTACTGAAGTTCCAGTGGCAAAAATCCGAACA

GAACAGGAAAGCAAAGGCCCCACCACCCGCCGACTACTACTGCACGAAGT

CCCCACTGGAGAAGTCTGGGTCCGCTTTGACCTGCAACTTTTTTGAACAA

AAAACTCTCCTTTGAGGGCCTGGGGAAGCCAGAACCAGGGGAGCTGCCCA

CAAGGCTGGGTCTAAAGACAGATTTTGCTCTCCCAGGACAGAGGAGCATC

ACATGGCTTCATCCATCAAACAGCCACACTCGCTGGGCCTGTATTTTATT

GCACACTAAATTGCTAGCAATCTATGCAAACATGATCTTT

Mouse Ese2 Alternative Partial Protein Containing C2 Membrane-Binding Domains—Sequence ID NO:8

VFHISHIDRVYTLRTDNINERTAWVQKIKGASEQYIDTEKKKREKAYQAR

SQKTSGIGRLMVHVIEATELKACKPNGKSNPYCEVSMGSQSYTTRTLQDT

LNPKWNFNCQFFIKDLYQDVLCLTMFDRDQFSPDDFLGRTEVPVAKIRTE

QESKGPTTRRLLLHEVPTGEVWVRFDLQLFEQKTLL

Novel Ese-coiled-coil Interacting Clones:

Mouse Homologue of C07E3.1 Protein (Clone 65):—Sequence ID NO:9

GAATTCGGCACGAGGGCTGAGAGAAGCGGACTCCGAGGACTCTGATGCTG

AAGAGAAGCCTGTTAAGCAGGAGGACTTCCCGAAGATTTAGGACCAAAG

AAGTTAAAGACGGGTGGCAATTTTAAGCCCAGCCAGAAAGGCTTTTCAGG

AGGAACCAAGTCCTTCATGGACTTTGGCAGCTGGGAGAGACACACGAAAG

GGATCGGGCAGAAGCTGCTGCAGAAGATGGGCTACGTCCCTGGGCGTGGC

CTGGGGAAGAACGCACAGGGGATCATCAACCCCATCGAAGCCAAACAGA

GAAAAGGCAAGGGAGCCGTGGGGGCCTATGGCTCGGAGAGGACCACTCA

GTCTCTGCAGGACTTCCCCGTGGCCGACTCGGAAGAGGAGGCAGAAGAGG

AGTTTCAGAAGGAGCTGAGCCAATGGAGGAAAGACCCCAGCGGGAGCAA

GAAGAAGCCAAAGTACTCTTACAAGACTGTGGAGGAGCTGAAGGCCAAG

GGCAGGGTCAGCAAGAAGCTCACAGCACCTCAGAAGGAACTGTCTCAGGT

CAAGGTGATCGACATGACAGGCCGGGAGCAGAAGGTGTACTACAGCTAC

AGCCAAATCAGCCACAAGCACAGCGTGCCCGATGAAGGGGTGCCATTGCT

GGCGCAGCTGCCCCCCACAGCCGGCAAGGAAGCCAGGATGCCGGGCTTTG

CACTGCCTGAGCTGGAGCACAACCTGCAGCTGCTCATTGAGCGCACGGAG

CAGGAGATCATCCAGAGCGACCGGCAGCTCCAGTATGAGCGGGACATGGT

GGTCAGCCTGTCGCATGAGCTGGAGAAGACGGCCGAGGTTCTTGCACATG

AGGAGCGTGTCATCTCTAACCTCAGCAAGGTGCTGGCCCTGGTGGAGGAA

TGTGAGCGCCGCATGCAGCCCCATGGCACCGACCCCCTCACTCTGGATGA

GTGTGCCCGCATCTTTGAGACACTACAGGACAAGTATTATGAGGAGTACC

GCCTGGCGGACCGCGCAGACCTCGCTGTGGCCATTGTCTACCCGCTCGTG

AAGGACTACTTTAAGGATTGGCACCCCTCGAGGG

Mouse Partial C07E3.1 Protein (Clone 65):—Sequence ID NO: 10

GTKSFMDFGSWERHTKGIGQKLLQKMGYVPGRGLGKNAQGIINPIEAKQR

KGKGAVGAYGSERTTQSLQDFPVADSEEEAEEEFQKELSQWRKDPSGSKK

KPKYSYKTVEELKAKGRVSKKLTAPQKELSQVKVIDMTGREQKVYYSYSQ

ISHKHSVPDEGVPLLAQLPPTAGKEARMPGFALPELEHNLQLLIERTEQE

IIQSDRQLQYERDMVVSLSHELEKTAEVLAHEERVISNLSKVLALVEECE

RRMQPHGTDPLTLDECARIFETLQDKYYEEYRLADRADLAVAIVYPLVKD

YFKDWHPSR

Mouse Novel cDNA Clone 42/Est Accession #W29719 and #AA915044:—Sequence ID NO:11

CATGGCGGCGGCTGCGGAGGGCGTCCCGGCGACGCGACGGAGGACGAGC

CACCTCGAGATGATGCTGCGGTGGAGACAGCCGAGGAAGCAAAGGAGC

Mouse Novel cDNA Clone 70:—Sequence ID NO:12

CTTGAGTCTACTGAAAATACCCTGCAGGAAGCTACATCATCCATGTCTTT

GATGACCCAATTTGAACAGGAAGTATCTGGCCTCCAAAGACCATACGTGA

TATTGAGACTAGCGAAGAGATGC

Mouse Novel cDNA Clone 83/Est Accession #AA589041 and W98708:—Sequence ID NO:13

GAATTCGGCACGAGGGAGTCTGGTTCTGGAAAGCCGACAGAAGCTGAGCT

TGTCAACTTAGATTTCTTGGGAGATTTGGATGTTCCGGTATCTGCCCCAC

CCCTGTGTGTCTGAGCTCGAGTCTCTCTGCTGGACTATGG

Novel Ese-SH3 Interacting Clones:

Mouse YNK1 Partial cDNA:—Sequence ID NO: 14

CTTTACGAGCAGAGGGAGCCAAATTCAGAGCCGTTTTAGATAAAGCTGTG

CAAGCGGATGGACAGGTGAAGGAGCGCTACCAGTCCCATCGAGACACCA

TCGCACTTCTGTGTAAGCCGGAGCCAGAGCTGAATGCTGCCATCCCCTCT

GCTAACCCAGCAAAGACCATGCAGGGCAGCGAGGTTGTAAGTGTCTTAAA

GTCCTTATTATCAAATCTTGATGAAATCAAGAAGGAAAGAGAGAGTCTTG

AGAATGACCTGAAGTCAGTGAATTTTGACATGACAAGCAAGTTTTTGACA

GCTCTGGCCCAAGATGGCGTGATAAATGAGGAGGCTCTCTCTGTCACTGA

GCTGGATCGGATCTATGGCGGTCTAACAAGTAAAGTTCAAGAGTCTCTGA

AGAAACAAGAGGGACTTCTAAAAAATATACAGGTCTCACACCAAGAATTC

TCCAAAATGAAGCAATCTAACAACGAGGCTAACTTGAGAGAAGAAGTTCT

GAAGAACCTAGCAACTGCGTATGACAACTTTGTTGAGCTTGTAGCTAACT

TGAAGGAGGGCACAAAGTTTTACAATGAGCTGACTGAGATCCTGGTCAGG

TTCCAGAACAAATGCAGTGACATAGTGTTTGCACGGAAGACAGAAAGAGA

CGAGCTCTTGAAGGATCTGCAGCAGAGCATTGCCAGAGAGCCCAGCGCTC

CTTCAATCCCTCCTCCAGCCTATCAGTCCTCCCCAGCAGCGGGGCATGCA

GCAGCGCCTCCAACTCCAGCCCCAAGAACCATGCCGCCTGCTAAGCCCCA

GCCTCCAGCCCGGCCTCCACCTCCTGTGCTTCCTGCAAACCGAGTTCCTC

CTGCTTCTGCTGCTGCTGCCCCTGCAGGCGTGGGGACGGCTTCAGCAGCG

CCGCCACAGACCCCTGGCTCTGCTCCCCCGCCACAGGCTCAGGGACCACC

ATACCCTACCTATCCAGGATATCCCGGGTATTGCCAAATGCCCATGCCCA

TGGGCTACAACCCCTACGCATATGGCCAGTACAATATGCCGTACCCACCG

GTGTATCACCAGAGCCCCGGACAGGCTCCATACCCAGGACCCCAGCAGCC

TACCTACCCCTTCCCTCAGCCCCCGCAGCAGTCCTACTATCCACAGCAGT

AACGCTGCCACGTGCTGCTGGTTCAGATCAGAGCGACAGGACAGCAGCTG

CCACCAGCTCTAAGCCACGCTCTGGCCACTCGAGAGTATCTTGCTCTATT

GATTGCTGTGGATGATTTCTGTCTGTGGCTAAAGCCGAAGGCTGGGCCCC

ACCTCCACATTTGATCGCACTCGTGAGATTCTGCTGCTGTTGCAGTATAA

ACGCTAGCTATAATAGCATTTGAAAAAAATTACAGTTCCATAAAATGCTG

AAAATGAGAAATTAAACCTGCAAGTGAAACATTTGAAATTAGCATACTTT

ATAAGATGCAGTTGGGACAAAGATGGCTTAAGTACTGATATTTAAGGAAA

AAGTTTTCTTTCTCTTTTGGTTTATTGATTTAGTTTAATTTCTATTATGA

TATTTTGCATAATCAAGGCATTGTAAATCTTATAATTTAAAAATAAATTA

CTTACGAACAGTTGTCATTGTTATGTTTTGTCATTGATTCTCATTGCTGT

CTAGTTCCTTTCTGGTATTAGCCTCTCCTTCTGTATGTTCACAGGCTCCA

TTACTGTGTTGAATTGCGTGACGTCAGGTGAGCAGTCAGGGAGGGCTGCT

CTGCGGACGCCAAGCGCACACCAGCTTGTCTCAGGCTCAGCAGTCAGCTC

ATCTGGACATTTCTATTTAAAAGTCCTTTAATGTGGAAGATACACACAAT

TGTTACCAAAGGTTCTTCCAATTAATTTTACAATTTAAAAAGTATGTATT

AATGTTTTATTGTTAGATTTTCCAAAAAAATGATGCAAATTCTGGTAATA

TTCATTTCCCTCACCCATAATTTGGTTAAAATGAGTAGTTTTAGCCATAC

AGTCTCATCTGCTGTGGAGGAACCTGGAGAAAGTCCCCTGTGCCTTTCTA

GCCCTTGGGTTCTATTCTTATCCTGCAATGTCTACTGCACAGTGTGTTTG

AGCAGATCCTAACCCTCCTTTTACAGTTTCTTCTTCTTACTTCTTTATTC

TTTTTGTGGCTCCTGAAATCTGAGGTTATTTTGTAATTCAGGAGCATGCA

GGACAATTGTTGGGACATGTGCCTAGTCCGGAATACAGCCCAGGACAGCA

AGGAGATGCGTCCTGCACCAGGAAGCCGTGCAGGCAGGAGCTGTCCAAGG

TCCCGGCGGCTCTGCCTGTGTGAGGCAGGAGAATGAGCAGATTCCCTAAT

CTATGTTCTCGAAGTTTAATGCTGATGTTGTCTTGCCTTATCCTCATTTA

ACTGATACTGTCACCCAGTCCACCTTTGCTCTCATTGCAAAGTGATAGTG

TAATTTCAAATGTAAGACTGAAGATACGATTGTAAAAGGGAGTAAACTGG

TTTAAACGTGTTATTCTAAAGCACCTTACTTTGTTGTTGTATGCAGAAAA

CACAGATGCGCTAATTCAGTATAAATGACTGATTGCCTGGAATTTGGACG

TTGGCTTAAAGTCCGATAGCTAAACCTTGGCAAAACATAACAAACATTTC

ATTGCTCAGCCTCAGTGCTCTGGAGTATTCAGTGTATGAGACAGGTTTAT

TTGAGTCCTCTGTAAATGGCATTTGAATTTTATATTCTCCCCTCCCGAGT

ATCTTATAAGACATCCCCTGAGTTAGGGAGTTCCCAGACTGCTACTCTAT

TCCTTATGAATGCAAAACAACCACCAATAGAACAAAAAAAAAAAAAAAAA

CTCGAG

Mouse YNK1 Partial Coding cDNA—Sequence ID NO:15

CTTTACGAGCAGAGGGAGCCAAATTCAGAGCCGTTTTAGATAAAGCTGTG

CAAGCGGATGGACAGGTGAAGGAGCGCTACCAGTCCCATCGAGACACCAT

CGCACTTCTGTGTAAGCCGGAGCCAGAGCTGAATGCTGCCATCCCCTCTG

CTAACCCAGCAAAGACCATGCAGGGCAGCGAGGTTGTAAGTGTCTTAAAG

TCCTTATTATCAAATCTTGATGAAATCAAGAAGGAAAGAGAGAGTCTTGA

GAATGACCTGAAGTCAGTGAATTTTGACATGACAAGCAAGTTTTTGACAG

CTCTGGCCCAAGATGGCGTGATAAATGAGGAGGCTCTCTCTGTCACTGAG

CTGGATCGGATCTATGGCGGTCTAACAAGTAAAGTTCAAGAGTCTCTGAA

GAAACAAGAGGGACTTCTAAAAAATATACAGGTCTCACACCAAGAATTCT

CCAAAATGAAGCAATCTAACAACGAGGCTAACTTGAGAGAAGAAGTTCTG

AAGAACCTAGCAACTGCGTATGACAACTTTGTTGAGCTTGTAGCTAACTT

GAAGGAGGGCACAAAGTTTTACAATGAGCTGACTGAGATCCTGGTCAGGT

TCCAGAACAAATGCAGTGACATAGTGTTTGCACGGAAGACAGAAAGAGAC

GAGCTCTTGAAGGATCTGCAGCAGAGCATTGCCAGAGAGCCCAGCGCTCC

TTCAATCCCTCCTCCAGCCTATCAGTCCTCCCCAGCAGCGGGGCATGCAG

CAGCGCCTCCAACTCCAGCCCCAAGAACCATGCCGCCTGCTAAGCCCCAG

CCTCCAGCCCGGCCTCCACCTCCTGTGCTTCCTGCAAACCGAGTTCCTCC

TGCTTCTGCTGCTGCTGCCCCTGCAGGCGTGGGGACGGCTTCAGCAGCGC

CGCCACAGACCCCTGGCTCTGCTCCCCCGCCACAGGCTCAGGGACCACCA

TACCCTACCTATCCAGGATATCCCGGGTATTGCCAAATGCCCATGCCCAT

GGGCTACAACCCCTACGCATATGGCCAGTACAATATGCCGTACCCACCGG

TGTATCACCAGAGCCCCGGACAGGCTCCATACCCAGGACCCCAGCAGCCT

ACCTACCCCTTCCCTCAGCCCCGCAGCAGTCCTACTATCCACAGCAG

TAA

Mouse YNK1 Partial Protein—Sequence ID NO:16

LRAEGAKFRAVLDKAVQADGQVKERYQSHRDTIALLCKPEPELNAAIPSA

NPAKTMQGSEVVSVLKSLLSNLDEIKKERESLENDLKSVNFDMTSKFLTA

LAQDGVINEEALSVTELDRIYGGLTSKVQESLKKQEGLLKNIQVSHQEFS

KMKQSMMEANLREEVLKNLATAYDNFVELVANLKEGTKFYNELTEILVRF

QNKCSDIVFARKTERDELLKDLQQSIAREPSAPSIPPPAYQSSPAAGHAA

APPTPAPRTMPPAKPQPPARPPPPVLPANRVPPASAAAAPAGVGTASAAP

PQTPGSAPPPQAQGPPYPTYPGYPGYCQMPMPMGYNPYAYGQYNMPYPPV

YHQSPGQAPYPGPQQPTYPFPQPPQQSYYPQQ

Mouse Novel cDNA Clone 4:—Sequence ID NO:17

GGTCTTGGCTAGAATTTTAAATTTCTTCTCATTTGAGTAAAATGTTGCAT

TCTGAAGTCCCATGCTACCTGAAGTTGCATTTGGAGTCCCAAGCTACTGG

AATGTTTATATGTGACCGTTTCCCAGGAGGCTTACACTGCAGAAGGAAGA

ATGAATCTAGGTGAGGTGGGCAGCTGCTTGGCAGTCCTCTCTTGTGCCCC

AACTGTAAACCAGATAGAAATGTTCAGGGGAGGATACTTTCATTATTGTG

GTTTGTAGTGTTAAGATGATTGCTTCTGCCTTGGAAATACCTCAAGCTGT

TCTTATTTAACAGGTAAGTGACTGAGTATAATATTCCAGAAAAATTTGAA

ATCCTAATTTCTTCCATATTTCATTAAATTTTTTGCATACAGGTCTAACA

AATATGGATATGTATACACATCCTCTTTAATGAAGGTATTATTTTGGTTA

CTTTTCCTAAGATATACCTTAAAAGATGTTCTATACATTTCCTACTTAAA

TTCTGGGGATTTGGAGTATGTACATGATAAAAAAGATTATAATATATCG

ATTGAAGTTACTTTATTTTCTAATTAGAATTATTTTAATAGTCCTTTATT

GAATAAGTGCTGTAATTTGTTTGCTATGAGACTTATTCCTGATGTGAATG

TAAATTATTTTTCCACATGCATGAAAAAATGTATGTACTAATCAGAGTTG

TCTCCATTGCATTGAAATTACTTGTTTTGAACTAAAGTAACTCATATTTA

TGTAGTAGAATGCTTATGTTTTCAGACTTTGTAATGATTTCCTTTGGATG

TATTTTAAATCAATCGGTCTGGGTAACATATCAGTTTAGATTAATATGTG

CTTAAAAGAAGAAAAAAATTCAATGGTTCATAGTAGAAATGTGCCACACT

TAAATAAGCTCTGTATGACATGAAATTCTGTTAAAACATTGTAATTCATG

GTGACTTTTAACTTATAAAAATACTACTTGCACGGGTTACTTGATTTATG

GATATATGAAAACTTCTCAGGACGAAAGTTCTTCTTTCTCTAGAACTATT

CTTCTGTCGGTCATGCAGAATGCTGTTATTCTGAAAAGTGTCCCTGTTGC

ATATGATGGTCACTTTATTTGGGGGGATTCTTCATAAGATGTGAGATGTT

GATGCCAGTCTTTCCCAAGTAAGTGCTCGTAAAAAAGGACTACTAACTAG

CCTGCATCTGTCTCTAACTGGGACCAAGGGGTCTGCTGAAGGAAACTGAA

GAGCTCTAACATTTTCACAGCTTGGAGAAGATAGAATCTTTAAAAGTACA

ACTGAAGCTTGATCTATTTTACAAGTGCATTGATGGCCCCTGTCCTTCTC

TGGTTCCTGTCATTTGAAACCAACTCCTGTTGTAAATAGGAAGAATATGG

GACATTCATATTTAAGAAAATTTGATGTCATTAGGTGACTAAGTAGAAGG

CTTAGAAAAATGTATTCATTTGCAAGTATTTTGGCACAAGAAATTTTCCA

ACTGAATAGTAAGCAAAAGCTAAGTTGTTTCATTGAAATCATAAGGCAGT

TTAAGATAAACTGGAGAAGATAACTGTTCTAATAGAGGATAATCGAATTG

ATTGTCAAGTGGATGTTATTTATTGGATAGTGACAGAGTTTATTTGTAAC

CTTAATTATATTAAAAGTTATTCTGTTAGGATGTTTTGTATTAATAAACG

TGAACAAAATTAAAAAAAAAAAAAAAAAAAACTCGAGGG

Mouse Novel cDNA Clone 8/47/52:—Sequence ID NO:18

GAGAAGGCGGCCTGCCGCAGCGGGACAACCTAGAGCGCGACGTGGAGGC

GCGTAGCGGAGCTGGAGCAACTGCGCACCGAGGTGGATGTGCGCATTAGC

GCNNTGGACACCTGCGTCAAGGCCAAGTCGCTGCCAGCCGTCCCGCCGAG

AGTCTCAGGCCCACCCCCGAACCCTCCACCCATTGATCCAGCTAGCCTGG

AGGAATTCAAGAAAAGGATCCTGGAGTCTCAGCGGCTCCCTGTAGTCAAC

CCTGCWGCCCAACCCAGCGGTTGAGRACCCAGCTGCCGCAGGACGCTGG

GTGCCAGAATCGCCCACCTGTGGATGGGGCAGCCAGGTGCCCACAGTGC

TGGACACCCGCCGTGCCTGCCGGCAGCCTCCACCCCCAGCGCCTTCTCTG

GCACCCCTTCACTGTCCCSTGCATCCCCRCCATTCSSCASWSASKGGATT

TAAGGCACACACAGCTGTGAGATGACTTCACATCGACCCCTTGTGCAGTG

ACCCGGATGGTGCCCCACCCACACATGAAGCACCCACAGCTCAGCTGCCA

CCCTAGGCAACTCCTCCGGTTTCCTATCACTCTGCTCCTGACCCGGGAGG

TGAGAACAGGAAGCCCAGCCTTCAGCTCCCTTGGGAGTTTCCAGCCTCCC

TCTTAAAGGCCACTAGGGTTTCCAGATCCTATTTGAGAGTCTCCAGGCCT

CCCCTGAAGGGTTCTAGCCACCACGCCCACAGGATTCCCATTAGGTTTTA

AAGTCTTTTCCAGAGTCCGCTGGTTCCCCTCCTCCTCACAAGGAAGGGCC

TCAATTGTAGATGAGCGTTCCGGGTGGATCTTAGAGCCCTAGAGGGAGGC

TTTTGCTTGTARCCCCCTAAAGATATTACTGGCACATAATAAATATGAAA

-continued

```
GTCCTTTGAAAGTTGGACACTGCGCAAATGGGGCTCTCCATGGACCGCAG

CCCATACGCCCGCACGGGGGACCAGCAGCGCGGCTCTGGTTCTACCTGCG

CTATTTCTTCCTCTTCGTGTCGCTCATTCAGTTCCTCATCATCCTGGGCC

TGGTCCTCTTCATGATCTATGGCAATGTGCACGCCACCACTGAGTCCAGC

CTGCGCGCCACGGAGATCCGCGCCGACAGCCTGTACAGCCAGGTGGTTGG

ACTATCGGCCTCACAGGCTAACCTGAGCAAACAGCTGAACATCAGCTTGC

TTGTCAAGGAAACAGTCATGCAGCAACTGTTGACTACGCGACGTGAGATG

GAGCGCATCAACGCCAGCTTCCGCCAGTGCCAAGGCGACCTGATCACCTA

CATAAACTATAATCGCTTCATCGCCGCTATCATCCTGAGCGAGAAGCAGT

GCCAGGAACAGCTGAAGGAGGTCAACAAGACCTGCGAACTTTACTCTTCA

AGCTGGGAGAAAAGTTAAGACACTGGAGATGGAGGTGGCCAAGGAGAAG

GCAGTGTGCTCCAAGGACAAGGAGAGCCTGCTGGCAGGAAAGCGGCAGAC

GGAAGAGCAGCTGGAGGCCTGTG
```

Mouse Novel cDNA Clone 18/25:—Sequence ID NO: 19
5'end of Partial Clone

```
TGTGCGCCGCCTCTAGAACTAGTGGATCCCCCGGGCCTGCAGGAATTCCG

GCACGACGGCCGAGCGCCGCGGACCACCCGCGGCTGCCCGCCGAGCCGTC

GACATGTGGGGGACTGGGGTGGGAGCGGCCGGAGCAGCGCCAGGTACC

CGGGCGCGCAGAACCATGGCTCTCGCTCGCCTGTCCTGACCTGGCTTGCT

CGCCCCACCGAAGAATGTCAGCCAAGTCCAAGGGGAACCCTCCTCGTCCT

CCGCAGCCGAGGGACCGCCGGCAGCCTCCAAAACCAAGGTGAAGGAGCAG

ATCAAGATCATAGTGGAGGATCTGGAATTAGTCCTGGGCGACCTGAAGGA

CGTGGCCAAAGAACTTAAGGAGGTGGTTGACCAGATTGACACCCTGACCT

CTGATCTACAGCTGGAAGATGAGATGACCGACAGCTCCAAAACAGACACT

CTGAACAGCAGCTCCAGTGGGACAACAGCCTCCAGCATAGAGAAGATCA

AAGAACAGGCCAATGCTCCCCTCATTAAACCTCCAGCACACCCGTCTGCT

ATCCTGACTGTCCTGAGAAAGCCAAACCCTCCACCGCCTCCTCCAAGGTT

GACACCCGTGAGGTGTGAAGAGCCTCAGAGAGTGGTGCCGACTGCCAACC

CTGTAAAGACCAATGGCACTCTTCTGCGGAATGGAGGCTTAGCGGGGAGG

CCCAACAAAATTCCAAATGGAG
```

3' end—Sequence ID NO:20

```
CTCGAGTTTTTTTTTTTTTTTTTTTTTTTTCATTATTTACTATTATT

TATTGACATATTTCCAAAGCTCAAAATATTTTATTATACATATAGTTGAA

CATATGTTTCAAATTGTATAGTATAGAAAATAAACTTTTTTGTAGTGTCC

TCAGCATTTCATGATGCAAAACTATTGACAAACATCTTTAGAAAAATAAT

AAAATAGTCCTTCGGTATTAAAATTCTTATTAAAAAGCATTAGATCAAAG

GGAGAACTATGACATCATCAATGCATAGATGAGATAGGCATGAATGGAAT

GAGTTGCCCTGGCTTTATCAACAAATCAAAATATCTGACATCCCAGCTCT
```

-continued

```
TATAATAGACCAAAATACTTGGAATCAGAAGGTCACAGTTTGTTTTAGGT

CAATCACAAAAAAATAAAATTCATTCATACTTTCTCAATTTTCCGCAGTT

TCTGATGATGGAACATAGAAAACAATGTACGTCCAGGACAGAGGCGCTAC

TCTGCATACTTACCACGTGATTTTTTATGCCACTTTGTTGAATGCAGATT

AATATATTTGGGCTTTTTATTGCTTGAGTAGAAAGTGCTCATTACTTATT

ATTTTACGTTTATCATATAGAAAATTAAAAACAAACAGAACGTTTTCTTA

AATGGCAGATATCACACTGTGGTAGTGGTGGATTTCCTCAGGATGGTCTT

CTGTGGTTTTGGTGCAGCGGGAGGAGGCACGGTTGCAGGTGTGGGAGGGG

GGAAACTGTTACTGTGGCTTATTCCCAGTCCCCCATTTTCTAATGGGAA

AT
```

Mouse Novel cDNA Clone 95/EST Accession #AA119951:—Sequence ID NO:21

```
GCACAGCCCCCTCCATCCTGAA-
GAAAACCTCAGCGTATGGGCCTCCAGC

TTCGGGCCGTGTCTATCCTTCCTCTC-
CTGGGACATGGTGTTCCCCGCTTG

CCCCCCTGGCAGAAAACCG
```

Mouse Ese1L cDNA: Sequence ID NO:22

```
CGGCACGAGGAGGAGTGGAGCGGCGCGGGGAGGGCGCGCAGCTTGGTTG

CTCCGTAGTACGGCGGCTCGCAAGGGAGCATCCCGAGCGGGCTCCGGGAC

GGCCGGGAGGCAGGCAGGCGGGCGGGCGGGGATGGTGTGCGCGGCTGCG

GACTCGGCGTTCCTCGCGCGGCGTGCGGGCTGCACTGATTTGTGTGAGGG

GCGGCCGCGCGCACCCGCCCGGAGATGAGGCGTCGATCAGCAAGGTGAA

CGTAATAGAACCATGGCTCAGTTTCCCACACCTTTCGGTGGTAGCCTGGA

TGTCTGGGCCATAACTGTGGAGGAAAGGGCCAAGCATGACCAGCAGTTCC

TTAGCCTGAAGCCGATAGCGGGATTTATTACTGGTGATCAAGCGAGGAAC

TTTTTTTTCCAATCTGGGTTACCTCAGCCTGTCTTAGCACAAATATGGGC

GCTAGCGGACATGAATAACGATGGAAGGATGGATCAAGTGGAATTTTCCA

TAGCCATGAAGCTTATCAAACTGAAGCTACAAGGATATCAGCTCCCCTCC

ACACTTCCCCCTGTCATGAAACAGCAACCAGTGGCTATTTCCAGTGCACC

AGCATTTGGTATAGGAGGGATTGCTAGCATGCCACCACTCACAGCTGTTG

CTCCTGTGCCAATGGGCTCCATTCCAGTTGTTGGAATGTCTCCACCCTTA

GTATCTTCTGTCCCTCCAGCAGCAGTGCCTCCCCTGGCTAACGGGGCTCC

TCCCGTCATACAGCCTCTGCCTGCGTTTGCGCATCCTGCAGCCACATGGC

CAAAGAGTTCTTCCTTCAGCAGATCTGGTCCAGGGTCACAATTAAACACT

AAGTTACAGAAGGCACAATCATTCGATGTCGCCAGCGCCCCTCCAGCAGC

AGAATGGGCTGTGCCTCAGTCATCAAGGCTGAAATACAGGCAGTTATTCA

ACAGCCACGACAAAACTATGAGTGGACACTTAACAGGTCCCCAGGCAAGA
```

```
ACTATTCTCATGCAATCAAGTTTACCCCAGGCTCAGCTGGCTTCAATATG
GAATCTTTCTGACATTGATCAAGATGGAAAACTCACTGCAGAAGAATTTA
TCCTAGCTATGCACCTAATTGATGTTGCCATGTCTGGTCAGCCACTGCCG
CCCGTCCTGCCTCCAGAATACATCCCTCCTTCCTTCAGAAGAGTTCGCTC
CGGCAGTGGGATGTCCGTCATAAGCTCTTCTTCTGTGGATCAGAGGCTGC
CTGAGGAGCCGTCGTCAGAGGATGAGCAGCAGCCAGAGAAGAAACTGCCT
GTGACATTTGAAGATAAGAAGCGGGAGAACTTCGAGCGAGGCAGTGTGGA
GCTGGAGAAGCGCCGGCAAGCGCTCTTGGAGCAGCAGCGCAAAGAGCAGG
AGCGGTTGGCTCAGCTGGAGCGCGCCGAGCAGGAGAGGAAAGAGCGGGAG
CGCCAGGAGCAGGAGGCCAAGCGGCAGCTGGAGCTGGAGAAGCAGCTGGA
GAAGCAGCGGGAGCTGGAGCGGCAGCGAGAGGAGGAGAGGAGGAAGGAGA
TCGAGAGGCGCGAGGCCGCAAAACGGGAACTGGAAAGGCAGCGACAACTT
GAATGGGAACGGAACCGGAGACAGGAACTCCTGAATCAGAGGAACAAGGA
GCAGGAGGGCACCGTGGTCCTGAAGGCAAGGAGGAAGACTCTGGAGTTTG
AGTTAGAAGCTCTGAATGACAAAAAGCATCAGCTAGAAGGAAAACTTCAG
GATATCAGGTGTCGACTGGCAACCCAGAGGCAAGAAATTGAGAGCACGAA
CAAGTCTAGAGAGCTAAGAATTGCTGAAATCACCCACTTACAGCAGCAGT
TGCAGGAATCTCAGCAAATGCTTGGAAGACTTATTCCAGAGAAACAGATA
CTCAGTGACCAGTTAAAACAAGTCCAGCAGAACAGTTTGCATAGAGACTC
GCTTCTTACCCTCAAAAGAGCCTTGGAAGCAAAGGAGCTGGCCCGGCAGC
AGCTCCGGGAGCAGCTGGACGAGGTGGAGAGAGAGACCAGGTCAAAGCTG
CAGGAGATTGATGTTTTCAACAACCAGCTGAAGGAACTGAGAGAGATACA
TAGCAAACAGCAACTCCAGAAGCAGAGGTCCCTGGAGGCAGCGCGACTGA
AGCAGAAAGAGCAGGAGAGGAAGAGCCTGGAGTTAGAGAAGCAAAAGG
AAGACGCTCAGAGACGAGTTCAGGAAAGGGACAAGCAATGGCTGGAGCA
TGTGCAGCAGGAGGAGCAGCCACGCCCCCGGAAACCCCACGAGGAGGAC
AGACTGAAGAGGGAAGACAGTGTCAGGAAGAAGGAGGCGGAAGAGAGA
GCCAAGCCGGAAATGCAAGACAAGCAGAGTCGGCTTTTCCATCCGCATCA
GGAGCCAGCTAAGCTGGCCACCCAGGCACCCTGGTCTACCACAGAGAAAG
GCCCGCTTACCATTTCTGCACAGGAGAGTGTAAAAGTGGTATATTACCGA
GCGCTGTACCCCTTTGAATCCAGAAGTCACGATGAGATCACCATCCAGCC
AGGAGATATAGTCATGGTGGATGAAAGCCAGACTGGAGAGCCAGGATGG
CTTGGAGGAGAGCTGAAAGGGAAGACGGGATGGTTCCCTGCAAACTATGC
AGAAAAGATTCCAGAAAATGAGGTTCCCACTCCAGCCAAACCAGTGACCG
ATCTGACATCTGCCCCTGCCCCCAAACTGGCTCTGCGTGAGACCCCTGCT
CCTTTGCCAGTGACCTCTTCTGAGCCCTCCACAACCCCCAACAACTGGGC
AGACTTCAGTTCCACGTGGCCCAGCAGCTCAAACGAGAAGCCAGAAACGG
ACAACTGGGATACGTGGGCGGCTCAGCCTTCTCTGACCGTACCTAGTGCT
GGCCAGTTACGGCAGAGATCAGCCTTTACCCCAGCCACAGCCACTGGCTC
CTCCCCATCTCCCGTCCTGGGCCAGGGTGAAAAGGTGGAAGGGCTACAAG
CGCAAGCCCTGTATCCCTGGAGAGCCAAAAAAGACAACCACTTAAATTTT
AACAAAAGTGACGTCATCACCGTTCTGGAACAGCAAGACATGTGGTGGTT
TGGAGAAGTTCAAGGTCAGAAGGGTTGGTTCCCCAAGTCTTACGTGAAAC
TCATTTCAGGGCCCGTAAGGAAATCCACAAGCATCGATACTGGCCCTACT
GAAAGTCCTGCTAGTCTAAAGAGAGTGGCTTCCCCGGCCGCCAAGCCAGC
CATTCCCGGAGAAGAGTTTATTGCCATGTACACATACGAGAGTTCTGAGC
AAGGAGATTTAACCTTTCAGCAAGGGGATGTGATTGTGGTTACCAAGAAA
GATGGTGACTGGTGGACGGGAACGGTGGGCGACAAGTCCGGAGTCTTCCC
TTCTAACTATGTGAGGCTTAAAGATTCAGAGGGCTCTGGAACTGCTGGGA
AAACAGGGAGTTTAGGAAAAAAACCTGAAATTGCCCAGGTTATTGCTTCC
TACGCTGCTACTGGTCCCGAACAACTCACCCTGGCTCCTGGGCAGCTGAT
TCTGATCCGGAAAAAGAACCCAGGTGGATGGTGGGAAGGAGAACTGCAAG
CTCGAGGGAAAAAGCGCCAGATAGGGTGGTTTCCAGCAAATTATGTCAAA
CTTCTAAGCCCCGGAACAAGCAAAATCACCCCAACTGAGCTACCCAAGAC
CGCAGTGCAGCCAGCAGTGTGCCAGGTGATCGGGATGTACGATTACACCG
CCCAGAACGATGACGAACTAGCCTTCAGCAAAGGCCAGATCATCAACGTC
CTCAACAAGGAGGACCCGGACTGGTGGAAAGGAGAAGTCAGTGGGCAAGT
TGGGCTCTTCCCATCCAATTATGTAAAGCTGACCACAGACATGGACCCCA
GCCAGCAATGGTGCTCAGACCTGCATCTCTTAGATATGCTGACCCCGACT
GAGAGGAAGCGGCAAGGCTACATCCATGAACTCATTGTCACGGAGGAGAA
CTACGTGAACGACTTGCAGCTGGTCACAGAGATCTTTCAGAAACCCCTGA
CGGAGTCTGAGCTGCTGACAGAAAAAGAGGTTGCTATGATTTTTGTTAAC
TGGAAGGAGCTGATCATGTGTAATATCAAACTGCTGAAAGCGCTGAGAGT
CCGCAAGAAGATGTCTGGGGAGAAGATGCCGGTGAAGATGATTGGCGACA
TCCTGAGCGCCCAGCTGCCGCACATGCAGCCTTACATCCGCTTCTGCAGC
TGCCAGCTCAATGGGCTGCCCTCATCCAGCAGAAGACGGACGAGGCTCC
AGACTTCAAGGAGTTCGTCAAAAGACTGGCAATGGACCCTCGGTGCAAAG
GAATGCCTCTGTCCAGCTTTATACTGAAGCCTATGCAGCGTGTCACAAGA
TACCCGCTGATCATTAAAAACATCCTGGAAAACACTCCTGAGAACCATCC
AGACCACAGCCACCTGAAGCATGCCCTGGAAAAGGCGGAGGAGCTGTGCT
CCCAGGTGAACGAGGGAGTTCGAGAGAAGGAGAACTCAGACCGGCTGGAG
TGGATCCAAGCCCACGTGCAGTGTGAAGGCCTTTCTGAGCAACTGGTGTT
CAATTCAGTGACCAACTGCTTGGGACCACGCAAGTTTCTGCACAGCGGGA
AGCTCTACAAGGCCAAGAGCAATAAAGAACTGTATGGCTTCCTCTTCAAC
GACTTCCTCCTGCTGACCCAAATCACAAAGCCCTTAGGCTCTTCCGGCAC
CGACAAAGTCTTCAGCCCCAAATCTAACCTTCAGTATAAAATGTACAAAA
CGCCCATTTTCTTAAATGAGGTTCTAGTAAAATTGCCCACGGACCCTTCT
GGAGATGAGCCTATCTTCCACATTTCCCACATCGACCGGGTCTACACCCT
CCGAGCAGAGAGCATAAATGAGAGGACTGCCTGGGTGCAGAAAATCAAGG
CGGCGTCTGAGCTCTACATAGAGACGGAGAAAAAGAAGCGAGAGAAGGCG
```

-continued

TACCTGGTCCGTTCCCAGCGGGCGACCGGTATTGGAAGGTTGATGGTGAA

CGTGGTAGAAGGCATTGAGCTGAAGCCCTGTCGGTCACATGGAAAGAGCA

ACCCGTACTGTGAGGTGACCATGGCTCTCAGTGCCACATCACCAAGACA

ATCCAGGACACGCTAAACCCCAAGTGGAATTCTAACTGCCAGTTCTTCAT

CAGAGACCTGGAGCAGGAGGTTCTCTGCATCACAGTGTTTGAGAGGGACC

AGTTCTCGCCTGATGATTTTTTGGGTCGGACAGAGATCCGAGTGGCCGAC

ATCAAGAAAGACCAGGGCTCCAAGGGGCCGGTTACGAAGTGTCTCCTGCT

GCATGAGGTCCCCACGGGAGAGATTGTGGTCCGCCTTGACCTGCAGTTGT

TTGATGAGCCGTAGCAGCCCTGCGATGATCGTAGATGACTTCCTCCTCAA

GGCCCCGTGCGGGCGTGCTGTCTGGTGGTCAGCCTCAGAGCAACGGGAT

GAAGCAAAGACGAAGCCCCTCGAGGCTGCTAGGAGTCGTTCTCGACAATC

CTGCCCTTCAAACCATGTCTCATTTTATGAATCCAAATTCTCTTTTCCTT

TGCTCTCCCTATGGTCTCATCATGGCTTCTAGAGTCTCTGAAATCTGTGA

CCTTTAACTAGGTTCCATTGGGAGCCTGGCTCCTTCCCTGGGCTGGAGGT

GTGGGTCTGGTTTCTATAAAATAGATTATAAACTCGAGAATCACTAGT

Mouse Ese1L Coding: Sequence ID NO:23

ATGGCTCAGTTTCCCACACCTTTCGGTGGTAGCCTGGATGTCTGGGCCAT

AACTGTGGAGGAAAGGGCCAAGCATGACCAGCAGTTCCTTAGCCTGAAGC

CGATAGCGGGATTTATTACTGGTGATCAAGCGAGGAACTTTTTTTTCCAA

TCTGGGTTACCTCAGCCTGTCTTAGCACAAATATGGGCGCTAGCGGACAT

GAATAACGATGGAAGGATGGATCAAGTGGAATTTTCCATAGCCATGAAGC

TTATCAAACTGAAGCTACAAGGATATCAGCTCCCCTCCACACTTCCCCCT

GTCATGAAACAGCAACCAGTGGCTATTTCCAGTGCACCAGCATTTGGTAT

AGGAGGGATTGCTAGCATGCCACCACTCACAGCTGTTGCTCCTGTGCCAA

TGGGCTCCATTCCAGTTGTTGGAATGTCTCCACCCTTAGTATCTTCTGTC

CCTCCAGCAGCAGTGCCTCCCCTGGCTAACGGGGCTCCTCCCGTCATACA

GCCTCTGCCTGCGTTTGCGCATCCTGCAGCCACATGGCCAAAGAGTTCTT

CCTTCAGCAGATCTGGTCCAGGGTCACAATTAAACACTAAGTTACAGAAG

GCACAATCATTCGATGTCGCCAGCGCCCCTCCAGCAGCAGAATGGGCTGT

GCCTCAGTCATCAAGGCTGAAATACAGGCAGTTATTCAACAGCCACGACA

AAACTATGAGTGGACACTTAACAGGTCCCCAGGCAAGAACTATTCTCATG

CAATCAAGTTTACCCCAGGCTCAGCTGGCTTCAATATGGAATCTTTCTGA

CATTGATCAAGATGGAAAACTCACTGCAGAAGAATTTATCCTAGCTATGC

ACCTAATTGATGTTGCCATGTCTGGTCAGCCACTGCCGCCCGTCCTGCCT

CCAGAATACATCCCTCCTTCCTTCAGAAGAGTTCGCTCCGGCAGTGGGAT

GTCCGTCATAAGCTCTTCTTCTGTGGATCAGAGGCTGCCTGAGGAGCCGT

CGTCAGAGGATGAGCAGCAGCCAGAGAAGAAACTGCCTGTGACATTTGAA

GATAAGAAGCGGGAGAACTTCGAGCGAGGCAGTGTGGAGCTGGAGAAGCG

-continued

CCGGCAAGCGCTCTTGGAGCAGCAGCGCAAAGAGCAGGAGCGGTTGGCTC

AGCTGGAGCGCGCCGAGCAGGAGAGGAAAGAGCGGGAGCGCCAGGAGCAG

GAGGCCAAGCGGCAGCTGGAGCTGGAGAAGCAGCTGGAGAAGCAGCGGGA

GCTGGAGCGGCAGCGAGAGGAGGAGAGGAGGAAGGAGATCGAGAGGCGCG

AGGCCGCAAAACGGGAACTGGAAAGGCAGCGACAACTTGAATGGGAACGG

AACCGGAGACAGGAACTCCTGAATCAGAGGAACAAGGAGCAGGAGGGCAC

CGTGGTCCTGAAGGCAAGGAGGAAGACTCTGGAGTTTGAGTTAGAAGCTC

TGAATGACAAAAAGCATCAGCTAGAAGGAAAACTTCAGGATATCAGGTGT

CGACTGGCAACCCAGAGGCAAGAAATTGAGAGCACGAACAAGTCTAGAG

AGCTAAGAATTGCTGAAATCACCCACTTACAGCAGCAGTTGCAGGAATCT

CAGCAAATGCTTGGAAGACTTATTCCAGAGAAACAGATACTCAGTGACCA

GTTAAAACAAGTCCAGCAGAACAGTTTGCATAGAGACTCGCTTCTTACCC

TCAAAAGAGCCTTGGAAGCAAAGGAGCTGGCCCGGCAGCAGCTCCGGGA

GCAGCTGGACGAGGTGGAGAGAGAGACCAGGTCAAAGCTGCAGGAGATT

GATGTTTTCAACAACCAGCTGAAGGAACTGAGAGAGATACATAGCAAACA

GCAACTCCAGAAGCAGAGGTCCCTGGAGGCAGCGCGACTGAAGCAGAAA

GAGCAGGAGAGGAAGAGCCTGGAGTTAGAGAAGCAAAAGGAAGACGCTC

AGAGACGAGTTCAGGAAAGGGACAAGCAATGGCTGGAGCATGTGCAGCA

GGAGGAGCAGCCACGCCCCCGGAAACCCCACGAGGAGGACAGACTGAAG

AGGGAAGACAGTGTCAGGAAGAAGGAGGCGGAAGAGAGAGCCAAGCCG

GAAATGCAAGACAAGCAGAGTCGGCTTTTCCATCCGCATCAGGAGCCAGC

TAAGCTGGCCACCCAGGCACCCTGGTCTACCACAGAGAAAGGCCCGCTTA

CCATTTCTGCACAGGAGAGTGTAAAAGTGGTATATTACCGAGCGCTGTAC

CCCTTTGAATCCAGAAGTCACGATGAGATCACCATCCAGCCAGGAGATAT

AGTCATGGTGGATGAAAGCCAGACTGGAGAGCCAGGATGGCTTGGAGGA

GAGCTGAAAGGGAAGACGGGATGGTTCCCTGCAAACTATGCAGAAAAGAT

TCCAGAAAATGAGGTTCCCACTCCAGCCAAACCAGTGACCGATCTGACAT

CTGCCCCTGCCCCAAACTGGCTCTGCGTGAGACCCCTGCTCCTTTGCCA

GTGACCTCTTCTGAGCCCTCCACAACCCCCAACAACTGGGCAGACTTCAG

TTCCACGTGGCCCAGCAGCTCAAACGAGAAGCCAGAAACGGACAACTGGG

ATACGTGGCGGCTCAGCCTTCTCTGACCGTACCTAGTGCTGGCCAGTTA

CGGCAGAGATCAGCCTTTACCCCAGCCACAGCCACTGGCTCCTCCCCATC

TCCCGTCCTGGGCCAGGGTGAAAAGGTGGAAGGGCTACAAGCGCAAGCCC

TGTATCCCTGGAGAGCCAAAAAAGACAACCACTTAAATTTTAACAAAAGT

GACGTCATCACCGTTCTGGAACAGCAAGACATGTGGTGGTTTGGAGAAGT

TCAAGGTCAGAAGGGTTGGTTCCCCAAGTCTTACGTGAAACTCATTTCAG

GGCCCGTAAGGAAATCCACAAGCATCGATACTGGCCCTACTGAAAGTCCT

GCTAGTCTAAAGAGAGTGGCTTCCCCGGCCGCCAAGCCAGCCATTCCCGG

AGAAGAGTTTATTGCCATGTACACATACGAGAGTTCTGAGCAAGGAGATT

TAACCTTTCAGCAAGGGGATGTGATTGTGGTTACCAAGAAAGATGGTGAC

-continued

```
TGGTGGACGGGAACGGTGGGCGACAAGTCCGGAGTCTTCCCTTCTAACTA
TGTGAGGCTTAAAGATTCAGAGGGCTCTGGAACTGCTGGGAAAACAGGGA
GTTTAGGAAAAAAACCTGAAATTGCCCAGGTTATTGCTTCCTACGCTGCT
ACTGGTCCCGAACAACTCACCCTGGCTCCTGGGCAGCTGATTCTGATCCG
GAAAAAGAACCCAGGTGGATGGTGGGAAGGAGAACTGCAAGCTCGAGGGA
AAAAGCGCCAGATAGGGTGGTTTCCAGCAAATTATGTCAAACTTCTAAGC
CCCGGAACAAGCAAAATCACCCCAACTGAGCTACCCAAGACCGCAGTGCA
GCCAGCAGTGTGCCAGGTGATCGGATGTACGATTACACCGCCCAGAACG
ATGACGAACTAGCCTTCAGCAAAGGCCAGATCATCAACGTCCTCAACAAG
GAGGACCCGGACTGGTGGAAAGGAGAAGTCAGTGGGCAAGTTGGGCTCTT
CCCATCCAATTATGTAAAGCTGACCACAGACATGGACCCCAGCCAGCAAT
GGTGCTCAGACCTGCATCTCTTAGATATGCTGACCCCGACTGAGAGGAAG
CGGCAAGGCTACATCCATGAACTCATTGTCACGGAGGAGAACTACGTGAA
CGACTTGCAGCTGGTCACAGAGATCTTTCAGAAACCCCTGACGGAGTCTG
AGCTGCTGACAGAAAAGAGGTTGCTATGATTTTTGTTAACTGGAAGGAG
CTGATCATGTGTAATATCAAACTGCTGAAAGCGCTGAGAGTCCGCAAGAA
GATGTCTGGGGAGAAGATGCCGGTGAAGATGATTGGCGACATCCTGAGCG
CCCAGCTGCCGCACATGCAGCCTTACATCCGCTTCTGCAGCTGCCAGCTC
AATGGGGCTGCCCTCATCCAGCAGAAGACGGACGAGGCTCCAGACTTCAA
GGAGTTCGTCAAAAGACTGGCAATGGACCCTCGGTGCAAAGGAATGCCTC
TGTCCAGCTTTATACTGAAGCCTATGCAGCGTGTCACAAGATACCCGCTG
ATCATTAAAAACATCCTGGAAAACACTCCTGAGAACCATCCAGACCACAG
CCACCTGAAGCATGCCCTGGAAAAGGCGGAGGAGCTGTGCTCCCAGGTGA
ACGAGGGAGTTCGAGAGAAGGAGAACTCAGACCGGCTGGAGTGGATCCAA
GCCCACGTGCAGTGTGAAGGCCTTTCTGAGCAACTGGTGTTCAATTCAGT
GACCAACTGCTTGGGACCACGCAAGTTTCTGCACAGCGGGAAGCTCTACA
AGGCCAAGAGCAATAAAGAACTGTATGGCTTCCTCTTCAACGACTTCCTC
CTGCTGACCCAAATCACAAAGCCCTTAGGCTCTTCCGGCACCGACAAAGT
CTTCAGCCCCAAATCTAACCTTCAGTATAAAATGTACAAAACGCCCATTT
TCTTAAATGAGGTTCTAGTAAAATTGCCCACGGACCCTTCTGGAGATGAG
CCTATCTTCCACATTTCCCACATCGACCGGGTCTACACCCTCCGAGCAGA
GAGCATAAATGAGGACTGCCTGGGTGCAGAAAATCAAGGCGGCGTCTG
AGCTCTACATAGAGACGGAGAAAAAGAAGCGAGAAGGCGTACCTGGTC
CGTTCCCAGCGGGCGACCGGTATTGGAAGGTTGATGGTGAACGTGGTAGA
GGCATTGAGCTGAAGCCCTGTCGGTCACATGAAAGAGCAACCCGTACTG
TGAGGTGACCATGGGCTCTCAGTGCCACATCACCAAGACAATCCAGGACA
CGCTAAACCCCAAGTGGAATTCTAACTGCCAGTTCTTCATCAGAGACCTG
GAGCAGGAGGTTCTCTGCATCACAGTGTTTGAGAGGGACCAGTTCTCGCC
TGATGATTTTTGGGTCGGACAGAGATCCGAGTGGCCGACATCAAGAAG
ACCAGGGCTCCAAGGGGCCGGTTACGAAGTGTCTCCTGCTGCATGAGGTC
```

-continued

```
CCCACGGGAGAGATTGTGGTCCGCCTTGACCTGCAGTTGTTTGATGAGCC
GTAG
```

Murine Ese1L Protein: Sequence ID NO:24

```
MAQFPTPFGGSLDVWAITVEERAKHDQQFLSLKPIAGFITGDQARNFFFQ
SGLPQPVLAQIWALADMNNDGRMDQVEFSIAMKLIKLKLQGYQLPSTLPP
VMKQQPVAISSAPAFGIGGIASMPPLTAVAPVPMGSIPVVGMSPPLVSSV
PPAAVPPLANGAPPVIQPLPAFAHPAATWPKSSSFSRSGPGSQLNTKLQ
KAQSFDVASAPPAAEWAVPQSSRLKYRQLFNSHDKTMSGHLTGPQARTIL
MQSSLPQAQLASIWNLSDIDQDGKLTAEEFILAMHLIDVAMSGQPLPPVL
PPEYIPPSFRRVRSGSGMSVISSSSVDQRLPEEPSSEDEQQPEKKLPVTF
EDKKRENFERGSVELEKRRQALLEQQRKEQERLAQLERAEQERKERERQE
QEAKRQLELEKQLEKQRELERQREEERRKEIERREAAKRELERQRQLEWE
RNRRQELLNQRNKEQEGTVVLKARRKTLEFELEALNDKKHQLEGKLQDIR
CRLATQRQEIESTNKSRELRIAEITHLQQQLQESQQMLGRLIPEKQILSD
QLKQVQQNSLHRDSLLTLKRALEAKELARQQLREQLDEVERETRSKLQEI
DVFNNQLKELREIHSKQQLQKQRSLEAARLKQKEQERKSLELEKQKEDA
QRRVQERDKQWLEHVQQEEQPRPRKPHEEDRLKREDSVRKKEAEERAKPE
MQDKQSRLFHPHQEPAKLATQAPWSTTEKGPLTISAQESVKVVYYRALY
PFESRSHDEITIQPGDIVMVDESQTGEPGWLGGELKGKTGWFPANYAEKI
PENEVPTPAKPVTDLTSAPAPKLALRETPAPLPVTSSEPSTTPNNWADFS
STWPSSSNEKPETDNWDTWAAQPSLTVPSAGQLRQRSAFTPATATGSSPS
PVLGQGEKVEGLQAQALYPWRAKKDNHLNFNKSDVITVLEQQDMWWFGEV
QGQKGWFPKSYVKLISGPVRKSTSIDTGPTESPASLKRVASPAAKPAIPG
EEFIAMYTYESSEQGDLTFQQGDVIVVTKKDGDWWTGTVGDKSGVFPSNY
VRLKDSEGSGTAGKTGSLGKKPEIAQVIASYAATGPEQLTLAPGQLILRK
KNPGGWWEGELQARGKKRQIGWFPANYVKLLSPGTSKITPTELPKTAVQP
AVCQVIGMYDYTAQNDDELAFSKGQIINVLNKEDPDWWKGEVSGQVGLFP
SNYVKLTTDMDPSQQWCSDLHLLDMLTPTERKRQGYIHELIVTEENYVND
LQLVTEIFQKPLTESELLTEKEVAMIFVNWKELIMCNIKLLKALRVRKK
MSGEKMPVKMIGDILSAQLIHMQPYIRFCSCQLNGAALIQQKTDEAPDF
KEFVKRLAMDPRCKGMPLSSFILKPMQRVTRYPLIIKNILENTPENHPDH
SHLKHALEKAEELCSQVNEGVREKENSDRLEWIQAHVQCEGLSEQLVFNS
VTNCLGPRKFLHSGKLYKAKSNKELYGFLFNDFLLLTQITKPLGSSGTDK
VFSPKSNLQYKMYKTPIFLNEVLVKLPTDPSGDEPIFHISHIDRVYTLRA
ESINERTAWVQKIKAASELYIETEKKKREKAYLVRSQRATGIGRLMVNV
VEGIELKPCRSHGKSNPYCEVTMGSQCHITKTIQDTLNPKWNSNCQFFIR
DLEQEVLCITVFERDQFSPDDFLGRTEIRVADIKKDQGSKGPVTKCLLLH
EVPTGEIVVRLDLQLFDEP
```

Mouse Ese2L cDNA: Sequence ID NO:25

CCCTTCCTTTCCTTTTTTGTGTTCGCCTTCGGCCGTGCCGGCTGAGAGC
CCAGCAGCCGTGACAGGCTGCGCAACAGGTTCGCTGCGGCCGGCCTGACG
ACTGACCCGGCGGCGGCCGCGGCACGGCAGGGTCTTCCCGGAGCTTG
GCCGCGCCCACGCGCCGGTGTCGAGGAGCGCGCGGGGTCGCGCCGGGACG
TGCGCGAGGCGCCAGATGGCTGAGAGCTGCAAGAAGAAGTCAGGATCATG
ATGGCTCAGTTTCCCACAGCGATGAATGGAGGGCCAAATATGTGGGCTAT
TACATCTGAAGAACGTACTAAGCATGATAAACAGTTTGATAACCTCAAAC
CTTCAGGAGGTTACATAACAGGTGATCAAGCCCGTACTTTTTCCTACAG
TCAGGTCTGCCGGCCCCGGTTTTAGCTGAAATATGGGCCTTATCAGATCT
GAACAAGGATGGGAAGATGGACCAGCAAGAGTTCTCTATAGCTATGAAAC
TCATCAAGTTAAAGTTGCAGGGCCAACAGCTGCCTGTAGTCCTCCCTCCT
ATCATGAAACAACCCCCTATGTTCTCTCCACTAATCTCTGCTCGTTTTGG
GATGGGAAGCATGCCCAATCTGTCCATTCATCAGCCATTGCCTCCAGTTG
CACCTATAGCAACACCCTTGTCTTCTGCTACGTCAGGGACCAGTATTCCT
CCCCTAATGATGCCTGCTCCCCTAGTGCCTTCTGTTAGTACATCCTCATT
ACCAAATGGAACTGCCAGTCTCATTCAGCCTTTATCCATTCCTTATTCTT
CTTCAACATTGCCTCATGCATCATCTTACAGCCTGATGATGGGAGGATTT
GGTGGTGCTAGTATCCAGAAGGCCCAGTCTCTGATTGATTTAGGATCTAG
TAGCTCAACTTCCTCAACTGCTTCCCTCTCAGGGAACTCACCTAAGACAG
GGACCTCAGAGTGGGCAGTTCCTCAGCCTTCAAGATTAAAGTATCGGCAA
AAATTTAATAGTCTAGACAAAGGCATGAGCGGATACCTCTCAGGTTTTCA
AGCTAGAAATGCCCTTCTTCAGTCAAATCTCTCTCAAACTCAGCTAGCTA
CTATTTGGACTCTGGCTGACATCGATGGTGACGGACAGTTGAAAGCTGAA
GAATTTATTCTGGCGATGCACCTCACTGACATGGCCAAAGCTGGACAGCC
ACTACCACTGACGTTGCCTCCCGAGCTTGTCCCTCCATCTTTCAGAGGGG
GAAAGCAAGTTGATTCTGTTAATGGAACTCTGCCTTCATATCAGAAAACA
CAAGAAGAAGAGCCTCAGAAGAAACTGCCAGTTACTTTTGAGGACAAACG
GAAAGCCAACTATGAACGAGGAAACATGGAGCTGGAGAAGCGACGCCAAG
TGTTGATCGAGCAGCAGCAGAGGGAGGCTGAACGCAAAGCCCAGAAAGAG
AAGGAAGAGTGGGAGCGGAAACAGAGAGAACTGCAAGAGCAAGAATGGAA
GAAGCAGCTGGAGTTGGAGAAACGCTTGGAGAAACAGAGAGAGCTGGAGA
GACAGCGGAGGAAGAGAGGAGAAAGGAGATAGAAAGACGAGAGGCAGCA
AAACAGGAGCTTGAGAGACAACGCCGTTTAGAATGGGAAAGACTCCGTCG
GCAGGAGCTGCTCAGTCAGAAGACCAGGGAACAAGAAGACATTGTCAGGC
TGAGCTCCAGAAAGAAAAGTCTCCACCTGGAACTGGAAGCAGTGAATGGA
AAACATCAGCAGATCTCAGGCAGACTACAAGATGTCCAAATCAGAAAGCA
AACACAAAAGACTGAGCTAGAAGTTTTGGATAAACAGTGTGACCTGGAAA
TTATGGAAATCAAACAACTTCAACAAGAGCTTAAGGAATATCAAAATAAG
CTTATCTATCTGGTCCCTGAGAAGCAGCTATTAAACGAAAGAATTAAAAA

CATGCAGCTCAGTAACACACCTGATTCAGGGATCAGTTTACTTCATAAAA
AGTCATCAGAAAAGGAAGAATTATGCCAAAGACTTAAAGAACAATTAGAT
GCTCTTGAAAAAGAAACTGCATCTAAGCTCTCAGAAATGGATTCATTTAA
CAATCAGCTGAAGGAACTCAGAGAAAGCTATAATACACAGCAGTTAGCCC
TTGAACAACTTCATAAAATCAAACGTGACAAATTGAAGGAAATCGAAAGA
AAAAGATTAGAGCAAATTCAAAAAAAGAAACTAGAAGATGAGGCTGCAAG
GAAAGCAAAGCAAGGAAAAGAAAACTTGTGGAGAGAAAGTATTAGAAAGG
AAGAAGAGGAAAAGCAAAAACGACTCCAGGAAGAAAAGTCACAGGACAAA
ACTCAAGAAGAGGAACGAAAAGCTGAGGCAAAACAAAGTGAGACAGCCA
GTGCTTTGGTGAATTACAGAGCACTGTACCCTTTTGAAGCAAGAAACCAT
GATGAGATGAGTTTTAGTTCTGGGGATATAATTCAGGTTGATGAAAAAAC
TGTAGGAGAGCCTGGTTGGCTTTATGGTAGTTTTCAGGGAAAGTTTGGCT
GGTTCCCCTGCAACTATGTAGAAAAAGTGCTGTCAAGTGAAAAAGCTCTG
TCTCCTAAGAAGGCCTTACTTCCTCCTACAGTGTCTCTCTCTGCTACCTC
AACTTCTTCCCAGCCACCAGCATCAGTGACTGATTATCACAATGTATCCT
TCTCAAACCTTACTGTTAATACAACATGGCAGCAGAAGTCAGCTTTTACC
CGCACTGTGTCCCCTGGATCTGTGTCCCCCATTCACGGACAGGGGCAGGC
TGTAGAAAACCTGAAAGCCCAGGCCCTTTGTTCCTGGACGGCAAAGAAGG
AGAACCACCTGAACTTCTCAAAGCACGACGTCATCACTGTCCTGGAGCAG
CAGGAAAACTGGTGGTTTGGGGAGGTGCACGGAGGAAGAGGATGGTTCCC
CAAGTCTTATGTCAAGCTCATTCCTGGGAATGAAGTACAGCGAGGAGAGC
CAGAAGCTTTGTATGCAGCTGTGACTAAGAAACCTACCTCCACAGCCTAT
CCAGTTACCTCCACAGCCTATCCAGTTGGAGAAGACTACATTGCACTTTA
TTCATACTCAAGTGTAGAGCCCGGGGATTTGACTTTCACTGAAGGTGAAG
AAATTCTAGTGACCCAGAAAGATGGAGAGTGGTGGACAGGAAGTATTGGA
GAGAGAACTGGAATCTTCCCGTCCAACTACGTCAGACCAAAGGATCAAGA
GAATTTTGGGAATGCTAGCAAATCTGGAGCATCAAACAAAAAACCCGAGA
TCGCTCAAGTAACTTCAGCATATGCTGCTTCAGGGACTGAGCAGCTCAGC
CTTGCGCCAGGACAGTTAATATTAATCTTAAAGAAAAACACAAGCGGGT
GGTGGCAAGGAGAGCTACAGGCCAGAGGGAAGAAACGACAGAAGGGATGG
TTTCCTGCCAGCCATGTAAAGCTGCTAGGTCCAAGCAGTGAAAGAACCAT
GCCTACTTTTCACGCTGTATGTCAAGTGATTGCTATGTATGACTACATGG
CGAATAACGAAGATGAGCTCAATTTCTCCAAAGGACAGCTGATTAATGTT
ATGAACAAAGATGACCCTGACTGGTGGCAAGGAGAAACCAATGGTCTGAC
TGGTCTCTTTCCTTCAAACTATGTTAAGATGACAACAGACTCAGATCCAA
GTCAACAGTGGTGTGCTGACCTCCAAGCCCTGGACACAATGCAGCCTACG
GAGAGGAAGCGACAGGGCTACATTCACGAGCTCATTCAGACAGAGGAGCG
GTACATGGACGACGACCTGCAGCTGGTCATCGAGGTCTTCCAGAAACGGA
TGGCTGAGGAAGGCTTCCTCACTGAAGCAGACATGGCTCTGATCTTTGTG
AACTGGAAAGAGCTCATCATGTCCAACACGAAGCTGCTGAGGGCCTTGCG

-continued
GGTGAGGAAGAAGACTGGGGGTGAGAAGATGCCAGTTCAGATGATTGGAG
ACATCCTGGCGGCAGAGCTGTCCCACATGCAGGCCTACATCCGCTTCTGC
AGCTGTCAGCTTAATGGGGCAACCCTGTTACAGCAGAAGACAGACGAGGA
CACGGACTTCAAGGAATTTCTAAAGAAGTTGGCATCAGACCCACGATGCA
AAGGGATGCCCCTCTCCAGCTTCCTGCTGAAGCCCATGCAGAGGATCACT
CGCTACCCGCTGCTCATCCGAAGTATCCTGGAGAACACTCCACAGAGTCA
TGTTGACCACTCCTCCCTGAAGCTGGCCCTAGAACGTGCTGAGGAGCTGT
GCTCTCAGGTGAACGAGGGAGTCCGGGAGAAGGAAAATTCAGACCGGCTG
GAGTGGATCCAGGCACACGTGCAGTGCGAAGGCTTGGCAGAGCAACTTAT
TTTCAACTCCCTCACCAACTGCCTGGGCCCCCGGAAGCTTCTGCACAGCG
GGAAGCTGTACAAGACCAAGAGCAATAAGGAGCTGCACGCCTTCCTCTTC
AACGACTTCCTGCTGCTCACCTACCTGGTCAGGCAGTTTGCCGCCGCCTC
TGGCCACGAGAAGCTCTTCAACTCCAAGTCCAGTGCTCAGTTCCGGATGT
ACAAAACGCCCATTTTCCTGAATGAAGTGTTGGTGAAACTTCCCACAGAC
CCTTCCGGCGATGAGCCCGTCTTCCACATTTCCCACATTGATCGTGTGTA
CACACTCCGAACAGACAACATCAACGAGAGGACGGCCTGGGTCCAGAAGA
TCAAGGGTGCCTCAGAGCAGTACATCGACACTGAGAAGAAGAAACGGGAA
AAGGCTTACCAAGCCCGTTCTCAAAAGACTTCAGGTATTGGGCGTCTGAT
GGTGCATGTCATTGAAGCTACAGAATTAAAAGCCTGCAAACCAAACGGGA
AAAGTAATCCATACTGTGAAGTCAGCATGGGCTCCCAAAGCTATACCACC
AGGACCCTGCAGGACACACTAAACCCCAAGTGGAACTTCAACTGCCAGTT
CTTCATCAAGGATCTTTACCAGGACGTTCTGTGTCTCACTATGTTTGACA
GAGACCAGTTTTCTCCAGATGACTTCTTGGGTCGTACTGAAGTTCCAGTG
GCAAAAATCCGAACAGAACAGGAAAGCAAAGGCCCCACCACCCGCCGACT
ACTACTGCACGAAGTCCCCACTGGAGAAGTCTGGGTCCGCTTTGACCTGC
AACTTTTTGAACAAAAAACTCTCCTTTGAGGGCCTGGGGAAGCCAGAACC
AGGGGAGCTGCCCACAAGGCTGGGTCTAAAGACAGATTTTGCTCTCCCAG
GACAGAGGAGCATCACATGGCTTCATCCATCAAACAGCCACACTCGCTGG
GCCTGTATTTTATTGCACACTAAATTGCTAGCAATCTATGCAAACATGAT
CTTTTAAACAAACGCCACAGCACAGTGCCTTGTACTAGTGTTAACCTGTT
CAGCTGTGTTAGATGCCAGGGTTTCCATTTTCAGGGCTATAAAAGTATTA
TGTGGAAATGAGGCATCAGACCACCGGACGTTACCACTTGGCAAATCTGT
CCACTGTGGAGTTGGTGATGTTGGAACCATTCCACACTATGTGACCTCTG
CTGGGTCACACACTCAGGAGGTGAAGGGCTGAGATGAAATGCTGCAGCCT
TGGGGCTTGTGCAGCCTGATACTGAAATAGCATCCACTTGTGCACTGAAT
AAATAGAAACTTGATCGTTTTATTCTGACTAGATATTATCATTCTCTGCT
AAGACAAATATAGTTTGAAATATTATGTTTGAATATAAGGAGGAAAGCTT
GATGTACTTTAAATATACTGTGAACTCTAATAATGTGGGGATATTTTTCA
ACTTTAATTTTCTTAAGTATAAATTATTTATGTAAATTCTTTGTTTTGCA
TATTTCATAGAACATGCATCTTTAAGCTTTATCATTGCCAACAATGTACA -continued
GAAAGAGAATAAAAGTATAAGTTTATGAATGTAAAAAAAAAAAAAAAAAA
AAAAAAAAAAAAAAAA Murine Ese2L Coding: Sequence ID NO: 26

ATGGCTCAGTTTCCCACAGCGATGAATGGAGGGCCAAATATGTGGGCTAT
TACATCTGAAGAACGTACTAAGCATGATAAACAGTTTGATAACCTCAAAC
CTTCAGGAGGTTACATAACAGGTGATCAAGCCCGTACTTTTTTCCTACAG
TCAGGTCTGCCGGCCCCGGTTTTAGCTGAAATATGGGCCTTATCAGATCT
GAACAAGGATGGGAAGATGGACCAGCAAGAGTTCTCTATAGCTATGAAAC
TCATCAAGTTAAAGTTGCAGGGCCAACAGCTGCCTGTAGTCCTCCCTCCT
ATCATGAAACAACCCCCTATGTTCTCTCCACTAATCTCTGCTCGTTTTGG
GATGGGAAGCATGCCCAATCTGTCCATTCATCAGCCATTGCCTCCAGTTG
CACCTATAGCAACACCCTTGTCTTCTGCTACGTCAGGGACCAGTATTCCT
CCCCTAATGATGCCTGCTCCCCTAGTGCCTTCTGTTAGTACATCCTCATT
ACCAAATGGAACTGCCAGTCTCATTCAGCCTTTATCCATTCCTTATTCTT
CTTCAACATTGCCTCATGCATCATCTTACAGCCTGATGATGGGAGGATTT
GGTGGTGCTAGTATCCAGAAGGCCCAGTCTCTGATTGATTTAGGATCTAG
TAGCTCAACTTCCTCAACTGCTTCCCTCTCAGGGAACTCACCTAAGACAG
GGACCTCAGAGTGGGCAGTTCCTCAGCCTTCAAGATTAAAGTATCGGCAA
AAATTTAATAATAGTCTAGACAAAGGCATGAGCGGATACCTCTCAGGTTT
TCAAGCTAGAAATGCCCTTCTTCAGTCAAATCTCTCAAACTCAGCTAG
CTACTATTTGGACTCTGGCTGACATCGATGGTGACGACAGTTGAAAGCT
GAAGAATTTATTCTGGCGATGCACCTCACTGACATGGCCAAAGCTGGACA
GCCACTACCACTGACGTTGCCTCCCGAGCTTGTCCCTCCATCTTTCAGAG
GGGGAAAGCAAGTTGATTCTGTTAATGGAACTCTGCCTTCATATCAGAAA
ACACAAGAAGAAGCCTCAGAAGAAACTGCCAGTTACTTTTGAGGACAA
ACGGAAAGCCAACTATGAACGAGGAAACATGGAGCTGGAGAAGCGACGCC
AAGTGTTGATGGAGCAGCAGCAGAGGGAGGCTGAACGCAAAGCCCAGAAA
GAGAAGGAAGAGTGGGAGCGGAAACAGAGAGAACTGCAAGAGCAAGAATG
GAAGAAGCAGCTGGAGTTGGAGAAACGCTTGGAGAAACAGAGAGAGCTGG
AGAGACAGCGGAGGAAGAGAGGAGAAAGGAGATAGAAAGACGAGAGGCA
GCAAAACAGGAGCTTGAGAGACAACGCCGTTTAGAATGGGAAAGACTCCG
TCGGCAGGAGCTGCTCAGTCAGAAGACCAGGGAACAAGAAGACATTGTCA
GGCTGAGCTCCAGAAAGAAAGTCTCCACCTGGAACTGGAAGCAGTGAAT
GGAAAACATCAGCAGATCTCAGGCAGACTACAAGATGTCCAAATCAGAAA
GCAAACACAAAAGACTGAGCTAGAAGTTTTGGATAAACAGTGTGACCTGG
AAATTATGGAAATCAAACAACTTCAACAAGAGCTTAAGGAATATCAAAAT
AAGCTTATCTATCTGGTCCCTGAGAAGCAGCTATTAAACGAAAGAATTAA
AAACATGCAGCTCAGTAACACACCTGATTCAGGGATCAGTTTACTTCATA
AAAAGTCATCAGAAAAGGAAGAATTATGCCAAAGACTTAAAGAACAATTA

-continued

```
GATGCTCTTGAAAAAGAAACTGCATCTAAGCTCTCAGAAATGGATTCATT
TAACAATCAGCTGAAGGAACTCAGAGAAAGCTATAATACACAGCAGTTAG
CCCTTGAACAACTTCATAAAATCAAACGTGACAAATTGAAGGAAATCGAA
AGAAAAAGATTAGAGCAAATTCAAAAAAAGAAACTAGAAGATGAGGCTGC
AAGGAAAGCAAAGCAAGGAAAAGAAAACTTGTGGAGAGAAAGTATTAGAA
AGGAAGAAGAGGAAAAGCAAAAACGACTCCAGGAAGAAAAGTCACAGGA
CAAAACTCAAGAAGAGGAACGAAAAGCTGAGGCAAAACAAAGTGAGACA
GCCAGTGCTTTGGTG
AATTACAGAGCACTGTACCCTTTTGAAGCAAGAAACCATGATGAGATGAG
TTTTAGTTCTGGGGATATAATTCAGGTTGATGAAAAAACTGTAGGAGAGC
CTGGTTGGCTTTATGGTAGTTTTCAGGGAAAGTTTGGCTGGTTCCCCTGC
AACTATGTAGAAAAAGTGCTGTCAAGTGAAAAAGCTCTGTCTCCTAAGAA
GGCCTTACTTCCTCCTACAGTGTCTCTCTCTGCTACCTCAACTTCTTCCC
AGCCACCAGCATCAGTGACTGATTATCACAATGTATCCTTCTCAAACCTT
ACTGTTAATACAACATGGCA
GCAGAAGTCAGCTTTTACCCGCACTGTGTCCCCTGGATCTGTGTCCCCCA
TTCACGGACAGGGGCAGGCTGTAGAAAACCTGAAAGCCCAGGCCCTTTGT
TCCTGGACGGCAAAGAAGGAGAACCACCTGAACTTCTCAAAGCACGACGT
CATCACTGTCCTGGAGCAGCAGGAAAACTGGTGGTTTGGGGAGGTGCACG
GAGGAAGAGGATGGTTCCCCAAGTCTTATGTCAAGCTCATTCCTGGGAAT
GAAGTACAGCGAGGAGAGCCAGAAGCTTTGTATGCAGCTGTGACTAAGAA
ACCTACCTCCACAGCCTATCCAGTTACCTCCACAGCCTATCCAGTTGGAG
AAGACTACATTGCACTTTATTCATACTCAAGTGTAGAGCCCGGGGATTTG
ACTTTCACTGAAGGTGAAGAAATTCTAGTGACCCAGAAAGATGGAGAGTG
GTGGACAGGAAGTATTGGAGAGAGAACTGGAATCTTCCCGTCCAACTACG
TCAGACCAAAGGATCAAGAGAATTTTGGGAATGCTAGCAAATCTGGAGCA
TCAAACAAAAAACCCGAGATCGCTCAAGTAACTTCAGCATATGCTGCTTC
AGGGACTGAGCAGCTCAGCCTTGCGCCAGGACAGTTAATATTAATCTTAA
AGAAAAACACAAGCGGGTGGTGGCAAGGAGAGCTACAGGCCAGAGGGAAG
AAACGACAGAAGGGATGGTTTCCTGCCAGCCATGTAAAGCTGCTAGGTCC
AAGCAGTGAAAGAACCATGCCTACTTTTCACGCTGTATGTCAAGTGATTG
CTATGTATGACTACATGGCGAATAACGAAGATGAGCTCAATTTCTCCAAA
GGACAGCTGATTAATGTTATGAACAAAGATGACCCTGACTGGTGGCAAGG
AGAAACCAATGGTCTGACTGGTCTCTTTCCTTCAAACTATGTTAAGATGA
CAACAGACTCAGATCCAAGTCAACAGTGGTGTGCTGACCTCCAAGCCCTG
GACACAATGCAGCCTACGGAGAGGAAGCGACAGGGCTACATTCACGAGCT
CATTCAGACAGAGGAGCGGTACATGGACGACGACCTGCAGCTGGTCATCG
AGGTCTTCCAGAAACGGATGGCTGAGGAAGGCTTCCTCACTGAAGCAGAC
ATGGCTCTGATCTTTGTGAACTGGAAAGAGCTCATCATGTCCAACACGAA
GCTGCTGAGGGCCTTGCGGGTGAGGAAGAAGACTGGGGGTGAGAAGATGC
```

```
CAGTTCAGATGATTGGAGACATCCTGGCGGCAGAGCTGTCCCACATGCAG
GCCTACATCCGCTTCTGCAGCTGTCAGCTTAATGGGGCAACCCTGTTACA
GCAGAAGACAGACGAGGACACGGACTTCAAGGAATTTCTAAAGAAGTTGG
CATCAGACCCACGATGCAAAGGGATGCCCCTCTCCAGCTTCCTGCTGAAG
CCCATGCAGAGGATCACTCGCTACCCGCTGCTCATCCGAAGTATCCTGGA
GAACACTCCACAGAGTCATGTTGACCACTCCTCCCTGAAGCTGGCCCTAG
AACGTGCTGAGGAGCTGTGCTCTCAGGTGAACGAGGGAGTCCGGGAGAAG
GAAAATTCAGACCGGCTGGAGTGGATCCAGGCACACGTGCAGTGCGAAGG
CTTGGCAGAGCAACTTATTTTCAACTCCCTCACCAACTGCCTGGGCCCCC
GGAAGCTTCTGCACAGCGGGAAGCTGTACAAGACCAAGAGCAATAAGGAG
CTGCACGCCTTCCTCTTCAACGACTTCCTGCTGCTCACCTACCTGGTCAG
GCAGTTTGCCGCCGCCTCTGGCCACGAGAAGCTCTTCAACTCCAAGTCCA
GTGCTCAGTTCCGGATGTACAAAACGCCCATTTTCCTGAATGAAGTGTTG
GTGAAACTTCCCACAGACCCTTCCGGCGATGAGCCCGTCTTCCACATTTC
CCACATTGATCGTGTGTACACACTCCGAACAGACAACATCAACGAGAGGA
CGGCCTGGGTCCAGAAGATCAAGGGTGCCTCAGAGCAGTACATCGACACT
GAGAAGAAGAAACGGGAAAAGGCTTACCAAGCCCGTTCTCAAAAGACTTC
AGGTATTGGGCGTCTGATGGTGCATGTCATTGAAGCTACAGAATTAAAAG
CCTGCAAACCAAACGGGAAAAGTAATCCATACTGTGAAGTCAGCATGGGC
TCCCAAAGCTATACCACCAGGACCCTGCAGGACACACTAAACCCCAAGTG
GAACTTCAACTGCCAGTTCTTCATCAAGGATCTTTACCAGGACGTTCTGT
GTCTCACTATGTTTGACAGAGACCAGTTTTCTCCAGATGACTTCTTGGGT
CGTACTGAAGTTCCAGTGGCAAAATCCGAACAGAACAGGAAAGCAAAGGC
CCCACCACCCGCCGACTACTACTGCACGAAGTCCCCACTGGAGAAGTCTG
GGTCCGCTTTGACCTGCAACTTTTTGAACAAAAAACTCTCCTTTGA
```

Mouse Ese2L Protein: Sequence ID NO:27

MAQFPTAMNGGPNMWAITSEERTKHDKQFDNLKPSGGYITGDQARTFFLQ

SGLPAPVLAEIWALSDLNKDGKMDQQEFSIAMKLIKLKLQGQQLPVVLPP

LMKQPPMFSPLISARFGMGSMPNLSIHQPLPPVAPIATPLSSATSGTSIP

PLMMPAPLVPSVSTSSLPNGTASLIQPLSIPYSSSTLPHASSYSLMMGGF

GGASIQKAQSLIDLGSSSSTSSTASLSGNSPKTGTSEWAVPQPSRLKYRQ

KFNSLDKGMSGYLSGFQARNALLQSNLSQTQLATIWTLADIDGDGQLKAE

EFILAMHLTDMAKAGQPLPLTLPPELVPPSFRGGKQVDSVNGTLPSYQKT

QEEEPQKKLPVTFEDKRKANYERGNMELEKRRQVLMEQQQREAERKAQKE

KEEWERKQRELQEQEWKKQLELEKRLEKQRELERQREEERRKEIERREAA

KQELERQRRLEWERLRRQELLSQKTREQEDIVRLSSRKKSLHLELEAVNG

KHQQISGRLQDVQIRKQTQKTELEVLDKQCDLEIMEIKQLQQELKEYQNK

LIYLVPEKQLLNERIKNMQLSNTPDSGISLLHKKSSEKEELCQRLKEQLD

```
-continued
ALEKETASKLSEMDSFNNQLKELRESYNTQQLALEQLHKIKRDKLKEIER

KRLEQIQKKKLEDEAARKAKQGKENLWRESIRKEEEEKQKRLQEEKSQDK

TQEEERKAEAKQSETASALVNYRALYPFEARNHDEMSFSSGDIIQVDEKT

VGEPGWLYGSFQGKFGWFPCNYVEKVLSSEKALSPKKALLPPTVSLSATS

TSSQPPASVTDYHNVSFSNLTVNTTWQQKSAFTRTVSPGSVSPIHGQGQA

VENLKAQALCSWTAKKENHLNFSKHDVITVLEQQENWWFGEVHGGRGWFP

KSYVKLIPGNEVQRGEPEALYAAVTKKPTSTAYPVTSTAYPVGEDYIALY

SYSSVEPGDLTFTEGEEILVTQKDGEWWTGSIGERTGIFPSNYVRPKDQE

NFGNASKSGASNKKPEIAQVTSAYAASGTEQLSLAPGQLILILKKNTSGW

WQGELQARGKKRQKGWFPASHVKLLGPSSERTMPTFHAVCQVIAMYDYMA

NNEDELNFSKGQLINVMNKDDPDWWQGETNGLTGLFPSNYVKMTTDSDPS

QQWCADLQALDTMQPTERKRQGYIHELIQTEERYMDDDLQLVIEVFQKRM

AEEGFLTEADMALIFVNWKELIMSNTKLLRALRVRKKTGGEKMPVQMIGD

ILAAELSHMQAYIRFCSCQLNGATLLQQKTDEDTDFKEFLKKLASDPRCK

GMPLSSFLLKPMQRITRYPLLIRSILENTPQSHVDHSSLKLALERAEELC

SQVNEGVREKENSDRLEWIQAHVQCEGLAEQLIFNSLTNCLGPRKLLHSG

KLYKTKSNKELHAFLFNDFLLLTYLVRQFAAASGHEKLFNSKSSAQFRMY

KTPIFLNEVLVKLPTDPSGDEPVFHISHIDRVYTLRTDNINERTAWVQKI

KGASEQYIDTEKKKREKAYQARSQKTSGIGRLMVHVIEATELKACKPNGK

SNPYCEVSMGSQSYTTRTLQDTLNPKWNFNCQFFIKDLYQDVLCLTMFDR

DQFSPDDFLGRTEVPVAKIRTEQESKGPTTRRLLLHEVPTGEVWVRFDLQ

LFEQKTLL
```

REFERENCES

1. H. Riezman, P. G. Woodman, G. van Meer, M. Marsh. Molecular mechanisms of Endocytosis. Cell 91: 731–738, 1997.
2. S. L. Schmid. Clathrin-coated vesicle formation and protein sorting: an integrated process. Annu. Rev. Biochem. 66: 511–548, 1997.
3. M. S. Robinson. Coats and budding vesicles. Trends Cell. Biol. 7: 99–102, 1997.
4. D. E. Warnock, S. L. Schmid. Dynamin GTPase, a force-generating molecular switch. BioEssays 18: 885–893, 1996.
5. R. Urrutia, J. R. Henley, T. Cook, M. A. McNiven. The dynamins: redundant or distinct functions for an expanding family of related GTPases? Proc. Natl. Acad. Sci. USA 94: 377–384, 1997.
6. P. Wigge, K. Kohler, Y. Vallis, C. A. Doyle, D. Owen, S. P. Hunt, H. T. McMahon. Amphiphysin Heterodimers: Potential Role in Clathrin-mediated Endocytosis. Molecular Biology of the Cell 8: 2003–2015, 1997.
7. A. L. Munn, B. J. Stevenson, M. I. Geli, H. Riezman. end5, end6 and end7:mutations that cause actin delocalization and block the internalization step of endocytosis in Saccharomyces cerevisiae. Molecular Biology of the Cell 6: 1721–1742, 1995.
8. O. Shupliakov, P. Low, D. Grabs, H. Gad, H. Chen, C. David, K. Takei, P. De Camilli, L. Brodin. Synaptic vesicle endocytosis impaired by disruption of dynamin-SH3 domain interactions. Science 276: 259–263, 1997.
9. P. Wigge, Y. Vallis, H. T. McMahon. Inhibition of receptor-mediated endocytosis by the amphiphysin SH3 domain. Current Biology 7: 554–560, 1997.
10. H. McLauchlan, J. Newell, N. Morrice, A. Osborne, M. West, E. Smythe. A novel role for Rab5-GDI in ligand sequestration into clathrin-coated pits. Current Biology 8: 34–45, 1997.
11. P. J. Robinson, J.-M. Sontag, J.-P. Liu, E. M. Fykse, C. Slaughter, H. McMahon, T. C. Sudhof. Dynamin GTPase regulated by protein kinase C phosphorylation in nerve terminals. Nature 365: 163–166, 1993.
12. J.-P. Liu, A. T. R. Sim, P. J. Robinson. Calcineurin inhibition of Dynamin GTPase activity coupled to nerve terminal depolarization. Science 265: 970–973, 1994.
13. A. Wilde, F. M. Brodsky. In vivo phosphorylation of Adaptors regulates their interaction with Clathrin. The Journal of Cell Biology 135: 635–645, 1996.
14. R. Bauerfeind, K. Takei, P. De Camilli. Amphiphysin I is associated with coated endocytic intermediates and undergoes stimulation-dependent dephosphorylation in nerve terminals. J. Biol. Chem. 272: 30984–30992, 1997.
15. S. van Delft, R. Govers, G. J. Strous, A. J. Verkleij, P. M. P. van Bergen en Henegouwen. Epidermal growth factor induces ubiquitination of Eps15. Journal of Biological Chemistry 272: 14013–14016, 1997.
16. J.-M. Galan, R. Haguenauer-Tsapis. Ubiquitin Lys63 is involved in ubiquitination of a membrane plasma membrane protein. EMBO J 16: 5847–5854, 1997.
17. J. Terrel, S. Shih, R. Dunn, L. Hicke. A function for monoubiquitination in the internalization of a G protein-coupled receptor. Molecular Cell 1: 193–202, 1998.
18. R. Govers, P. van Kerkhof, A. L. Schwartz. G. J. Strous. Linkage of the ubiquitin-conjugating system and the endocytic pathway in ligand-induced internalization of the growth hormone receptor. EMBO J. 16: 4851–4858, 1997.
19. P. De Camilli, S. D. Emr, P. S. McPherson, P. Novick. Phosphoinositides as regulators in membrane traffic. Science 271: 1533–1539, 1996.
20. E. Kubler, H. Riezman. Actin and fimbrin are required for the internalization step of endocytosis in yeast. EMBO J. 12: 2855–2862, 1993.
21. H. Benedetti, S. Raths, F. Crausaz, H. Riezman. The END3 gene encodes a protein that is required for the internalization step of endocytosis and for actin cytoskeleton organization in yeast. Mol. Biol. Cell. 5: 1023–1037, 1994.
22. M. I. Geli, H. Riezman. Role of Type I Myosin in receptor-mediated endocytosis in yeast. Science 27: 533–535, 1996.
23. H.-Y. Tang, M. Cai. The EH-domain-containing protein Pan1 is required for normal organization of the actin cytoskeleton in Saccaromyces cerevisiae. Mol. Cell. Biol. 16: 4897–4914, 1996.
24. V. Moreau, J.-M. Galan, G. Devilliers, R. Haguenauer-Tsapis, B. Winsor. The yeast Actin-related protein Arp2p is required for the internalization step of endocytosis. Molecular Biology of the Cell 8: 1361–1375, 1997.
25. B. Wendland, S. D. Emr. Pan1p, Yeast eps15, functions as a multivalent adaptor that coordinates protein-protein interactions essential for endocytosis. Journal of Cell Biology 141: 71–84, 1998.

26. F. Fazioli, L. Minichiello, B. Matoskova, W. T. Wong, P. P. Di Fiore. eps15. A novel tyrosine kinase substrate, exhibits transforming activity. Mol. Cell. Biol. 13: 5814–5828, 1993.
27. A. Benmerah, J. Gagnon, B. Begue, B. Megarbane, A. Dautry-Varsat, N. Cerf-Bensussan. The Tyrosine kinase substrate EPS15 is constitutively associated with the plasma membrane adaptor AP2. J. Cell Biol. 131: 1831–1838, 1995.
28. F. Tebar, T. Sorkina, A. Sorkin, M. Ericsson, T. Kirchausen. Eps15 Is a component of Clathrin-coated Pits and Vesicles and is located at the Rim of Coated Pits. Journal of Biological Chemistry 271: 28727–28730, 1996.
29. F. Tebar, S. Confalonieri, R. E. Carter, P. P. Di Fiore, A. Sorkin. Eps15 is Constitutively Oligomerized due to Homolphilic interaction of its Coiled-coil domain. Journal of Biological Chemistry 272: 15413–15418, 1997.
30. R. Carbone, S. Fre, G. Iannolo, F. Belleudi, M. P., P. G. Pelicci, M. R. Torrisi, P. P. Di Fiore. eps15 and eps15R are essential components of the endocytic pathway. Cancer Research 57: 5498–5504, 1997.
31. A. Benmerah, C. Lamaze, B. Begue, S. L. Schmid, A. Dautry-Varsat, N. Cerf-Bensussan. AP-2/Eps 15 interaction is required for receptor-mediated endocytosis. Journal of Cell Biology 140: 1055–1062, 1998.
32. W. T. Wong, C. Schumacher, A. E. Salcini, A. Romano, P. Castagnino, P. G. Pelicci, P. P. Di Fiore. A protein-binding domain. EH, identified in the receptor tyrosine kinase substrate EPS15 and conserved in evolution. Proc. Natl. Acad. Sci. USA 92: 9530–9534, 1995.
33. P. P. Di Fiore, P. G. Pelicci, A. Sorkin. EH: a novel protein—protein interaction domain potentially involved in intracellular sorting. Trends. Biochem. Sci. 22: 411–413, 1997.
34. C. Schumacher, B. S. Knudsen, T. Ohuchi, P. P. Di Fiore, R. H. Glassman, H. Hanafusa. The SH3 domain of Crk binds specifically to a conserved proline-rich motif in Eps15 and Eps15R. Journal of Biological Chemistry 270: 15341–15347, 1995.
35. A. Benmerah, B. Begue, A. Dautry-Vasat, N. Cerf-Bensussan. The Ear of alpha-Adaptin interacts with the COOH-terminal domain of the EPS15 protein. Journal of Biological Chemistry 271: 12111–12116, 1996.
36. G. Iannolo, A. E. Salcini, I. Gaidarov, O. B. J. Goodman, J. Baulida, G. Carpenter, P. G. Pelicci, P. P. Di Fiore, J. H. Keen. Mapping of the molecular determinants involved in the interaction between Eps15 and AP2. Cancer Research 57: 240–245, 1997.
37. L. Coda, A. E. Salcini, S. Confalonieri, G. Pelicci, T. Sorkina, A. Sorkin, P. G. Pelicci, P. P. Di Fiore. Eps15R is a tyrosine kinase substrate with characteristics of a docking protein possibly involved in coated pits-mediated internalization. Journal of Biological Chemistry 273: 3003–3012, 1998.
38. B. Wendland, J. M. McCaffery, Q. Xiao, S. D. Emr. A Novel Fluorescence-activated Cell Sorter-based screen for yeast Endocytosis mutants identifies a yeast homologue of mammalian eps15. J. Cell Biol. 135: 1485–1500, 1996.
39. S. Raths, J. Rohrer, F. Crausaz, H. Riezman. end3 and end4: Two mutants defective in receptor-mediated and fluid-phase endocytosis in *Saccaromyces cerevisiae*. The Journal of Cell Biology 120: 55–65, 1993.
40. H. Y. Tang, A. Munn, M. Cai. EH domain proteins Pan1p and End3p are components of a complex that plays a dual role in organization of the cortical actin cytoskeleton and endocytosis in *Saccharomyces cerevisiae*. Mol. Cell. Biol. 17: 4294–4304, 1997.
41. T. Zoladek, A. Tobiasz, G. Vaduva, M. Boguta, N. C. Martin, A. K. Hopper. MDP1, a *Saccharomyces cerevisiae* gene involved in mitochondrial/cytoplasmic protein distribution, is identical to the ubiquitin-protein ligase gene RSP5. Genetics 145: 595–603, 1997.
42. P. S. McPherson, E. P. Garcia, V. I. Slepnev, C. David, X. Zhang, D. Grabs, W. S. Sossin, R. Bauerfeind, Y. Nemoto, P. De Camilli. A presynaptic inositol-5-phosphatase. Nature 379: 353–357, 1996.
43. A. E. Saicini, S. Confalonieri, M. Doria, E. Santolini, E. Tassi, O. Minencova, G. Cesareni, P. G. Pelicci, P. P. Di Fiore. Binding specificty and in vivo targets of the EH domain, a novel protein—protein interaction module. Genes & Development 11: 2239–2249, 1997.
44. I. Gout, R. Dhand, I. D. Hiles, M. J. Fry, G. Panayotou, P. Das, O. Truong, N. F. Totty, J. Hsuan, G. W. Booker, I. D. Campbell, M. D. Waterfield. The GTPase dynamin binds to and is activated by a subset of SH3 domains. Cell 75: 25–36, 1993.
45. C. David, P. S. McPherson, O. Mundigl, P. De Camilli. A role of amphiphysin in synaptic vesicle endocytosis suggested by its binding to dynamin in nerve terminals. Proc. Natl. Acad. Sci. USA 93: 331–335, 1996.
46. M. H. Butler, C. David, G.-C. Ochoa, Z. Freyberg, L. Daniell, D. Grabs, O. Cremona, P. De Camilli. Amphiphysin II (SH3P9:BIN1), a member of the Amphiphysin/Rvs family, is concentrated in the cortical cytomatrix of axon initial segments and Nodes of Ranvier in brain and around T Tubules in skeletal muscle. Journal of Cell Biology 137: 1355–1367, 1997.
47. C. Leprince, F. Romero, D. Cussac, B. Vayssiere, R. Berger, A. Tavitian, J. H. Camonis. A new member of the Amphiphysin family connecting endocytosis and signal transduction pathways. J. Biol. Chem. 272: 15101–15105, 1997.
48. A. R. Ramjaun, K. D. Micheva, I. Bouchelet, P. S. McPherson. Identification and characterization of a nerve terminal-enriched amphiphysin isoform. J. Biol. Chem. 272: 16700–16706, 1997.
49. A. Wesp, L. Hicke, J. Palecek, R. Lombardi, T. Aust, A. L. Munn, H. Riezman. End4p/Sla2p Interacts with Actin-associated proteins for endocytosis in *Saccharomyces cerevisiae*. Molecular Biology of the Cell 8: 2291–2306, 1997.
50. E. de Heuvel, A. W. Bell, A. R. Ramjaun, K. Wong, W. S. Sossin, P. S. McPherson. Identification of the major Synaptojanin-binding proteins in the brain. J. Biol. Chem. 272: 8710–8716, 1997.
51, N. Ringstad, Y. Nemoto, P. De Camilli. The SH3p4/SH3p8/SH3p13 protein family: binding partners for synaptojanin and dynamin via a Grb2-like Src homology 3 domain. Proc. Natl. Acad. Sci. USA 94: 8569–8574, 1997.
52. Z. Wang, M. F. Moran. Requirement for the Adapter protein Grb2 in EGF receptor endocytosis. Science 272: 1935–1939, 1996.
53. A. B. Sparks, N. G. Hoffman, S. J. McConnel, D. M. Fowlkes, B. K. Kay. Cloning of ligand targets: Sytematic isolation of SH3 domain-containing proteins. Nature Biotechnology 14: 741–744, 1996.
54. P. Cupers, E. ter Haar, W. Boll, T. Kirchhausen. Parallel dimers and anti-parallel tetramers formed by Epidermal Growth Factor Receptor Pathway Substrate Clone 15 (Eps15). Journal of Biological Chemistry 272: 33430–33434, 1997.

55. H. Stenmark, C. Bucci, M. Zerial. Expression of Rab GTPases using recombinant vaccinia virus. Meth. Enzymol. 257: 155–164, 1995.
56. S. van Delft, C. Schumacher, W. Hage, A. J. Verkleij, P. M. P. van Bergen en Henegouwen. Association and Colocalization of Eps15 with Adaptor Protein-2 and Clathrin. The Journal of Cell Biology 136: 811–821, 1997.
57. M. Toth, J. Grimsby, G. Buzsaki, G. P. Donovan. Epileptic seizures caused by inactivation of a novel gene, jerky, related to centromere binding protein-B in transgenic mice. Nature Genetics 11: 71–75, 1995.
58. J. Sambrook, E. F. Fritsch, T. Maniatis, *Molecular Cloning, a laboratory manual. Second Edition.* (Cold Spring Harbor Press, Cold Spring Harbor. 1989).
59. Roos, J. and Kelly, R. B. Dap160, a Nerual-specific Eps115 homology and multiple SH3 domain-containing protein that interacts with *Drosophila* Dynamin. *J. Biol. Chem.* 273, 19108–19119, 1998.
60. Ren, R., Mayer, B. J. Cicchetti, P. and Baltimore, D. Identification of a Ten-Amino Acid Proline-Rich SH3 Binding Site. *Science.* 259, 1157–1161, 1993.
61. Hall, A. Rho GTPases and the actin cytoskeleton. *Science.* 279, 509–514, 1998.
62. Nalefski, E. A. and Falke, J. J. The C2 domain calcium-binding motif: Structural and functional diversity. *Protein Science.* 5, 2375–2390, 1996.
63. Chen. H., et al. Epsin is an EH-domain binding protein implicated in clathrin-mediated endocytosis. *Nature.* 394, 793–797.
64. Stukenberg, P. T. et al., Systematic identification of mitotic phosphoproteins. *Current Biology.* 7, 338–348, 1997.
65. Tang, H. Y. and Cai, M. The EH-domain containing protein Pan1 is required for normal organization of the actin cytoskeleton in *Saccaromyces cerevisiae. Mol. Cell. Biol.* 16, 4897–4914, 1996.

TABLE 1

Ese Proteins

| | | |
|---|---|---|
| Ese1 | MAQFPTPFGGSLDVWAITVEERAKHDQQFLSLKPIAGFITGDQARNPFFQ | |
| | :::::: : :::: ::: ::: :: ::: : ::::::: :: : | |
| Ese2 | MAQFPTAMNGGPNMWAITSEERTKHDKQFDNLKPSGGYITGDQARTFFLQ | |
| | | |
| EH1 | SGLPQPVLAQIWALADMNNDGRMDQVEFSIAMKLIKLKLQGYQLPSTLPP | 100 |
| | :::: :::: :::: : : :: ::: ::::::::::::: ::: ::: | |
| | SGLPAPVLAEIWALSDLNKDGKMDQQEFSIAMKLIKLKLQGQQLPVVLPP | 100 |
| | | |
| | VMKQQPVAISSAPA-FGIGGIASMP---PLTAVAPV--PMGSIPVVGMSP | |
| | ::: : : :: : :: ::: : : | |
| | IMKQPPMFSPLISARFGMGSMPNLSIHQPLPPVAPIATPLSSATSGTSIP | |
| | | |
| | PLVSS---VPPAAVPPLANGAPPVIQPLPAFAHPAATWPKSSSFSRSGPG | 191 |
| | :: :: : :: :::: : : :: : : | |
| | PLMMPAPLVPSVSTSSLPNGTASLIQPLS-IPYSSSTLPHASSYSLMMGG | 199 |
| | | |
| | SQLNTKLQKAQSF-DVASAPPAA---------------EWAVPQSSRLKY | |
| | ::::: : : :::::: ::::: | |
| | FG-GASIQKAQSLIDLGSSSSTSSTASLSGNSPKTGTSEWAVPQPSRLKY | |
| | | |
| EH2 | RQLFNSHDKTMSGHLTGPQARTILMQSSLPQAQLASIWNLSDIDQDGKLT | 275 |
| | :: ::: :: ::: : : ::: : :: : : ::: :: : ::: :: : | |
| | RQKFNSLDKGMSGYLSGFQARNALLQSNLSQTQLATIWTLADIDGDGQLK | 298 |
| | | |
| | AEEFILAMHLIDVAMSGQPLPPVLPPEYIPPSFRRVRSGSGMSVISSSSV | |
| | :::::::::: : : ::::: :::: ::::: :: : :: | |
| | AEEFILAMHLTDMAKAGQPLPLTLPPELVPPSFR-----GGKQV---DSV | |
| | | |
| | DQRLPEEPSSEDEQQPEKKLPVTFEDKKRENFERGSVELEKRRQALLEQQ | 375 |
| | :: : : :::::::::: : ::: ::::::: : ::: | |
| | NGTLPSYQKTQEEE-PQKKLPVTFEDKRKANYERGNMELEKRRQVLMEQQ | 389 |
| | | |
| | RKEQERLAQLERAEQERKERERQEQEAKRQLELEKQLEKQRELERQREEE | |
| | : :: :: : : ::: :: :::: : :::::: ::::::::::::: | |
| | QREAERKAQKEKEEWERKQRELQEQEWKKQLELEKRLEKQRELERQREEE | |
| | | |
| | RRKEIERREAAKRELERQRQLEWERNRRQELLNQRNKEQEGTVVLKARRK | 475 |
| | :::::::::::: :::::: ::::: :::::: : ::: : : : : | |
| | RRKEIERREAAKQELERQRRLEWERLRRQELLSQKTREQEDIVRLSSRKK | 489 |
| | | |
| C-C | TLEFELEALNDKKHQLEGKLQDIRCRLATQRQEIESTNKSRELRIAEITH | |
| | : :::: : : : ::: : : ::: : : :: | |
| | SLHLELEAVNGKHQQISGRLQDVQIRKQTQKTELEVLDKQCDLEIMEIKQ | |
| | | |
| | LQQQLQESQQMLGRLIPEKQILSDQLKQVQQN--SLHRDSLLTLKRALEA | 573 |
| | ::: : : : : :::: : : ::: : : | |
| | LQQELKEYQNKLIYLVPEKQLLNERIKNMQLSNTPDSGISLLHKKSS-E- | 587 |
| | | |
| | KELARQQLREQLDEVERETRSKLQEIDVFNNQLKELREIHSKQQLQKQRS | |
| | :: : : :::: : :: ::: : : ::::::::::: ::: | |
| | KEELCQRLKEQLDALEKETASKLSEMDSFNNQLKELRESYNTQQLALEQL | |

TABLE 1-continued

Ese Proteins

```
         LEAARLKQEQERKSLE-LEKQKED--AQRRV-QERDKQWLEHVQQEEQP         669
         : : :: ::: ::   : :    : :   :    : :       ::
         HKIKRDKLKEIERKRLEQIQKKKLEDEAARKAKQGKENLWRESIRKEEEE        687

RPRKPHEEDRLKREDSVRKKEAEEERAKPEMQDKQSRLFHPHQEPAKLATQ
         ::    : :    :    ::: : :    :::
         KQK------RLQEEKSQDKTQEEER-KAEA--KQSET-------------

SH3A     APWSTTEKGPLTISAQESVKVVYYRALYPFESRSHDEITIGPGDIVMVDE        769
                            : :::::::: : :::     :::   :::
         -----------------ASALVNYRALYPFEARNHDEMSFSSGDIIGVDE        748

SGTGEPGWLGGELKGKTGWPPANYAEKIPENEVPTPAKPVTDLTSAPAPK
         :::::: :    :: :::: :: ::       :              : ::
         KTVGEPGWLYGSFGGKFGWFPCNYVEKVLSSE------------KALSPK

LALRETPAPLPVTSSEPSTTPNNWADFSSTWPSSSNEKPETDNWDTWAAQ        869
         ::     : :  ::   :    :        :         :
         KALLPPTVSLSATST-SSQPPASVTDYHNV---SFSNLTVNTTWQ-----        827

PSLTVPSAGQLRQRSAFTPATATGSSPSPVLGQGEKVEGLQAQALYPWRA
                     : ::::       :: :: :::   :: : :::: : :
         ------------QKSAFTRTVSPGSV-SPIHGQGQAVENLKAQALGSWTA

SH3B     KKDNHLNPNKSDVITVLEQQDMWWFGEVGGGKGWFPKSYVKLISGPVRKS        969
         :: ::::: : :::::::::  :::::: ::  : :::::::::: :
         KKENHLNFSKHDVITVLEQQENWWFGEVHGGRGWFPKSYVKLIPGNEVQR        914

TSIDTGPTESPASLKRVASPAAKPAIP-GEEFIAMYTYESSEGGDLTPQQ
         : :       :  : :::  :: : : :  : :    :::::
         GEPEALYAAVTKKPTSTAYPVTSTAYPVGEDYIALYSYSSVEPGDLTFTE

SH3C     GDVIVVTKKDGDWWTGTVGDKSGVFPSNYVRLKDSEGSGTAGKTGSLGKK        1068
         :  : ::  ::: :::: ::     : :::::: :: :    : ::    ::
         GEEILVTGKDGEWWTGSIGERTGIFPSNYVRPKDQENFGNASKSGASNKK        1014

SH3D     PEIAQVIASYAATGPEGLTLAPGCLILIRKKNPGGWWEGELGARGKKRGI
         ::::::  :::  : :::  ::::::::::  :::  :::  ::::::::::
         PEIAQVTSAYAASGTEGLSLAPGGLILILKKNTSGWWGGELQARGKKRQK

GWFPANYVKLLSPGTSKITPTELPKTAVQPAVCQVIGMYDYTAQNDDELA        1168
         :::::  :::: :    ::         ::::: :::: : : :::
         GWFPASHVKLLGPSSERTMPT-------FHAVCQVIAMYDYMANNEDELN        1107

SH3E     FSKGGIINVLNKEDPDWWKGEVSGGVGLFPSNYVKLTTDMDPSQQ            1213
         :::: ::: :: ::::: ::  :  :::::::::::: ::: :::::
         FSKGQLINVMNKDDPDWWGGETNGLTGLFPSNYVKMTTDSDPSQQWCADL        1157

QALDTMQPTERKRQGYIHELIQTEERYMDDLQLFEQKTLL                 1197
```

Ese Proteins

TABLE 2

TABLE 2 (CONT'D.)

TABLE 2 (CONT'D.)

We claim:

1. An isolated nucleic acid comprising a nucleotide sequence selected from the group consisting of:
   (a) a nucleotide sequence encoding the amino acid sequence of SEQ ID NO:3;
   (b) Sequence ID NO:1;
   (c) Sequence ID NO:2; and
   (d) a nucleotide sequence completely complementary to the sequence of any of (a) to (c).

2. An isolated nucleic acid fragment of a nucleotide sequence selected from the group consisting of SEQ ID NO:1, SEQ ID NO:2 and a sequence completely complementary to either of said nucleic acid sequences, said fragment consisting of at least 10 consecutive nucleotides of said nucleotide sequence.

3. The nucleic acid of claim 2, wherein said sequence is used as a probe or a primer.

4. A recombinant vector comprising the isolated nucleic acid of claim 1.

5. An isolated host cell comprising the recombinant vector of claim 4.

6. A process for recombinantly producing a protein comprising culturing an isolated host cell comprising a recombinant vector comprising the nucleic acid of claim 1 under conditions whereby the encoded protein is expressed and isolating the expressed protein.

7. A recombinant vector comprising the isolated nucleic acid of claim 2.

8. An isolated host cell comprising the recombinant vector of claim 7.

* * * * *

UNITED STATES PATENT AND TRADEMARK OFFICE
CERTIFICATE OF CORRECTION

PATENT NO. : 7,118,886 B1 Page 1 of 1
APPLICATION NO. : 09/674237
DATED : October 10, 2006
INVENTOR(S) : Egan et al.

It is certified that error appears in the above-identified patent and that said Letters Patent is hereby corrected as shown below:

Column 191,
Line 24 should read -- mentary to either of said nucleotide sequences, said --

Signed and Sealed this

Twentieth Day of May, 2008

JON W. DUDAS
*Director of the United States Patent and Trademark Office*